US008367702B2

(12) United States Patent
Onda et al.

(10) Patent No.: US 8,367,702 B2
(45) Date of Patent: Feb. 5, 2013

(54) QUINOLONE DERIVATIVE

(75) Inventors: Kenichi Onda, Tokyo (JP); Kenichiro Imamura, Tokyo (JP); Fumie Sato, Tokyo (JP); Hiroyuki Moritomo, Tokyo (JP); Yasuharu Urano, Tokyo (JP); Yuki Sawada, Tokyo (JP); Naoki Ishibashi, Tokyo (JP); Keita Nakanishi, Tokyo (JP); Kazuhiro Yokoyama, Tokyo (JP); Shigetada Furukawa, Tokyo (JP); Kazuhiro Momose, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 376 days.

(21) Appl. No.: 12/680,301

(22) PCT Filed: Sep. 25, 2008

(86) PCT No.: PCT/JP2008/067325
§ 371 (c)(1),
(2), (4) Date: Mar. 26, 2010

(87) PCT Pub. No.: WO2009/041521
PCT Pub. Date: Apr. 2, 2009

(65) Prior Publication Data
US 2010/0256113 A1 Oct. 7, 2010

(30) Foreign Application Priority Data

Sep. 26, 2007 (JP) .................. 2007-248877

(51) Int. Cl.
*A61K 31/04* (2006.01)
*C07D 215/38* (2006.01)

(52) U.S. Cl. ...................... 514/312; 546/159
(58) Field of Classification Search ............. 546/159; 514/312
See application file for complete search history.

(56) References Cited

U.S. PATENT DOCUMENTS

| 5,817,674 | A | 10/1998 | Clemence et al. |
| 6,004,979 | A | 12/1999 | Clemence et al. |
| 6,635,655 | B1 | 10/2003 | Jayyosi et al. |
| 2002/0143030 | A1 | 10/2002 | Cutler et al. |
| 2003/0225117 | A1 | 12/2003 | Gronberg et al. |
| 2007/0082910 | A1 | 4/2007 | Yamamoto et al. |

FOREIGN PATENT DOCUMENTS

| EP | 0 374 765 | 6/1990 |
| EP | 0 811 613 | 12/1997 |
| GB | 1 207 771 | 3/1969 |
| JP | 55 151511 | 11/1980 |
| JP | 4 346974 | 12/1992 |
| JP | 8 311032 | 11/1996 |
| JP | 10 279561 | 10/1998 |
| JP | 2001 97866 | 4/2001 |
| JP | 2002 543073 | 12/2002 |
| JP | 2005 523004 | 8/2005 |
| WO | 97 12864 | 4/1997 |
| WO | 01 81340 | 11/2001 |
| WO | 2004 089412 | 10/2004 |

OTHER PUBLICATIONS

Extended European Search Report issued on Oct. 20, 2011 in the corresponding European Application No. 08834496.5.
Steck, E. A. et al., "Quinolines. V. Some Polysubstituted 4- (4'-Diethylamino-1'-methylbutylamino)-quinolines", Journal of the American Chemical Society, vol. 70, pp. 1012-1015, (1948).
Chung, K.H. et al., "New 4-Hydroxypyridine and 4-Hydroxyquinoline Derivatives as Inhibitors of NADH-ubiquione Reductase in the Respiratory Chain", Z. Naturforsch, pp. 609-616, (1989).
Chung, K.H. et al., "Fungicidal activity of synthetic piericidin analogs as inhibitors of NADH-ubiquinone oxidoreductase on the respiratory chain", J. Korean Agric. Chem., Soc., vol. 33, No. 3, pp. 264-267, (1990).
Chung, K.H. et al., "Biologocal Activity of quinoline derivatives as inhibitors of NADH-ubiquinone oxidoreductase in the respiratory chain", J. Korean. Agric., Chem., Soc., vol. 34, No. 1, pp. 43-48, (1991).
Brand, D. Martin et al., "Serial Review: The Powerhouse Takes Control of the Cell: the Role of Mitochondria in Signal Transduction Mitochondrial Supeoxide: Production, Biological Effects, and Activation of Uncoupling Proteins", Free Radical Biology & Medicine, vol. 37, No. 6, pp. 755-767, (2004).
Raha, Sandeep et al., "Mitocondria, oxygen free radicals, disease and ageing", Trends Biochem., Sci., pp. 502-508, (2000).
Hongo, Toshinori et al., Hyojun Seirigaku, pp. 662-663, (2005), (with partial English translation).
Brownlee, Michael "Biochemistry and molecular cell biology of diabetic complications", Nature, vol. 414, pp. 813-820, (Dec. 13, 2001).
Griendling, K. Kathy et al., "NAD(P)H Oxidase: Role in Cardiovascular Biology and Disease", Circulation Research, Journal of the American Heart Association, vol. 86, pp. 494-501, ISSN: 0009-7330, (2000).
Blair, S. Anne et al., "Regulation of Glucose Transport and Glycogen Synthesis in L6 Muscle Cells during Oxidative Stress", The Journal of Biological Chemistry, vol. 274, No. 51, pp. 36293-36299, (1999).

(Continued)

*Primary Examiner* — D M Seaman
(74) *Attorney, Agent, or Firm* — Oblon, Spivak, McClelland, Maier & Neustadt, L.L.P.

(57) ABSTRACT

As a result of extensive studies on NAD(P)H oxidase inhibitors, the present inventors found that a quinolone derivative having, at the 2-position, an alkyl group substituted with a heteroatom or the like has an excellent NAD(P)H oxidase inhibitory activity, and accomplished the present invention. The compound of the present invention has a reactive oxygen species production inhibitory activity based on the NAD(P)H oxidase inhibitory activity, and therefore can be used as an agent for preventing and/or treating diabetes, impaired glucose tolerance, hyperlipidemia, fatty liver, diabetic complications and the like.

21 Claims, No Drawings

OTHER PUBLICATIONS

Rudich, Assaf et al., "Prolonged Oxidative Stress Impairs Insulin-Induced GLUT4 Translocation in 3T3-L1 Adipocytes", Diabetes, vol. 47, pp. 1562-1569, (Oct. 1998).

Ihara, Yu et al., "Hyperglycemia Causes Oxidative Stress in Pancreatic β-Cells of GK Rats, a Model of Type 2 Diabetes", Diabetes, vol. 48, pp. 927-932, (Apr. 1999).

Furukawa, Shigetada et al., "Increased oxidative stress in obesity and its impact on metabolic syndrome", The Journal of Clinical Investigation, vol. 114, No. 12, pp. 1752-1761, (Dec. 2004).

Fukui, Toshiki et al., "p22phox mRNA Expression and NADPH Oxidase Activity Are Increased in Aortas From Hypertensive Rats", Circulation Research, vol. 80, pp. 45-51, (1997).

Inoguchi, Toyoshi et al., "NAD(P)H Oxidase Activation: A Potential Target Mechanism for Diabetic Vascular Complications, Progressive β-Cell Dysfunction and Metabolic Syndrome", Current Drug Targets, vol. 6, pp. 495-501, (2005).

Browning, D. Jeffrey et al., "Molecular mediators of hepatic steatosis and liver injury", The Journal of Clinical Investigation, vol. 114, No. 2, pp. 147-152 (Jul. 2004).

Arbiser, L. Jack et al., "Reactive oxygen generated by Nox1 triggers the angiogenic switch", Proceedings of the National Acadamy of Science, vol. 99, No. 2, pp. 715-720, (Jan. 22, 2002).

Zhu, Xiongwei et al., "Oxidative stress signalling in Alzheimer's disease", Brain Research, vol. 1000, pp. 32-39, (2004).

Imamura, Yutaka et al., "Drusen, choroidal neovascularization, and retinal pigment epithelium dysfunction in SOD1-deficient mice: A model of age-related macular degeneration", Proceedings of the National Academy of Science, vol. 103, No. 30, pp. 11282-11287, (Jul. 25, 2006).

Droege, Wulf "Free Radicals in the Physiological Control of Cell Function", Physiological Reviews, vol. 82, pp. 47-95, (2002).

Braun v. Julius et al., "Imid- und Amid- chloride nicht- aromatischer Saeurenm VI.: Ein Neuer Weg in die Chnolin-Reihe", Berichit Der Deutshen Chemischen Gesellshaft, vol. 63B, pp. 3191-3203, (1930).

QUINOLONE DERIVATIVE

TECHNICAL FIELD

The present invention relates to a medicament, and specifically to a novel quinolone derivative or a salt thereof, which is useful as an agent for preventing and/or treating diabetes.

BACKGROUND ART

Diabetes is a syndrome mainly characterized by chronic continuance of a high concentration of glucose in blood (blood glucose level) and is a disease caused by relative or absolute deficiency of insulin which is a blood glucose-lowering hormone.

The number of diabetic patients throughout the world is currently estimated to be 194,000,000 (2003, adults), accounting for 5.1% of the adult population (3,800,000,000), which corresponds to a diabetic morbidity of one in twenty people. Further, this number is predicted to rise to 333,000,000 by 2025 (Diabetes Atlas, 2003, $2^{nd}$ edition, p. 15-71).

Further, there is a serious increase in the number of people with impaired glucose tolerance which can be said to be a pre-diabetes state. Impaired glucose tolerance raises a pathogenic risk of hypertension or hyperlipidemia as well as a pathogenic risk of diabetes. The number of people with impaired glucose tolerance in the adult population is already estimated to be 314,000,000, and is said to be increased to 472,000,000 by 2025. Therefore, it is said to the extent that diabetes and impaired glucose tolerance are called the most significant medical problem of the $21^{st}$ century, there is a great social demand associated with the treatment of this diseases.

In healthy people, saccharides from dietary intake are absorbed by the digestive tract and then transported into blood, resulting in elevation of the blood glucose level. Correspondingly, insulin is secreted from the pancreas, whereby release of glucose from the liver is lowered while increasing glucose uptake into muscle or adipose tissues. Then, the blood glucose level is decreased. As a result, homeostasis of blood glucose is maintained. However, in a diabetic condition, it is caught in chronic dysfunction of the blood glucose control known as postprandial hyperglycemia or fasting hyperglycemia due to incomplete secretion of insulin, or insulin resistance (insufficiency of insulin action).

Chronic duration of a hyperglycemic state leads to an enhancement in the production of reactive oxygen in vivo, which consequently increases oxidative stress to vascular endothelial cells. Indeed, it has been reported that the level of an oxidative stress marker in blood is elevated in diabetic patients. It is considered that oxidative stress stemming from such a hyperglycemic condition is closely correlated with not only the progression of diabetes (hyperglycemic symptom), but also the pathogenesis of microvascular diabetic complications such as diabetic retinopathy, neuropathy, and nephropathy (Non-Patent Citation 1).

Excessive reactive oxygen also acts on lipids in vivo to cause the formation of lipid peroxides such as oxidized LDL, which, in turn, brings about inflammatory reactions including the accumulation of monocytes and macrophages in the vascular endothelium, and macrovascular complications (arteriosclerosis) accompanying the risk of cardiovascular events.

In vivo oxidative stress arises from the excessive production of reactive oxygen species (ROS) such as superoxide anions. NAD(P)H oxidase in neutrophils or phagocytes has been conventionally known as a principle production source of ROS for a long time. Recently, the production of ROS by NAD(P)H oxidase has also been confirmed in several cellular species such as vascular endothelial cells or smooth muscle cells, and the possibility has been pointed to that ROS is implicated in functions of cells and the pathogenesis of diseases in a variety of tissues (Non-Patent Citation 2).

In insulin target cells such as L6 myocytes or 3T3-L1 adipocytes, it has been reported that long-term exposure of ROS to such cells inhibits glucose uptake by insulin stimulation (Non-Patent Citations 3 and 4), and it is believed that oxidative stress induces insulin resistance. Besides, it is believed that ROS produced by chronic hyperglycemia results in dysfunction or apoptosis of pancreatic β cells, consequently lowering insulin secretion (Non-Patent Citation 5).

In diabetic model mice, it has been reported that an expression level of NAD(P)H oxidase is increased in adipose tissues, thus enhancing the production of ROS, and apocynin, an NAD(P)H oxidase inhibitor, inhibits ROS production lower the blood glucose level in diabetes model mice (Non-Patent Citation 6). In addition, it has been reported that diphenyleneiodonium (DPI), another NAD(P)H oxidase inhibitor, promotes glucose uptake into L6 myocytes and improves insulin sensitivity in diabetes model mice (Patent Citation 1).

From these findings, a compound inhibiting the NAD(P)H oxidase activity, based on an inhibitory action of ROS production, is expected to be a drug for improving hyperglycemic symptoms in diabetes through the promotion of glucose uptake in peripheral tissues. Further, with regard to the pancreas or other organs vulnerable to disorders through diabetic hyperglycemia, such a compound also provides a feasibility of a drug having an active protective action via the relief of oxidative stress.

Apocynin, which is an NAD(P)H oxidase inhibitor, has been reported to improve the elevation of triglyceride levels in blood and hepatic tissues in diabetes model mice (Non-Patent Citation 6), and a compound inhibiting an NAD(P)H oxidase activity is also considered to be useful for preventing and treating hyperlipidemia or fatty liver.

Besides, elevation of blood pressure due to a rise of ROS production in vascular walls through the action of NAD(P)H oxidase has been reported in spontaneous hypertension model rats, or hypertension model rats with continuous administration of angiotensin II (Non-Patent Citation 7), and an NAD(P)H oxidase inhibitor is expected to remedy hypertension.

Further, it is considered that a rise of ROS production through the action of NAD(P)H oxidase is involved in the pathogenesis and progression of diabetic complications (such as retinopathy, nephropathy, and neuropathy), peripheral circulatory disturbance, and arteriosclerosis, by the development of vascular endothelial cell disorders and chronic inflammatory reactions (Non-Patent Citation 8), and there is a possibility that the NAD(P)H oxidase inhibitor inhibits these diseases.

Additionally, as diseases associated with an enhancement of ROS production, there are known metabolic syndromes (Non-Patent Citation 5), Non-Alcoholic Fatty Liver Disease (NAFLD) and Non-Alcoholic Steato-Hepatitis (NASH) (Non-Patent Citation 9), cancer (Non-Patent Citation 10), Alzheimer's type dementia (Non-Patent Citation 11), age-related macular degeneration (Non-Patent Citation 12), neurodegenerative diseases, cerebral stroke, ischemic diseases, arthritis, inflammatory diseases, etc. (Non-Patent Citation 13). The NAD(P)H oxidase inhibitor is expected to ameliorate these diseases.

As the NAD(P)H oxidase inhibitor, bicyclic pyridazine compounds have been reported to be effective for treating diabetes, hypertension, and the like (Patent Citation 2).

Meanwhile, there have been reported Patent Citations 3 through 8, Non-Patent Citation 14, and the like relating to quinolone derivative compounds.

It has been reported in Patent Citation 3 that a compound of the formula (A) exhibits a leucotriene D4 antagonistic action and is effective for allergic diseases. However, there is no disclosure of groups described in $R^2$ of the present invention compound, and no disclosure of an NAD(P)H oxidase inhibitory activity.

[Chem. 1]

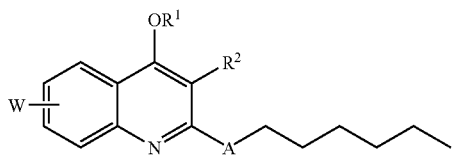

(A)

(In the formula, A represents —$CH_2CH=CH$—, —$CH(OH)CH=CH$—, —$CH(OH)C\equiv C$—, —$CH=CHCH_2$—, or —$CH_2C\equiv C$—. See the above-referenced document for other symbols in the formula.)

It has been reported in Patent Citation 4 that a compound of the formula (B) exhibits an anti-*helicobacter pylori* action. However, there is no disclosure of groups described in $R^2$ of the present invention compound, and no disclosure of an NAD(P)H oxidase inhibitory activity and effectiveness for diabetes.

[Chem. 2]

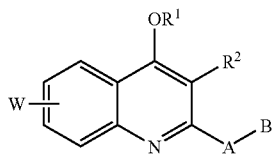

(B)

(In the formula, A represents —$CH(OH)CH=CH$—, —$CH(OH)C\equiv C$—, —$CH=CHCH_2$—, —$(CH_2)_n$—, —$CH=CHCH_2$—, —$CH=CHCH=CH$—, —$COCH_2$—, or —$CH_2CH=CH$—, and B represents a hydrogen atom, —$(CH_2)_p$—$CH_3$, $(CH_2)_q$—$CO_2H$, or —$CH_2CH=C(CH_3)$ $CH_2CH_2CH=C(CH_3)$—$CH_3$. See the above-referenced document for other symbols in the formula.)

It has been reported in Patent Citation 5 that a wide range of compounds represented by the formula (C) exhibit an anti-*helicobacter pylori* action. However, there is no disclosure of groups described in $R^2$ of the present invention compound, and no disclosure of an NAD(P)H oxidase inhibitory activity and effectiveness for diabetes.

[Chem. 3]

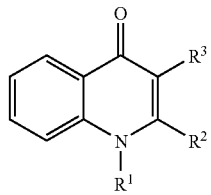

(C)

(In the formula, $R^2$ means

[Chem. 4]

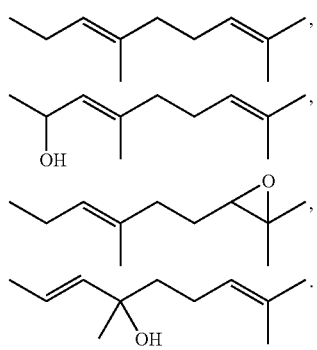

See the above-referenced document for other symbols in the formula.)

It has been reported in Patent Citation 6 that a compound of the formula (D) exhibits an anti-*helicobacter pylori* action. However, there is no disclosure of groups described in $R^2$ of the present invention compound, and no disclosure of an NAD(P)H oxidase inhibitory activity and effectiveness for diabetes.

[Chem. 5]

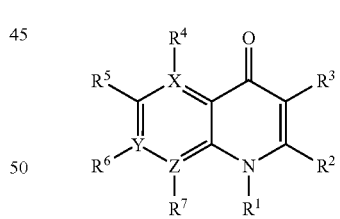

(D)

(In the formula, $R^2$ represents $C_{1-10}$ alkyl, $C_{2-10}$ alkenyl, ($C_{1-10}$ alkyl)phenyl, ($C_{2-10}$ alkenyl)phenyl, $C_{2-10}$ alkynyl, ($C_{2-10}$ alkynyl)phenyl, phenyl, naphthyl, thiophenyl, or pyridyl (provided that a cyclic group may be substituted). See the above-referenced document for other symbols in the formula.)

It has been reported in Patent Citation 7 that a wide range of compounds represented by the formula (E) exhibit an inosine monophosphate dehydrogenase (IMPDH) inhibitory activity. However, there is no specific disclosure of the present invention compound, and no disclosure of an NAD (P)H oxidase inhibitory activity and effectiveness for diabetes.

[Chem. 6]

$$R^2 \underset{X^5}{\overset{X^6}{\diagdown}} \underset{X^4}{\overset{X^1}{\diagdown}} \underset{X^3}{\overset{X^2}{\diagdown}} R^1 \quad (E)$$

(In the formula, $R^1$ represents alkyl, substituted alkyl, alkenyl, substituted alkenyl, alkynyl, substituted alkynyl, $NR^8R^9$, $SR^{20}$, cycloalkyl, substituted cycloalkyl, aryl, heterocycloalkyl, or heteroaryl. See the above-referenced document for other symbols in the formula.)

It has been reported in Patent Citation 8 that 2-(2-heptenyl)-3-methyl-4(1H)-quinolone, 2-(2-cis-heptenyl)-3-methyl-4(1H)-quinolone, and 2-(2-trans-heptenyl)-3-methyl-4(1H)-quinolone exhibit an anti-*helicobacter pylori* action. However, there is no disclosure of an NAD(P)H oxidase inhibitory activity and effectiveness for diabetes.

It has been reported in Patent Citation 9 that a wide range of compounds represented by the formula (F) exhibits a PPAR receptor inhibitory activity. However, there is no specific disclosure of the present invention compound, and no disclosure of an NAD(P)H oxidase inhibitory activity.

[Chem. 7]

$$\text{Ar I} - \text{Link}_1 - \text{Ar II} - \text{Link}_2\text{-z} \quad (F)$$

(In the formula, Ar I and Ar II represent aryl, heteroaryl, or the like. See the above-referenced document for other symbols in the formula.)

It has been reported in Patent Citation 14 that 3-methyl-2-(5-phenoxypentyl)quinolin-4(1H)-one and 3-ethyl-2-(5-phenoxypentyl)quinolin-4(1H)-one have an NADH-ubiquinone reductase inhibitory action. However, there is no disclosure of an NAD(P)H oxidase inhibitory activity and effectiveness for diabetes.

It has been reported in Patent Citation 15 that 3-methyl-2-[2-(4-phenoxyphenyl)ethyl]quinolin-4(1H)-one has an NADH-ubiquinone reductase inhibitory action. However, there is no disclosure of NAD(P)H oxidase inhibitory activity and effectiveness for diabetes.

A synthesis method of 3-chloro-2-(piperidin-1-ylmethyl)quinolin-4(1H)-one has been reported in Patent Citation 16. However, there is no disclosure of NAD(P)H oxidase inhibitory activity and effectiveness for diabetes.

[Patent Citation 1] Pamphlet of International Publication No. WO2003/087399

[Patent Citation 2] Pamphlet of International Publication No. WO2004/089412

[Patent Citation 3] European Patent Application Laid-open Publication No. 374765

[Patent Citation 4] JP-A-2001-97866

[Patent Citation 5] Pamphlet of International Publication No. WO97/12864

[Patent Citation 6] European Patent Application Laid-open Publication No. 811613

[Patent Citation 7] Pamphlet of International Publication No. WO01/81340

[Patent Citation 8] JP-A-10-279561

[Patent Citation 9] Pamphlet of International Publication No. WO00/064888

[Non-Patent Citation 1] Brownlee, Nature, 2001, Vol. 414, p. 813-820

[Non-Patent Citation 2] Griendling et al., Circulation Research, 2000, Vol. 86, p. 494-501

[Non-Patent Citation 3] Blair et al., The Journal of Biological Chemistry, 1999, Vol. 274, p. 36293-36299

[Non-Patent Citation 4] Rudich et al., Diabetes, 1998, Vol. 47, p. 1562-1569

[Non-Patent Citation 5] Ihara et al., Diabetes, 1999, Vol. 48, p. 927-932

[Non-Patent Citation 6] Furukawa et al., The Journal of Clinical Investigation, 2004, Vol. 114, p. 1752-1761

[Non-Patent Citation 7] Fukui et al., Circulation Research, 1997, Vol. 80, p. 45-51

[Non-Patent Citation 8] Inoguchi et al., Current Drug Targets, 2005, Vol. 6, p. 495-501

[Non-Patent Citation 9] Browning et al., The Journal of Clinical Investigation, 2004, Vol. 114, p. 147-152

[Non-Patent Citation 10] Arbiser et al., Proceedings of the National Academy of Science, 2002, Vol. 99, p. 715-720

[Non-Patent Citation 11] Zhu et al., Brain Research, 2004, Vol. 1000, p. 32-39

[Non-Patent Citation 12] Imamura et al., Proceedings of the National Academy of Science, 2006, Vol. 103, p. 11282-11287

[Non-Patent Citation 13] Droge et al., Physiological Reviews, 2002, Vol. 82, p. 47-95

[Non-Patent Citation 14] Chung et al., Journal of Bioscience, 1989, Vol. 44, p. 609-616

[Non-Patent Citation 15] Chung et al., Journal of Korean Agricultural Chemical Society, 1990, Vol. 33, p. 264-267

[Non-Patent Citation 16] Braun et al., Berichte der Deutschen Chemischen Gesellshaft, 1930, Vol. 63(B), p. 3291-3203

DISCLOSURE OF THE INVENTION

Problem to be Solved by the Invention

It is an object of the present invention to provide a novel medicament having an NAD(P)H oxidase inhibitory action, in particular a novel compound which is useful as an agent for preventing and/or treating diabetes.

Means for Solving the Problem

As a result of extensive studies on NAD(P)H oxidase inhibitors, the present inventors found that a quinolone derivative having, at the 2-position, an alkyl group substituted with a heteroatom or the like has an excellent NAD(P)H oxidase inhibitory activity, and completed this invention.

Thus, the present invention relates to a compound of the formula (I) or a salt thereof as well as a pharmaceutical composition comprising the compound of the formula (I) or a salt thereof and an excipient:

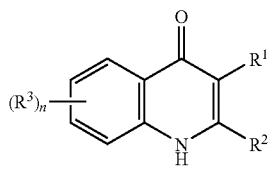

In formula (I),

R$^1$: lower alkyl, halogen, halogeno-lower alkyl, or cycloalkyl;

R$^2$: —X—Y—R$^{20}$, —X-a heterocyclic group which may be substituted, or

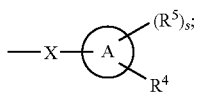

Ring A: aryl;

R$^3$: the same or different, and lower alkyl, halogen, halogeno-lower alkyl, aryl which may be substituted, a heterocyclic group which may be substituted, —CO$_2$R$^0$, —OR$^0$, or —O-halogeno-lower alkyl;

X: C$_{1-10}$ alkylene which may be substituted;

Y: *—C(O)N(R$^7$)—, —O—, *—OC(O)—, *—OC(O)N(R$^7$)—, —S—, —S(O)—, —S(O)$_2$—, —N(R$^8$)—, *—N(R$^7$)C(O)—, *—N(R$^7$)C(O)O—, —N(R$^7$)C(O)N(R$^7$)—, or *—N(R$^7$)S(O)$_2$—;

* in Y means a binding point to X;

R$^7$: the same or different, and R$^0$, cycloalkyl, or lower alkylene-cycloalkyl;

R$^8$: the same or different, and R$^7$ or —C(O)R$^7$;

R$^0$: the same or different, and H or lower alkyl;

n: 0, 1, 2, or 3;

s: 0, 1, 2, or 3;

R$^{20}$: C$_{1-10}$ alkyl, halogeno-lower alkyl, cycloalkyl which may be substituted, aryl which may be substituted, a heterocyclic group which may be substituted, lower alkylene-cycloalkyl which may be substituted, lower alkylene-aryl which may be substituted, lower alkylene-a heterocyclic group which may be substituted, lower alkylene-N(R$^0$)$_2$, —W—R$^0$, —W-halogeno-lower alkyl, —W-cycloalkyl which may be substituted, —W-aryl which may be substituted, —W-a heterocyclic group which may be substituted, —W-lower alkylene-cycloalkyl which may be substituted, —W-lower alkylene-aryl which may be substituted, or —W-lower alkylene-a heterocyclic group which may be substituted;

W: *-lower alkylene-C(O)N(R$^7$)—, *-lower alkylene-C(O)—, *-lower alkylene-O—, *-lower alkylene-OC(O)—, *-lower alkylene-OC(O)N(R$^7$)—, *-lower alkylene-O-lower alkylene-O—, *-lower alkylene-S—, *-lower alkylene-S(O)—, *-lower alkylene-S(O)$_2$—, *-lower alkylene-N(R$^8$)—, *-lower alkylene-N(R$^7$)C(O)—, *-lower alkylene-N(R$^7$)C(O)O—, *-lower alkylene-N(R$^7$)C(O)N(R$^7$)—, or *-lower alkylene-N(R$^7$)S(O)$_2$—;

* in W means a binding point to Y;

R$^4$: cycloalkyl which may be substituted, aryl which may be substituted, a heterocyclic group which may be substituted, lower alkylene-cycloalkyl which may be substituted, lower alkylene-aryl which may be substituted, lower alkylene-a heterocyclic group which may be substituted, lower alkylene-OR$^0$, —O-lower alkylene-OR$^0$, -J-cycloalkyl which may be substituted, -J-aryl which may be substituted, -J-a heterocyclic group which may be substituted, -J-lower alkylene-cycloalkyl which may be substituted, -J-lower alkylene-aryl which may be substituted, or -J-lower alkylene-a heterocyclic group which may be substituted;

R$^5$: the same or different, and C$_{1-10}$ alkyl, halogen, halogeno-lower alkyl, cycloalkyl which may be substituted, aryl which may be substituted, a heterocyclic group which may be substituted, —CO$_2$R$^0$, —CN, oxo, lower alkylene-cycloalkyl which may be substituted, lower alkylene-aryl which may be substituted, lower alkylene-a heterocyclic group which may be substituted, lower alkylene-CO$_2$R$^0$, -J-R$^0$, -J-halogeno-lower alkyl, -J-cycloalkyl which may be substituted, -J-aryl which may be substituted, -J-a heterocyclic group which may be substituted, -J-lower alkylene-cycloalkyl which may be substituted, -J-lower alkylene-aryl which may be substituted, or -J-lower alkylene-a heterocyclic group which may be substituted;

J: the same or different, and *—C(O)N(R$^7$)—, —C(O)—, —O—, —S—, —S(O)—, —S(O)$_2$—, —N(R$^8$)—, *—N(R$^7$)C(O)—, *—N(R$^7$)C(O)O—, —N(R$^7$)C(O)N(R$^7$)—, *-lower alkylene-C(O)N(R$^7$)—, *-lower alkylene-C(O)—, *-lower alkylene-O—, *-lower alkylene-S—, *-lower alkylene-S(O)—, *-lower alkylene-S(O)$_2$—, *-lower alkylene-N(R$^8$)—, *-lower alkylene-N(R$^7$)C(O)—, *-lower alkylene-N(R$^7$)C(O)O—, *-lower alkylene-N(R$^7$)C(O)N(R$^7$)—, *—O-lower alkylene-C(O)—, —O-lower alkylene-O—, or *—O-lower alkylene-N(R$^8$)—;

* in J means a binding point to ring A;

provided that the following compounds are excluded:
3-methyl-2-(5-phenoxypentyl)quinolin-4(1H)-one,
3-ethyl-2-(5-phenoxypentyl)quinolin-4(1H)-one,
3-methyl-2-[2-(4-phenoxyphenyl)ethyl]quinolin-4(1H)-one,
3-chloro-2-(piperidin-1-ylmethyl)quinolin-4(1H)-one, and
5-({4-[(3,4-dihydro-3-methyl-4-oxoquinolin-2-yl)methoxy]phenyl}methyl)thiazolidine-2,4-dione.

In the present specification, the symbols as defined above are used as having the same meaning unless otherwise particularly specified.

In the present specification, the "disease associated with NAD(P)H oxidase" means a "disease that can be treated by the inhibition of NAD(P)H oxidase-mediated ROS production".

Examples of an embodiment having the "disease associated with NAD(P)H oxidase" include diabetes (types 1 and 2), impaired glucose tolerance, hyperlipidemia, fatty liver, metabolic syndrome, NAFLD, NASH, arteriosclerosis, diabetic complications (retinopathy, nephropathy, neurosis, etc.), peripheral circulatory disturbance, hypertension, cancer, Alzheimer's type dementia, age-related macular degeneration, neurodegenerative diseases, cerebral stroke, ischemic diseases, arthritis, and inflammatory diseases.

Examples of another embodiment having the "disease associated with NAD(P)H oxidase" include diabetes (types 1 and 2), impaired glucose tolerance, hyperlipidemia, fatty liver, metabolic syndrome, NAFLD, NASH, arteriosclerosis, diabetic complications (retinopathy, nephropathy, neurosis, etc), and peripheral circulatory disturbance.

Examples of a further embodiment having the "disease associated with NAD(P)H oxidase" include diabetes (types 1 and 2), glucose tolerance disorder, hyperlipidemia, fatty liver, NAFLD, NASH, and diabetic complications (retinopathy, nephropathy, neurosis, etc.).

Further, the present invention relates to a pharmaceutical composition for preventing and/or treating diseases associated with NAD(P)H oxidase, comprising the compound of the formula (I) or a salt thereof as an active ingredient, that is, an agent for preventing and/or treating diseases associated with NAD(P)H oxidase, comprising the compound of the formula (I) or a salt thereof as an active ingredient.

Further, the present invention relates to use of the compound of the formula (I) or a salt thereof, for the manufacture of a pharmaceutical composition for treating and/or preventing diseases associated with NAD(P)H oxidase.

Further, the present invention relates to a method for preventing and/or treating diseases associated with NAD(P)H oxidase, comprising administering to a patient an effective amount of a compound of the formula (I) or a salt thereof.

Further, the present invention relates to an NAD(P)H oxidase inhibitor comprising the compound of the formula (I) or a salt thereof.

Further, the present invention relates to a method for producing a pharmaceutical composition for preventing or treating diseases associated with NAD(P)H oxidase, comprising mixing a compound of the formula (I) or a salt thereof, and a pharmaceutically acceptable carrier, solvent, or excipient.

Further, the present invention relates to a commercial package, comprising a pharmaceutical composition containing a compound of the formula (I) or a salt thereof; and a description that the compound of the formula (I) or a salt thereof is capable of being used or should be used for treating and/or preventing diseases associated with NAD(P)H oxidase.

Effects of the Invention

The compound of the formula (I) can be used as an agent for preventing and/or treating diseases associated with NAD(P)H oxidase, since it has an NAD(P)H oxidase inhibitory action.

Best Mode For Carrying Out the Invention

Hereinafter, the present invention will be described in detail.

In the definitions of the present specification, the "alkyl", "alkylene", and "alkenylene" mean a linear or branched hydrocarbon chain unless otherwise particularly specified.

The "lower alkyl" means alkyl having 1 to 6 carbon atoms (hereinafter, referred to as "$C_{1-6}$"), and examples thereof include methyl, ethyl, n-propyl, isopropyl, n-butyl, isobutyl, sec-butyl, tert-butyl, n-pentyl, n-hexyl groups, and the like. In another embodiment, the lower alkyl is $C_{1-4}$ alkyl. In yet another embodiment, the lower alkyl is methyl, ethyl, n-propyl, isopropyl, or tert-butyl.

The "lower alkylene" means $C_{1-6}$ alkylene and examples thereof include methylene, ethylene, trimethylene, tetramethylene, pentamethylene, hexamethylene, propylene, methylmethylene, ethylethylene, 1,2-dimethylethylene, 1,1,2,2-tetramethylethylene groups, and the like. In another embodiment, the lower alkylene is $C_{1-5}$ alkylene. In yet another embodiment, the lower alkylene is methylene, ethylene, trimethylene, tetramethylene, or pentamethylene.

The "lower alkenylene" means linear or branched $C_{2-6}$ alkenylene, and examples thereof include vinylene, ethylidene, propenylene, butenylene, pentenylene, hexenylene, 1,3-butadienylene, 1,3-pentadienylene groups, and the like. In another embodiment, it is $C_{2-4}$ alkenylene. In yet embodiment, it is vinylene.

The "halogen" means F, Cl, Br, or I.

The "halogeno-lower alkyl" is lower alkyl substituted with one or more halogens. In another embodiment, the halogeno-lower alkyl is lower alkyl substituted with 1 to 5 halogens. In yet another embodiment, the halogeno-lower alkyl is trifluoromethyl, 3,3,3-trifluoropropyl, or 4,4,4-trifluorobutyl.

The "cycloalkyl" is a $C_{3-10}$ saturated hydrocarbon ring group which may have a bridge. Examples of the cycloalkyl include cyclopropyl, cyclobutyl, cyclopentyl, cyclohexyl, cycloheptyl, cyclooctyl, bicyclo[2.2.1]heptyl, adamantyl groups and the like. In another embodiment, the cycloalkyl is $C_{3-8}$ cycloalkyl. In yet another embodiment, the cycloalkyl is cyclopropyl, cyclobutyl, cyclopentyl, or cyclohexyl.

The "aryl" is a $C_{6-14}$ monocyclic to tricyclic aromatic hydrocarbon ring group which contains a ring group fused with $C_{5-8}$ cycloalkene at the double bond site thereof. Examples of the aryl include phenyl, naphthyl, tetrahydronaphthalenyl, indanyl, indenyl, fluorenyl groups, and the like. In another embodiment, the aryl is phenyl, naphthyl, indanyl, or indenyl. In yet another embodiment, the aryl is phenyl.

The "heterocyclic" group means a cyclic group selected from i) a monocyclic 3- to 8-membered, and in another embodiment, 5- to 7-membered monocyclic hetero ring, containing 1 to 4 hetero atoms selected from O, S and N, and ii) a bicyclic to tricyclic hetero ring containing 1 to 5 hetero atoms selected from O, S and N, and formed by ring fusion of the monocyclic hetero ring with one or two rings which are selected from the group consisting of a monocyclic hetero ring, a benzene ring, C5-8 cycloalkane, and C5-8 cycloalkene. The ring atom, S or N, may be oxidized to form an oxide or a dioxide. Further, it may form a bridged ring or a Spiro ring.

Examples of the heterocyclic group includes aziridinyl, azetidyl, pyrrolidinyl, piperidyl, azepanyl, piperazinyl, homopiperazinyl, oxiranyl, oxetanyl, tetrahydrofuranyl, tetrahydropyranyl, tetrahydrothiopyranyl, morpholinyl, homomorpholinyl, thiomorpholinyl, pyrrolyl, indolyl, imidazolyl, pyrazolyl, pyridyl, pyrimidinyl, pyrazinyl, triazolyl, tetrazolyl, furyl, thienyl, oxazolyl, isoxazolyl, oxadiazolyl, thiazolyl, thiadiazolyl, oxazolidinyl, dihydropyridinyl, benzimidazolyl, quinolyl, quinazolyl, quinoxalinyl, benzofuranyl, benzothiophenyl, benzoxazolyl, benzthiazolyl, carbazolyl, indolinyl, tetrahydroquinolinyl, tetrahydroisoquinolinyl, quinuclidinyl, dibenzofuranyl, dihydrobenzofuranyl, benzodioxynyl, chromenyl, isothiazolidinyl, 8-azaspiro[4,5]decanyl, 1-oxa-8-azaspiro[4,5]decanyl, dihydrobenzofuranyl, dihydrobenzodioxynyl, dioxopiperazinyl, etc.

In another embodiment, the heterocyclic group is a monocyclic to bicyclic 5- to 10-membered heterocyclic group.

In yet another embodiment, the heterocyclic group is azetidyl, pyrrolidinyl, piperidyl, azepanyl, piperazinyl, homopiperazinyl, oxiranyl, oxetanyl, tetrahydrofuranyl, tetrahydropyranyl, tetrahydrothiopyranyl, morpholinyl, homomorpholinyl, thiomorpholinyl, indolyl, imidazolyl, pyridyl, pyrimidinyl, pyrazinyl, triazolyl, tetrazolyl, furyl, thienyl, oxazolyl, isoxazolyl, thiadiazolyl, oxazolidinyl, dihydropyridinyl, benzimidazolyl, tetrahydroquinolinyl, tetrahydroisoquinolinyl, dibenzofuranyl, dihydrobenzofuranyl, benzodioxynyl, chromenyl, isothiazolidinyl, 8-azaspiro[4,5] decanyl, 1-oxa-8-azaspiro[4,5]decanyl, dihydrobenzofuranyl, or dihydrobenzodioxynyl.

The "saturated heterocyclic" group means that a ring-forming bond in the "heterocyclic" group consists only of single bonds.

Examples of the "saturated heterocyclic" group include azetidyl, pyrrolidinyl, piperidyl, azepanyl, piperazinyl, homopiperazinyl, oxiranyl, oxetanyl, tetrahydrofuranyl, tetrahydropyranyl, tetrahydrothiopyranyl, morpholinyl, homomorpholinyl, thiomorpholinyl, oxazolidinyl, isothiazolidinyl, 1,4-dioxa-8-azaspiro[4,5]decanyl, 8-azaspiro[4,5]decanyl, 1-oxa-8-azaspiro[4,5]decanyl, and the like.

In another embodiment, the saturated heterocyclic group is azetidyl, pyrrolidinyl, piperidyl, azepanyl, morpholinyl, homomorpholinyl, thiomorpholinyl, oxazolidinyl, or isothiazolidinyl.

In yet another embodiment, the saturated heterocyclic group is oxetanyl, tetrahydrofuranyl, or tetrahydropyranyl.

The "which may be substituted" in the present specification means "not substituted" or "substituted with 1 to 5 substituents". Further, if there are multiple substituents, the substituents may be the same or different from each other.

The substituents for the "heterocyclic group which may be substituted" in the definition of $R^2$, and the "cycloalkyl which may be substituted", "aryl which may be substituted" and/or "heterocyclic group which may be substituted" in the definition of $R^{20}$ include, for example, groups selected from Group $G^1$, and in another embodiment, groups selected from Group $G^3$.

Group $G^1$: $C_{1-10}$ alkyl, halogen, halogeno-lower alkyl, cycloalkyl which may be substituted, aryl which may be substituted, a heterocyclic group which may be substituted, —$CO_2R^0$, —CN, oxo, lower alkylene-cycloalkyl which may be substituted, lower alkylene-aryl which may be substituted, lower alkylene-a heterocyclic group which may be substituted, lower alkylene-$CO_2R^0$, -$J^1$-$R^0$, -$J^1$-halogeno-lower alkyl, -$J^1$-cycloalkyl which may be substituted, -$J^1$-aryl which may be substituted, -$J^1$-a heterocyclic group which may be substituted, -$J^1$-lower alkylene-cycloalkyl which may be substituted, -$J^1$-lower alkylene-aryl which may be substituted, and -$J^1$-lower alkylene-a heterocyclic group which may be substituted; wherein $J^1$: —C(O)N($R^7$)—*, —C(O)—, —C(O)-lower alkylene-O—*, —O—, —S—, —S(O)—, —S(O)$_2$—, —N($R^8$)—, —N($R^7$)C(O)—*, —N($R^7$)C(O)O—*, —N($R^7$)C(O)N($R^7$)—, —N($R^7$)S(O)$_2$—*, —N($R^7$)C(O)-lower alkylene-O—*, -lower alkylene-C(O)N($R^0$)—*, -lower alkylene-C(O)—*, -lower alkylene-O—*, -lower alkylene-OC(O)—*, -lower alkylene-S—*, -lower alkylene-S(O)—*, -lower alkylene-S(O)$_2$—*, -lower alkylene-N($R^8$)—*, -lower alkylene-N($R^7$)C(O)—*, —O-lower alkylene-C(O)—*, —O-lower alkylene-O—, or —O—lower alkylene-N($R^8$)—*;

wherein * in $J^1$ means a binding point to a remnant of the group in Group $G^1$.

The substituents for the "cycloalkyl which may be substituted", "aryl which may be substituted", and/or "heterocyclic group which may be substituted" in Group $G^1$ include, for example, groups selected from Group $G^2$.

Group $G^2$: $C_{1-10}$ alkyl, halogen, halogeno-lower alkyl, cycloalkyl which may be substituted, aryl which may be substituted, a heterocyclic group which may be substituted, —$CO_2R^0$, —CN, oxo, lower alkylene-cycloalkyl which may be substituted, lower alkylene-aryl which may be substituted, lower alkylene-a heterocyclic group which may be substituted, lower alkylene-$CO_2R^0$, -$J^2$—$R^0$, -$J^2$-halogeno-lower alkyl, -$J^2$-cycloalkyl which may be substituted, -$J^2$-aryl which may be substituted, -$J^2$-a heterocyclic group which may be substituted, -$J^2$-lower alkylene-cycloalkyl which may be substituted, -$J^2$-lower alkylene-aryl which may be substituted, and -$J^2$-lower alkylene-a heterocyclic group which may be substituted; wherein $J^2$: —C(O)N($R^7$)—*, —C(O)—, —C(O)-lower alkylene-O—*, —O—, —S—, —S(O)—, —S(O)$_2$—, —N($R^8$)—, —N($R^7$)C(O)—*, —N($R^7$)C(O)O—*, —N($R^7$)C(O)N($R^7$)—, —N($R^7$)S(O)$_2$—*, —N($R^7$)C(O)-lower alkylene-O—*, -lower alkylene-C(O)N($R^0$)—*, -lower alkylene-C(O)—*, -lower alkylene-O—*, -lower alkylene-OC(O)—*, -lower alkylene-S—*, -lower alkylene-S(O)—*, -lower alkylene-S(O)$_2$—*, -lower alkylene-N($R^8$)—*, -lower alkylene-N($R^7$)C(O)—*, —O-lower alkylene-C(O)—*, —O-lower alkylene-O—, or —O—lower alkylene-N($R^8$)—*;

wherein * in $J^2$ means a binding point to a remnant of the group in Group $G^2$.

The substituents for the "cycloalkyl which may be substituted", "aryl which may be substituted", and/or "heterocyclic group which may be substituted" in Group $G^2$ include, for example, lower alkyl, halogen, halogeno-lower alkyl, oxo, —$OR^7$, and —O-halogeno-lower alkyl.

Group $G^3$: lower alkyl, halogen, halogeno-lower alkyl, cycloalkyl which may be substituted, aryl which may be substituted, a heterocyclic group which may be substituted, —$CO_2R^0$, —CN, oxo, lower alkylene-cycloalkyl which may be substituted, lower alkylene-aryl which may be substituted, lower alkylene-a heterocyclic group which may be substituted, lower alkylene-$CO_2R^0$, lower alkylene-$OR^0$, —C(O)$R^0$, —$OR^0$, —O-lower alkylene-$OR^0$, —N($R^7$)S(O)$_2$-lower alkyl, —O-halogeno-lower alkyl, —C(O)-cycloalkyl which may be substituted, —O-lower alkylene-cycloalkyl which may be substituted, and —O-lower alkylene-a heterocyclic group which may be substituted.

The substituents for the "cycloalkyl which may be substituted" and/or "heterocyclic group which may be substituted" in Group $G^3$ include, for example, lower alkyl, halogen, halogeno-lower alkyl, oxo, —$OR^7$, —O-halogeno-lower alkyl, and —O-lower alkylene-$OR^7$.

In another embodiment, the substituents for the "heterocyclic group which may be substituted" in the definition of $R^2$, and the "cycloalkyl which may be substituted", "aryl which may be substituted", and/or "heterocyclic group which may be substituted" in the definition of $R^{20}$ include, for example, groups selected from Groups $G^4$ to $G^{26}$.

Group $G^4$: —$NR^{200}R^{201}$, wherein $R^{200}$: H or lower alkyl;

$R^{201}$: —C(O)-lower alkyl, —C(O)-(cycloalkyl which may be substituted with lower alkyl or —$OR^0$), —C(O)-lower alkylene-(cycloalkyl which may be substituted with lower alkyl or —$OR^0$, —C(O)-lower alkylene-$OR^0$, —C(O)-lower alkylene-(a saturated heterocyclic group which may be substituted with lower alkyl or —$OR^0$), —C(O)O-lower alkyl, —C(O)N($R^0$)-lower alkyl, —S(O)$_2$-lower alkyl, or —S(O)$_2$-(cycloalkyl which may be substituted with lower alkyl or —$OR^0$; or $R^{200}$ and $R^{201}$, taken together with N to which they are attached, forms a saturated heterocyclic group which may be substituted with lower alkyl, oxo, or —$OR^0$.

Group $G^5$: a group in which $R^{201}$ in Group $G^4$ is —C(O)-lower alkyl, —C(O)-(cycloalkyl which may be substituted with lower alkyl or —$OR^0$), —C(O)-lower alkylene-(cycloalkyl which may be substituted with lower alkyl or —$OR^0$, —C(O)-lower alkylene-$OR^0$, or —C(O)-lower alkylene-(a saturated heterocyclic group which may be substituted with lower alkyl or —$OR^0$).

Group $G^6$: a group in which cycloalkyl of $R^{201}$ in Group $G^5$ is cyclopropyl, cyclobutyl, cyclopentyl, or cyclohexyl, and the saturated heterocyclic group is oxetanyl, tetrahydrofuranyl, or tetrahydropyranyl.

Group $G^7$: a group in which $R^{201}$ in Group $G^4$ is —C(O)O-lower alkyl.

Group $G^8$: a group in which $R^{201}$ in Group $G^4$ is —C(O)N($R^0$)-lower alkyl.

Group $G^9$: a group in which $R^{201}$ in Group $G^4$ is —S(O)$_2$-lower alkyl, or —S(O)$_2$-(cycloalkyl which may be substituted with lower alkyl or —$OR^0$.

Group $G^{10}$: a group in which $R^{200}$ and $R^{201}$ in Group $G^4$, taken together with N to which they are attached, form a saturated heterocyclic group which may be substituted with lower alkyl, oxo, or —$OR^O$.

Group $G^{11}$: H, lower alkyl, halogen, halogeno-lower alkyl, —$OR^O$, —$CO_2R^O$, —$C(O)R^O$, and —CN.

Group $G^{12}$: H, lower alkyl, halogen, halogeno-lower alkyl, and —$OR^O$.

Group $G^{13}$: lower alkyl, halogen, halogeno-lower alkyl, lower alkylene-a saturated heterocyclic group, lower alkylene-$OR^O$, —$OR^O$, —O-lower alkylene-$OR^O$, —O-halogeno-lower alkyl, cycloalkyl which may be substituted with —O-lower alkylene-oxo, and —O-lower alkylene-a saturated heterocyclic group; provided that the saturated heterocyclic group may be substituted with lower alkyl, —$OR^O$, —C(O)-lower alkyl, or —$S(O)_2$-lower alkyl.

Group $G^{14}$: lower alkylene-a saturated heterocyclic group, lower alkylene-$OR^O$, —O-lower alkylene-$OR^O$, and —O-lower alkylene-a saturated heterocyclic group; provided that the saturated heterocyclic group is oxetanyl, tetrahydrofuranyl, or tetrahydropyranyl, each of which may be substituted with lower alkyl or —$OR^O$.

Group $G^{15}$:

[Chem. 10]

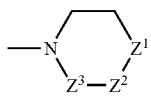

[In the formula,
$Z^1$: —$C(R^O)_2$— or —O—;
$Z^2$: a bond, —$C(R^O)_2$—, or —$C(R^O)_2C(R^O)_2$—; and
$Z^3$: —$C(R^O)_2C(R^O)_2$— or —C(O)—.]

Group $G^{16}$: a group in which $Z^3$ in Group $G^{15}$ is —C(O)—.

Group $G^{17}$: lower alkyl, halogen, halogeno-lower alkyl, cyclohexyl which may be substituted with —$OR^O$, lower alkylene-a saturated heterocyclic group, lower alkylene-$OR^O$, —$OR^O$, —O-lower alkylene-$OR^O$, —O-halogeno-lower alkyl, and —O-lower alkylene-a saturated heterocyclic group; provided that the saturated heterocyclic group may be substituted with lower alkyl, —$OR^O$, —C(O)-lower alkyl, or —$S(O)_2$-lower alkyl.

Group $G^{18}$: lower alkylene-a saturated heterocyclic group, and —O-lower alkylene-a saturated heterocyclic group; provided that the saturated heterocyclic group is oxetanyl, tetrahydrofuranyl, or tetrahydropyranyl, each of which may be substituted with lower alkyl or —$OR^O$.

Group $G^{19}$: lower alkyl, halogen, halogeno-lower alkyl, lower alkylene-a saturated heterocyclic group, lower alkylene-$OR^O$, —$OR^O$, —O-lower alkylene-$OR^O$, —O-halogeno-lower alkyl, and —O-lower alkylene-a saturated heterocyclic group; provided that the saturated heterocyclic group may be substituted with lower alkyl or —$OR^O$.

Group $G^{20}$: lower alkylene-a saturated heterocyclic group, lower alkylene-$OR^O$, —O-lower alkylene-$OR^O$, and —O-lower alkylene-a saturated heterocyclic group; provided that the saturated heterocyclic group is oxetanyl, tetrahydrofuranyl, or tetrahydropyranyl, each of which may be substituted with lower alkyl or —$OR^O$.

Group $G^{21}$: —C(O)-lower alkyl, —C(O)-(a saturated heterocyclic group which may be substituted with lower alkyl or —$OR^O$, —C(O)-lower alkylene-$OR^O$, and —C(O)-lower alkylene-(a saturated heterocyclic group which may be substituted with lower alkyl or —$OR^O$.

Group $G^{22}$: a group in which the saturated heterocyclic group in Group $G^{21}$ is oxetanyl, tetrahydrofuranyl, or tetrahydropyranyl.

Group $G^{23}$: —C(O)-lower alkyl, —C(O)-(cycloalkyl which may be substituted with lower alkyl or —$OR^O$, —C(O)-lower alkylene-(cycloalkyl which may be substituted with lower alkyl or —$OR^O$, —C(O)-lower alkylene-$OR^O$, —C(O)-lower alkylene-(a saturated heterocyclic group which may be substituted with lower alkyl or —$OR^O$, —C(O)O-lower alkyl, —$C(O)N(R^O)$-lower alkyl, —$S(O)_2$-lower alkyl, and —$S(O)_2$-(cycloalkyl which may be substituted with lower alkyl or —$OR^O$.

Group $G^{24}$: —C(O)-lower alkyl, —C(O)-(cycloalkyl which may be substituted with lower alkyl or —$OR^O$, —C(O)-lower alkylene-(cycloalkyl which may be substituted with lower alkyl or —$OR^O$, —C(O)-lower alkylene-$OR^O$, and —C(O)-lower alkylene-(a saturated heterocyclic group which may be substituted with lower alkyl or —$OR^O$.

Group $G^{25}$: a group in which the cycloalkyl in Group $G^{24}$ is cyclopropyl, cyclobutyl, cyclopentyl, or cyclohexyl, and the saturated heterocyclic group is oxetanyl, tetrahydrofuranyl, or tetrahydropyranyl.

Group $G^{26}$: —$S(O)_2$-lower alkyl, and —$S(O)_2$-(cycloalkyl which may be substituted with lower alkyl or —$OR^O$.

The substituents for the "$C_{1-10}$ alkylene which may be substituted" in the definition of X include, for example, halogen and —$OR^O$.

The substituents for the "aryl which may be substituted" and "heterocyclic group which may be substituted" in the definition of $R^3$ include, for example, lower alkyl, halogen, halogeno-lower alkyl, oxo, —$OR^O$, and —O-halogeno-lower alkyl.

The substituents for the "cycloalkyl which may be substituted", "aryl which may be substituted", and/or "heterocyclic group which may be substituted" in the definition of $R^4$ and $R^5$ include, for example, groups selected from the Group $G^2$.

Some embodiments of the compound of the formula (I) of the present invention will be described below.

The compound of the formula (I) wherein
$R^2$: —X—Y—$R^{20}$;
$R^3$: the same or different, and halogen, lower alkyl, halogeno-lower alkyl, —$OR^O$, —O-halogeno-lower alkyl, —$CO_2R^O$, aryl which may be substituted, or a heterocyclic group which may be substituted;
Y: —O—, *—OC(O)—, *—$OC(O)N(R^O)$—, —S—, —S(O)—, —$S(O)_2$—, —$N(R^O)$—, —$N[C(O)R^O]$—, *—$N(R^O)S(O)_2$—, *—$N(R^O)C(O)$—, *—$C(O)N(R^O)$—, *—$N(R^O)C(O)O$—, or —$N(R^O)C(O)N(R^O)$—;
$R^{20}$: $C_{1-10}$ alkyl, halogeno-lower alkyl, cycloalkyl which may be substituted, aryl which may be substituted, a heterocyclic group which may be substituted, lower alkylene-cycloalkyl which may be substituted, lower alkylene-aryl which may be substituted, lower alkylene-a heterocyclic group which may be substituted, —W—$R^O$, —W-halogeno-lower alkyl, —W-cycloalkyl which may be substituted, —W-aryl which may be substituted, —W-a heterocyclic group which may be substituted, —W-lower alkylene-cycloalkyl which may be substituted, —W-lower alkylene-aryl which may be substituted, or —W-lower alkylene-a heterocyclic group which may be substituted;
W: *-lower alkylene-O—, *-lower alkylene-$OC(O)N(R^O)$—, *-lower alkylene-S—, *-lower alkylene-S(O)—, *-lower alkylene-$S(O)_2$—, *-lower alkylene-$N(R^O)$—, *-lower alkylene-$N[C(O)R^O]$—, *-lower alkylene-$N(R^O)S(O)_2$—, *-lower alkylene-$C(O)N(R^O)$—, *-lower alkylene-N ($R^0$)C(O)—, *-lower alkylene-N($R^0$)C(O)O—, *-lower alkylene-N($R^0$)C(O)N($R^0$)—, or *-lower alkylene-O-lower alkylene-O—;

$R^5$: the same or different, and halogen, —CN, $C_{1-10}$ alkyl, halogeno-lower alkyl, —$CO_2R^0$, lower alkylene-$CO_2R^0$, —N($R^0$)C(O)N($R^0$)$_2$, oxo, cycloalkyl which may be substituted, aryl which may be substituted, a heterocyclic group which may be substituted, lower alkylene-cycloalkyl which may be substituted, lower alkylene-aryl which may be substituted, lower alkylene-a heterocyclic group which may be substituted, -J-$R^0$, -J-halogeno-lower alkyl, -J-cycloalkyl which may be substituted, -J-aryl which may be substituted, -J-a heterocyclic group which may be substituted, -J-lower alkylene-cycloalkyl which may be substituted, -J-lower alkylene-aryl which may be substituted, or -J-lower alkylene-a heterocyclic group which may be substituted; and J: the same or different, and —O—, *-lower alkylene-O—, —O-lower alkylene-O—, *—O-lower alkylene-N($R^0$)—, *—O-lower alkylene-N[C(O)$R^0$]—, *—O-lower alkylene-C(O)—, —C(O)—, *-lower alkylene-C(O)—, —N($R^0$)—, —N[C(O)$R^0$]—, *-lower alkylene-N($R^0$)—, *-lower alkylene-N[C(O)$R^0$]—, *—N($R^0$)C(O)—, *-lower alkylene-N($R^0$)C(O)—, *—C(O)N($R^0$)—, *-lower alkylene-C(O)N($R^0$)—, —S—, —S(O)—, —S(O)$_2$—, *-lower alkylene-S—, *-lower alkylene-S(O)—, or *-lower alkylene-S(O)$_2$—.

Other embodiments of the compound of formula (I) of the present invention will be described below.

(1) The compound wherein $R^1$ is lower alkyl or halogen. In another embodiment, the compound wherein $R^1$ is lower alkyl. In yet another embodiment, the compound wherein $R^1$ is methyl.

(2) The compound wherein $R^2$ is —X—Y—$R^{20}$, or —X-a heterocyclic group which may be substituted. In another embodiment, the compound wherein $R^2$ is —X-piperidyl which may be substituted, or —X—Y—$R^{20}$. In yet another embodiment, the compound wherein $R^2$ is —X-piperidyl which may be substituted. In yet another embodiment, the compound wherein $R^2$ is —X—Y—$R^{20}$.

(3) The compound wherein Ring A in $R^2$ is phenyl.

(4) The compound wherein X is lower alkylene. In another embodiment, the compound wherein X is $C_{1-4}$ alkylene. In yet another embodiment, the compound wherein X is —$CH_2$—.

(5) The compound wherein Y is *—C(O)N($R^7$)—, —O—, *—OC(O)—, *—OC(O)N($R^7$)—, —S—, —S(O)—, —S(O)$_2$—, —N($R^8$)—, *—N($R^7$)C(O)—, or *—N($R^7$)C(O)O—. In another embodiment, the compound wherein Y is —O—, —S—, —S(O)—, or —S(O)$_2$—. In another embodiment, the compound wherein Y is —O—. In yet another embodiment, the compound wherein Y is —S—, —S(O)—, or —S(O)$_2$—. Here, * means a binding point to X.

(6) The compound wherein $R^3$, which are the same or different from each other, are lower alkyl, halogen, halogeno-lower alkyl, phenyl, pyridyl, pyrimidinyl, piperidyl which may be substituted with oxo, —$CO_2R^0$, —$OR^0$, or —O-halogeno-lower alkyl. In another embodiment, the compound wherein $R^3$ are the same or different from each other, and are halogen. In yet another embodiment, the compound wherein $R^3$ are F.

(7) The compound wherein $R^3$ is a substituent at the 6-position.

(8) The compound wherein n is 0 or 1. In another embodiment, the compound wherein n is 0. In yet another embodiment, the compound wherein n is 1.

(9) The compound wherein when $R^2$ is —X-a heterocyclic group which may be substituted, the "heterocyclic group which may be substituted" is 1-substituted piperidin-4-yl.

(10) The compound wherein $R^{20}$ is cycloalkyl which may be substituted, aryl which may be substituted, or a heterocyclic group which may be substituted. In another embodiment, the compound wherein $R^{20}$ is cyclohexyl which may be substituted, phenyl which may be substituted, pyridyl which may be substituted, tetrahydroquinolinyl which may be substituted, or tetrahydroisoquinolinyl which may be substituted. In another embodiment, the compound wherein $R^{20}$ is phenyl which may be substituted, or pyridyl which may be substituted. In another embodiment, the compound wherein $R^{20}$ is cyclohexyl which may be substituted. In another embodiment, the compound wherein $R^{20}$ is phenyl which may be substituted. In another embodiment, the compound wherein $R^{20}$ is pyridyl which may be substituted. In another embodiment, the compound wherein $R^{20}$ is pyrimidinyl which may be substituted. In yet another embodiment, the compound wherein $R^{20}$ is tetrahydroquinolinyl which may be substituted, or tetrahydroisoquinolinyl which may be substituted.

(11) The compound wherein when $R^{20}$ is cycloalkyl which may be substituted, the "cycloalkyl which may be substituted" is 3- or 4-substituted cyclohexyl. In another embodiment, the compound wherein the "cycloalkyl which may be substituted" is 3-substituted cyclohexyl. In another embodiment, the compound wherein the "cycloalkyl which may be substituted" is 4-substituted cyclohexyl.

(12) The compound wherein when $R^{20}$ is aryl which may be substituted, the "aryl which may be substituted" is 3- and 5-substituted phenyl. In another embodiment, the compound wherein the "aryl which may be substituted" is 3-substituted phenyl. In yet another embodiment, the compound wherein the "aryl which may be substituted" is 4-substituted phenyl.

(13) The compound wherein when $R^{20}$ is a heterocyclic group which may be substituted, the "heterocyclic group which may be substituted" is pyridin-2-yl which may be substituted. In another embodiment, the compound wherein the "heterocyclic group which may be substituted" is pyridin-3-yl which may be substituted. In yet another embodiment, the compound wherein the "heterocyclic group which may be substituted" is pyridin-4-yl which may be substituted.

(14) The compound wherein when $R^{20}$ is a heterocyclic group which may be substituted, the "heterocyclic group which may be substituted" is 4-substituted pyridin-2-yl. In another embodiment, the compound wherein the "heterocyclic group which may be substituted" is 2-substituted pyridin-4-yl.

(15) The compound wherein when $R^{20}$ is a heterocyclic group which may be substituted, the "heterocyclic group which may be substituted" is tetrahydroquinolinyl substituted on a nitrogen atom in the ring, or tetrahydroisoquinolinyl substituted on a nitrogen atom in the ring.

(16) The compound wherein when $R^{20}$ is a cycloalkyl which may be substituted, a substituent in the "cycloalkyl which may be substituted" is a group selected from Group $G^1$. In another embodiment, the compound wherein a substituent in the "cycloalkyl which may be substituted" is a group selected from Groups $G^4$ to $G^{10}$.

(17) The compound wherein when $R^{20}$ is aryl which may be substituted, a substituent in the "aryl which may be substituted" is a group selected from Group $G^1$. In another embodiment, the compound wherein a substituent in the "aryl which may be substituted" is a group selected from Groups $G^{11}$ to $G^{18}$. In another embodiment, the compound wherein a substituent in the "aryl which may be substituted" is a group selected from pyrrolidinyl, piperidyl, azepanyl, morpholinyl, homomorpholinyl, and oxazolidinyl, each of which may be substituted with lower alkyl or oxo.

(18) The compound wherein when $R^{20}$ is a heterocyclic group which may be substituted, a substituent in the "heterocyclic group which may be substituted" is a group selected from Group $G^1$. In another embodiment, the compound wherein a substituent in the "heterocyclic group which may be substituted" is a group selected from Groups $G^{19}$ to $G^{22}$.

(19) The compound wherein when $R^2$ is —X-a heterocyclic group which may be substituted, a substituent in the "heterocyclic group which may be substituted" is a group selected from Group $G^1$. In another embodiment, the compound wherein a substituent in the "heterocyclic group which may be substituted" is a group selected from Groups $G^{23}$ to $G^{26}$, —C(O)O-lower alkyl, and —C(O)N($R^0$)-lower alkyl.

(20) The compound which is a combination of any two or more of groups described in the above (1) to (19).

Other embodiments of the compound of formula (I) of the present invention will be described below.

(21) The compound of the formula (I) wherein
$R^1$ is lower alkyl or halogen;
$R^2$ is -lower alkylene-(a heterocyclic group which may be substituted with group(s) selected from Group $G^1$), or -lower alkylene-O—$R^{20}$;
$R^3$ is halogen;
n is 0 or 1; and
$R^{20}$ is cycloalkyl which may be substituted with group(s) selected from Group $G^1$, aryl which may be substituted with group(s) selected from Group $G^1$, or a heterocyclic group which may be substituted with group(s) selected from Group $G^1$.

(22) The compound described in (21), wherein
$R^1$ is lower alkyl;
$R^2$ is -lower alkylene-(piperidyl which may be substituted with group(s) selected from Group $G^1$), or -lower alkylene-O—$R^{20}$; and
$R^{20}$ is cyclohexyl which may be substituted with group(s) selected from Group $G^1$, phenyl which may be substituted with group(s) selected from Group $G^1$, pyridyl which may be substituted with group(s) selected from Group $G^1$, tetrahydroquinolinyl which may be substituted with group(s) selected from Group $G^1$, or tetrahydroisoquinolinyl which may be substituted with group(s) selected from Group $G^1$.

(23) The compound described in (22), wherein $R^2$ is -lower alkylene-O-(phenyl which may be substituted with group(s) selected from Group $G^1$), or -lower alkylene-O-(pyridyl which may be substituted with group(s) selected from Group $G^1$).

(24) The compound described in (23), wherein $R^2$ is -lower alkylene-O-(phenyl which may be substituted with group(s) selected from Group $G^1$).

(25) The compound described in (24), wherein $R^2$ is

[Chem. 11]

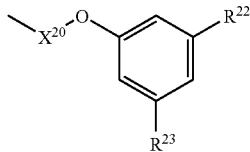

[In the formula, $X^{20}$ is lower alkylene, $R^{22}$ is a group selected from Group $G^1$, and $R^{23}$ is a group selected from Group $G^{11}$. The same shall apply hereinafter.]

(26) The compound described in (25), wherein $R^{23}$ is a group selected from Group $G^{12}$.

(27) The compound described in (26), wherein $R^{22}$ is a group selected from Group $G^{13}$.

(28) The compound described in (27), wherein $R^{22}$ is a group selected from Group $G^{14}$.

(29) The compound described in (26), wherein $R^{22}$ is a group selected from Group $G^{15}$.

(30) The compound described in (29), wherein $R^{22}$ is a group selected from Group $G^{16}$.

(31) The compound described in (24), wherein $R^2$ is

[Chem. 12]

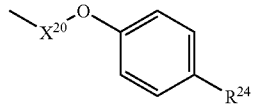

[In the formula, $R^{24}$ is a group selected from Group $G^1$.]

(32) The compound described in (31), wherein $R^{24}$ is a group selected from Group $G^{17}$.

(33) The compound described in (32), wherein $R^{24}$ is a group selected from Group $G^{18}$.

(34) The compound described in (23), wherein $R^2$ is -lower alkylene-O-(pyridyl which may be substituted with group(s) selected from Group $G^1$).

(35) The compound described in (34), wherein $R^2$ is

[Chem. 13]

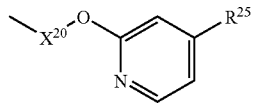

[In the formula, $R^{25}$ is a group selected from Group $G^1$. The same shall apply hereinafter.]

(36) The compound described in (35), wherein $R^{25}$ is a group selected from Group $G^{19}$.

(37) The compound described in (36), wherein $R^{25}$ is a group selected from Group $G^{20}$.

(38) The compound described in (22), wherein $R^2$ is

[Chem. 14]

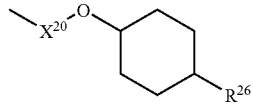

[In the formula, $R^{26}$ is a group selected from Group $G^4$].

(39) The compound described in (38), wherein $R^{26}$ is a group selected from Group $G^5$.

(40) The compound described in (39), wherein $R^{26}$ is a group selected from Group $G^6$.

(41) The compound described in (38), wherein $R^{26}$ is a group selected from Group $G^7$.

(42) The compound described in (38), wherein $R^{26}$ is a group selected from Group $G^8$.

(43) The compound described in (38), wherein $R^{26}$ is a group selected from Group $G^9$.

(44) The compound described in (38), wherein $R^{26}$ is a group selected from Group $G^{10}$.

(45) The compound described in (22), wherein $R^2$ is

[Chem. 15]

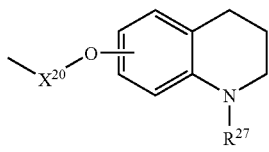

[Chem. 16]

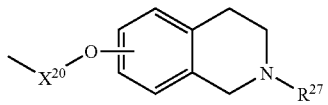

[In the formula, $R^{27}$ is a group selected from Group $G^{21}$. The same shall apply hereinafter.]

(46) The compound described in (45), wherein $R^{27}$ is a group selected from Group $G^{22}$.

(47) The compound described in (21), wherein $R^2$ is

[Chem. 17]

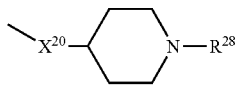

[In the formula, $R^{28}$ is a group selected from Group $G^{23}$. The same shall apply hereinafter.]

(48) The compound described in (47), wherein $R^{28}$ is a group selected from Group $G^{24}$.

(49) The compound described in (48), wherein $R^{28}$ is a group selected from Group $G^{25}$.

(50) The compound described in (47), wherein $R^{28}$ is —C(O)O-lower alkyl.

(51) The compound described in (47), wherein $R^{28}$ is —C(O)N($R^0$)-lower alkyl.

(52) The compound described in (47), wherein $R^{28}$ is a group selected from Group $G^{26}$.

Examples of the specific compounds encompassed by the present invention include the following compounds.

3-methyl-2-{[3-(tetrahydro-2H-pyran-4-ylmethoxy)phenoxy]methyl}quinolin-4(1H)-one,
N-{trans-4-[(3-methyl-4-oxo-1,4-dihydroquinolin-2-yl)methoxy]cyclohexyl}ethanesulfonamide,
3-methyl-2-[({4-[2-(tetrahydro-2H-pyran-4-yl)ethoxy]pyridin-2-yl}oxy)methyl]quinolin-4(1H)-one,
3-methyl-2-{[3-(3-oxomorpholin-4-yl)phenoxy]methyl}quinolin-4(1H)-one,
4-{4-[(3-methyl-4-oxo-1,4-dihydroquinolin-2-yl)methoxy]butoxy}benzonitrile,
2-({4-[4-(2-methoxyethyl)phenoxy]butoxy}methyl)-3-methyl quinolin-4(1H)-one,
2-({3-[(1-acetylpiperidin-4-yl)methoxy]phenoxy}methyl)-3-methylquinolin-4(1H)-one,
3-methyl-2-{[3-(2-pyridin-4-ylethoxy)phenoxy]methyl}quinolin-4(1H)-one,
2-{[3-(3-hydroxy-3-methylbutoxy)phenoxy]methyl}-3-methylquinolin-4(1H)-one,
6-fluoro-3-methyl-2-({[4-(tetrahydro-2H-pyran-4-ylmethoxy)pyridin-2-yl]oxy}methyl)quinolin-4(1H)-one,
2-({[4-(3-hydroxy-3-methylbutoxy)pyridin-2-yl]oxy}methyl)-3-methylquinolin-4(1H)-one,
6-fluoro-3-methyl-2-({[1-(tetrahydro-2H-pyran-4-ylacetyl)-1,2,3,4-tetrahydroquinolin-7-yl]oxy}methyl)quinolin-4(1H)-one,
3-methyl-2-{[6-(tetrahydro-2H-pyran-4-ylmethoxy)-3,4-dihydroisoquinolin-2(1H)-yl]methyl}quinolin-4(1H)-one,
2-({[4-(3-methoxy-3-methylbutoxy)pyridin-2-yl]oxy}methyl)-3-methylquinolin-4(1H)-one,
2-[({4-[(4-hydroxy-4-methylpentyl)oxy]pyridin-2-yl}oxy)methyl]-3-methylquinolin-4(1H)-one,
2-{[3-(4-hydroxypiperidin-1-yl)phenoxy]methyl}-3-methylquinolin-4(1H)-one,
2-{[3-(4-hydroxy-4-methylpiperidin-1-yl)phenoxy]methyl}-3-methylquinolin-4(1H)-one,
N-cyclohexyl-N-{2-[(3-methyl-4-oxo-1,4-dihydroquinolin-2-yl)methoxy]ethyl}tetrahydro-2H-pyrane-4-carboxamide,
ethyl 4-[2-(3-methyl-4-oxo-1,4-dihydroquinolin-2-yl)ethyl]piperidine-1-carboxylate,
2-{2-[1-(ethylsulfonyl)piperidin-4-yl]ethyl}-3-methylquinolin-4(1H)-one, and
(3-methyl-4-oxo-1,4-dihydroquinolin-2-yl)methyl(3-phenylpropyl)carbamate.

The compound of formula (I) may in some cases exist in the form of tautomers, geometrical isomers and stereoisomers, depending on the kind of substituents. In the present specification, the compound formula (I) may be described only in one form of isomers, but the present invention includes these isomers as well as isolated forms or mixtures thereof.

Further, the compound of formula (I) may have asymmetric carbon atoms or axial asymmetries in some cases, and correspondingly, it may exist in the form of optical isomers. Isolates or mixtures of optical isomers of the compound of formula (I) are also included in the present invention.

Further, a pharmaceutically acceptable prodrug of the compound of formula (I) is also included in the present invention. As used herein, the "pharmaceutically acceptable prodrug" is a compound having a group which can be converted into an amino group, a hydroxyl group, a carboxyl group or the like by solvolysis or under a physiological condition. Examples of the group for forming a prodrug include those as described, for example, in Prog. Med., 5, 2157-2161 (1985) or "Iyakuhin no Kaihatsu (Development of Pharmaceuticals)" (Hirokawa Shoten Ltd., 1990), Vol. 7, "Bunshi Sekkei (Molecular Design)", pp. 163-198.

In addition, the salt of the compound of formula (I) is a pharmaceutically acceptable salt of the compound of formula (I). The compound of formula (I) may form an acid addition salt or a salt with a base, depending on the kind of substituents. Specifically, examples of such salts include acid addition salts with inorganic acids such as hydrochloric acid, hydrobromic acid, hydroiodic acid, sulfuric acid, nitric acid, and phosphoric acid, or with organic acids such as formic acid, acetic acid, propionic acid, oxalic acid, malonic acid, succinic acid, fumaric acid, maleic acid, lactic acid, malic acid, mandelic acid, tartaric acid, dibenzoyl tartaric acid, ditoluoyl tartaric acid, citric acid, methanesulfonic acid, ethanesulfonic acid, benzenesulfonic acid, p-toluenesulfonic acid, aspartic acid, and glutamic acid, salts with inorganic bases such as sodium, potassium, magnesium, calcium, and aluminum, or with organic bases such as methylamine, ethylamine, ethanolamine, lysine, and ornithine, salts with various amino acids and amino acid derivatives such as acetylleucine, ammonium salts, and the like.

Further, the present invention also includes various hydrates or solvates, and crystalline polymorphs of the compound of formula (I) and a salt thereof. Further, compounds labeled with various radioactive or non-radioactive isotopes are also included in the present invention.

(Production Method)

The compound of formula (I) and a salt thereof can be produced by utilizing the characteristics based on the types of its basic skeleton or substituents and by applying various known synthetic methods. It is sometimes effective, in terms of production techniques, that the functional group is replaced by an appropriate protecting group (a group that can be readily converted into the functional group) in the stage of a starting material to intermediate depending on the type of the functional group during the production. Examples of such functional groups include an amino group, a hydroxyl group, a carboxyl group, and the like, and examples of such protecting groups include protecting groups described for example in "Protective Groups in Organic Synthesis", 3rd ed., 1999, edited by Greene and Wuts, or the like. These protecting groups may be appropriately selected and used depending on the reaction conditions. According to such a method, a desired compound can be obtained by introducing the protecting group and carrying out the reaction, and then removing the protecting group, if desired.

In addition, the prodrug of the compound of formula (I) can be produced in the same manner as the case of the protecting groups, by carrying out the reaction after introducing a specific group at the stage of starting materials to intermediates or using the obtained compound of formula (I). The reaction can be carried out by applying methods known to those skilled in the art, such as the usual esterification, amidation, dehydration and the like.

Hereinafter, the representative production processes for the compound of formula (I) will be described. Each of the production processes may also be carried out with reference to References appended to the corresponding description. Further, the production processes of the present invention are not limited to the examples as shown below.

(Production Process 1)

[Chem. 18]

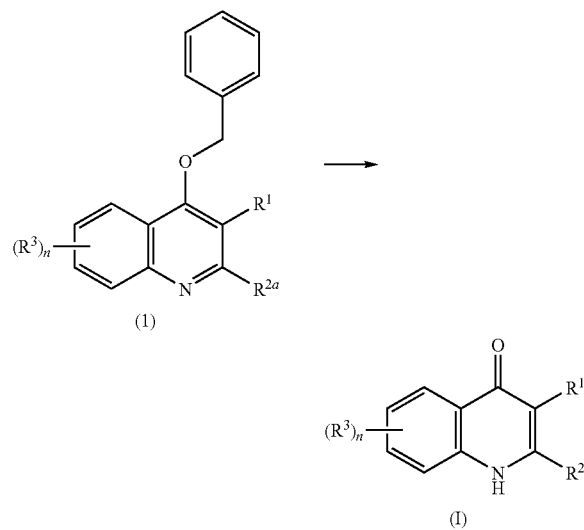

(In the formula, $R^{2a}$ represents $R^2$ or $-X^a-Y-R^{20}$; and $X^a$ represent $C_{2-10}$ alkenylene which may be substituted. The same shall apply hereinafter.)

This production process is a method in which the compound of the formula (I) is obtained by debenzylation of compound (1) through hydrogenation thereof.

The hydrogenation reaction can be carried out using a catalyst such as palladium-carbon or platinum oxide, from under normal pressure to under a pressurized hydrogen atmosphere, from under room temperature to under heating. This reaction may also be carried out using cyclohexene or the like as a hydrogen source in place of hydrogen gas. Examples of the solvent used in this reaction include aromatic hydrocarbons such as benzene, toluene, and xylene; alcohols such as methanol, ethanol, and propanol; ethers such as diethyl ether, tetrahydrofuran (THF), and dioxane; N,N-dimethylformamide (DMF), N,N-dimethylacetamide (DMA), N-methylpyrrolidone (NMP), acetic acid, and water. These materials may be used alone or in any combination thereof.

Further, when $R^{2a}$ is $-X^a-Y-R^{20}$, reduction of a double bond can also be carried out concurrently with debenzylation under these reaction conditions. Further, when an oxygen or nitrogen atom contained in $R^{2a}$ is protected by a benzyl or benzyloxycarbonyl group, deprotection can also be simultaneously carried out under these reaction conditions.

(Production Process 2)

[Chem. 19]

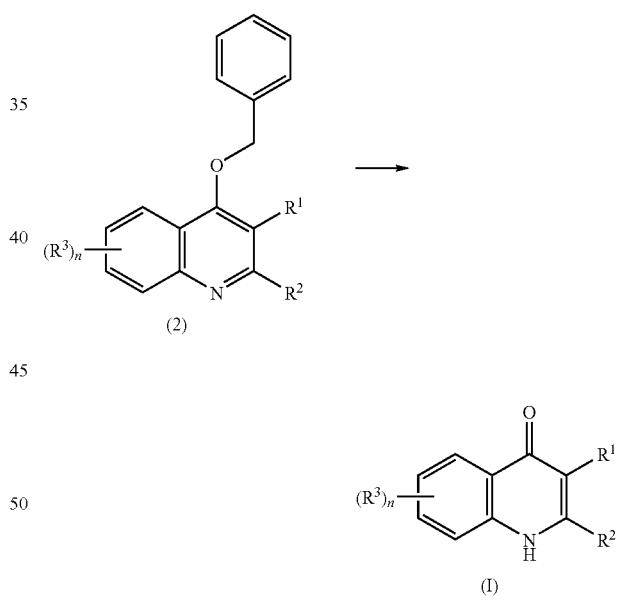

This production process is a method in which the compound of the formula (I) is obtained by debenzylation of the compound (2) using trifluoroacetic acid (TFA).

The debenzylation reaction can be carried out in the presence of TFA, from under room temperature to under heating. An addition of thioanisole, anisole or the like may be advantageous in some cases for the progress of the reaction, depending on types of compounds. Examples of the solvent used in this reaction include aromatic hydrocarbons, halogenated hydrocarbons such as dichloromethane, dichloroethane, and chloroform, and TFA.

(Production Process 3)

[Chem. 20]

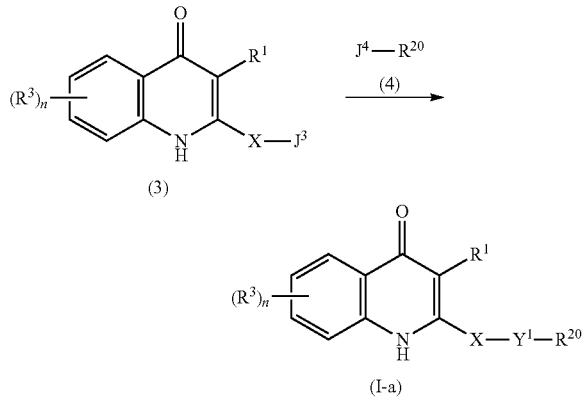

(In the formula, one of $J^3$ and $J^4$ represents —$NHR^7$, and the other represents —C(O)-$L^1$; $L^1$ represents a leaving group or hydroxyl group, and $Y^1$ represents —N($R^7$)C(O)— or —C(O)N($R^7$)—. The same shall apply hereinafter.)

This production process is a method in which the compound of the formula (I-a) is obtained by amidation of the compound (3). The leaving group of $L^1$ may be an organosulfonic acid group such as methanesulfonyloxy or p-toluenesulfonyloxy, halogen, or the like. Alternatively, a variety of acid anhydrides may be used as the leaving group.

When $L^1$ is a hydroxyl group, the reaction can be carried out in the presence of a condensing agent such as N,N'-dicyclohexylcarbodiimide (DCC), 1-ethyl-3-(3'-dimethylaminopropyl)carbodiimide (WSC), 1,1'-carbonyldiimidazole (CDI), diphenylphosphoryl azide (DPPA), phosphorus oxychloride/pyridine, or triphenylphosphine/N-bromosuccinimide and, if necessary, also in the presence of an additive (for example, N-hydroxysuccinimide (HONSu), 1-hydroxybenzotriazole (HOBt), etc.).

When $L^1$ is a leaving group, it may be preferable in some cases to carry out the reaction in the presence of an inorganic base such as sodium carbonate, potassium carbonate, sodium hydrogen carbonate, or potassium hydrogen carbonate, or an organic base such as triethylamine, diisopropylethylamine or pyridine.

Examples of the solvent used in this reaction include solvents such as aromatic hydrocarbons, ethers, halogenated hydrocarbons, acetonitrile, ethyl acetate, and pyridine. These materials may be used alone or in any combination thereof. Further, the compounds (3) and (4) are appropriately used in equimolar amounts or in excess amounts, depending on reactions or compounds.

(Production Process 4)

[Chem. 21]

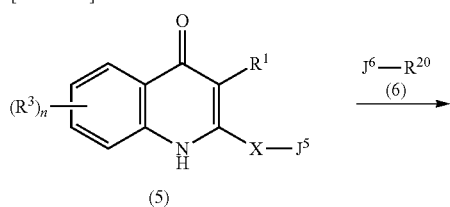

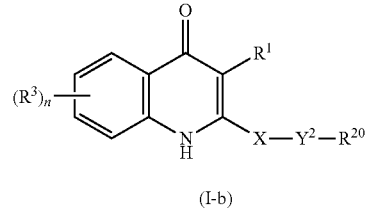

(In the formula, one of $J^5$ and $J^6$ represents —$NHR^7$, and the other represents —OC(O)-$L^2$, or $J^5$ represents —OH, $J^6$ represents —N=C=O; $L^2$ represents a leaving group, and $Y^2$ represents —N($R^7$)C(O)O— or —OC(O)N($R^7$)—. The same shall apply hereinafter.)

This production process is a method in which the compound of the formula (I-b) is obtained by carbamation of the compound (5). The leaving group of $L^2$ may be an organosulfonic acid group such as methanesulfonyloxy or p-toluenesulfonyloxy, halogen, or the like. Alternatively, a variety of acid anhydrides may be used as the leaving group.

The carbamation reaction can be carried out using the compound (5) and the compound (6) in equimolar amounts or one of them in an excess amount, from under cooling to under heating. Examples of the solvent used in this reaction include solvents such as aromatic hydrocarbons, ethers, halogenated hydrocarbons, acetonitrile, ethyl acetate, and pyridine. These materials may be used alone or in any combination thereof. Depending on the compounds, it may be preferable in some cases to carry out the reaction in the presence of an inorganic base such as sodium carbonate, potassium carbonate, sodium hydrogen carbonate, or potassium hydrogen carbonate, or an organic base such as triethylamine, diisopropylethylamine or pyridine.

(Production Process 5)

[Chem. 22]

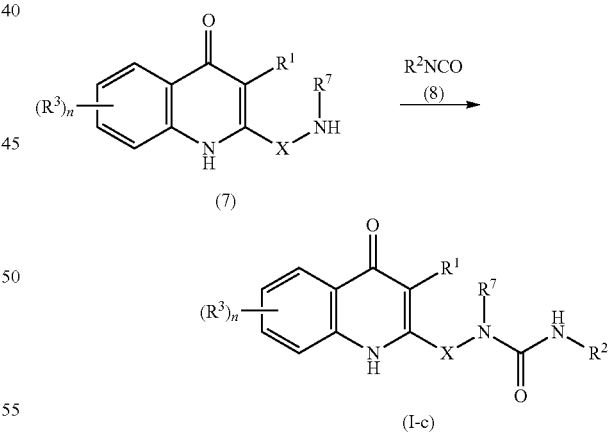

This production process is a method in which the compound of the formula (I-c) is obtained by ureation of the compound (7).

The ureation reaction can be carried out using the compounds (7) and (8) in equimolar amounts or one of them in an excess amount, from under cooling to under heating. Examples of the solvent used in this reaction include solvents such as aromatic hydrocarbons, ethers, halogenated hydrocarbons, acetonitrile, and ethyl acetate. These materials may be used alone or in any combination thereof.

(Production Process 6)

[Chem. 23]

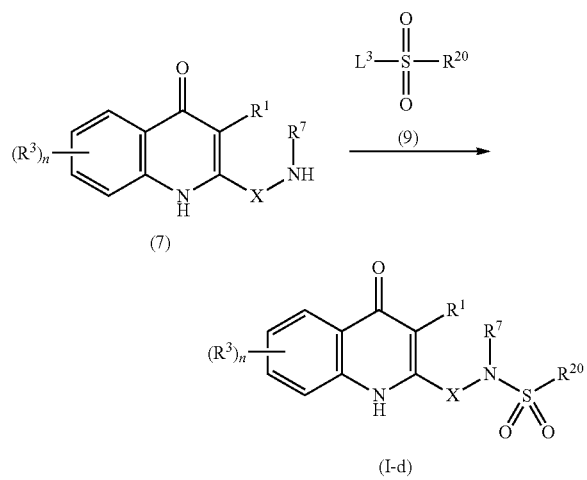

(In the formula, $L^3$ represents a leaving group. The same shall apply hereinafter.)

This production process is a method in which the compound of the formula (I-d) is obtained by sulfonamidation of the compound (7). The leaving group of $L^3$ may be a halogen or the like.

The sulfonamidation reaction can be carried out using the compounds (7) and (9) in equimolar amounts or one of them in an excess amount, from under cooling to under heating. Examples of the solvent used in this reaction include solvents such as aromatic hydrocarbons, ethers, halogenated hydrocarbons, acetonitrile, ethyl acetate. These materials may be used alone or in any combination thereof. Depending on the compounds, it may be preferable in some cases to carry out the reaction in the presence of an inorganic base such as sodium carbonate, potassium carbonate, sodium hydrogen carbonate, or potassium hydrogen carbonate, or an organic base such as triethylamine, diisopropylethylamine or pyridine.

(Production Process 7)

[Chem. 24]

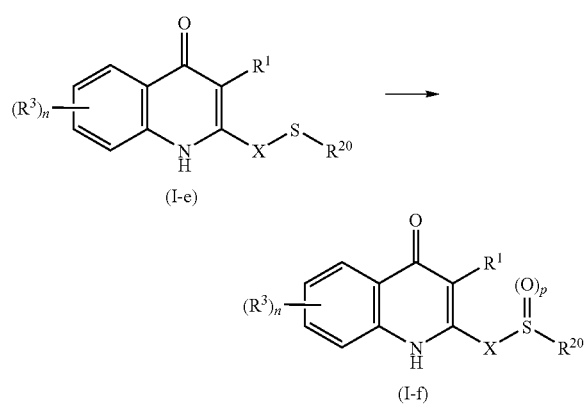

(In the formula, p represents 1 or 2. The same shall apply hereinafter.)

This production process is a method in which the compound of the formula (I-f) is obtained by oxidation of the compound (I-e).

The oxidation reaction can be carried out using the compound (I-e) and an oxidizing agent (such as m-chloroperbenzoic acid, peracetic acid, or hydrogen peroxide solution) in equimolar amounts or one of them in an excess amount, from under cooling to under heating. Examples of the solvent used in this reaction include solvents such as aromatic hydrocarbons, and halogenated hydrocarbons. These materials may be used alone or in any combination thereof.

Further, various substituents on groups $R^1$, $R^2$ and $R^3$ in formula (I) can be easily converted into other functional groups by using the compound of formula (I) as a starting material and applying reactions described in the following Examples, reactions apparent to those skilled in the art, or modifications thereof. For example, such conversion reactions can be carried out by any combination of processes that can be conventionally employed by those skilled in the art, for example O-alkylation, N-alkylation, acylation, oxidation, reduction, hydrolysis, amidation, and the like.

(Production of Starting Compounds)

The starting compounds in the above-mentioned production processes can be produced, for example, by the following methods, methods described in the following Production Examples, known methods, or modifications thereof.

(Starting Material Synthesis 1)

[Chem. 25]

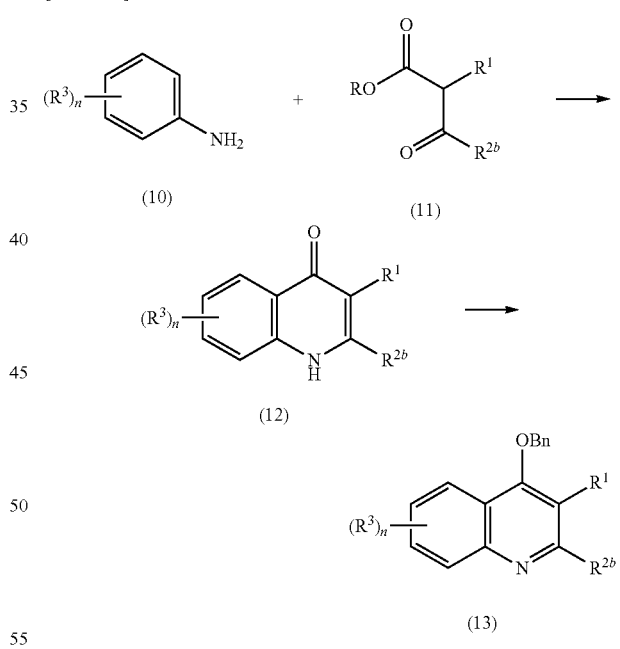

(In the formula, $R^{2b}$ represents lower alkyl or $-CO_2R$, R represents lower alkyl, and Bn represents a benzyl group. The same shall apply hereinafter.)

The compound (12) can be obtained by dehydration, condensation and cyclization of the compound (10) and the compound (11). This reaction is carried out using the compound (10) and the compound (11) in the presence of an acid such as acetic acid, hydrochloric acid, or sulfuric acid, usually stirring under heating in a solvent such as aromatic hydrocarbon.

The compound (13) can be obtained by benzylation of the compound (12). The benzylation is carried out using the compound (12) and a benzylating agent such as benzyl bromide in the presence of a base, in a solvent such as ethers, aromatic hydrocarbons, halogenated hydrocarbons, or DMF, usually stirring from under cooling to under heating. Examples of the base include an inorganic base such as sodium carbonate, potassium carbonate, sodium hydrogen carbonate, or potassium hydrogen carbonate, or an organic base such as triethylamine, N,N-diisopropylethylamine or pyridine.

(Starting Material Synthesis 2)

[Chem. 26]

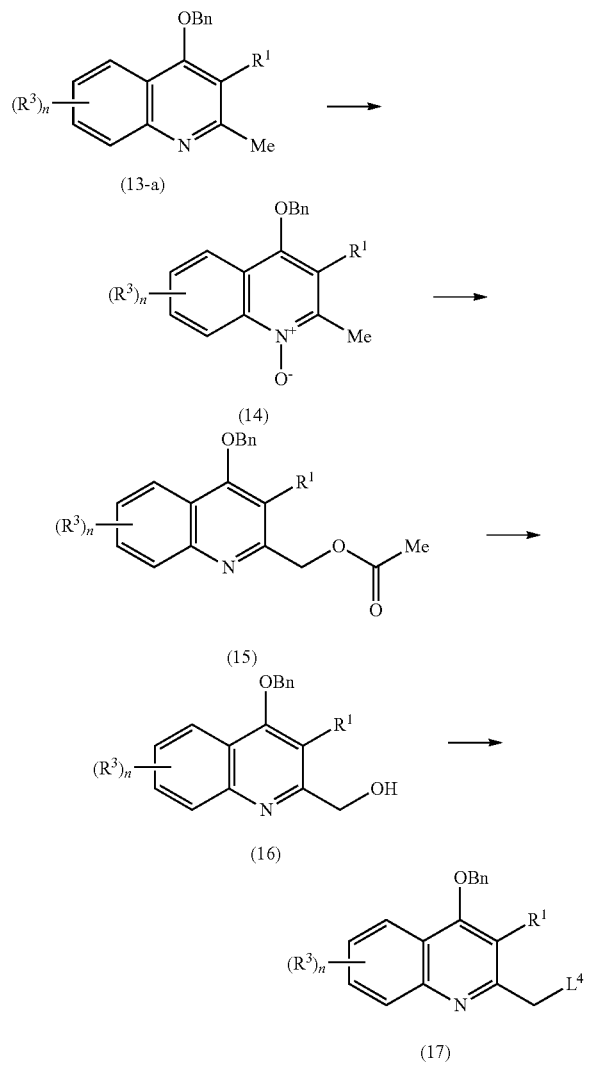

(In the formula, Me represents a methyl group, and $L^4$ represents a leaving group. The same shall apply hereinafter.)

The compound (14) can be obtained by oxidation of the compound (13-a). The oxidation is carried out using an oxidizing agent such as m-chloroperbenzoic acid, peracetic acid, hydrogen peroxide solution, in a solvent such as aromatic hydrocarbons, or halogenated hydrocarbons, usually stirring from under cooling to under heating.

The compound (15) can be obtained by rearrangement reaction of the compound (14). The rearrangement reaction is carried out using the compound (14) and an excess of acetic anhydride, without a solvent or in a solvent such as aromatic hydrocarbons, halogenated hydrocarbons, or ethers, stirring from under room temperature to under heating.

The compound (16) can be obtained by hydrolysis of the compound (15). The hydrolysis is carried out in the presence of an alkali such as sodium hydroxide or potassium hydroxide, in a solvent such as alcohols, ethers or water, usually stirring from under room temperature to under heating.

The compound (17) can be obtained by functional group transformation reaction of the compound (16). The leaving group of $L^4$ may be an organosulfonic acid group such as methanesulfonyloxy or p-toluenesulfonyloxy, halogen, or the like. The functional group transformation reaction is carried out using a sulfonylating agent such as methane sulfonyl chloride or p-toluene sulfonyl chloride, or a halogenating agent such as thionyl chloride, in a solvent such as aromatic hydrocarbons, halogenated hydrocarbons, or ethers, usually stirring from under cooling to under room temperature. It may be advantageous in some cases for smooth progress of the reaction to carry out the reaction in the presence of an inorganic base such as sodium carbonate, potassium carbonate, sodium hydrogen carbonate, or potassium hydrogen carbonate, or an organic base such as triethylamine, N,N-diisopropylethylamine or pyridine.

(Starting Material Synthesis 3)

[Chem. 27]

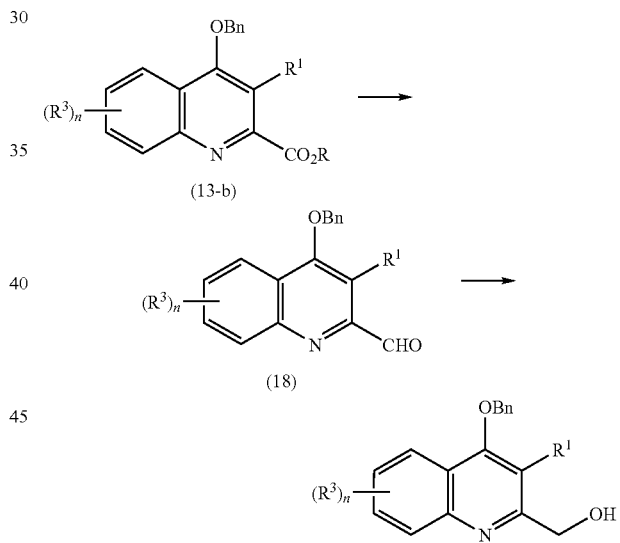

The compound (18) can be obtained by reduction of the compound (13-b) into an aldehyde. The reduction is carried out using a reducing agent such as diisobutylaluminum hydride, in a solvent such as aromatic hydrocarbons or ethers, usually stirring from under cooling.

The compound (16) can be obtained by reduction of the compound (18). The reduction is carried out using a reducing agent such as sodium borohydride, in a solvent such as alcohols, usually stirring from under cooling to under room temperature.

The compound (16) can also be obtained by carrying out the reduction reaction of the compound (13-b) under reaction conditions such as room temperature.

(Starting Material Synthesis 4)

[Chem. 28]

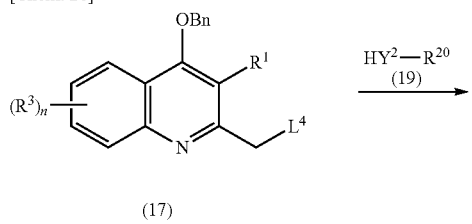

(In the formula, $Y^2$ represents —O—, —S—, or —N($R^7$)—. The same shall apply hereinafter.)

The compound (1-a) can be obtained by reaction of the compound (17) with the compound (19). This reaction is carried out using the compound (17) and the compound (19) in equivalent amounts or one of them in an excess amount, in the presence of a base, from under cooling to under heating at reflux, preferably at 0° C. to 80° C. usually stirring for 0.1 hour to 5 days, in a reaction-inert solvent. There is no particular limit to the solvent that can be used herein. Examples of such a solvent include aromatic hydrocarbons such as benzene, toluene, and xylene; ethers such as diethyl ether, tetrahydrofuran, dioxane, and dimethoxyethane; halogenated hydrocarbons such as dichloromethane, 1,2-dichloroethane, and chloroform; N,N-dimethylformamide, dimethylsulfoxide, ethyl acetate, acetonitrile, and a mixture thereof. Examples of the base include organic bases such as triethylamine, diisopropylethylamine, 1,8-diazabicyclo[5.4.0]-7-undecene and n-butyllithium, or inorganic bases such as sodium carbonate, potassium carbonate, sodium hydride, or potassium tert-butoxide. It may be advantageous in some cases to carry out the reaction in the presence of a phase-transfer catalyst such as tetra-n-butylammonium chloride.

(Starting Material Synthesis 5)

[Chem. 29]

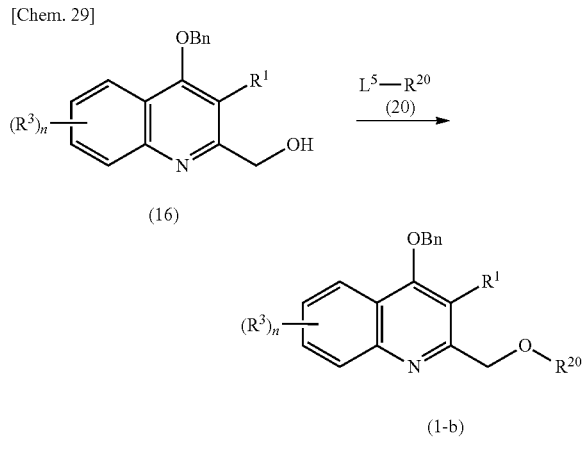

The compound (1-b) can be obtained by reaction of the compound (16) with the compound (20). The leaving group of $L^5$ may be an organosulfonic acid group such as methanesulfonyloxy or p-toluenesulfonyloxy, halogen, or the like. The reaction conditions are the same as in "Starting material synthesis 4".

(Starting Material Synthesis 6)

[Chem. 30]

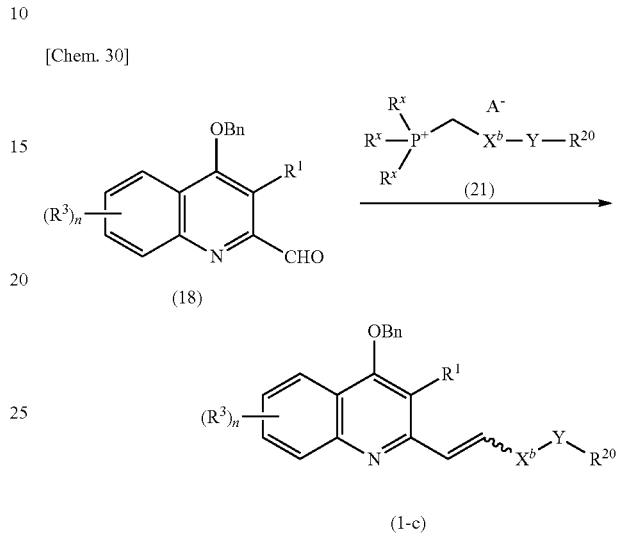

(In the formula, $R^x$ represents a remnant of a Wittig reagent, $A^-$ represents a counter anion, and $X^b$ represents $C_{1-8}$ alkylene. The same shall apply hereinafter.)

The compound (1-c) can be obtained by Wittig reaction of the compound (18) with the compound (21). This reaction is carried out using the compound (18) and compound (21) in the presence of a base such as potassium carbonate, potassium tert-butoxide, sodium hydride, n-butyllithium, or lithium hexamethyldisilazide, in a solvent such as aromatic hydrocarbons, ethers, halogenated hydrocarbons, DMF, DMA, NMP, dimethylsulfoxide (DMSO), or acetonitrile, usually stirring from under cooling to under heating.

(Starting Material Synthesis 7)

[Chem. 31]

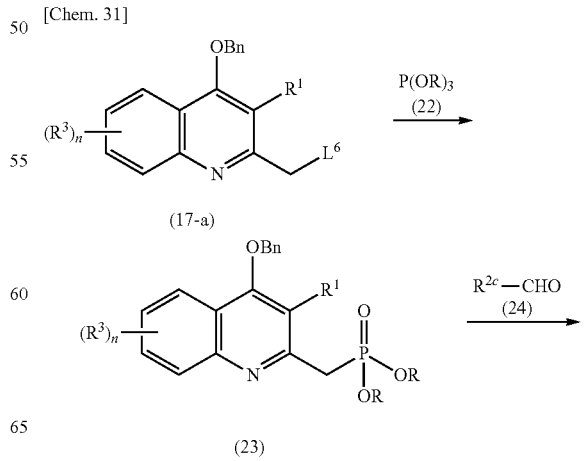

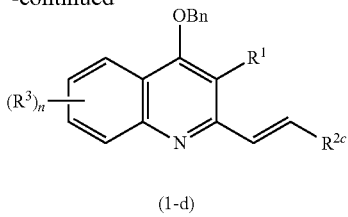

(1-d)

(In the formula, $L^6$ represents halogen, $R^{2c}$ represents —$X^c$-aryl which may be substituted, —$X^c$-a heterocyclic group which may be substituted, or —$X^d$—Y—$R^{20}$; and $X^c$ represents a bond or $X^d$ and $X^d$ represent $C_{1-8}$ alkylene which may be substituted. The same shall apply hereinafter.)

The compound (23) can be obtained by Arbuzov reaction of the compound (17-a) with the compound (22). This reaction is carried out using the compound (17-a) and an excess of the compound (22), stirring under heating, without a solvent or in a solvent such as aromatic hydrocarbons or ethers.

The compound (1-d) can be obtained by Horner-Emmons reaction of the compound (23) with the compound (24). This reaction is carried out using the compound (23) and compound (24) in the presence of a base such as potassium carbonate, potassium tert-butoxide, sodium hydride, n-butyllithium, or lithium hexamethyldisilazide, in a solvent such as aromatic hydrocarbons, ethers, halogenated hydrocarbons, DMF, DMA, NMP, DMSO, or acetonitrile, usually stirring from under cooling to under heating.

(Starting Material Synthesis 8)

[Chem. 32]

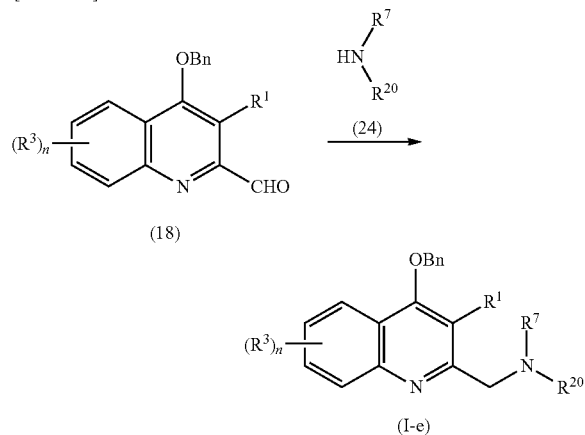

The compound (1-e) can be obtained by reductive amination of the compound (18) and the compound (24). This reaction is carried out using the compound (18) and the compound (24) in equivalent amounts or one of them in an excess amount, from under room temperature to under heating, stirring from under cooling, in a solvent such as halogenated hydrocarbons, aromatic hydrocarbons, or esters (such as ethyl acetate), ethers, alcohols, acetic acid, in the presence of a reducing agent such as sodium borohydride, sodium triacetoxy borohydride.

The compound of the formula (I) is isolated and purified as its free compound, or a pharmaceutically acceptable salt, hydrate, solvate or crystalline polymorph thereof. The pharmaceutically acceptable salt of the compound of the formula (I) can also be prepared in accordance with a conventional method for a salt formation reaction.

Isolation and purification are carried out by employing common chemical operations such as extraction, fractional crystallization, and various types of fraction chromatography.

Various isomers can be prepared by selecting an appropriate starting compound, or can be separated by making use of the difference in the physicochemical properties between isomers. For example, the optical isomer can be derived into an optically pure isomer by means of general optical resolution methods of racemic forms (for example, fractional crystallization for inducing diastereomers with optically active bases or acids, chromatography using a chiral column, etc., and the like). In addition, the isomers can also be prepared from an appropriate optically active starting compound.

(Pharmacological Test)

The pharmacological activity of the compound of the formula (I) was confirmed by the following tests.

Test 1: Inhibitory Activity on ROS Production Derived from NADPH Oxidase

This activity was measured by using Human Umbilical Vein Endothelial Cells (HUVECs). The test method is as follows.

$3\times10^4$ cells/well (100 μL) of HUVECs were seeded into a 96-well plate coated with collagen. The culture medium was MCDB131 medium containing 10% fetal bovine serum, 2 mM glutamine, 100 U/mL penicillin, 100 U/mL streptomycin, and 10 ng/mL recombinant human basic-FGF. On the next day, the culture medium was removed by an aspirator, and 100 μL/well of phosphate buffered saline containing 25 mM glucose, 200 μM NADPH, 0.2% nitrotetrazolium blue, and test compounds followed by culturing at 37° C. Nitrotetrazolium blue reacts with intracellularly produced ROS and turns into a water-insoluble blue pigment. After 2 hours, the supernatant was discarded, and the wells were washed three times with phosphate buffered physiological saline. Then, 100 μL/well of 90% DMSO water containing 0.04M sodium hydroxide was added to each well to completely dissolve the pigment, and an absorbance at a wavelength of 715 nm was measured. By taking an absorbance with no addition of a test compound as A, an absorbance with no addition of a test compound as B, and an absorbance with addition of glucose, NADPH and a test compound as C, ROS production inhibitory rate was calculated according to the following equation.

Inhibition rate (%)=$(A-B)/(A-C)\times100$

Table 1 shows the results obtained upon addition of 1.0 μM test compound. Abbreviation "Ex" in the table represents Example Compound No. which will follow, and abbreviation "Inh" represents an ROS production inhibition rate. It was confirmed that the compounds of the formula (I) of the present invention have an excellent ROS production inhibitory activity.

TABLE 1

| Ex | Inh(%)(1.0 μM) |
|---|---|
| 2 | 91.9 ± 5.2 |
| 4 | 84.7 ± 2.1 |
| 6 | 79.9 ± 1.2 |
| 8 | 91.5 ± 4.7 |
| 9 | 88.7 ± 1.5 |
| 19 | 99.1 ± 0.0 |
| 49 | 90.8 ± 5.2 |
| 50 | 80.5 ± 2.5 |
| 55 | 57.3 ± 2.3 |
| 98 | 101.5 ± 1.9 |
| 127 | 85.3 ± 2.9 |

TABLE 1-continued

| Ex | Inh(%)(1.0 μM) |
|---|---|
| 128 | 77.7 ± 3.9 |
| 166 | 84.3 ± 2.4 |
| 180 | 69.5 ± 1.3 |
| 198 | 97.5 ± 6.1 |
| 199 | 93.1 ± 1.1 |
| 228 | 66.3 ± 2.1 |
| 276 | 118.2 ± 4.0 |
| 279 | 98.9 ± 1.0 |
| 283 | 61.6 ± 1.7 |
| 284 | 64.2 ± 0.1 |
| 285 | 67.3 ± 0.1 |
| 291 | 118.8 ± 0.4 |

Test 2: Oral Glucose Tolerance Test Using Mice

This test is intended to evaluate an inhibitory action of a test compound on elevation of the blood glucose level after glucose loading, using mice. A test method is described hereinafter.

Male ICR or C57BL/6 J mice (6 weeks old, available from CLEA JAPAN, Inc.) pre-bred for one week were fasted overnight and used as test animals. A test compound was suspended in 10% PEG-60 Hydrogenated Castor Oil (HCO-60) aqueous solution, and was orally administered (3 mg/kg) to animals 5 minutes prior to oral glucose loading (2 g/kg). The control group was given a 10% HCO-60 aqueous solution. According to the following equation, a blood glucose-lowering rate (%) at 30 minutes after glucose loading was calculated for the test compound-treated group relative to the control group. An increase in the blood glucose level of the test compound-treated group and an increase in the blood glucose level of the control group were taken as A and B, respectively.

Blood glucose-lowering rate (%)=100−[(*A*/*B*)×100]

As a result, it was confirmed that the compound of the formula (I) of this invention has an excellent blood glucose-lowering action. Compounds of Examples 2, 4, 8, 141, 153, 186, 188, and 284 exhibited a blood glucose-lowering rate of 70 to 105%. For example, the compounds of Examples 2, 8, 188, and 248 exhibited a blood glucose-lowering rate of 93%, 70%, 105%, and 89%, respectively.

As a result of the above respective tests, it was confirmed that the compound of the formula (I) has an ROS production inhibitory activity based on the NAD(P)H oxidase inhibitory action, and possess an excellent blood glucose-lowering action. Therefore, the compound of the formula (I) can be used as an agent for preventing and/or treating diseases associated with NAD(P)H oxidase.

A preparation containing one or two or more kinds of the compound of formula (I) or a salt thereof as an active ingredient can be prepared in accordance with a generally used method, using a pharmaceutical carrier, excipient, or the like, that is usually used in the art.

The administration can be carried out by oral administration via tablets, pills, capsules, granules, powders, liquid preparations, or the like, or parenteral administration via injections such as intraarticular injection, intravenous injection, intramuscular injection, or the like, as well as suppositories, eye drops, eye ointments, percutaneous liquid preparations, ointments, percutaneous patches, transmucosal liquid preparations, transmucosal patches, inhalations, and the like.

As solid compositions for oral administration according to the present invention, tablets, powders, granules, or the like are used. In such a solid composition, one or two or more kinds of active ingredients are mixed with at least one inert excipient such as lactose, mannitol, glucose, hydroxypropylcellulose, microcrystalline cellulose, starch, polyvinyl pyrrolidone, and/or magnesium aluminometasilicate. According to a conventional method, the composition may contain inert additives such as a lubricant such as magnesium stearate, a disintegrator such as sodium carboxymethyl starch, a stabilizing agent, and a solubilizing aid. As occasion demands, the tablets or the pills may be coated with a film of a sugar coating, or a gastric or enteric coating agent.

Liquid compositions for oral administration include pharmaceutically acceptable emulsions, solutions, suspensions, syrups, elixirs, or the like, and contain a generally used inert diluent such as purified water or ethanol. In addition to the inert diluent, the liquid composition may contain an adjuvant such as a solubilizing agent, a moistening agent, and a suspending agent, a sweetener, a flavor, an aromatic, and a preservative.

Injections for parenteral administration include sterile aqueous or non-aqueous solutions, suspensions and emulsions. The aqueous solvent includes, for example, distilled water for injection and physiological saline. Examples of the non-aqueous solvent include propylene glycol, polyethylene glycol, vegetable oils such as olive oil, alcohols such as ethanol, Polysorbate 80 (Japanese Pharmacopeia), and the like. Such a composition may further contain a tonicity agent, a preservative, a moistening agent, an emulsifying agent, a dispersing agent, a stabilizing agent, or a solubilizing agent. These are sterilized, for example, by filtration through a bacteria-retaining filter, blend of a sterilizing agent, or irradiation. In addition, these can also be used by preparing a sterile solid composition, and dissolving or suspending it in sterile water or a sterile solvent for injection prior to use.

External preparations include ointments, plasters, creams, jellies, adhesive skin patches, sprays, lotions, eye drops, eye ointments, and the like. The external preparation contains generally used ointment bases, lotion bases, aqueous or non-aqueous liquids, suspensions, emulsions, and the like. Examples of the ointment or lotion bases include polyethylene glycol, propylene glycol, white Vaseline, white beeswax, polyoxyethylene hydrogenated castor oil, glyceryl monostearate, stearyl alcohol, cetyl alcohol, lauromacrogol, sorbitan sesquioleate, and the like.

Transmucosal preparations such as inhalations and transnasal preparations are used in a solid, liquid or semi-solid form and may be prepared in accordance with a conventionally known method. For example, a known excipient, and also a pH-adjusting agent, a preservative, a surfactant, a lubricant, a stabilizing agent, a thickening agent, or the like may be appropriately added thereto. For their administration, an appropriate device for inhalation or blowing may be used. For example, a compound may be administered alone or as a powder of formulated mixture, or as a solution or suspension in combination with a pharmaceutically acceptable carrier, using a conventionally known device or sprayer, such as a measured administration inhalation device. The dry powder inhaler or the like may be for single or multiple administration use, and a dry powder or a powder-containing capsule may be used. Alternatively, it may be in a form such as a pressurized aerosol spray or the like which uses an appropriate propellant, for example, a suitable gas such as chlorofluoroalkane, hydrofluoroalkane, or carbon dioxide.

In oral administration, the daily dose is generally from about 0.001 to 100 mg/kg, preferably from 0.1 to 30 mg/kg, and more preferably 0.1 to 10 mg/kg, per body weight, administered in one portion or in 2 to 4 divided portions. In the case of intravenous administration, the daily dose is suitably administered from about 0.0001 to 10 mg/kg per body weight, once a day or two or more times a day. In addition, a transmucosal agent is administered at a dose from about 0.001 to 100 mg/kg per body weight, once a day or two or more times a day. The dose is appropriately decided in response to the individual case by taking the symptoms, the age, and the gender, and the like into consideration.

The compounds of formula (I) can be used in combination with various agents for treating or preventing for the diseases for which the aforementioned compounds of formula (I) are considered to be effective. The combined preparation may be administered simultaneously, or separately and continuously, or at a desired time interval. The preparations to be co-administered may be a blend, or may be prepared individually.

EXAMPLES

Hereinafter, production processes of compounds of the formula (I) will be described in more detail with reference to Examples. The present invention compounds are not limited to compounds described in the following Examples. In addition, production processes of starting compounds are shown in Production Examples.

Production Example 1

To a solution of 4-bromoaniline (25 g) and diethyl 2-methyl-3-oxo succinate (30 mL) in benzene (300 mL) was added dropwise acetic acid (3.3 mL) at room temperature, followed by refluxing using a Dean-Stark reflux apparatus for 12 hours. After the reaction mixture was concentrated under reduced pressure, the residue was gradually added dropwise to 100 mL of diphenyl ether which had been previously heated to 270° C., followed by stirring at the same temperature for 1 hour. The reaction mixture was allowed to cool to room temperature, and hexane was added thereto. The precipitated solid was collected by filtration to obtain ethyl 6-bromo-3-methyl-4-oxo-1,4-dihydroquinoline-2-carboxylate (19 g).

Production Example 2

To a solution of ethyl 3-chloro-4-oxo-1,4-dihydroquinoline-2-carboxylate (1.1 g) in DMF (30 mL) were added benzyl bromide (0.57 mL) and potassium carbonate (720 mg) at room temperature, followed by stirring for 15 hours. Water was added to the reaction mixture, followed by extraction with ethyl acetate. The organic layer was washed sequentially with water and saturated brine and dried over anhydrous sodium sulfate, and the solvent was evaporated. The residue was purified by silica gel column chromatography (eluent: hexane/ethyl acetate=85/15) to obtain ethyl 4-(benzyloxy)-3-chloroquinoline-2-carboxylate (1.24 g).

Production Example 3

To an ice-cold solution of 4-(benzyloxy)-2,3,6-trimethylquinoline (1.36 g) in chloroform (25 mL) was added m-chloroperbenzoic acid (75%, 1.35 g), and the mixture was stirred for 4.5 hours. A 1M aqueous sodium hydroxide solution (10 mL) and water (10 mL) were added to the reaction mixture, followed by extraction with chloroform (20 mL). The organic layer was washed sequentially with water and saturated brine, and the solvent was evaporated under reduced pressure. The residue was purified by silica gel column chromatography (eluent: chloroform/methanol=95/5) to obtain 4-(benzyloxy)-2,3,6-trimethylquinoline-1-oxide (1.20 g).

Production Example 4

4-(Benzyloxy)-2,3,6-trimethylquinoline-1-oxide (1.18 g) was dissolved in acetic anhydride (32 mL), followed by stirring at room temperature for 2 hours. After the solvent was evaporated under reduced pressure, water (50 mL) was added to the residue, followed by extraction with ethyl acetate (100 mL). The organic layer was washed sequentially with water and saturated brine, and dried. The solvent was evaporated under reduced pressure, and the residue was purified by silica gel column chromatography (eluent: chloroform) to obtain [4-(benzyloxy)-3,6-dimethylquinolin-2-yl]methyl acetate (1.25 g).

Production Example 5

To a mixture of 4-benzyloxy-2,3-dimethylquinoline-1-oxide (21.2 g), potassium carbonate (20.9 g), and acetonitrile (400 mL) was added p-toluenesulfonyl chloride (18.8 g), followed by stirring at room temperature for 12 hours. Insolubles were removed by filtration, and the filtrate was concentrated under reduced pressure. Water (500 mL) was added to the residue, followed by twice extractions with ethyl acetate (500 mL). The organic layer was washed with saturated brine and then dried over anhydrous magnesium sulfate. The solvent was evaporated under reduced pressure, and the residue was purified by silica gel column chromatography (eluent: hexane/ethyl acetate=5/1) to obtain p-toluenesulfonic acid [4-(benzyloxy)-3-methylquinolin-2-yl]methyl ester (13.4 g).

Production Example 6

To a solution of [4-(benzyloxy)-3,6-dimethylquinolin-2-yl]methyl acetate (1.20 g) in THF-methanol (1:3, 24 mL) was added a 1M aqueous sodium hydroxide solution (5.5 mL), followed by stirring at room temperature for 3 hours. The reaction solution was concentrated under reduced pressure and water was then added to the residue. The precipitated solid was collected by filtration, washed with water, and dried to obtain [4-(benzyloxy)-3,6-dimethylquinolin-2-yl]methanol (900 mg).

Production Example 7

Ethyl 4-(benzyloxy)-6-bromo-3-methylquinoline-2-carboxylate (2.37 g) was dissolved in THF (30 mL) and toluene (30 mL). A solution of 1M diisobutylaluminum hydride in toluene (7.10 mL) was gradually added dropwise to this solution at −78° C., followed by stirring at the same temperature for 3 hours. The reaction mixture was warmed to about 0° C., and water was added thereto, followed by stirring overnight. The precipitated insolubles were removed by filtration through Celite, and then the filtrate was concentrated. The resulting residue was dissolved in ethyl acetate, and powdered with gradual addition of hexane to obtain 4-(benzyloxy)-6-bromo-3-methylquinoline-2-carboxaldehyde (1.76 g).

Production Example 8

4-(Benzyloxy)-6-bromo-3-methylquinoline-2-carboxaldehyde (3.23 g) was dissolved in THF (50 mL) and ethanol (50 mL), and sodium borohydride (410 mg) was gradually added thereto under ice-cooling, followed by stirring at room temperature for 2 hours. The reaction mixture was ice-cooled, and water was added thereto, followed by stirring at room temperature for 1 hour. The reaction mixture was concentrated under reduced pressure, water was added to the residue, and the precipitated solid was collected by filtration. The resulting solid was suspended in ethanol, stirred for a while, and collected by filtration to obtain [4-(benzyloxy)-6-bromo-3-methylquinolin-2-yl]methanol (3.20 g).

Production Example 9

To a solution of ethyl 4-(benzyloxy)-8-methoxy-3-methylquinoline-2-carboxylate (1.95 g) in toluene (30 mL) was added dropwise a solution of diisobutylaluminum hydride in toluene (0.99M, 6.1 mL) at room temperature under nitrogen flow, followed by stirring. After 1 hour and 2 hours, a solution of diisobutylaluminum hydride in toluene (0.99M, each 6.1 mL) was added thereto, followed by stirring for 3 hours. Water was added to the reaction mixture to stop the reaction, and then anhydrous sodium sulfate was added thereto, followed by stirring. Insolubles were removed by filtration through Celite. The filtrate was concentrated under reduced pressure, and then the residue was purified by silica gel column chromatography (eluent: hexane/ethyl acetate=50/50~ethyl acetate, then chloroform~chloroform/methanol=95/5) to obtain [4-(benzyloxy)-8-methoxy-3-methylquinolin-2-yl]methanol (551 mg).

Production Example 10

[4-(Benzyloxy)-6-fluoro-3-methylquinolin-2-yl]methanol (4.02 g) was dissolved in THF (50 mL) and toluene (50 mL), and 10 drops of pyridine were added thereto. Thionyl chloride (1.50 mL) was gradually added dropwise thereto under ice-cooling, and the reaction mixture was stirred at the same temperature for 1 hour, and further stirred at room temperature for 1 hour. After the precipitated solid was collected by filtration, ethyl acetate and a saturated aqueous sodium hydrogen carbonate solution were gradually added with stirring to the filtrate under ice-cooling. After the foaming became stable, the organic layer was separated, washed sequentially with water and saturated brine and dried over anhydrous magnesium sulfate. The solvent was evaporated. The residue was purified by silica gel column chromatography (eluent: chloroform) to obtain 4-(benzyloxy)-2-(chloromethyl)-6-fluoro-3-methylquinoline (3.85 g).

Production Example 11

To a solution of 4-(benzyloxy)-2-(chloromethyl)-3-methylquinoline (5.0 g) in THF (50 mL) was added anhydrous lithium bromide (15 g), followed by heating under reflux for 3 hours. The reaction mixture was cooled to room temperature, and then the solvent was evaporated under reduced pressure. Water was added to the residue, followed by stirring, and the resulting solid was collected by filtration. This solid was dried under vacuum at 60° C. to obtain 5.73 g of 4-(benzyloxy)-2-(bromomethyl)-3-methylquinoline as a white solid.

Production Example 12

A mixture of 4-(benzyloxy)-2-(chloromethyl)-3-methylquinoline (1.00 g) and triethyl phosphite (3.84 g) was stirred at 150° C. for 6 hours. The reaction mixture was allowed to cool to room temperature, and then concentrated under reduced pressure. The residue was purified by silica gel column chromatography (eluent: chloroform/methanol=98/2) to obtain diethyl {[4-(benzyloxy)-3-methylquinolin-2-yl]methyl}phosphonate (1.12 g).

Production Example 13

To a solution of 4-(benzyloxy)-2-[4-(benzyloxy)-1-buten-1-yl]-3-methylquinoline (2.57 g) in ethanol (26 mL) were added cyclohexene (13 mL) and 20% palladium hydroxide-activated carbon powder (1.5 g), followed by stirring under reflux for 2 hours. The catalyst was removed by filtration, and then the solvent was evaporated. The residue was purified by silica gel column chromatography (eluent: chloroform/methanol=93/7) to obtain 2-(4-hydroxybutyl)-3-methylquinolin-4(1H)-one (1.10 g).

Production Example 14

A mixture of 4-(benzyloxy)-3-methylquinoline-2-carboxyaldehyde (570 mg), n-heptylamine (240 mg), sodium triacetoxy borohydride (530 mg), acetic acid (0.1 mL), and 1,2-dichloroethane (15 mL) was stirred at room temperature for 14.5 hours. Water (15 mL) was added to the reaction mixture, followed by extraction with chloroform (30 mL). The organic layer was washed with saturated brine, and then dried over anhydrous magnesium sulfate. The solvent was evaporated under reduced pressure, and the residue was purified by silica gel column chromatography (eluent: chloroform/methanol=10/1) to obtain N-{[4-(benzyloxy)-3-methylquinolin-2-yl]methyl}heptane-1-amine (740 mg).

Production Example 15

To a solution of N-benzyl-1-[4-(benzyloxy)-3-methylquinolin-2-yl]methaneamine (2.21 g) in ethyl acetate (50 mL) was added a 4M hydrogen chloride-ethyl acetate solution (4 mL), and the solvent was evaporated under reduced pressure. The residue was washed with diethyl ether, and dried to obtain a solid (1.10 g). This solid (1.00 g) was dissolved in a mixed solvent of ethanol-THF-water (10:5:1, 32 mL), and 10% palladium-activated carbon (400 mg) was added thereto, followed by stirring at room temperature under hydrogen atmosphere for 3 hours. To reaction mixture were added water (10 mL) and 10% palladium-activated carbon (400 mg), followed by stirring at room temperature under hydrogen atmosphere for 6 hours. The catalyst was removed by filtration, and then the solvent was evaporated under reduced pressure. The residue was dissolved in ethyl acetate-ethanol (1:1, 10 mL), and a 4M hydrogen chloride-ethyl acetate solution (2 mL) was added thereto. The solvent was evaporated under reduced pressure and the resulting residue was dried to obtain 2-(aminomethyl)-3-methylquinolin-4(1H)-one dihydrochloride (560 mg).

Production Example 16

To a solution of N-{[4-(benzyloxy)-3-methylquinolin-2-yl]methyl}heptane-1-amine (153 mg) in pyridine (5 mL) was added acetic anhydride (0.06 mL), followed by stirring at room temperature for 24 hours. The reaction mixture was concentrated under reduced pressure, and water (10 mL) and 1M hydrochloric acid (10 mL) were added to the residue, followed by extraction with ethyl acetate (50 mL). The organic layer was washed sequentially with water and saturated brine, and dried over anhydrous magnesium sulfate. The solvent was evaporated under reduced pressure, and the residue was purified by silica gel column chromatography (eluent: chloroform/methanol=20/1) to obtain N-{[4-(benzyloxy)-3-methylquinolin-2-yl]methyl}-N-heptylacetamide (158 mg).

Production Example 17

1-Heptanethiol (250 mg) was dissolved in methanol (5 mL), to which a solution of 28% sodium methoxide in methanol (0.37 mL) was then added, followed by stirring at room temperature for 15 minutes. The reaction mixture was added to a solution of p-toluenesulfonic acid [4-(benzyloxy)-3-methylquinolin-2-yl]methyl ester (464 mg) in methanol-THF (1:1, 10 mL), followed by stirring at room temperature for 30 minutes. The reaction mixture was concentrated under reduced pressure, and water (100 mL) was added to the resulting residue, followed by extraction with ethyl acetate (100 mL). The organic layer was washed with saturated brine, and then dried over anhydrous magnesium sulfate. The solvent was evaporated under reduced pressure, and the residue was purified by silica gel column chromatography (eluent: hexane/ethyl acetate=5/1) to obtain 4-(benzyloxy)-2-[(heptylsulfanyl)methyl]-3-methylquinoline (380 mg).

Production Example 18

To a solution of 4-(benzyloxy)-2-[(heptylsulfanyl)methyl]-3-methylquinoline (106 mg) in dichloromethane (5 mL) was added m-chloroperbenzoic acid (75%, 68 mg) at −30° C., followed by stirring for 5 hours while warming to room temperature. A 0.2M aqueous sodium hydroxide solution (20 mL) was added to the reaction mixture, followed by extraction with chloroform (50 mL). The organic layer was washed sequentially with water and saturated brine and then dried over anhydrous magnesium sulfate, and the solvent was evaporated under reduced pressure. The residue was purified by silica gel column chromatography (eluent: chloroform/methanol=10/1) to obtain 4-(benzyloxy)-2-[(heptylsulfinyl)methyl]-3-methylquinoline (75 mg).

Production Example 19

A solution of 1-(4-bromobutoxy)-4-fluorobenzene (2.56 g) and triphenylphosphine (2.72 g) in toluene (10 mL) was heated under reflux for 24 hours. The reaction mixture was allowed to cool to room temperature, and the precipitated solid was collected by filtration and dried to obtain [4-(4-fluorophenoxy)butyl]triphenylphosphonium bromide (2.06 g).

Production Example 20

60% Sodium hydride (160 mg) was added to DMSO (20 mL), followed by stirring at 40° C. for 1 hour, and [4-(4-fluorophenoxy)butyl]triphenylphosphonium bromide (2.00 g) was added thereto. The reaction mixture was stirred at 40° C. for 1.5 hours, and then 4-(benzyloxy)-3-methylquinoline-2-carboxyaldehyde (910 mg) was added thereto, followed by stirring at room temperature for 3 hours. Water (100 mL) was added to the reaction mixture, followed by extraction with diethyl ether (100 mL). The organic layer was washed with saturated brine, and then dried over anhydrous magnesium sulfate. The solvent was evaporated under reduced pressure, and the residue was purified by silica gel column chromatography (eluent: hexane/ethyl acetate=5/1) to obtain 4-(benzyloxy)-2-[5-(4-fluorophenoxy)pent-1-en-1-yl]-3-methylquinoline (816 mg) as an E/Z mixture.

Production Example 21

1-Heptanol (470 mg) was dissolved in THF (10 mL), and potassium tert-butoxide (450 mg) was added thereto, followed by stirring at room temperature for 30 minutes. 4-(Benzyloxy)-2-[(chloromethyl)-3-methylquinoline (1.00 g) was added to the reaction mixture, followed by stirring at room temperature for 1 hour. A saturated aqueous ammonium chloride solution (50 mL) was added to the reaction mixture, followed by extraction with ethyl acetate (60 mL). The organic layer was dried over anhydrous magnesium sulfate, and the solvent was evaporated under reduced pressure. The residue was purified by silica gel column chromatography (eluent: hexane/ethyl acetate=5/1) to obtain 4-(benzyloxy)-2-[(heptyloxy)methyl]-3-methylquinoline (1.13 g).

Production Example 22

To a solution of [4-(benzyloxy)-3-methylquinolin-2-yl]methanol (105 mg) in THF (3 mL) was added pentylisocyanate (45 mg), followed by stirring at room temperature for 1 hour. Pentylisocyanate (20 mg) was further added to the reaction mixture, followed by stirring at room temperature for 16 hours. Methanol (2 mL) was added to the reaction mixture, and then the solvent was evaporated under reduced pressure. The residue was purified by silica gel column chromatography (eluent: chloroform) to obtain [4-(benzyloxy)-3-methylquinolin-2-yl]methylpentylcarbamate (150 mg).

Production Example 23

A mixture of ethyl 3-{[4-(benzyloxy)-3-methylquinolin-2-yl]methoxy}-5-hydroxybenzoate (2.10 g), 4-(bromomethyl)tetrahydro-2H-pyrane (2.29 g), potassium carbonate (0.98 g), and DMF (40 mL) was stirred at 80° C. for 13 hours. The reaction mixture was concentrated under reduced pressure, and then water was added to the residue, followed by extraction with ethyl acetate (150 mL). The organic layer was washed sequentially with water and saturated brine, and dried. The solvent was evaporated under reduced pressure, and the residue was purified by silica gel column chromatography (eluent: chloroform/methanol=20/1) to obtain ethyl 3-{[4-(benzyloxy)-3-methylquinolin-2-yl]methoxy}-5-(tetrahydro-2H-pyran-4-ylmethoxy)benzoate (2.50 g).

Production Example 24

To a solution of {[4-(2,2-dimethylpropoxy)butoxy]methyl}benzene (1.50 g) in acetic acid (30 mL) was added 10% palladium-activated carbon (500 mg), followed by stirring under hydrogen atmosphere for 3 hours. The catalyst was removed by filtration, and the solvent was evaporated under reduced pressure to obtain 4-(2,2-dimethylpropoxy)butan-1-ol (267 mg).

Production Example 25

To a solution of diethyl {[4-(benzyloxy)-3-methylquinolin-2-yl]methyl}phosphonate (1.85 g) in THF (40 mL) was added lithium hexamethyldisilazide (1.0M hexane solution, 4.76 mL) at 5 to 6° C. under nitrogen atmosphere, followed by stirring at the same temperature for 30 minutes. A solution of tetrahydrofuran-2-ol (675 mg) in THF (10 mL) was added to the reaction mixture, followed by stirring at the same temperature for 5 hours. Water (100 mL) was added to the reaction mixture, followed by extraction with ethyl acetate (300 mL). The organic layer was washed with saturated brine, and dried over anhydrous magnesium sulfate. The solvent was evaporated under reduced pressure, and the residue was purified by silica gel column chromatography (eluent: hexane/ethyl acetate=19/1-1/1) to obtain (4E)-5-[4-(benzyloxy)-3-methylquinolin-2-yl]penten-1-ol (427 mg).

Production Example 26

2,3,5-trichloro-6-(tetrahydro-2H-pyran-4-ylmethoxy)pyridine (214 mg) and [4-(benzyloxy)-3-methylquinolin-2-yl]

methanol (222 mg) were dissolved in DMF (5 mL), and 60% sodium hydride (40 mg) was added thereto, followed by stirring at room temperature for 3 hours. Water (30 mL) was added to the reaction mixture, followed by extraction with ethyl acetate (80 mL). The organic layer was washed sequentially with water and saturated brine, and then dried over anhydrous magnesium sulfate. The solvent was evaporated under reduced pressure to obtain 4-(benzyloxy)-2-({[3,5-dichloro-6-(tetrahydro-2H-pyran-4-ylmethoxy)pyridin-2-yl]oxy}methyl)-3-methylquinoline (250 mg).

Production Example 27

To a solution of ethyl (2E,4E)-5-(2,3-dihydro-1,4-benzodioxin-6-yl)penta-2,4-dienoate (5.00 g) in ethanol (100 mL) was added 10% palladium-activated carbon (1.0 g), followed by stirring at room temperature under hydrogen atmosphere (4 atm.) for 5 hours. The catalyst was removed by filtration, and then the solvent was evaporated under reduced pressure. The residue was purified by silica gel column chromatography (eluent: hexane/ethyl acetate=85/15) to obtain ethyl 5-(2,3-dihydro-1,4-benzodioxin-6-yl)pentanoate (2.94 g).

Production Example 28

To a suspension of lithium aluminum hydride (418 mg) in anhydrous THF (25 mL) was added dropwise under ice-cooling a solution of ethyl 5-(2,3-dihydro-1,4-benzodioxin-6-yl)pentanoate (2.91 g) in anhydrous THF (10 mL) under nitrogen atmosphere. The mixture was stirred under ice-cooling for 30 minutes, and then a saturated aqueous sodium sulfate solution was added dropwise thereto, followed by stirring at room temperature for 1 hour. Ethyl acetate was added thereto, and the organic layer was washed with saturated brine and dried over anhydrous magnesium sulfate. The solvent was evaporated under reduced pressure. The residue was purified by silica gel column chromatography (eluent: hexane/ethyl acetate=65/35) to obtain 5-(2,3-dihydro-1,4-benzodioxin-6-yl)pentan-1-ol (2.17 g).

Production Example 29

4-Fluorophenol (500 mg) and benzyl 4-bromobutyl ether (1.1 g) were dissolved in DMF (20 mL), and potassium carbonate (1.0 g) was added thereto at room temperature, followed by stirring at 100° C. for 18 hours. The reaction mixture was allowed to cool to room temperature, and water was added thereto, followed by extraction with ethyl acetate. The organic layer was washed sequentially with water and saturated brine and dried over anhydrous sodium sulfate, and the solvent was evaporated. The residue was purified by silica gel column chromatography (eluent: hexane/ethyl acetate=90/10) to obtain 1-[4-(benzyloxy)butoxy]-4-fluorobenzene (851 mg).

Production Example 30

Under reaction conditions as described in J. Org. Chem. 1997, 62, 1560, {[4-(vinyloxy)butoxy]methyl}benzene was obtained using 4-(benzyloxy)butan-1-ol as a starting material. That is, 1,10-phenanthroline (1.00 g) and palladium(II) acetate (2.50 g) were added to a mixture of ethyl vinyl ether (25 mL) and dichloromethane (15 mL), followed by stirring for 15 minutes, and then 4-(benzyloxy)butan-1-ol (5.00 g) was added thereto, followed by stirring at room temperature for 60 hours. The reaction mixture was purified by silica gel column chromatography (eluent: hexane/ethyl acetate=95/5) to obtain {[4-(vinyloxy)butoxy]methyl}benzene (3.24 g).

Production Example 31

To a solution of {[4-(vinyloxy)butoxy]methyl}benzene (3.16 g) in diethyl ether (63 mL) was added diethyl zinc (1.0M, hexane solution) (30.6 mL) under nitrogen atmosphere, and a solution of diiodomethane (8.49 g) in diethyl ether (13 mL) was added dropwise thereto. The reaction liquid was stirred under reflux for 1 hour, followed by stirring at room temperature for 12 hours. A saturated aqueous ammonium acetate solution (80 mL) was added to the reaction liquid, followed by extraction with diethyl ether (400 mL). The organic layer was washed sequentially with a saturated aqueous ammonium acetate solution and saturated brine and dried over anhydrous magnesium sulfate, and the solvent was evaporated under reduced pressure. The residue was purified by silica gel column chromatography (eluent: hexane/ethyl acetate=95/5) to obtain {[4-(cyclopropyloxy)butoxy]methyl}benzene (2.41 g).

Production Example 32

To a solution of 2-(tetrahydro-2H-pyran-4-yl)ethyl p-toluenesulfonate (465 mg) in DMF (5 mL) were added 2,4-dihydroxypyridine (363 mg) and potassium carbonate (339 mg), and the mixture was stirred at 80° C. for 6 hours. The reaction mixture was allowed to cool to room temperature, and water (50 mL) was added thereto, followed by extraction with ethyl acetate (20 mL×3). The organic layer was washed with saturated brine and dried over anhydrous sodium sulfate, and the solvent was evaporated under reduced pressure. The residue was purified by silica gel column chromatography (eluent: methanol/chloroform=0/100~10/90) to obtain 4-[2-(tetrahydro-2H-pyran-4-yl)ethoxy]pyridin-2-ol (160 mg) as a major product, and 2-[2-(tetrahydro-2H-pyran-4-yl)ethoxy]pyridin-4-ol (Production Example 347) (43 mg) as a minor product.

Production Example 33

4-(cyclopropyloxy)butan-1-ol (400 mg) was dissolved in a mixture of DMSO (3.5 mL), dichloromethane (10 mL), and triethylamine (2.14 mL), and a solution of a sulfur trioxide pyridine complex (1.47 g) in DMSO (3.5 mL) added dropwise thereto under ice-cooling. The reaction mixture was stirred under ice-cooling for 1 hour, and then poured into water (20 mL). The mixture was extracted with diethyl ether (200 mL), the organic layer was washed sequentially with water and saturated brine and dried over anhydrous sodium sulfate, and the solvent was evaporated under reduced pressure. The residue was purified by silica gel column chromatography (eluent: hexane/ethyl acetate=80/20) to obtain 4-(cyclopropyloxy)butanal (233 mg).

Production Example 34

To a solution of 4-(benzyloxy)butan-1-ol (3.00 g), 6-(trifluoromethyl)pyrimidin-4-ol (3.00 g), and triphenylphosphine (5.25 g) in THF (30 mL) was added diisopropyl azodicarboxylate (4.05 g), and the mixture was stirred at room temperature for 30 minutes. The reaction mixture was concentrated under reduced pressure, and then the residue was purified by silica gel column chromatography (eluent: hexane/ethyl acetate=9/1) to obtain 4-[4-(benzyloxy)butoxy]-6-(trifluoromethyl)pyrimidine (2.83 g).

Production Example 35

8-{[3-(Benzyloxy)phenoxy]methyl}-1,4-dioxaspiro[4.5]decane (817 mg) was dissolved in a mixed solvent of ethanol (15 mL) and THF (15 mL), and cyclohexene (4.67 mL) and 20% palladium hydroxide-activated carbon (218 mg) were added thereto, followed by heating under reflux for 4 hours. The reaction mixture was allowed to cool to room temperature, the catalyst was removed by filtration, and the solvent was evaporated under reduced pressure. The residue was purified by silica gel column chromatography (eluent: chloroform/methanol=100/0-95/5) to obtain 3-(1,4-dioxaspiro[4.5]dec-8-ylmethoxy)phenol (567 mg).

Production Example 36

1-(3-Phenylpropanoyl)piperazine hydrochloride (1.0 g) was dissolved in acetonitrile, and 1,1'-carbonyldiimidazole (950 mg) was added thereto at room temperature, followed by stirring at the same temperature for 3 hours. The reaction mixture was concentrated under reduced pressure, and water was added to the residue, followed by extraction with chloroform. The organic layer was washed with saturated brine and dried over anhydrous sodium sulfate, and the solvent was evaporated. The residue was purified by silica gel column chromatography (eluent: chloroform/methanol=95/5) to obtain 1-(1H-imidazol-1-ylcarbonyl)-4-(3-phenylpropanoyl)piperazine (1.13 g).

Production Example 37

To a solution of 1-(1H-imidazol-1-ylcarbonyl)-4-(3-phenylpropanoyl)piperazine (1.03 g) in acetonitrile (20 mL) was added dropwise methyl iodide (1.40 mL) and triethylamine (2.20 mL) at room temperature, followed by stirring at 60° C. for 5 hours. The reaction mixture was allowed to cool to room temperature, and then [4-(benzyloxy)-3-methylquinolin-2-yl]methanol (300 mg) was added thereto, followed by dropwise addition of triethylamine (0.50 mL) and stirring at 70° C. for 15 hours. The reaction mixture was concentrated under reduced pressure, and water (20 mL) was added to the residue, followed by extraction with ethyl acetate (50 mL). The organic layer was washed with saturated brine and then dried over anhydrous magnesium sulfate, and the solvent was evaporated under reduced pressure. The residue was purified by silica gel column chromatography (eluent: hexane/ethyl acetate=90/10) to obtain [4-(benzyloxy)-3-methylquinolin-2-yl]methyl 4-(3-phenylpropanoyl)piperazine-1-carboxylate (405 mg).

Production Example 38

Diethyl malonate (597 mg) was dissolved in THF (6 mL) under nitrogen atmosphere, and 60% sodium hydride (150 mg) was added thereto under ice-cooling, followed by stirring for 20 minutes. A solution of 4-(benzyloxy)-2-(chloromethyl)-3-methylquinoline (1.11 g) in THF (5 mL) was added thereto, followed by stirring at 50° C. for 9 hours. The reaction mixture was allowed to cool to room temperature, and water (30 mL) was added thereto, followed by extraction with ethyl acetate (300 mL). The organic layer was washed sequentially with water and saturated brine and then dried over anhydrous magnesium sulfate, and the solvent was evaporated under reduced pressure. The residue was purified by silica gel column chromatography (eluent: hexane/ethyl acetate=95/5) to obtain {[4-(benzyloxy)-3-methylquinolin-2-yl]methyl}diethyl malonate (1.08 g).

Production Example 39

To a solution of {[4-(benzyloxy)-3-methylquinolin-2-yl]methyl}diethyl malonate (1.04 g) in THF (5 mL) were added a solution of potassium hydroxide (555 mg) in water (0.60 mL) and methanol (4 mL), followed by stirring at 45° C. for 2 hours. The reaction mixture was concentrated under reduced pressure and then neutralized with 1M hydrochloric acid, followed by extraction with ethyl acetate. The organic layer was washed with saturated brine and dried over anhydrous magnesium sulfate, and the solvent was evaporated under reduced pressure. The residue was heated at 130° C. for 2 hours and then purified by silica gel column chromatography (eluent: chloroform/methanol=98/2) to obtain 3-[4-(benzyloxy)-3-methylquinolin-2-yl]propionic acid (230 mg).

Production Example 40

3-[4-(Benzyloxy)-3-methylquinolin-2-yl]propionic acid (213 mg) and 1-hydroxybenzotriazole hydrate (107 mg) were dissolved in DMF (4 mL). 1-ethyl-3-(3-dimethylaminopropyl)carbodiimide hydrochloride (140 mg), 3-phenylpropylamine (134 mg), and N,N-diisopropylethylamine (0.14 mL) were added thereto, and the mixture was stirred at room temperature for 72 hours. A saturated aqueous sodium hydrogen carbonate solution (20 mL) was added to the reaction mixture, followed by extraction with ethyl acetate (200 mL). The organic layer was washed sequentially with water and saturated brine and then dried over anhydrous magnesium sulfate, and the solvent was evaporated under reduced pressure. The residue was purified by silica gel column chromatography (eluent: chloroform/methanol=30/1) to obtain 3-[4-(benzyloxy)-3-methylquinolin-2-yl]-N-(3-phenylpropyl)propanamide (90 mg).

Production Example 41

3-Sulfanylphenol (250 mg) was dissolved in methanol (5 mL), and a 28% sodium methoxide-methanol solution (0.5 mL) was added thereto, followed by stirring at room temperature for 10 minutes. 4-(Bromomethyl)tetrahydro-2H-pyrane (410 mg) was added to the reaction mixture, followed by stirring at room temperature for 3 hours. The solvent was evaporated under reduced pressure, and then water was added to the residue, followed by extraction with ethyl acetate. The organic layer was washed with saturated brine and dried. The solvent was evaporated under reduced pressure, and the residue was washed with hexane to obtain 3-[(tetrahydro-2H-pyran-4-ylmethyl)sulfanyl]phenol (265 mg).

Production Example 42

To a solution of 1,4-dioxaspiro[4.5]dec-8-ylmethanol (946 mg), 3-(benzyloxy)phenol (1 g), and triphenylphosphine (1.57 g) in THF (15 mL) was added azodicarboxylate diethyl (944 µL) under ice-cooling, and the mixture was stirred at room temperature overnight. The reaction liquid was concentrated under reduced pressure, benzene was added to the residue, and insolubles were removed by filtration. The filtrate was concentrated under reduced pressure, and the residue was purified by silica gel column chromatography (elu-

Production Example 43

To an ice-cold solution of 4-[(3-{[4-(benzyloxy)-3-methylquinolin-2-yl]methoxy}phenoxy)methyl]piperidine-1-carbamic acid tert-butyl ester (735 mg) in ethyl acetate-ethanol (3:1, 20 mL) was added a 4M hydrogen chloride-ethyl acetate solution (15 mL), and the mixture was stirred at room temperature for 1.5 hours. The reaction mixture was concentrated under reduced pressure, and then a 5% aqueous sodium hydrogen carbonate solution was added to the residue, followed by extraction with ethyl acetate (80 mL). The organic layer was washed with saturated brine and then dried over anhydrous magnesium sulfate, and the solvent was evaporated under reduced pressure. The residue was purified by silica gel column chromatography (eluent: chloroform/methanol=20/1) to obtain 4-(benzyloxy)-3-methyl-2-{[3-(piperidin-4-ylmethoxy)phenoxy]methyl}quinoline (545 mg).

Production Example 44

4-{[3-(Benzyloxy)phenoxy]methyl}piperidine hydrochloride (1.5 g) was dissolved in chloroform (30 mL), and diisopropyl ethylamine (3.13 mL) and methanesulfonyl chloride (0.52 mL) were added thereto under ice-cooling, followed by stirring at room temperature for 2 hours. Saturated aqueous sodium bicarbonate solution was added to the reaction liquid, followed by extraction with chloroform. The organic layer was washed with saturated brine and then dried over anhydrous magnesium sulfate, and the solvent was evaporated under reduced pressure. The residue was powdered and purified from chloroform/hexane to obtain 4-{[3-(benzyloxy)phenoxy]methyl}-1-(methylsulfonyl)piperidine (1.508 g).

Production Example 45

To a solution of (3-hydroxyphenoxy)acetic acid (246 mg) in DMF (10 mL) were added N-[3-(dimethylamino)propyl]-N'-ethylcarbodiimide hydrochloride (336 mg), 1H-benzotriazol-1-ol hydrate (268 mg) and morpholine (153 μL) at room temperature, followed by overnight stirring at room temperature. The solution was concentrated under reduced pressure, and water was added to the residue, followed by extraction with ethyl acetate. The organic layer was washed sequentially with water and saturated brine and then dried over anhydrous magnesium sulfate, and the solvent was evaporated under reduced pressure. The residue was purified by silica gel column chromatography (eluent: chloroform/methanol=100/0-95/5) to obtain 3-(2-(morpholin-4-yl)-2-oxoethoxy)phenol (305 mg).

Production Example 46

4-(Benzyloxy)-6-bromo-3-methyl-2-{[3-(tetrahydro-2H-pyran-4-ylmethoxy)phenoxy]methyl}quinoline (500 mg) was dissolved in DMSO (30 mL) and ethanol (10 mL), and palladium(II) acetate (60 mg), 1,3-bis(diphenylphosphino)propane (230 mg), and triethylamine (0.19 mL) were added thereto at room temperature, followed by stirring under carbon monoxide atmosphere at 80° C. for 5 hours. The reaction mixture was allowed to cool to room temperature and concentrated under reduced pressure, and water was added to the residue, followed by extraction with ethyl acetate. The separated organic layer was washed with saturated brine and then dried over anhydrous sodium sulfate, and the solvent was evaporated. The residue was purified by silica gel column chromatography (eluent: hexane/ethyl acetate=60/40) to obtain ethyl 4-(benzyloxy)-3-methyl-2-{[3-(tetrahydro-2H-pyran-4-ylmethoxy)phenoxy]methyl}quinoline-6-carboxylate (257 mg).

Production Example 47

To a solution of 4-(benzyloxy)-6-bromo-3-methyl-2-{[3-(tetrahydro-2H-pyran-4-ylmethoxy)phenoxy]methyl}quinoline (300 mg) in dioxane (10 mL) were added pyridin-3-yl boric acid (135 mg), tetrakis(triphenylphosphine)palladium(0) (65 mg), and a 1M aqueous sodium carbonate solution (1.60 mL), followed by stirring at 80° C. for 2 hours. The reaction mixture was allowed to cool to room temperature, and water (20 mL) was added thereto, followed by extraction with chloroform (50 mL). The organic layer was washed sequentially with a saturated aqueous sodium hydrogen carbonate solution and saturated brine and then dried over anhydrous magnesium sulfate, and the solvent was evaporated. The residue was purified by silica gel column chromatography (eluent: hexane/ethyl acetate=15/85) to obtain 4-(benzyloxy)-3-methyl-6-(pyridin-3-yl)-2-{[3-(tetrahydro-2H-pyran-4-ylmethoxy)phenoxy]methyl}quinoline (265 mg).

Production Example 48

To a solution of 4-(benzyloxy)-6-bromo-3-methyl-2-{[3-(tetrahydro-2H-pyran-4-ylmethoxy)phenoxy]methyl}quinoline (400 mg) in dioxane (10 mL) were added piperidin-2-one (90 mg), tris(dibenzylideneacetone)dipalladium(0) (35 mg), cesium carbonate (360 mg), and (9,9-dimethyl-9H-xanthen-4,5-diyl)bis(diphenylphosphine) (65 mg), and the mixture was stirred at 100° C. for 30 hours. The reaction mixture was allowed to cool to room temperature and then concentrated under reduced pressure. The residue was purified by silica gel column chromatography (eluent: chloroform/methanol=97/3) to obtain 1-[4-(benzyloxy)-3-methyl-2-{[3-(tetrahydro-2H-pyran-4-ylmethoxy)phenoxy]methyl}quinolin-6-yl]piperidin-2-one (328 mg).

Production Example 49

To a solution of 3-(1,4-dioxaspiro[4.5]dec-8-ylmethoxy)phenol (536 mg) in acetone (9.6 mL) was added 1M hydrochloric acid (9.6 mL), followed by stirring at room temperature for 6 hours. The solvent was evaporated under reduced pressure, and then water was added to the residue, followed by extraction with ethyl acetate. The organic layer was washed with saturated brine and then dried over anhydrous magnesium sulfate. The solvent was evaporated under reduced pressure to obtain 4-[(3-hydroxyphenoxy)methyl]cyclohexanone (446 mg).

Production Example 50

To a solution of tetrahydro-2H-pyran-4-yl methanol (1.00 g) and 2,6-difluoropyridine (1.19 g) in DMF (10 mL) was added 60% sodium hydride (410 mg), and the mixture was stirred at 80° C. for 8 hours. Water (50 mL) was added dropwise to the reaction mixture, followed by extraction with ethyl acetate (100 mL). The organic layer was washed sequentially with water and saturated brine and dried, and the solvent was evaporated under reduced pressure. The residue (continuing from column 1, top) ent: hexane/ethyl acetate=92/8-85/15) to obtain 8-{[3-(benzyloxy)phenoxy]methyl}-1,4-dioxaspiro[4.5]decane (846 mg).

was purified by silica gel column chromatography (eluent: hexane/ethyl acetate=80/20) to obtain 2-fluoro-6-(tetrahydro-2H-pyran-4-ylmethoxy)pyridine (1.36 g).

Production Example 51

To a solution of 1-(benzyloxy)-3-bromobenzene (1.00 g) in 1,2-dimethoxyethane (15 mL) were added tris(dibenzylideneacetone)dipalladium(0) (180 mg), 2'-[dicyclohexylphosphino]-N,N-dimethylbiphenyl-2-amine (150 mg), piperidine (500 µL), and tripotassium phosphate (2.5 g) at room temperature, and the mixture was stirred at 110° C. for 21 hours. After the reaction mixture was cooled to room temperature, insolubles were separated by filtration and the solvent was concentrated under reduced pressure. The residue was purified by silica gel column chromatography (eluent: hexane/ethyl acetate=100/0-85/15) to obtain 1-[3-(benzyloxy)phenyl]piperidine (722 mg).

Production Example 52

To an ice-cold solution of 2-(tetrahydro-2H-pyran-4-yl)ethanol (1.00 g) in pyridine (6.5 mL) was added p-toluenesulfonyl chloride (1.5 g), followed by stirring at the same temperature for 30 minutes, and at room temperature for 18 hours. The reaction mixture was concentrated under reduced pressure, and then diluted aqueous hydrochloric acid (20 mL) was added to the residue, followed by twice extractions with ethyl acetate (20 mL). The organic layers were combined, washed with saturated brine, and dried over anhydrous magnesium sulfate. The solvent was evaporated under reduced pressure, and the residue was purified by silica gel column chromatography (eluent: hexane/ethyl acetate=80/20-50/50) to obtain p-toluenesulfonic acid 2-(tetrahydro-2H-pyran-4-yl)ethyl ester (450 mg).

Production Example 53

1-[3-(Benzyloxy)phenoxy]acetone (1.77 g) was dissolved in THF (20 mL), and, a solution of 0.97M methyl magnesium bromide in THF (9.0 mL) was added dropwise thereto with cooling in an ice bath under nitrogen flow. The reaction mixture was stirred at room temperature for 2.5 hours. A saturated aqueous ammonium chloride solution was added to the reaction mixture, followed by extraction with ethyl acetate. The organic layer was washed with a 1M aqueous sodium hydroxide solution and saturated brine, and then dried over anhydrous magnesium sulfate. The solvent was concentrated under reduced pressure, and the residue was purified by silica gel column chromatography (eluent: hexane/ethyl acetate=100/0-85/15) to obtain 1-[3-(benzyloxy)phenoxy]-2-methylpropan-2-ol (997 mg).

Production Example 54

Palladium(II) chloride (112 mg) and copper(I) chloride (628 mg) were added to DMF-water (7:1, 8 mL), followed by stirring at room temperature under oxygen atmosphere for 1 hour. A solution of 1-(benzyloxy)-3-(pent-4-en-1-yloxy)benzene (1.70 g) in DMF (7 mL) was added dropwise to the reaction mixture, followed by vigorous stirring at room temperature for 2 hours. 0.5M Hydrochloric acid (60 mL) was added to the reaction mixture, followed by extraction with diethyl ether (100 mL). The organic layer was washed sequentially with water and saturated brine, and the solvent was evaporated under reduced pressure. The residue was purified by silica gel column chromatography (eluent: hexane/ethyl acetate=5/1) to obtain 5-[3-(benzyloxy)phenoxy]pentan-2-one (1.65 g).

Production Example 55

A mixture of 4-(benzyloxy)-2-(chloromethyl)-3-methylquinoline (200 mg), 1-hexanoylpiperazin (130 mg), potassium carbonate (111 mg), and DMF (6 mL) was stirred at room temperature for 2 hours. Water (30 mL) was added to the reaction mixture, followed by extraction with ethyl acetate (50 mL). The organic layer was washed sequentially with water and saturated brine, and then dried over anhydrous magnesium sulfate. The solvent was evaporated under reduced pressure, and then the residue was purified by silica gel column chromatography (eluent: hexane/ethyl acetate=1/1) to obtain 4-(benzyloxy)-2-[(4-hexanoylpiperazin-1-yl)methyl]-3-methylquinoline (241 mg).

Production Example 56

To a solution of [4-(benzyloxy)-8-methoxy-3-methylquinolin-2-yl]methanol (250 mg) in THF (10 mL) were added 3-(tetrahydro-2H-pyran-4-ylmethoxy)phenol (185 mg) and 1,1-(azodicarbonyl)dipiperidine (245 mg), followed by dropwise addition of tributylphosphine (0.24 mL) at room temperature and stirring. After 1 hour, tributyl phosphine (0.24 mL) was added thereto, followed by stirring for 12 hours. Ethyl acetate was added to the reaction mixture, and then insolubles were removed by filtration. The filtrate was concentrated under reduced pressure, and then the residue was purified by silica gel column chromatography twice (eluent for the first round: hexane/ethyl acetate=80/20~67/33~60/40, eluent for the second round: chloroform~chloroform/methanol=95/5), and also by thin layer silica gel chromatography (developer: chloroform/methanol=95/5) to obtain 4-(benzyloxy)-8-methoxy-3-methyl-2-{[3-(tetrahydro-2H-pyran-4-ylmethoxy)phenoxy]methyl}quinoline (340 mg).

Production Example 57

A mixture of 3-bromo-5-(tetrahydro-2H-pyran-4-ylmethoxy)pyridine (300 mg), copper(II) sulfate pentahydrate (130 mg), bronze (100 mg), sodium hydroxide (700 mg), and water (5 mL) was stirred in an autoclave at 210° C. for 6 hours. The reaction mixture was cooled to room temperature, followed by addition of methanol, and insolubles were removed by filtration. The filtrate was concentrated under reduced pressure and extracted with chloroform. The aqueous layer was neutralized by addition of 1M hydrochloric acid (3.5 mL), followed by extraction with ethyl acetate. The organic layers were combined and dried over anhydrous magnesium sulfate. The solvent was evaporated under reduced pressure to obtain 5-(tetrahydro-2H-pyran-4-ylmethoxy)pyridin-3-ol (137 mg).

Production Example 58

To a mixture of (2-fluoropyridin-4-yl)methanol (300 mg), triethylamine (239 mg), and dichloromethane (24 mL) was added anhydrous trifluoromethanesulfonic acid (666 mg) under ice-cooling, followed by stirring at the same temperature for 1 hour. (Tetrahydro-2H-pyran-4-yl)methanol (1.37 g) was added to the reaction liquid at room temperature, followed by stirring at the same temperature for 8 hours. A saturated aqueous sodium hydrogen carbonate solution (20 mL) was added to the reaction mixture, followed by extraction with chloroform (30 mL). The organic layer was washed with saturated brine and then dried over anhydrous magnesium sulfate. The solvent was evaporated under reduced pressure, and then the residue was purified by silica gel column chromatography (eluent: hexane/ethyl acetate=8/1) to obtain 2-fluoro-4-[(tetrahydro-2H-pyran-4-ylmethoxy)methyl]pyridine (132 mg).

Production Example 59

To a mixture of magnesium (35 mg) and THF (1.5 mL) was added one grain of iodine under nitrogen flow, followed by warming in an oil bath at 50° C. A solution of 1-(benzyloxy)-4-(2-bromoethyl)benzene (400 mg) in THF (3 mL) was added dropwise to the mixture over 20 minutes, and then the reaction liquid was heated under reflux for 4 hours. The reaction liquid was ice-cooled, and a solution of cyclobutanone (100 mg) in THF (4 mL) was added dropwise over 15 minutes, followed by stirring at room temperature for another 6 hours. The reaction liquid was adjusted to an acidic pH by adding 1M hydrochloric acid, followed by extraction with ethyl acetate. The organic layer was dried over anhydrous magnesium sulfate, and the solvent was evaporated under reduced pressure. The residue was purified by silica gel column chromatography (eluent: hexane/ethyl acetate=9:1-1/1) to obtain 1-{2-[4-(benzyloxy)phenyl]ethyl}cyclobutanol (80 mg).

Production Example 60

To a solution of 3-{[4-(benzyloxy)-3-methylquinolin-2-yl]methoxy}-2,2-dimethylpropan-1-ol (500 mg) in THF (10 mL) was added dropwise a solution of n-butyl lithium in hexane (1.55M, 1.1 mL) at an internal temperature of −20° C. under nitrogen flow, followed by stirring at the same temperature for 15 minutes. Morpholine-4-carbonylchloride (0.2 mL) was added to the reaction mixture, followed by stirring for 3 hours while warming to room temperature. Water was added to the reaction mixture, followed by extraction with ethyl acetate. The organic layer was washed with saturated brine, and dried over anhydrous magnesium sulfate. The solvent was evaporated under reduced pressure, and then the residue was purified by silica gel column chromatography (eluent: hexane/ethyl acetate=100/0~50/50), and the solvent was evaporated under reduced pressure. The resulting residue was dried under vacuum at room temperature to obtain 459 mg of 3-{[4-(benzyloxy)-3-methylquinolin-2-yl]methoxy}-2,2-dimethylpropylmorpholine-4-carboxylate as a yellow solid.

Production Example 61

To a mixture of magnesium (120 mg) and THF (1.5 mL) was added 1,4-dibromobutane (0.2 mL) at room temperature under nitrogen flow, followed by stirring for 1 hour. The reaction solution was ice-cooled, and a solution of ethyl 3-[4-(benzyloxy)phenyl]propanoate (400 mg) in THF (3 mL) was added dropwise thereto while maintaining an internal temperature of 10° C. or less. The reaction mixture was stirred under ice-cooling for 3 hours, and allowed to stand overnight at room temperature. The reaction liquid was ice-cooled and was adjusted to an acidic pH by adding 1M hydrochloric acid, followed by extraction with ethyl acetate. The organic layer was dried over anhydrous magnesium sulfate, and the solvent was evaporated under reduced pressure. The residue was purified by silica gel column chromatography (eluent: hexane/ethyl acetate=20/3-1/1) to obtain 1-{2-[4-(benzyloxy)phenyl]ethyl}cyclopentanol (145 mg).

Production Example 62

To a solution of 2-(benzyloxy)-5-bromopyridine (600 mg) in DMF (12 mL) were added 3-buten-2-one (400 mg), tris(dibenzylidene acetone) dipalladium(0) (74 mg), triethylamine (460 mg), and tris(o-tolyl)phosphine (70 mg) at room temperature under nitrogen flow, and the mixture was stirred at 100° C. for 24 hours. The reaction liquid was allowed to cool, and insolubles were filtered through Celite. Water was added to the filtrate, followed by three times extractions with ethyl acetate. The organic layer was washed sequentially with water and saturated brine, and then dried over anhydrous magnesium sulfate. The solvent was evaporated under reduced pressure, and then the residue was purified by silica gel column chromatography (eluent: hexane/ethyl acetate=9/1-3/2) to obtain (3E)-4-[6-(benzyloxy)pyridin-3-yl]but-3-en-2-one (220 mg).

Production Example 63

1-(trans-4-{[4-(Benzyloxy)-3-methylquinolin-2-yl]methoxy}cyclohexyl)-3-ethylurea was obtained from trans-4-{[4-(benzyloxy)-3-methylquinolin-2-yl]methoxy}cyclohexaneamine, in the same manner as in Example 15 which will follow.

Production Example 64

N-(trans-4-{[4-(Benzyloxy)-3-methylquinolin-2-yl]methoxy}cyclohexyl)ethanesulfonamide was obtained from trans-4-{[4-(benzyloxy)-3-methylquinolin-2-yl]methoxy}cyclohexaneamine, in the same manner as in Example 16 which will follow.

Production Example 65

To a solution of trans-4-{[4-(benzyloxy)-3-methylquinolin-2-yl]methoxy}cyclohexaneamine (300 mg) in dichloromethane (5 mL) were added 4-bromo butanoic acid chloride (0.11 mL) and triethylamine (0.15 mL) under ice-cooling, followed by stirring at the same temperature for 45 minutes. Water was added to the reaction mixture, followed by extraction with chloroform. The organic layer was washed with saturated aqueous sodium hydrogen carbonate solution and saturated brine, dried over anhydrous magnesium sulfate, and then concentrated under reduced pressure. The residue was dissolved in THF, and 60% sodium hydride (50 mg) was added thereto. The reaction mixture was stirred at room temperature for 2 hours, followed by stirring for another 15 hours while heating it in an oil bath at 60° C. 60% sodium hydride (50 mg) was added to the reaction mixture, followed by stirring for 4 hours while heating it in an oil bath at 60° C. The reaction mixture was cooled to room temperature, and water was then added thereto, followed by extraction with ethyl acetate. The organic layer was washed with saturated brine, and dried over anhydrous magnesium sulfate. The solvent was evaporated under reduced pressure, and then the residue was purified by silica gel column chromatography (eluent: chloroform/methanol=100/0~95/5). The solvent was evaporated under reduced pressure, and the residue was then dried under vacuum at room temperature to obtain 161 mg of 1-(trans-4-{[4-(benzyloxy)-3-methylquinolin-2-yl]methoxy}cyclohexyl)pyrrolidin-2-one as a yellow oily substance.

Production Example 66

To a mixed solution (10 mL) of N-(trans-4-{[4-(benzyloxy)-3-methylquinolin-2-yl]methoxy}cyclohexyl)cyclopentanecarboxamide (260 mg) in THF-DMF (1:1) was added 60% sodium hydride (45 mg) under ice-cooling, followed by stirring at the same temperature. Methyl iodide (0.055 mL) was added thereto, followed by stirring at room temperature for 3.5 hours. The reaction mixture was ice-cooled, and 60% sodium hydride (45 mg) and methyl iodide (0.055 mL) were added thereto, followed by stirring at room temperature for another 17 hours. Water was added to the reaction mixture, followed by extraction with ethyl acetate. The organic layer was washed with water and saturated brine, and dried over anhydrous magnesium sulfate. The solvent was evaporated under reduced pressure, the residue was purified by silica gel column chromatography (eluent: hexane/ethyl acetate=100/0~50/50), and the solvent was evaporated under reduced pressure. The residue was dried under vacuum at room temperature to obtain 93 mg of N-(trans-4-{[4-(benzyloxy)-3-methylquinolin-2-yl]methoxy}cyclohexyl)-N-methylcyclopentanecarboxamide as a colorless viscous substance.

Production Example 67

4-(Benzyloxy)-2-{[(5-bromopyrimidin-2-yl)oxy]methyl}-3-methylquinoline (1.5 g) was suspended in a mixed solvent (40 mL) of DMF-methanol (1:1), and triethylamine (1 mL) and dichlorobis(triphenylphosphine)palladium(II) (1.2 g) were added thereto, followed by stirring at 100° C. under a carbon monoxide atmosphere (1.0 MPa) for 5 hours. The reaction mixture was allowed to cool to room temperature, and water was added thereto, followed by extraction with ethyl acetate. The organic layer was washed water and saturated brine, and dried over anhydrous magnesium sulfate. The solvent was evaporated under reduced pressure, and then the residue was purified by silica gel column chromatography (eluent: hexane/ethyl acetate=100/0~50/50). The solvent was evaporated under reduced pressure, and ethyl acetate was added to the residue which was then warmed to be dissolved. Hexane was added to this solution, followed by stirring at room temperature, and the resulting solid was collected by filtration and dried under vacuum at room temperature to obtain 1.034 g of methyl 2-{[4-(benzyloxy)-3-methylquinolin-2-yl]methoxy}pyrimidine-5-carboxylate as a pale yellow solid.

Production Example 68

2-{[4-(Benzyloxy)-3-methylquinolin-2-yl]methoxy}pyrimidine-5-carboxylic acid was obtained from methyl 2-{[4-(benzyloxy)-3-methylquinolin-2-yl]methoxy}pyrimidine-5-carboxylate, in the same manner as in Example 20 which will follow.

Production Example 69

To a solution of 3-{[4-(benzyloxy)-3-methylquinolin-2-yl]methoxy}-5-methoxyphenol (104 mg) and pyridine (52 mg) in dichloromethane (4 mL) was gradually added a solution of anhydrous trifluoroacetic acid (110 mg) in dichloromethane (1 mL) under ice-cooling, followed by stirring under the same conditions for 30 minutes, and at room temperature for 3 hours. A saturated aqueous sodium hydrogen carbonate solution was added to the reaction liquid, followed by extraction with chloroform. The organic layer was dried over anhydrous magnesium sulfate, and the solvent was evaporated under reduced pressure. The residue was purified by silica gel column chromatography (eluent: hexane/ethyl acetate=3/1~1/1) to obtain 3-{[4-(benzyloxy)-3-methylquinolin-2-yl]methoxy}-5-methoxyphenyltrifluoromethanesulfonate (130 mg).

Compounds of Production Examples 70 to 565 shown in the following Tables were produced in the same manner as in Production Examples 1 to 69. Structures, Production methods and physicochemical data of Production Example Compounds are shown in Tables 2 to 96.

Example 1

4-(Benzyloxy)-2-[5-(4-fluorophenoxy)pent-1-en-1-yl]-3-methylquinoline (E/Z mixture, 810 mg) was dissolved in ethanol-THF (1:1, 20 mL), and 10% palladium-activated carbon (200 mg) was added thereto. The mixture was stirred at room temperature under hydrogen atmosphere for 3 hours. The catalyst was removed by filtration, and then the solvent was evaporated under reduced pressure. The residue was purified by silica gel column chromatography (eluent: chloroform/methanol=10/1) to obtain 2-[5-(4-fluorophenoxy)pentyl]-3-methylquinolin-4(1H)-one (572 mg).

Example 2

To a solution of 4-(benzyloxy)-3-methyl-2-{[3-(tetrahydro-2H-pyran-4-ylmethoxy)phenoxy]methyl}quinoline (330 mg) in ethanol-THF (1:1, 10 mL) was added 10% palladium-activated carbon (80 mg), and the mixture was stirred at room temperature under hydrogen atmosphere for 1 hour. The catalyst was removed by filtration, and then the solvent was evaporated under reduced pressure. The residue was purified by silica gel column chromatography (eluent: chloroform/methanol=10/1) to obtain 3-methyl-2-{[3-(tetrahydro-2H-pyran-4-ylmethoxy)phenoxy]methyl}quinolin-4(1H)-one (207 mg).

Example 3

To a solution of 1-[2-(4-{[4-(benzyloxy)-3-methylquinolin-2-yl]methoxy}phenyl)ethyl]cyclopentanol (128 mg) in ethanol-THF (1:1, 4 mL) was added 10% palladium-activated carbon (30 mg) under nitrogen atmosphere, followed by stirring at room temperature under hydrogen atmosphere for 3 hours. The catalyst was removed by filtration, and then the solvent was evaporated under reduced pressure. The resulting residue was purified by silica gel column chromatography (eluent: chloroform/methanol=92/8). The resulting solid was washed with ether and dried to obtain 2-({4-[2-(1-hydroxycyclopentyl)ethyl]phenoxy}methyl)-3-methylquinolin-4(1H)-one (51 mg) as a crystal.

Example 4

To a solution of 4-[(2-{[4-(benzyloxy)-3-methylquinolin-2-yl]methoxy}pyridin-4-yl)oxy]-2-methyl butan-2-ol (1.33 g) in ethanol-THF (1:4, 45 mL) was added 10% palladium-activated carbon (300 mg) under nitrogen atmosphere. The mixture was placed under hydrogen atmosphere, and then stirred at room temperature for 1 hour. The catalyst was removed by filtration, and then the solvent was evaporated under reduced pressure. The resulting residue was purified by silica gel column chromatography (eluent: chloroform/methanol=97/3) to obtain 2-({[4-(3-hydroxy-3-methylbutoxy)pyridin-2-yl]oxy}methyl)-3-methylquinolin-4(1H)-one (783 mg) as a crystal.

Example 5

To a solution of ethyl (trans-4-{[4-(benzyloxy)-3-methylquinolin-2-yl]methoxy}cyclohexyl)carbamate (153 mg) in ethanol-THF (1:1, 6 mL) was added 5% Pd—BaSO$_4$ (70 mg) under nitrogen atmosphere, followed by stirring at room temperature under hydrogen atmosphere for 1 hour. The catalyst was removed by filtration, and then the solvent was evaporated under reduced pressure. The resulting residue was purified by silica gel column chromatography (eluent: chloroform/methanol=95/5). The resulting solid was washed with ethyl acetate and dried to obtain ethyl {trans-4-[(3-methyl-4-oxo-1,4-dihydroquinolin-2-yl]methoxy]cyclohexyl}carbamate (88 mg) as a crystal.

Example 6

N-(trans-4-{[4-(Benzyloxy)-3-methylquinolin-2-yl]methoxy}cyclohexyl)ethanesulfonamide (315 mg) was subjected to debenzylation under the same reaction conditions as in Example 5, and then purified by silica gel column chromatography (eluent: chloroform/methanol=97/3) to obtain N-{trans-4-[(3-methyl-4-oxo-1,4-dihydroquinolin-2-yl)methoxy]cyclohexyl}ethanesulfonamide (168 mg) as a crystal.

Example 7

1-(trans-4-{[4-(Benzyloxy)-3-methylquinolin-2-yl]methoxy}cyclohexyl)pyrrolidin-2-one (158 mg) was subjected to debenzylation under the same reaction conditions as in Example 5, and then purified by silica gel column chromatography (eluent: chloroform/methanol=97/3) to obtain 3-methyl-2-({[trans-4-(2-oxopyrrolidin-1-yl)cyclohexyl]oxy}methyl)quinolin-4(1H)-one (72 mg) as a crystal.

Example 8

4-(Benzyloxy)-3-methyl-2-[({4-[2-(tetrahydro-2H-pyran-4-yl)ethoxy]pyridin-2-yl}oxy)methyl]quinoline (1.7 g) was subjected to debenzylation under the same reaction conditions as in Example 5, and then purified by silica gel column chromatography (eluent: chloroform/ethyl acetate=100/0~50/50) to obtain 3-methyl-2-[({4-[2-(tetrahydro-2H-pyran-4-yl)ethoxy]pyridin-2-yl}oxy)methyl]quinolin-4(1H)-one (1.34 g) as a crystal.

Example 9

4-(3-{[4-(Benzyloxy)-3-methylquinolin-2-yl]methoxy}phenyl)morpholine-3-one (160 mg) was subjected to debenzylation under the same reaction conditions as in Example 5, and then purified by thin layer silica gel chromatography (developer: chloroform/methanol=15/1) to obtain 3-methyl-2-{[3-(3-oxomorpholin-4-yl)phenoxy]methyl}quinolin-4(1H)-one (96 mg) as a crystal.

Example 10

4-(3-{[4-(Benzyloxy)-3-methylquinolin-2-yl]methoxy}-5-morpholin-4-ylphenoxy)-2-methylbutan-2-ol (510 mg) was subjected to debenzylation under the same reaction conditions as in Example 5, and then was purified by silica gel column chromatography (eluent: chloroform/methanol=90/10) to obtain 2-{[3-(3-hydroxy-3-methylbutoxy)-5-morpholin-4-ylphenoxy]methyl}-3-methylquinolin-4(1H)-one (279 mg) as a crystal.

Example 11

To a mixture of benzyl 4-{(E)-2-[4-(benzyloxy)-3-methylquinolin-2-yl]vinyl}piperidine-1-carboxylate (978 mg), THF (6 mL) and ethanol (6 mL) was added 10% palladium-activated carbon (200 mg) under nitrogen atmosphere. The mixture was stirred at room temperature under hydrogen atmosphere of 3 atms, for 4 hours. The catalyst was removed by filtration, and the filtrate was concentrated under reduced pressure. The resulting residue was purified by silica gel column chromatography (Fuji Silysia Chemical Ltd., NH, eluent: chloroform/methanol=97/3~92/8), and the solvent was evaporated. The residue was washed with ether, and collected by filtration to obtain 3-methyl-2-(2-piperidin-4-ylethyl)quinolin-4(1H)-one (490 mg).

Example 12

To a solution of 4-(benzyloxy)-2-[(heptylsulfanyl)methyl]-3-methylquinoline (150 mg) in trifluoroacetic acid (5 mL) was added thioanisole (150 mg), followed by stirring at room temperature for 16 hours. The reaction mixture was added dropwise to an ice-cold aqueous sodium hydrogen carbonate solution, followed by extraction with ethyl acetate (50 mL). The organic layer was washed with saturated brine, and then dried over anhydrous magnesium sulfate. The solvent was evaporated under reduced pressure, and the residue was purified by silica gel column chromatography (eluent: chloroform/methanol=10/1) to obtain 2-[(heptylsulfanyl)methyl]-3-methylquinolin-4(1H)-one (110 mg).

Example 13

To an ice-cold solution of 2-(aminomethyl)-3-methylquinolin-4(1H)-one dihydrochloride (160 mg) in pyridine (5 mL) was added heptanoic acid chloride (110 mg), and the mixture was stirred at room temperature for 45 minutes. The reaction mixture was concentrated under reduced pressure, and then water (40 mL) was added to the residue. The resulting solid was collected by filtration, washed with water, and dried. This solid was purified by silica gel column chromatography (eluent: chloroform/methanol=20/1) to obtain N-[(3-methyl-4-oxo-1,4-dihydroquinolin-2-yl)methyl]heptanamide (127 mg).

Example 14

To a solution of 2-(aminomethyl)-3-methylquinolin-4(1H)-one dihydrochloride (160 mg) in pyridine (8 mL) was added pentyl chloroformate (100 mg), followed by stirring at room temperature for 6 hours. The solvent was evaporated under reduced pressure, and the residue was purified by silica gel chromatography (eluent: chloroform/methanol) to obtain pentyl [(3-methyl-4-oxo-1,4-dihydroquinolin-2-yl)methyl]carbamate (104 mg).

Example 15

To a solution of 2-(aminomethyl)-3-methylquinolin-4(1H)-one dihydrochloride (160 mg) in chloroform (5 mL) were sequentially added triethylamine (0.26 mL) and pentyl isocyanate (0.09 mL), and the mixture was stirred at room temperature for 7 hours. The reaction mixture was concentrated under reduced pressure, and the residue was purified by silica gel column chromatography (eluent: chloroform/

Example 16

To a solution of 2-(aminomethyl)-3-methylquinolin-4 (1H)-one dihydrochloride (212 mg) in pyridine-DMF (8:1, 9 mL) was added hexanesulfonyl chloride (180 mg) under ice-cooling, and the mixture was stirred at room temperature for 12 hours. The reaction mixture was concentrated under reduced pressure, and water (50 mL) was added to the residue, followed by extraction with ethyl acetate (100 mL). The organic layer was washed sequentially with water and saturated brine, and then dried over anhydrous magnesium sulfate. The solvent was evaporated under reduced pressure, and then the residue was purified by silica gel column chromatography (eluent: chloroform/methanol=20/1) to obtain N-[(3-methyl-4-oxo-1,4-dihydroquinolin-2-yl)methyl]hexane-1-sulfonamide (56 mg).

Example 17

Sodium hydride (60%, 173 mg) was added to DMSO (20 mL), followed by stirring at room temperature for 1 hour. [(3-Benzyloxy)propyl]triphenylphosphonium bromide (2.13 g) was added to this mixture, followed by stirring at room temperature for 1.5 hours. 4-(Benzyloxy)-3-methylquinoline-2-carboxyaldehyde (1.00 g) was added to the reaction mixture, followed by stirring for 1.5 hours. Water (80 mL) was added to the reaction mixture, followed by extraction with diethyl ether. The organic layer was washed with saturated brine and dried. The solvent was evaporated under reduced pressure, and the residue was purified by silica gel column chromatography (eluent: hexane/ethyl acetate=5/1) to give an oily substance. To this oily substance were added ethanol (10 mL), THF (5 mL), and 10% palladium-activated carbon (200 mg), followed by stirring under hydrogen atmosphere for 3 hours. The catalyst was removed by filtration, and the solvent was evaporated under reduced pressure. The residue was purified by silica gel column chromatography (eluent: chloroform/methanol=10/1). The resulting solid was washed with diethyl ether to obtain 2-[4-(benzyloxy)butyl]-3-methylquinolin-4(1H)-one (490 mg).

Example 18

To a solution of [4-(benzyloxy)-3-methylquinolin-2-yl] methanol (400 mg) in THF (8 mL) was added (5-indanyl) isocyanate (498 mg), and the mixture was stirred at 40° C. for 15 hours. Methanol (2 mL) was added to the reaction liquid to stop the reaction. Ethanol (10 mL) and 10% palladium-activated carbon (200 mg) were added to this mixture. The mixture was stirred at room temperature under hydrogen atmosphere for 30 minutes. The catalyst was removed by filtration, and then the solvent was evaporated. The residue was purified by silica gel column chromatography (eluent: chloroform/methanol=98/2) to obtain (3-methyl-4-oxo-1,4-dihydroquinolin-2-yl)methyl(2,3-dihydro-1H-inden-5-yl)carbamate (356 mg).

Example 19

To a solution of 2-[(heptylsulfanyl)methyl]-3-methylquinolin-4(1H)-one (110 mg) in chloroform (5 mL) was added m-chloroperbenzoic acid (75%, 200 mg) at room temperature, and the mixture was stirred for 5 hours. A 0.2M aqueous sodium hydroxide solution (20 mL) was added to the reaction mixture, followed by extraction with chloroform (50 mL). The organic layer was washed sequentially with water and saturated brine, and then dried over anhydrous magnesium sulfate. The solvent was evaporated under reduced pressure, and the resulting powder was washed with diethyl ether and dried to obtain 2-[(heptylsulfonyl)methyl]-3-methylquinolin-4(1H)-one (70 mg).

Example 20

To ethyl 4-[(3-methyl-4-oxo-1,4-dihydroquinolin-2-yl) methoxy]-2-(tetrahydro-2H-pyran-4-ylmethoxy)benzoate (110 mg) were added ethanol (3 mL) and a 0.5M aqueous sodium hydroxide solution (10 mL), and the mixture was stirred at room temperature for 4 hours. The reaction mixture was adjusted to a pH of 7 by adding 1M hydrochloric acid under ice-cooling. The resulting solid was collected by filtration, washed with water, and dried to obtain 4-[(3-methyl-4-oxo-1,4-dihydroquinolin-2-yl)methoxy]-2-(tetrahydro-2H-pyran-4-ylmethoxy)benzoic acid (100 mg).

Example 21

4-[(3-Methyl-4-oxo-1,4-dihydroquinolin-2-yl)methoxy]-2-(tetrahydro-2H-pyran-4-ylmethoxy)benzoic acid (67 mg) and 1-hydroxybenzotriazole hydrate (25 mg) were dissolved in DMF (1.3 mL). To this solution were sequentially added 1-ethyl-3-(3-dimethylaminopropyl)carbodiimide hydrochloride (33 mg) and morpholine (15 mg), and the mixture was stirred at room temperature for 12 hours. A saturated aqueous sodium hydrogen carbonate solution (5 mL) to the reaction mixture, followed by extraction with ethyl acetate (50 mL). The organic layer was washed sequentially with water and saturated brine, and then dried over anhydrous magnesium sulfate. The solvent was evaporated under reduced pressure, and the residue was purified by silica gel column chromatography (eluent: chloroform/methanol=15/1) to obtain 3-methyl-2-{[4-(morpholin-4-ylcarbonyl)-3-(tetrahydro-2H-pyran-4-ylmethoxy)phenoxy]methyl}quinolin-4(1H)-one (73 mg).

Example 22

To a solution of 3-[(3-methyl-4-oxo-1,4-dihydropyridin-2-yl)methoxy]-5-(tetrahydro-2H-pyran-4-ylmethoxy)benzonitrile (100 mg) in DMF (2 mL) were added sodium azide (18 mg) and ammonium chloride (15 mg), followed by stirring at 100° C. for 24 hours. The reaction mixture was concentrated under reduced pressure, and the residue was dissolved in a 1M aqueous sodium hydroxide solution and washed with diethyl ether. The aqueous layer was adjusted to a pH of 2 by adding 1M hydrochloric acid, followed by extraction with chloroform and a mixed solvent of chloroform-methanol (5:1). The organic layer was washed with saturated brine, and then dried over anhydrous magnesium sulfate. The solvent was evaporated under reduced pressure, and the residue was purified by thin layer chromatography (developer: chloroform/methanol=6/1) and washed with ethyl acetate to obtain 3-methyl-2-{[3-(tetrahydro-2H-pyran-4-ylmethoxy)-5-(1H-tetrazol-5-yl)phenoxy]methyl}quinolin-4(1H)-one (37 mg).

Example 23

To an ice-cold suspension of ethyl 3-methyl-4-oxo-2-{[3-(tetrahydro-2H-pyran-4-ylmethoxy)phenoxy]methyl}-1,4-dihydroquinoline-6-benzoate (158 mg) in ethanol (5.0 mL)-THF (3.0 mL) was added dropwise a 4M aqueous potassium hydroxide solution (0.18 mL), and the mixture was stirred at 65° C. for 15 hours. The reaction mixture was ice-cooled, and adjusted to a pH of 7 by adding 1M hydrochloric acid. The resulting solid was collected by filtration, washed with water, and dried to obtain 3-methyl-4-oxo-2-{[3-(tetrahydro-2H-pyran-4-ylmethoxy)phenoxy]methyl}-1,4-dihydroquinoline-6-benzoic acid (103 mg).

Compounds of Examples 24 to 301 shown in the following Tables were produced using respective corresponding starting materials, in the same manner as in Examples 1 to 23. Structures of respective Example Compounds are shown in Tables 97 to 122, and Production methods and the physicochemical data of the compounds are shown in Tables 123 to 179.

In addition, structures of other compounds of the present invention are shown in Table 180. These compounds can be easily synthesized according to the above-mentioned production methods, methods described in Examples, and methods apparent to those skilled in the art, or modifications thereof.

The following abbreviations are used in Tables below.

PEx: Production Example numbers, Ex: Example numbers, Syn: Example numbers in which the corresponding compounds were produced using the same method, PSyn: Production Example numbers in which the corresponding compounds were produced using the same method, No: compound number, mp: melting point, dec.: decomposition, Str: Structural formula, DATA: physicochemical data, EI+: m/z values in mass analysis (ionization method EI, representing $(M)^+$ when not specified), CI+: m/z values in mass analysis (ionization method CI, representing $(M+H)^+$ when not specified), FAB+: m/z values in mass analysis (ionization method FAB, representing $(M+H)^+$ when not specified), ESI+: m/z values in mass analysis (ionization method ESI, representing $(M+H)^+$ when not specified), ESI−: m/z values in mass analysis (ionization method ESI, representing $(M-H)^-$ when not specified), NMR1: δ(ppm) in $^1$H NMR in DMSO-$d_6$), NMR1+TFA: δ(ppm) in $^1$H NMR in DMSO-$d_6$) (trifluoroacetic acid-D added), NMR2: δ(ppm) in $^1$H NMR in CDCl$_3$), NMR3: δ(ppm) in $^1$H NMR in CD$_3$OD), s: singlet (spectrum), d: doublet (spectrum), t: triplet (spectrum), q: quadruplet (spectrum), br: broad (spectrum) (e.g., br s), Me: methyl, Bn: benzyl. Further, HCl in the Structural formula represents hydrochloride, and the numeral before HCl represents a molar ratio. For example, 2HCl means dihydrochloride.

TABLE 2

| PEx | PSyn | Str | DATA |
|---|---|---|---|
| 1 | 1 | (structure) | ESI+: 310, 312 |
| 70 | 1 | (structure) | ESI−: 260 |
| 71 | 1 | (structure) | EI+: 249 |
| 2 | 2 | (structure) | NMR1: 1.38(3H, t, J = 7.2 Hz), 4.47(2H, q, J = 7.2 Hz), 5.39(2H, s), 7.38-7.49(3H, m), 7.56-7.62(2H, m), 7.71- 7.78(1H, m), 7.86-7.93(1H, m), 8.11(2H, d, J = 8.4 Hz) |
| 72 | 2 | (structure) | EI+: 339 |

TABLE 2-continued

| PEx | PSyn | Str | DATA |
|---|---|---|---|
| 73 | 2 | 6-MeO, 4-OBn, 3-Me, 2-Me quinoline | FAB+: 294 |

TABLE 3

| PEx | PSyn | Str | DATA |
|---|---|---|---|
| 74 | 2 | 4-OBn, 3-iPr, 2-Me quinoline | FAB+: 292 |
| 75 | 2 | 6-F, 4-OBn, 3-Me, 2-CO2Et quinoline | FAB+: 340 |
| 76 | 2 | 6-Me, 4-OBn, 3-Me, 2-Me quinoline | EI+: 277 |
| 77 | 2 | 6-Br, 4-OBn, 3-Me, 2-CO2Et quinoline | ESI+: 400, 402 |
| 78 | 2 | 8-OMe, 4-OBn, 3-Me, 2-CO2Et quinoline | ESI+: 352 |
| 3 | 3 | 6-Me, 4-OBn, 3-Me, 2-Me quinoline N-oxide | ESI+: 294 |

TABLE 4

| PEx | PSyn | Str | DATA |
|---|---|---|---|
| 79 | 3 | 6-MeO, 4-OBn, 3-Me, 2-Me quinoline N-oxide | ESI+: 310 |
| 80 | 3 | 4-OBn, 3-iPr, 2-Me quinoline N-oxide | FAB+: 308 |

TABLE 4-continued

| PEx | PSyn | Str | DATA |
|---|---|---|---|
| 4 | 4 | 6-Me, 4-OBn, 3-Me quinoline with 2-CH2-OC(O)Me | FAB+: 336 |
| 81 | 4 | 4-OBn, 3-CH(Me)2 quinoline with 2-CH2-OC(O)Me | FAB+: 350 |
| 82 | 4 | 6-OMe, 4-OBn, 3-Me quinoline with 2-CH2-OC(O)Me | ESI+: 352 |
| 5 | 5 | 4-OBn, 3-Me quinoline with 2-CH2-OTs (p-tolylsulfonate) | NMR2: 2.38(3H, s), 2.41(3H, s), 5.03(2H, s), 5.37(2H, s), 7.26(2H, d, J = 8.2 Hz), 7.37-7.54(6H, m), 7.62-7.69(1H, m), 7.80(2H, d, J = 8.3 Hz), 7.95-8.03(2H, m) |

TABLE 5

| PEx | PSyn | Str | DATA |
|---|---|---|---|
| 6 | 6 | 6-Me, 4-OBn, 3-Me quinoline with 2-CH2OH | FAB+: 294 |
| 83 | 6 | 4-OBn, 3-CH(Me)2 quinoline with 2-CH2OH | FAB+: 308 |
| 84 | 6 | 6-OMe, 4-OBn, 3-Me quinoline with 2-CH2OH | FAB+: 310 |
| 7 | 7 | 6-Br, 4-OBn, 3-Me quinoline with 2-CHO | ESI+: 356, 358 |
| 85 | 7 | 6-F, 4-OBn, 3-Me quinoline with 2-CHO | ESI+: 296 |

TABLE 5-continued

| PEx | PSyn | Str | DATA |
|---|---|---|---|
| 86 | 7 | 3-chloro-4-(benzyloxy)quinoline-2-carbaldehyde | ESI+: 298, 300 |
| 87 | 7 | 6-fluoro-4-(benzyloxy)-3-methylquinoline-2-carbaldehyde | EI+: 295 |

TABLE 6

| PEx | PSyn | Str | DATA |
|---|---|---|---|
| 8 | 8 | 6-bromo-4-(benzyloxy)-3-methyl-2-(hydroxymethyl)quinoline | ESI+: 358, 360 |
| 88 | 8 | 6-chloro-4-(benzyloxy)-3-methyl-2-(hydroxymethyl)quinoline | NMR1: 2.38(3H, s), 4.74(2H, d, J = 4.8 Hz), 5.11(2H, s), 5.29(1H, t, J = 4.8 Hz), 7.37-7.48(3H, m), 7.50-7.56(2H, m), 7.70(1H, dd, J = 8.8, 2.0 Hz), 7.91(1H, d, J = 2.0 Hz), 8.01(1H, d, J = 8.8 Hz) |
| 89 | 8 | 6-fluoro-4-(benzyloxy)-3-methyl-2-(hydroxymethyl)quinoline | ESI+: 298 |
| 90 | 8 | 3-chloro-4-(benzyloxy)-2-(hydroxymethyl)quinoline | NMR1: 4.83(2H, s), 5.30(2H, s), 5.37(1H, br s), 7.37-7.49(3H, m), 7.55-7.61(2H, m), 7.61-7.68(1H, m), 7.77-7.85(1H, m), 8.0$_{1-8}$.10(2H, m) |
| 91 | 8 | 6-fluoro-4-(benzyloxy)-3-methyl-2-(hydroxymethyl)quinoline | ESI+: 298 |
| 9 | 9 | 8-methoxy-4-(benzyloxy)-3-methyl-2-(hydroxymethyl)quinoline | ESI+: 310 |

TABLE 7

| PEx | PSyn | Str | DATA |
|---|---|---|---|
| 10 | 10 | 6-fluoro-4-benzyloxy-3-methyl-2-(chloromethyl)quinoline | NMR1: 2.46(3H, s), 4.99(2H, s), 5.13(2H, s), 7.37-7.48(3H, m), 7.51-7.57(2H, m), 7.61-7.69(2H, m), 8.07(1H, dd, J = 8.8, 5.6 Hz) |
| 92 | 10 | 6-methyl-4-benzyloxy-3-methyl-2-(chloromethyl)quinoline | FAB+: 312 |
| 93 | 10 | 4-benzyloxy-3-chloro-2-(chloromethyl)quinoline | NMR1: 5.06(2H, s), 5.34(2H, s), 7.38-7.49(3H, m), 7.57-7.62(2H, m), 7.67-7.73(1H, m), 7.82-7.89(1H, m), 8.04-8.10(2H, m) |
| 94 | 10 | 4-benzyloxy-3-isopropyl-2-(chloromethyl)quinoline | EI+: 325 |
| 95 | 10 | 6-methoxy-4-benzyloxy-3-methyl-2-(chloromethyl)quinoline | FAB+: 328 |
| 96 | 10 | 6-chloro-4-benzyloxy-3-methyl-2-(chloromethyl)quinoline | NMR1: 2.46(3H, s), 4.99(2H, s), 5.14(2H, s), 7.37-7.48(3H, m), 7.48-7.57(2H, m), 7.74(1H, dd, J = 9.2, 2.4 Hz), 7.94(1H, d, J = 2.4 Hz), 8.01(1H, d, J = 9.2 Hz) |

TABLE 8

| PEx | PSyn | Str | DATA |
|---|---|---|---|
| 97 | 10 | 6-bromo-4-benzyloxy-3-methyl-2-(chloromethyl)quinoline | NMR1: 2.47(3H, s), 4.98(2H, s), 5.14(2H, s), 7.38-7.48(3H, m), 7.49-7.55(2H, m), 7.85(1H, dd, J = 9.2, 2.4 Hz), 7.94(1H, d, J = 9.2 Hz), 8.08(1H, d, J = 2.4 Hz) |
| 11 | 11 | 4-benzyloxy-3-methyl-2-(bromomethyl)quinoline | ESI+: 342, 344 |

TABLE 8-continued
| PEx | PSyn | Str | DATA |
|---|---|---|---|
| 12 | 12 | 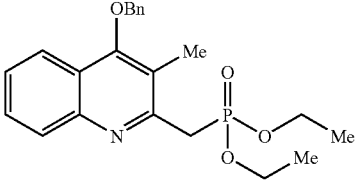 [SMILES: CCOP(=O)(Cc1nc2ccccc2c(OCc2ccccc2)c1C)OCC] | ESI+: 400 |
| 98 | 12 | 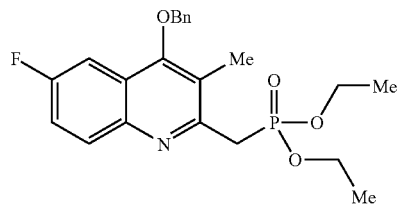 [SMILES: CCOP(=O)(Cc1nc2ccc(F)cc2c(OCc2ccccc2)c1C)OCC] | ESI+: 418 |
| 13 | 13 | 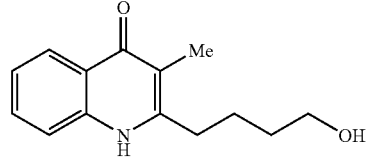 [SMILES: Cc1c(CCCCO)[nH]c2ccccc2c1=O] | ESI+: 232 |
| 99 | 2 | 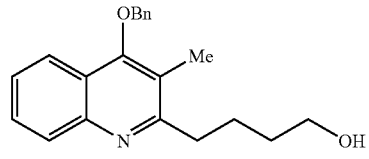 [SMILES: Cc1c(CCCCO)nc2ccccc2c1OCc1ccccc1] | ESI+: 322 |
TABLE 9
| PEx | PSyn | Str | DATA |
|---|---|---|---|
| 100 | 14 | 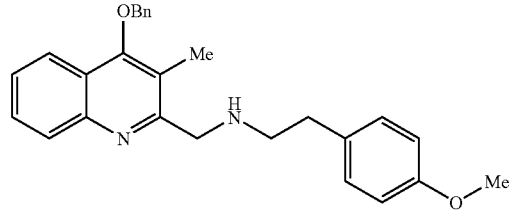 [SMILES: COc1ccc(CCNCc2nc3ccccc3c(OCc3ccccc3)c2C)cc1] | FAB+: 413 |
| 101 | 14 | 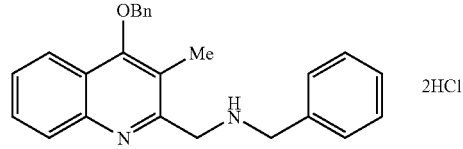 [SMILES: Cc1c(CNCc2ccccc2)nc2ccccc2c1OCc1ccccc1 ; "2HCl"] | FAB+: 369 |
| 15 | 15 | 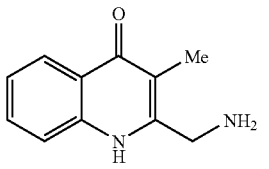 | NMR1: 2.11(3H, s), 4.20-4.26(2H, m), 7.31-7.36(1H, m), 7.64-7.70(2H, m), 8.12(1H, d, J = 7.9 Hz), 8.73(3H, br s), 8.85(1H, br s), 12.53(1H, br s) |

TABLE 9-continued

| PEx | PSyn | Str | DATA |
|---|---|---|---|
| 14 | 14 | 4-OBn, 3-Me quinoline, 2-CH₂NH-hexyl-Me | FAB+: 377 |
| 102 | 16 | 4-OBn, 3-Me quinoline, 2-CH₂-N(COMe)-CH₂CH₂-C₆H₄-OMe | FAB+: 455 |
| 16 | 16 | 4-OBn, 3-Me quinoline, 2-CH₂-N(COMe)-hexyl-Me | FAB+: 419 |

TABLE 10

| PEx | PSyn | Str | DATA |
|---|---|---|---|
| 103 | 14 | 4-OBn, 3-Me quinoline, 2-CH₂NH-(CH₂)₄-Ph | FAB+: 411 |
| 104 | 14 | 4-OBn, 3-Me quinoline, 2-CH₂NH-(CH₂)₄-C₆H₄-OMe | FAB+: 441 |
| 105 | 14 | 4-OBn, 3-Me quinoline, 2-CH₂NH-(CH₂)₃-Ph | FAB+: 397 |
| 17 | 17 | 4-OBn, 3-Me quinoline, 2-CH₂-S-hexyl-Me | FAB+: 394 |

TABLE 10-continued
| PEx | PSyn | Str | DATA |
|---|---|---|---|
| 18 | 18 | 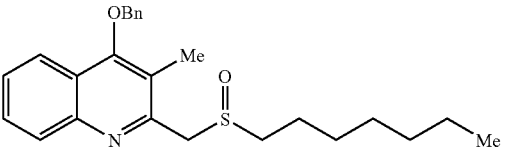 [SMILES: CCCCCCCS(=O)Cc1nc2ccccc2c(OCc2ccccc2)c1C] | FAB+: 410 |
| 19 | 19 | 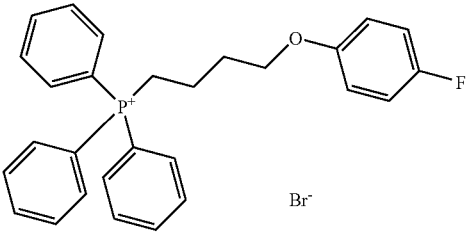 [SMILES: Fc1ccc(OCCCC[P+](c2ccccc2)(c2ccccc2)c2ccccc2)cc1 ; [Br-]] | ESI+: 429 |
TABLE 11
| PEx | PSyn | Str | DATA |
|---|---|---|---|
| 20 | 20 | 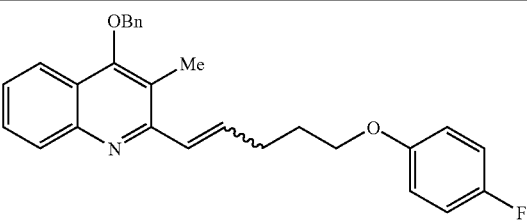 | FAB+: 428 |
| 106 | 19 | 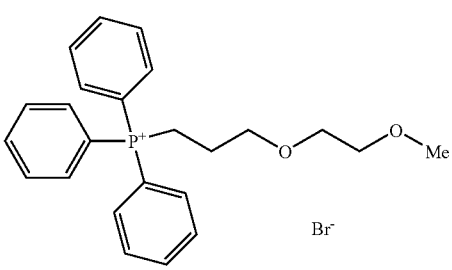 [SMILES: COCCOCCC[P+](c1ccccc1)(c1ccccc1)c1ccccc1 ; [Br-]] | ESI+: 379 |
| 107 | 20 | 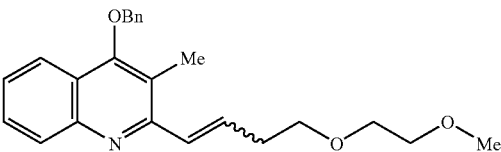 [SMILES: COCCOCCC=Cc1nc2ccccc2c(OCc2ccccc2)c1C] | ESI+: 378 |
| 21 | 21 | 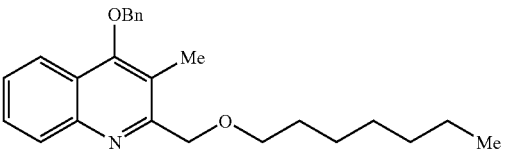 [SMILES: CCCCCCCOCc1nc2ccccc2c(OCc2ccccc2)c1C] | FAB+: 378 |
| 108 | 19 | 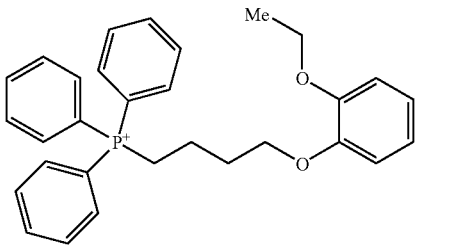 | ESI+: 455 |

TABLE 11-continued

| PEx | PSyn | Str | DATA |
|---|---|---|---|
| 109 | 20 | [Structure: 4-(benzyloxy)-3-methyl-2-[4-(2-ethoxyphenoxy)but-1-en-1-yl]quinoline] | ESI+: 454 |

TABLE 12

| PEx | PSyn | Str | DATA |
|---|---|---|---|
| 110 | 19 | [Structure: triphenyl[4-(2,4-difluorophenoxy)butyl]phosphonium bromide] | ESI+: 447 |
| 111 | 20 | [Structure: 4-(benzyloxy)-3-methyl-2-[4-(2,4-difluorophenoxy)but-1-en-1-yl]quinoline] | FAB+: 446 |
| 112 | 20 | [Structure: 4-(benzyloxy)-8-fluoro-3-methyl-2-[4-(2,4-difluorophenoxy)but-1-en-1-yl]quinoline] | ESI+: 464 |
| 113 | 20 | [Structure: 4-(benzyloxy)-6-fluoro-3-methyl-2-[4-(2,4-difluorophenoxy)but-1-en-1-yl]quinoline] | ESI+: 464 |
| 22 | 22 | [Structure: {[4-(benzyloxy)-3-methylquinolin-2-yl]methyl} pentylcarbamate] | FAB+: 393 |
| 114 | 23 | [Structure: BnO-(CH2)4-O-CH2-cyclopropyl] | CI+: 235 |

TABLE 12-continued
| PEx | PSyn | Str | DATA |
|-----|------|-----|------|
| 115 | 24 | 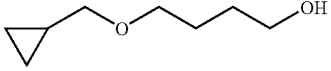 | CI+: 145 |
TABLE 13
| PEx | PSyn | Str | DATA |
|-----|------|-----|------|
| 116 | 21 | 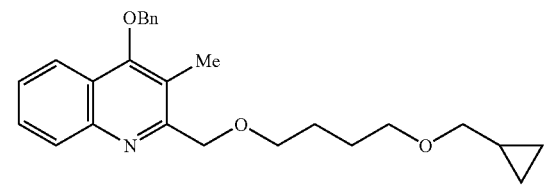 [SMILES: Cc1c(COCCCCOCC2CC2)nc2ccccc2c1OCc1ccccc1] | FAB+: 406 |
| 25 | 25 | 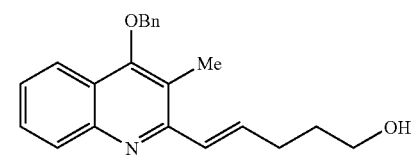 [SMILES: Cc1c(/C=C/CCCO)nc2ccccc2c1OCc1ccccc1] | ESI+: 334 |
| 117 | 26 | 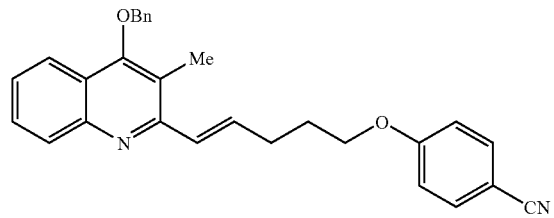 [SMILES: Cc1c(/C=C/CCCOc2ccc(C#N)cc2)nc2ccccc2c1OCc1ccccc1] | ESI+: 435 |
| 118 | 25 | 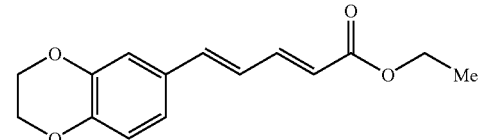 | EI+: 260 |
| 27 | 27 | 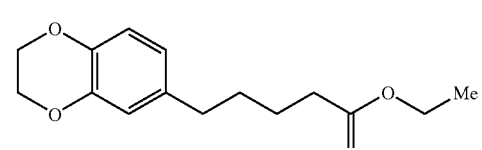 | EI+: 264 |
| 28 | 28 | 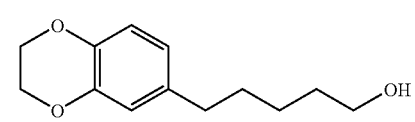 [SMILES: OCCCCCc1ccc2c(c1)OCCO2] | EI+: 222 |
| 119 | 21 | 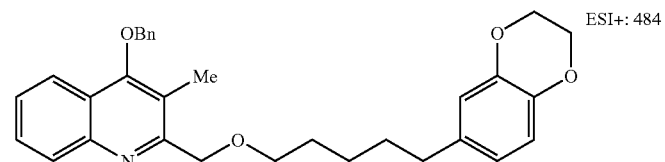 | ESI+: 484 |

TABLE 14
| PEx | PSyn | Str | DATA |
|---|---|---|---|
| 120 | 21 | 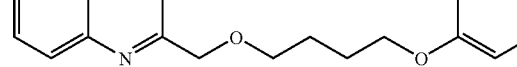 | ESI+: 429 |
| 121 | 21 | 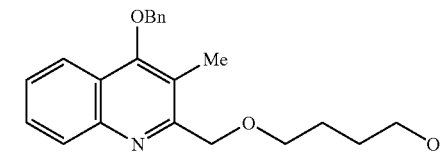 | FAB+: 352 |
| 122 | 22 | 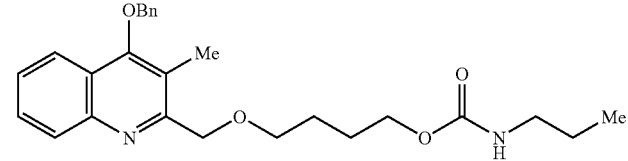 [SMILES: CCCNC(=O)OCCCCOCc1nc2ccccc2c(OCc2ccccc2)c1C] | FAB+: 437 |
| 123 | 21 | 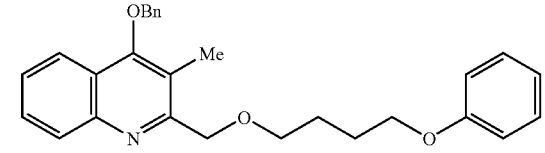 [SMILES: Cc1c(COCCCCOc2ccccc2)nc2ccccc2c1OCc1ccccc1] | ESI+: 428 |
| 124 | 29 | 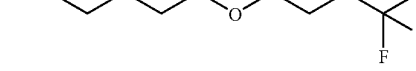 | CI+: 291 |
| 125 | 24 | 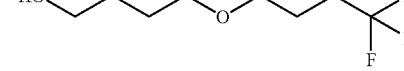 | CI+: 201 |
| 126 | 21 | 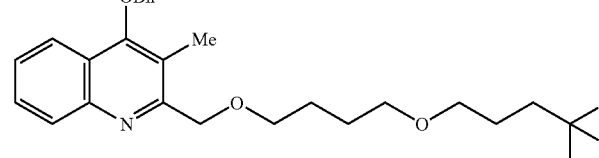 | ESI+: 462 |
| 127 | 21 | 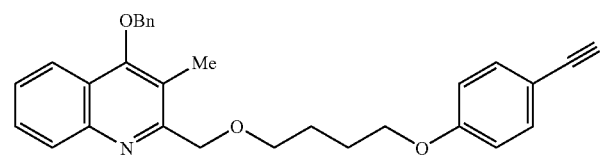 | FAB+: 453 |
TABLE 15
| PEx | PSyn | Str | DATA |
|---|---|---|---|
| 128 | 29 |  | EI+: 314 |

TABLE 15-continued
| PEx | PSyn | Str | DATA |
|---|---|---|---|
| 129 | 24 | 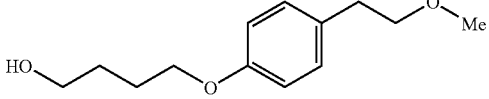 | EI+: 224 |
| 130 | 21 | 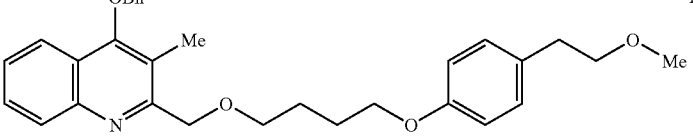 | ESI+: 486 |
| 29 | 29 | 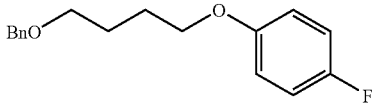 [SMILES: Fc1ccc(OCCCCOCc2ccccc2)cc1] | ESI+: 275 |
| 131 | 24 | 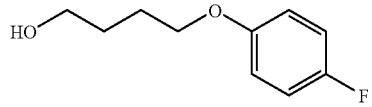 [SMILES: OCCCCOc1ccc(F)cc1] | NMR2: 1.70-1.81(2H, m), 1.81-1.93(2H, m), 3.73(2H, dd, J = 6.4, 6.4 Hz), 3.97(2H, dd, J = 6.4, 6.4 Hz), 6.83(2H, dd, J = 9.2, 4.4 Hz), 6.96(2H, dd, J = 9.2, 9.2 Hz) |
| 132 | 21 | 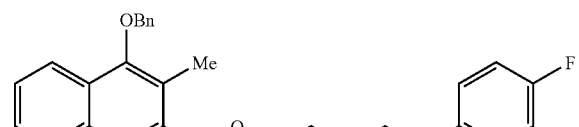 | ESI+: 446 |
| 133 | 21 | 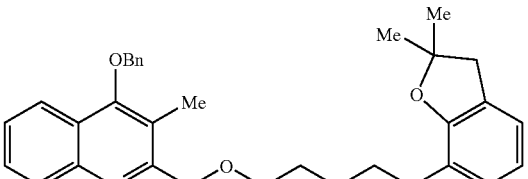 | ESI+: 498 |
| 134 | 29 | 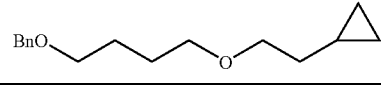 | CI+: 249 |
TABLE 16
| PEx | PSyn | Str | DATA |
|---|---|---|---|
| 135 | 24 | 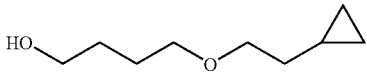 | CI+: 159 |
| 136 | 21 | 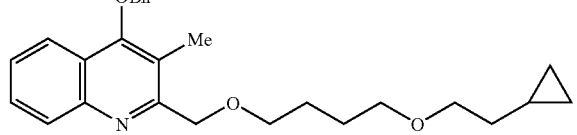 | FAB+: 420 |
| 137 | 21 | 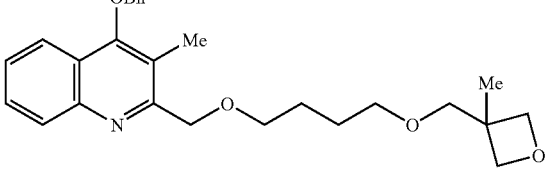 | FAB+: 436 |

TABLE 16-continued

| PEx | PSyn | Str | DATA |
|---|---|---|---|
| 138 | 29 | BnO–(CH₂)₄–O–CH₂CH₂–C(Me)₂–OMe | NMR2: 1.17(6H, s), 1.64-1.70(4H, m), 1.78(2H, t, J = 7.2 Hz), 3.18(3H, s), 3.40-3.44(2H, m), 3.45-3.51(4H, m), 4.50(2H, s), 7.26-7.35(5H, m) |
| 139 | 24 | HO–(CH₂)₄–O–CH₂CH₂–C(Me)₂–OMe | CI+: 191 |
| 140 | 21 | 4-OBn-3-Me-quinolin-2-yl-CH₂–O–(CH₂)₄–O–CH₂CH₂–C(Me)₂–OMe | FAB+: 452 |
| 141 | 29 | BnO–(CH₂)₄–O–CH₂CH₂–CF₃ | EI+: 276 |
| 142 | 24 | HO–(CH₂)₄–O–CH₂CH₂–CF₃ | CI+: 187 |

TABLE 17

| PEx | PSyn | Str | DATA |
|---|---|---|---|
| 143 | 21 | 4-OBn-3-Me-quinolin-2-yl-CH₂–O–(CH₂)₄–O–CH₂CH₂–CF₃ | FAB+: 448 |
| 144 | 21 | 4-OBn-3-Me-quinolin-2-yl-CH₂–O–(CH₂)₃–O–C(Me)₃ | FAB+: 408 |
| 145 | 29 | BnO–(CH₂)₄–O–(4-piperidinyl)–N–Boc | ESI+: 364 |
| 146 | 24 | HO–(CH₂)₄–O–(4-piperidinyl)–N–Boc | NMR2: 1.45(9H, s), 1.47-1.57(2H, m), 1.63-1.74(4H, m), 1.78-1.88(2H, m), 2.05(1H, br s), 3.03-3.14(2H, m), 3.43-3.50(1H, m), 3.48-3.54(2H, m), 3.62-3.68(2H, m), 3.71-3.80(2H, m) |
| 147 | 21 | 4-OBn-3-Me-quinolin-2-yl-CH₂–O–(CH₂)₄–O–(4-piperidinyl)–N–Boc | ESI+: 535 |

TABLE 17-continued
| PEx | PSyn | Str | DATA |
|---|---|---|---|
| 148 | 29 | 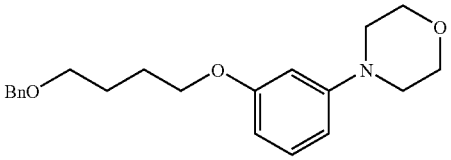 [SMILES: c1ccc(COCCCCOc2cccc(N3CCOCC3)c2)cc1] | ESI+: 342 |
| 149 | 24 | 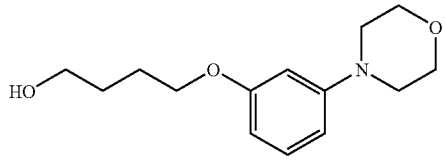 [SMILES: OCCCCOc1cccc(N2CCOCC2)c1] | ESI+: 252 |
TABLE 18
| PEx | PSyn | Str | DATA |
|---|---|---|---|
| 150 | 21 | 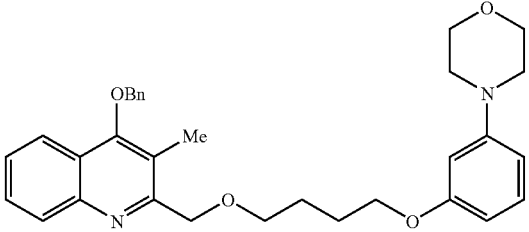 [SMILES: Cc1c(COCCCCOc2cccc(N3CCOCC3)c2)nc2ccccc2c1OCc1ccccc1] | ESI+: 513 |
| 30 | 30 | 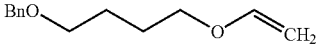 | CI+: 207 |
| 31 | 31 | 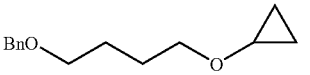 [SMILES: c1ccc(COCCCCOC2CC2)cc1] | CI+: 221 |
| 151 | 24 | 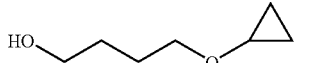 | CI+: 131 |
| 152 | 21 | 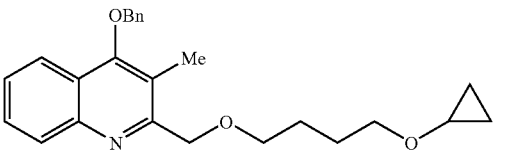 [SMILES: Cc1c(COCCCCOC2CC2)nc2ccccc2c1OCc1ccccc1] | ESI+: 392 |
| 153 | 29 | 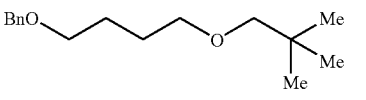 [SMILES: CC(C)(C)COCCCCOCc1ccccc1] | NMR2: 0.89(9H, s), 1.63-1.70(4H, m), 3.04(2H, s), 3.42(2H, t, J = 6.1 Hz), 3.50(2H, t, J = 6.3 Hz), 4.51(2H, s), 7.25-7.35(5H, m) |
| 24 | 24 | 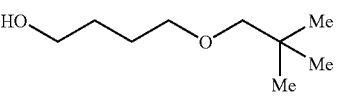 [SMILES: CC(C)(C)COCCCCO] | CI+: 161 |
| 154 | 21 | 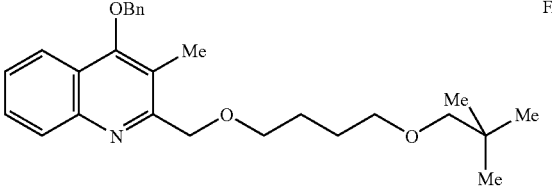 | FAB+: 422 |

TABLE 19
| PEx | PSyn | Str | DATA |
|---|---|---|---|
| 155 | 21 | 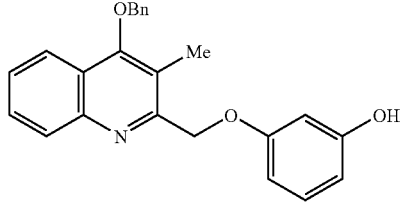 [SMILES: Cc1c(COc2cccc(O)c2)nc2ccccc2c1OCc1ccccc1] | FAB+: 372 |
| 156 | 21 | 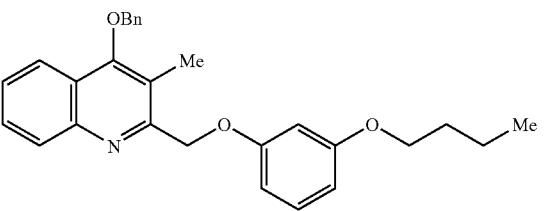 [SMILES: CCCCOc1cccc(OCc2nc3ccccc3c(OCc3ccccc3)c2C)c1] | FAB+: 428 |
| 157 | 22 | 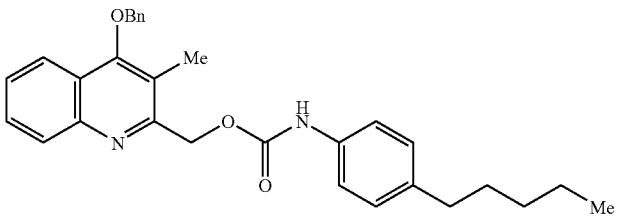 [SMILES: CCCCCc1ccc(NC(=O)OCc2nc3ccccc3c(OCc3ccccc3)c2C)cc1] | FAB+: 469 |
| 158 | 22 | 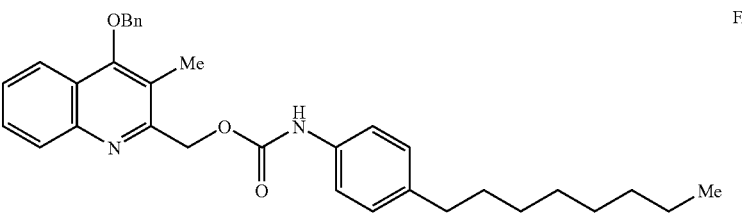 | FAB+: 511 |
| 159 | 22 | 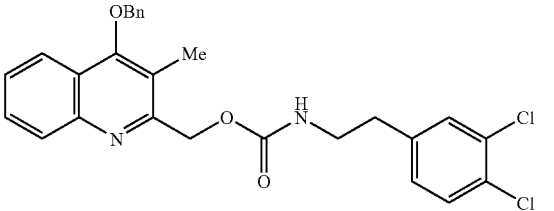 [SMILES: Cc1c(COC(=O)NCCc2ccc(Cl)c(Cl)c2)nc2ccccc2c1OCc1ccccc1] | FAB+: 495, 497 |
| 160 | 22 | 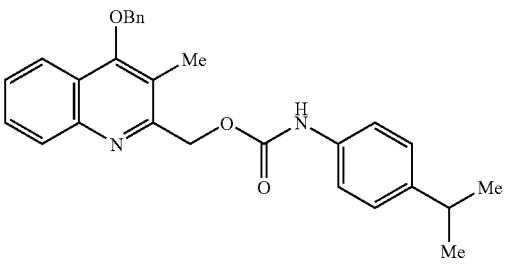 [SMILES: Cc1c(COC(=O)Nc2ccc(C(C)C)cc2)nc2ccccc2c1OCc1ccccc1] | FAB+: 441 |

TABLE 20

| PEx | PSyn | Str | DATA |
|---|---|---|---|
| 161 | 22 | 4-OBn, 3-Me-quinolin-2-yl-CH2-O-C(=O)-NH-(4-phenoxyphenyl) | FAB+: 491 |
| 162 | 22 | 4-OBn, 3-Me-quinolin-2-yl-CH2-O-C(=O)-NH-(4-SMe-phenyl) | FAB+: 445 |
| 163 | 22 | 4-OBn, 3-Me-quinolin-2-yl-CH2-O-C(=O)-NH-(4-SCF3-phenyl) | ESI+: 499 |
| 164 | 32 | 3-(4,4,4-trifluorobutoxy)phenol | EI+: 220 |
| 165 | 21 | 4-OBn, 3-Me-quinolin-2-yl-CH2-O-(3-(4,4,4-trifluorobutoxy)phenyl) | FAB+: 482 |
| 166 | 32 | 3-((tetrahydropyran-4-yl)methoxy)phenol | FAB+: 209 |

TABLE 21

| PEx | PSyn | Str | DATA |
|---|---|---|---|
| 167 | 21 | 4-OBn, 3-Me-quinolin-2-yl-CH2-O-(3-((tetrahydropyran-4-yl)methoxy)phenyl) | FAB+: 470 |

TABLE 21-continued

| PEx | PSyn | Str | DATA |
|---|---|---|---|
| 168 | 21 | 4-OBn, 3-Me quinoline, 2-CH2O-C6H4-CH2CH2OCH2CH2CH3 | ESI+: 442 |
| 169 | 32 | 3-hydroxyphenyl O-CH2-C(Me)2-OMe | EI+: 210 |
| 170 | 21 | 4-OBn, 3-Me quinoline, 2-CH2O-C6H4-O-CH2CH2-C(Me)2-OMe | FAB+: 472 |
| 33 | 33 | OHC-CH2CH2-O-cyclopropyl | CI+: 129 |
| 171 | 25 | 4-OBn, 3-Me quinoline, 2-CH=CH-CH2CH2CH2-O-cyclopropyl | ESI+: 374 |
| 172 | 22 | 4-OBn, 3-Me quinoline, 2-CH2-O-C(O)NH-(2,3-dihydrobenzofuran-5-yl) | ESI+: 441 |

TABLE 22

| PEx | PSyn | Str | DATA |
|---|---|---|---|
| 173 | 14 | 4-OBn, 3-Me quinoline, 2-CH2-N(piperazine)-C(O)OEt | ESI+: 420 |
| 174 | 26 | 4-OBn, 3-Me quinoline, 2-CH2CH2CH2CH2-O-C6H4-OEt | ESI+: 442 |

TABLE 22-continued

| PEx | PSyn | Str | DATA |
|---|---|---|---|
| 175 | 30 | BnO~~~~O-CH=CH2 | FAB+: 221 |
| 176 | 31 | BnO~~~~O-cyclopropyl | CI+: 235 |
| 177 | 24 | HO~~~~O-cyclopropyl | CI+: 145 |
| 178 | 21 | 4-OBn, 3-Me quinoline-2-CH2-O~~~~O-cyclopropyl | ESI+: 406 |
| 179 | 23 | 4-OBn, 3-Me quinoline-2-CH2-O-(1,3-phenylene)-O-CH2-(3-Me-oxetan-3-yl) | FAB+: 456 |
| 180 | 21 | 4-OBn, 3-Me quinoline-2-CH2-O-(piperidin-4-yl)-N-C(=O)-(CH2)4-Me | ESI+: 461 |

TABLE 23

| PEx | PSyn | Str | DATA |
|---|---|---|---|
| 181 | 21 | 4-OBn, 3-Me quinoline-2-CH2-O-(2-phenyl-4H-chromen-4-one-7-yl) | FAB+: 500 |

TABLE 23-continued

| PEx | PSyn | Str | DATA |
|---|---|---|---|
| 182 | 21 | | ESI+: 500 |
| 183 | 21 | | FAB+: 444 |
| 23 | 23 | | FAB+: 542 |
| 184 | 21 | | FAB+: 444 |

TABLE 24

| PEx | PSyn | Str | DATA |
|---|---|---|---|
| 185 | 23 | | FAB+: 542 |

TABLE 24-continued

| PEx | PSyn | Str | DATA |
|---|---|---|---|
| 186 | 21 | | FAB+: 408 |
| 187 | 23 | | FAB+: 506 |
| 188 | 25 | | ESI+: 466 |
| 34 | 34 | | FAB+: 327 |
| 189 | 35 | | CI+: 237 |

TABLE 25

| PEx | PSyn | Str | DATA |
|---|---|---|---|
| 190 | 33 | | CI+: 235 |
| 191 | 25 | | ESI+: 480 |

TABLE 25-continued

| PEx | PSyn | Str | DATA |
|---|---|---|---|
| 192 | 21 | | FAB+: 444 |
| 193 | 23 | | FAB+: 542 |
| 36 | 36 | | NMR2: 2.66 (2H, dd, J = 7.2, 7.2 Hz), 3.00 (2H, dd, J = 7.2, 7.2 Hz), 3.35-3.42 (2H, m), 3.42-3.49 (2H, m), 3.51-3.60 (2H, m), 3.66-3.76 (2H, m), 7.09-7.13 (1H, m), 7.15-7.19 (1H, m), 7.19-7.36 (5H, m), 7.86 (1H, s) |

TABLE 26

| PEx | PSyn | Str | DATA |
|---|---|---|---|
| 37 | 37 | | ESI+: 524 |
| 194 | 34 | | FAB+: 375 |
| 195 | 24 | | FAB+: 285 |

TABLE 26-continued
| PEx | PSyn | Str | DATA |
|---|---|---|---|
| 196 | 21 | 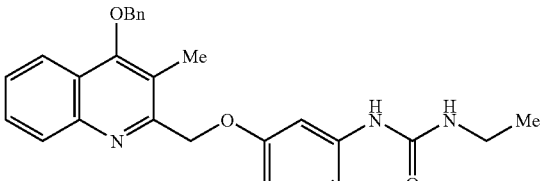 | FAB+: 546 |
| 197 | 36 |  | NMR2: 0.81-0.87 (2H, m), 1.00-1.07 (2H, m), 1.69-1.78 (1H, m), 3.55-3.73 (4H, m), 3.70-3.91 (4H, m), 7.13 (1H, s), 7.22 (1H, s), 7.91 (1H,s) |
| 198 | 37 | 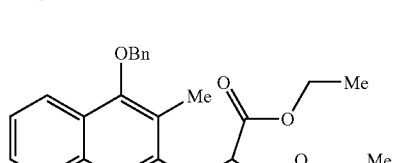 | ESI+: 460 |
TABLE 27
| PEx | PSyn | Str | DATA |
|---|---|---|---|
| 199 | 21 | | FAB+: 442 |
| 200 | 21 | | NMR2: 0.90 (3H, t, J = 7.2 Hz), 1.26-1.40 (2H, m), 1.45-1.52 (2H, m), 1.86-1.95 (2H, m), 2.48 (3H, s), 3.39 (2H, t, J = 6.9 Hz), 3.51 (2H, t, J = 6.3 Hz), 3.67 (2H, t, J = 6.3 Hz), 4.82 (2H, s), 5.09 (2H, s), 7.40-7.56 (6H, m), 7.60-7.70 (1H, m), 8.02-8.12 (2H, m) |
| 38 | 38 | | ESI+: 422 |

TABLE 27-continued

| PEx | PSyn | Str | DATA |
|---|---|---|---|
| 39 | 39 | | ESI+: 322 |
| 40 | 40 | | ESI+: 439 |

TABLE 28

| PEx | PSyn | Str | DATA |
|---|---|---|---|
| 201 | 21 | | FAB+: 390 |
| 202 | 23 | | FAB+: 488 |
| 203 | 32 | | EI+: 226 |
| 204 | 21 | | FAB+: 488 |

TABLE 28-continued

| PEx | PSyn | Str | DATA |
|---|---|---|---|
| 205 | 32 | | NMR2: 1.38-1.52 (2H, m), 1.71-1.78 (2H, m), 1.98-2.10 (1H, m), 2.27 (3H, s), 3.44 (2H, td, J = 11.9, 1.3 Hz), 3.76 (2H, d, J = 6.5 Hz), 4.01 (2H, dd, J = 10.4, 3.2 Hz), 4.69 (1H, s), 6.21 (1H, t, J = 2.2 Hz), 6.25 (1H, s), 6.31 (1H, s) |

TABLE 29

| PEx | PSyn | Str | DATA |
|---|---|---|---|
| 206 | 21 | | ESI+: 484 |
| 207 | 21 | | FAB+: 373 |
| 208 | 23 | | FAB+: 471 |
| 209 | 23 | | FAB+: 471 |
| 210 | 32 | | EI+: 238 |

TABLE 30

| PEx | PSyn | Str | DATA |
|-----|------|-----|------|
| 211 | 21 | (4-benzyloxy-3-methylquinolin-2-yl)methoxy-3-methoxy-5-((tetrahydropyran-4-yl)methoxy)benzene | ESI+: 500 |
| 212 | 32 | 3,5-dihydroxyphenyl (tetrahydropyran-4-yl)methyl ether | EI+: 224 |
| 213 | 21 | 3-((4-benzyloxy-3-methylquinolin-2-yl)methoxy)-5-((tetrahydropyran-4-yl)methoxy)phenol | FAB+: 486 |
| 214 | 32 | 3-hydroxy-5-((tetrahydropyran-4-yl)methoxy)benzamide | EI+: 251 |
| 215 | 21 | 3-((4-benzyloxy-3-methylquinolin-2-yl)methoxy)-5-((tetrahydropyran-4-yl)methoxy)benzamide | ESI+: 513 |

TABLE 31
| PEx | PSyn | Str | DATA |
|---|---|---|---|
| 216 | 32 | 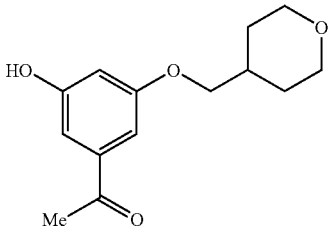 [SMILES: CC(=O)c1cc(O)cc(OCC2CCOCC2)c1] | ESI−: 249 |
| 217 | 21 | 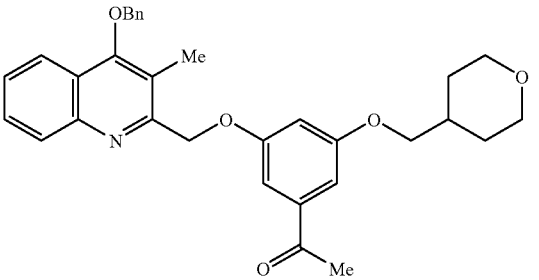 [SMILES: CC(=O)c1cc(OCc2nc3ccccc3c(OCc3ccccc3)c2C)cc(OCC2CCOCC2)c1] | ESI+: 512 |
| 41 | 41 | 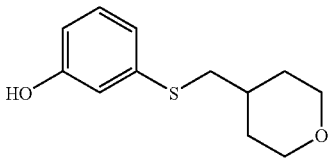 [SMILES: Oc1cccc(SCC2CCOCC2)c1] | EI+: 224 |
| 218 | 21 | 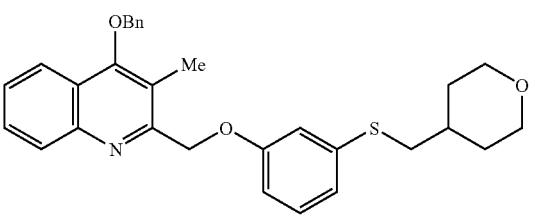 [SMILES: Cc1c(COc2cccc(SCC3CCOCC3)c2)nc2ccccc2c1OCc1ccccc1] | FAB+: 486 |
| 219 | 21 | 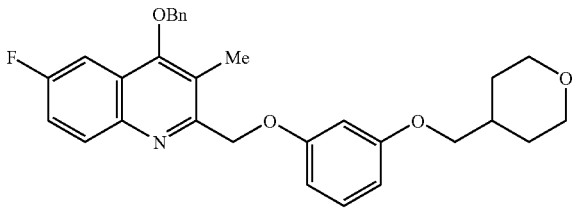 [SMILES: Cc1c(COc2cccc(OCC3CCOCC3)c2)nc2ccc(F)cc2c1OCc1ccccc1] | ESI+: 488 |
| 220 | 21 | 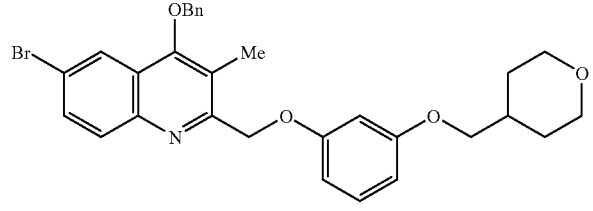 [SMILES: Cc1c(COc2cccc(OCC3CCOCC3)c2)nc2ccc(Cl)cc2c1OCc1ccccc1] | ESI+: 548, 550 |

TABLE 32

| PEx | PSyn | Str | DATA |
|-----|------|-----|------|
| 221 | 42 | (structure) | FAB+: 398 |
| 222 | 43 | (structure) | FAB+: 298 |
| 223 | 16 | (structure) | FAB+: 340 |
| 224 | 35 | (structure) | EI+: 249 |
| 225 | 21 | (structure) | FAB+: 511 |
| 226 | 21 | (structure) | ESI+: 462 |

TABLE 33

| PEx | PSyn | Str | DATA |
|---|---|---|---|
| 227 | 21 | | ESI+: 484 |
| 228 | 21 | | FAB+: 500 |
| 229 | 21 | | ESI+: 504, 506 |
| 44 | 44 | | FAB+: 376 |
| 230 | 35 | | FAB+: 286 |
| 231 | 21 | | FAB+: 547 |

TABLE 34

| PEx | PSyn | Str | DATA |
|---|---|---|---|
| 232 | 32 | 3-hydroxy-5-((tetrahydro-2H-pyran-4-yl)methoxy)benzonitrile | ESI−: 232 |
| 233 | 21 | 4-(benzyloxy)-2-((3-cyano-5-((tetrahydro-2H-pyran-4-yl)methoxy)phenoxy)methyl)-3-methylquinoline | ESI−: 493 |
| 234 | 42 | 4-((3-(benzyloxy)phenoxy)methyl)tetrahydro-2H-thiopyran 1,1-dioxide | FAB+: 347 |
| 235 | 35 | 4-((3-hydroxyphenoxy)methyl)tetrahydro-2H-thiopyran 1,1-dioxide | FAB+: 257 |
| 236 | 21 | 4-((3-((4-(benzyloxy)-3-methylquinolin-2-yl)methoxy)phenoxy)methyl)tetrahydro-2H-thiopyran 1,1-dioxide | ESI+: 518 |
| 237 | 42 | 4-(2-(3-(benzyloxy)phenoxy)ethyl)morpholine | ESI+: 314 |

TABLE 35

| PEx | PSyn | Str | DATA |
|---|---|---|---|
| 238 | 35 | 3-(2-morpholinoethoxy)phenol | FAB+: 224 |

TABLE 35-continued

| PEx | PSyn | Str | DATA |
|---|---|---|---|
| 239 | 21 | 4-(benzyloxy)-3-methyl-2-[[3-[2-(morpholin-4-yl)ethoxy]phenoxy]methyl]quinoline | FAB+: 485 |
| 45 | 45 | 1-(morpholin-4-yl)-2-(3-hydroxyphenoxy)ethan-1-one | CI+: 238 |
| 240 | 21 | 2-[3-[[4-(benzyloxy)-3-methylquinolin-2-yl]methoxy]phenoxy]-1-(morpholin-4-yl)ethan-1-one | ESI+: 499 |
| 46 | 46 | ethyl 4-(benzyloxy)-3-methyl-2-[[3-[(tetrahydro-2H-pyran-4-yl)methoxy]phenoxy]methyl]quinoline-6-carboxylate | ESI+: 542 |
| 241 | 21 | 5-[[4-(benzyloxy)-3-methylquinolin-2-yl]methoxy]pentan-1-amine | FAB+: 365 |
| 47 | 47 | 4-(benzyloxy)-3-methyl-6-(pyridin-3-yl)-2-[[3-[(tetrahydro-2H-pyran-4-yl)methoxy]phenoxy]methyl]quinoline | ESI+: 547 |

TABLE 36

| PEx | PSyn | Str | DATA |
|---|---|---|---|
| 242 | 16 | N-[5-[[4-(benzyloxy)-3-methylquinolin-2-yl]methoxy]pentyl]acetamide | ESI+: 407 |

TABLE 36-continued
| PEx | PSyn | Str | DATA |
|---|---|---|---|
| 243 | 42 | 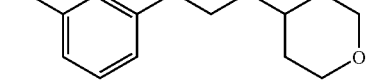 | CI+: 313 |
| 244 | 35 | 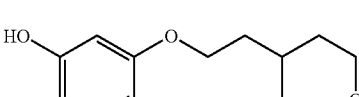 | EI+: 222 |
| 245 | 21 | 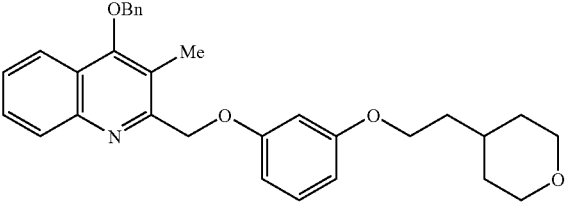 [SMILES: Cc1c(COc2cccc(OCCN3CCOCC3)c2)nc2ccccc2c1OCc1ccccc1] | ESI+: 484 |
| 246 | 42 | 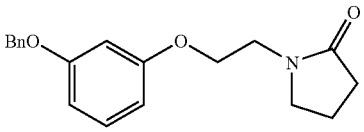 [SMILES: O=C1CCCN1CCOc1cccc(OCc2ccccc2)c1] | NMR2: 1.87-1.99 (2H, m), 2.22 (2H, t, J = 8.1), 3.44 (2H, t, J = 7.0), 3.53 (2H, t, J = 5.5), 4.06 (2H, t, J = 5.5 Hz), 5.09 (2H, s), 6.55 (1H, d, J = 2.0 Hz), 6.60-6.62 (2H, m), 7.16-7.20 (1H, m), 7.31-7.46 (5H, m) |
| 247 | 35 | 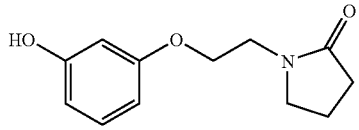 | CI+: 222 |
TABLE 37
| PEx | PSyn | Str | DATA |
|---|---|---|---|
| 248 | 21 | | ESI+: 483 |
| 249 | 21 | | ESI+: 490, 492 |
| 250 | 23 | | NMR2: 1.27-1.42 (2H, m), 1.62-1.70 (2H, m), 1.79-1.94 (1H, m), 3.34 (2H, d, J = 6.5 Hz), 3.40 (2H, ddd, J = 11.9, 11.6, 2.2 Hz), 3.54 (2H, dd, J = 4.7, 4.2 Hz), 3.74 (2H, dd, J = 4.9, 4.1 Hz), 3.98 (2H, dd, J = 9.0, 3.6 Hz) |

TABLE 37-continued

| PEx | PSyn | Str | DATA |
|---|---|---|---|
| 251 | 42 | BnO-C6H4-O-CH2CH2-O-CH2-(tetrahydropyran-4-yl) (3-substituted) | NMR2: 1.24-1.40 (2H, m), 1.63-1.71 (2H, m), 1.82-1.95 (1H, m), 3.34-3.44 (4H, m), 3.77 (2H, dd, J = 4.7, 4.7 Hz), 3.97 (2H, dd, J = 11.3, 4.5 Hz), 4.09 (2H, dd, J = 5.2, 4.5 Hz), 5.04 (2H, s), 6.51-6.61 (3H, m), 7.71 (1H, dd, J = 8.4, 8.1 Hz), 7.30-7.46 (5H, m) |
| 252 | 35 | HO-C6H4-O-CH2CH2-O-CH2-(tetrahydropyran-4-yl) (3-substituted) | ESI-: 251 |

TABLE 38

| PEx | PSyn | Str | DATA |
|---|---|---|---|
| 253 | 21 | 4-OBn-3-Me-quinoline-2-CH2-O-(3-substituted phenyl)-O-CH2CH2-O-CH2-(tetrahydropyran-4-yl) | ESI+: 514 |
| 254 | 17 | 4-OBn-3-Me-quinoline-2-CH2-S-(3-hydroxyphenyl) | ESI+: 388 |
| 255 | 23 | 4-OBn-3-Me-quinoline-2-CH2-S-(3-substituted phenyl)-O-CH2-(tetrahydropyran-4-yl) | ESI+: 486 |
| 256 | 42 | BnO-C6H4-O-CH2-(tetrahydropyran-4-yl) (4-substituted) | EI+: 298 |
| 257 | 35 | HO-C6H4-O-CH2-(tetrahydropyran-4-yl) (4-substituted) | EI+: 208 |

TABLE 38-continued

| PEx | PSyn | Str | DATA |
|---|---|---|---|
| 258 | 21 | (4-OBn, 3-Me quinoline-2-yl)methoxy-phenyl-O-CH2-tetrahydropyran | FAB+: 470 |
| 259 | 16 | 3-hydroxyphenyl-NH-C(O)-CH2-tetrahydropyran | EI+: 235 |

TABLE 39

| PEx | PSyn | Str | DATA |
|---|---|---|---|
| 260 | 21 | (4-OBn, 3-Me quinoline-2-yl)methoxy-phenyl-NH-C(O)-CH2-tetrahydropyran | FAB+: 497 |
| 261 | 45 | 3-hydroxyphenyl-CH2-C(O)-morpholine | EI+: 221 |
| 262 | 21 | (4-OBn, 3-Me quinoline-2-yl)methoxy-phenyl-CH2-C(O)-morpholine | FAB+: 483 |
| 263 | 21 | (4-OBn, 3-iPr quinoline-2-yl)methoxy-phenyl-O-CH2-tetrahydropyran | FAB+: 498 |
| 264 | 32 | 3-hydroxy-5-fluorophenyl-O-CH2-tetrahydropyran | ESI−: 225 |

TABLE 39-continued

| PEx | PSyn | Str | DATA |
|---|---|---|---|
| 265 | 21 | (4-(benzyloxy)-3-methyl-2-((3-fluoro-5-((tetrahydro-2H-pyran-4-yl)methoxy)phenoxy)methyl)quinoline) | ESI−: 486 |

TABLE 40

| PEx | PSyn | Str | DATA |
|---|---|---|---|
| 266 | 47 | (4-(benzyloxy)-3-methyl-6-(pyrimidin-5-yl)-2-((3-((tetrahydro-2H-pyran-4-yl)methoxy)phenoxy)methyl)quinoline) | ESI+: 548 |
| 267 | 42 | (3-(2-(3-(benzyloxy)phenoxy)ethyl)pyridine) | EI+: 305 |
| 268 | 35 | (3-(2-(pyridin-3-yl)ethoxy)phenol) | EI+: 215 |
| 269 | 21 | (4-(benzyloxy)-3-methyl-2-((3-(2-(pyridin-3-yl)ethoxy)phenoxy)methyl)quinoline) | ESI+: 477 |
| 270 | 42 | (4-(3-(3-(benzyloxy)phenoxy)propyl)tetrahydro-2H-pyran) | NMR2: 1.22-1.35 (2H, m), 1.35-1.47 (2H, m), 1.47-1.58 (1H, m), 1.58-1.68 (2H, m), 1.74-1.84 (2H, m), 3.38 (2H, td, J = 11.6, 1.7 Hz), 3.87-4.01 (4H, m), 5.01 (2H, s), 6.49-6.60 (3H, m), 7.17 (1H, dd, J = 8.5, 8.5 Hz), 7.28-7.49 (5H, m) |

TABLE 41

| PEx | PSyn | Str | DATA |
|---|---|---|---|
| 271 | 35 | (3-(3-(tetrahydro-2H-pyran-4-yl)propoxy)phenol) | NMR2: 1.23-1.36 (2H, m), 1.36-1.46 (2H, m), 1.46-1.57 (1H, m), 1.60-1.68 (2H, m), 1.75-1.84 (2H, m), 3.39 (2H, td, J = 12.2, 1.9 Hz), 3.92 (2H, dd, J = 6.9, 6.7 Hz), 3.97 (2H, dd, J = 10.9, 3.7 Hz), 4.92 (1H, s), 6.37-6.43 (2H, m), 6.46-6.50 (1H, m), 7.12 (1H, dd, J = 8.2, 7.7 Hz) |

TABLE 41-continued

| PEx | PSyn | Str | DATA |
|---|---|---|---|
| 272 | 21 | 4-OBn, 3-Me quinoline-2-CH2-O-(3-phenoxy)-O-CH2CH2CH2-(tetrahydropyran-4-yl) | ESI+: 498 |
| 273 | 42 | BnO-(3-phenoxy)-O-CH2CH2-(pyridin-2-yl) | EI+: 305 |
| 274 | 35 | HO-(3-phenoxy)-O-CH2CH2-(pyridin-2-yl) | ESI+: 216 |
| 275 | 21 | 4-OBn, 3-Me quinoline-2-CH2-O-(3-phenoxy)-O-CH2CH2-(pyridin-2-yl) | ESI+: 477 |
| 48 | 48 | 6-(2-oxopiperidin-1-yl)-4-OBn, 3-Me quinoline-2-CH2-O-(3-phenoxy)-O-CH2-(tetrahydropyran-4-yl) | ESI+: 567 |

TABLE 42

| PEx | PSyn | Str | DATA |
|---|---|---|---|
| 276 | 21 | 6-F, 4-OBn, 3-Me quinoline-2-CH2-O-(3-phenoxy)-O-CH2CH2-O-CH2-(tetrahydropyran-4-yl) | ESI+: 532 |
| 42 | 42 | BnO-(3-phenoxy)-O-CH2-(1,4-dioxaspiro[4.5]decan-8-yl) | FAB+: 355 |

TABLE 42-continued
| PEx | PSyn | Str | DATA |
|---|---|---|---|
| 35 | 35 | 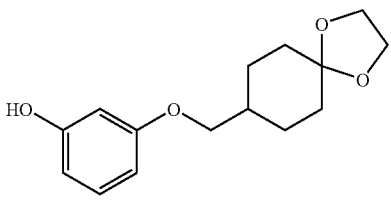 [SMILES: Oc1cccc(OCC2CCC3(CC2)OCCO3)c1] | EI+: 264 |
| 49 | 49 | 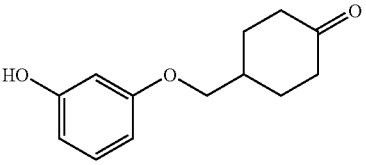 [SMILES: O=C1CCC(COc2cccc(O)c2)CC1] | EI+: 220 |
| 277 | 21 | 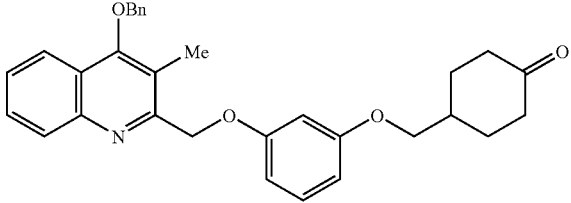 [SMILES: Cc1c(COc2cccc(OCC3CCC(=O)CC3)c2)nc2ccccc2c1OCc1ccccc1] | ESI+: 482 |
| 278 | 42 | 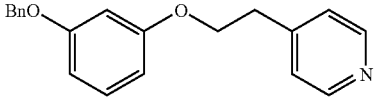 | EI+: 305 |
| 279 | 35 | 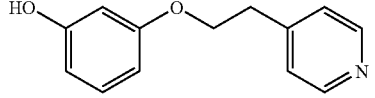 [SMILES: Oc1cccc(OCCc2ccncc2)c1] | ESI+: 216 |
TABLE 43
| PEx | PSyn | Str | DATA |
|---|---|---|---|
| 280 | 21 | 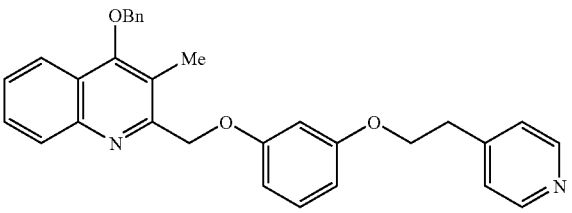 [SMILES: Cc1c(COc2cccc(OCCc3ccncc3)c2)nc2ccccc2c1OCc1ccccc1] | ESI+: 477 |
| 281 | 21 | 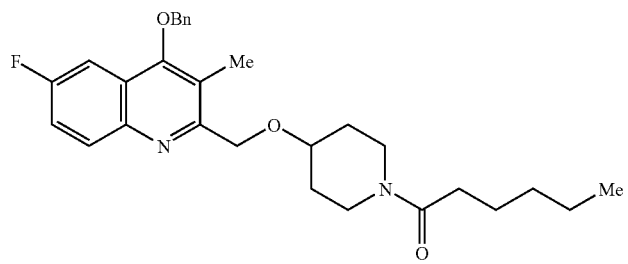 [SMILES: CCCCCC(=O)N1CCC(OCc2nc3ccc(F)cc3c(OCc3ccccc3)c2C)CC1] | ESI+: 479 |

TABLE 43-continued
| PEx | PSyn | Str | DATA |
|---|---|---|---|
| 282 | 50 | 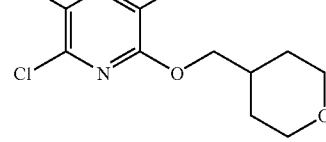 | CI+: 296 |
| 26 | 26 | 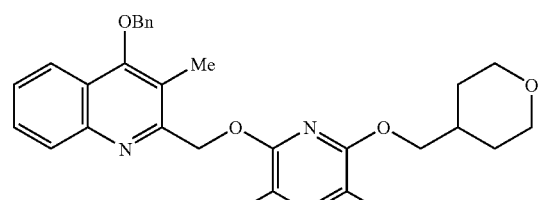 | ESI+: 539 |
| 283 | 32 | | ESI+: 210 |
| 284 | 21 | | ESI+: 471 |
TABLE 44
| PEx | PSyn | Str | DATA |
|---|---|---|---|
| 285 | 21 | 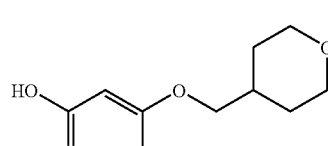 | FAB+: 503 |
| 57 | 57 | | ESI+: 210 |
| 286 | 21 | 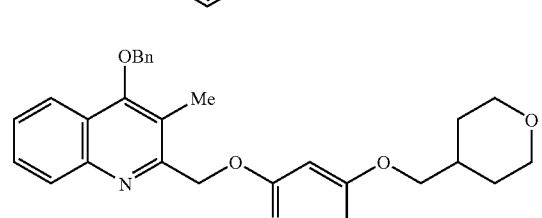 | FAB+: 489 |

TABLE 44-continued

| PEx | PSyn | Str | DATA |
|---|---|---|---|
| 287 | 51 | | EI+: 323 |
| 288 | 35 | | EI+: 233 |
| 289 | 21 | | ESI+: 495 |

TABLE 45

| PEx | PSyn | Str | DATA |
|---|---|---|---|
| 290 | 16 | | ESI+: 172 |
| 291 | 21 | | ESI+: 451 |
| 292 | 21 | | ESI+: 471 |
| 293 | 51 | | EI+: 341 |

TABLE 45-continued
| PEx | PSyn | Str | DATA |
|---|---|---|---|
| 294 | 35 | 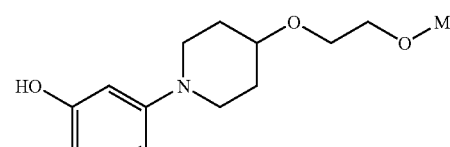 | EI+: 251 |
| 295 | 21 | 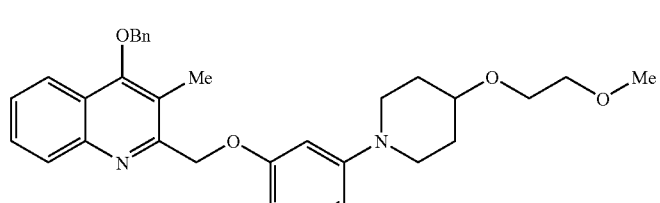 | ESI+: 513 |
| 51 | 51 | 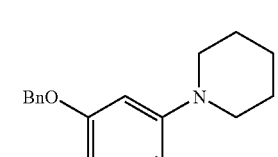 | EI+: 267 |
TABLE 46
| PEx | PSyn | Str | DATA |
|---|---|---|---|
| 296 | 35 | 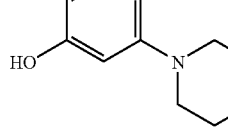 | ESI+: 178 |
| 297 | 21 | 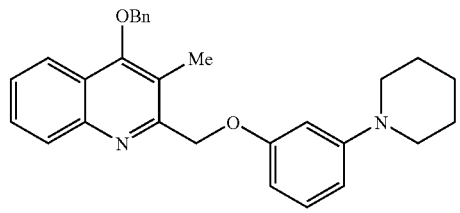 [SMILES: Cc1c(COc2cccc(N3CCCCC3)c2)nc2ccccc2c1OCc1ccccc1] | ESI+: 439 |
| 298 | 21 | 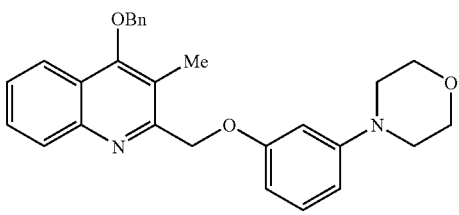 [SMILES: Cc1c(COc2cccc(N3CCOCC3)c2)nc2ccccc2c1OCc1ccccc1] | ESI+: 441 |
| 299 | 35 | 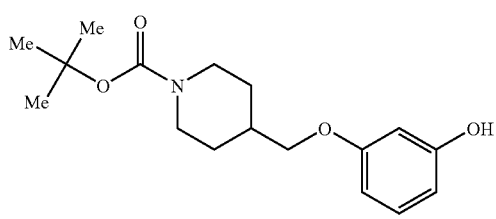 [SMILES: CC(C)(C)OC(=O)N1CCC(COc2cccc(O)c2)CC1] | EI+: 307 |

TABLE 46-continued

| PEx | PSyn | Str | DATA |
|---|---|---|---|
| 300 | 21 | [4-OBn-3-Me-quinolin-2-yl-CH2-O-(1,3-phenylene)-O-CH2-(piperidin-4-yl)-N-Boc] | ESI+: 569 |
| 43 | 43 | [4-OBn-3-Me-quinolin-2-yl-CH2-O-(1,3-phenylene)-O-CH2-(piperidin-4-yl)-NH] | ESI+: 469 |

TABLE 47

| PEx | PSyn | Str | DATA |
|---|---|---|---|
| 301 | 16 | [BnO-(piperidin-4-yl)-N-C(O)-CH2CH2-CH=CH2] | ESI+: 274 |
| 302 | 31 | [BnO-(piperidin-4-yl)-N-C(O)-CH2CH2-cyclopropyl] | ESI+: 288 |
| 303 | 35 | [HO-(piperidin-4-yl)-N-C(O)-CH2CH2-cyclopropyl] | NMR1: 0-0.06 (2H, m), 0.33-0.40 (2H, m), 0.64-0.77 (1H, m), 1.12-1.25 (1H, m), 1.25-1.37 (1H, m), 1.37 (2H, dd, J = 14.8, 7.2 Hz), 1.61-1.69 (1H, m), 1.69-1.77 (1H, m), 2.36 (2H, dd, J = 7.6, 7.2 Hz), 2.89-3.01 (1H, m), 3.08-3.19 (1H, m), 3.63-3.73 (2H, m), 3.85-3.96 (1H, m), 4.73 (1H, d, J = 4.0 Hz) |
| 304 | 21 | [6-F-4-OBn-3-Me-quinolin-2-yl-CH2-O-(piperidin-4-yl)-N-C(O)-CH2CH2-cyclopropyl] | ESI+: 477 |
| 305 | 23 | [BnO-(3-phenylene)-O-CH2CH2-C(Me)2-OH] | EI+: 286 |

TABLE 47-continued
| PEx | PSyn | Str | DATA |
|---|---|---|---|
| 306 | 35 | 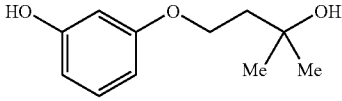 [SMILES: CC(C)(O)CCOc1cccc(O)c1] | EI+: 196 |
TABLE 48
| PEx | PSyn | Str | DATA |
|---|---|---|---|
| 307 | 21 | 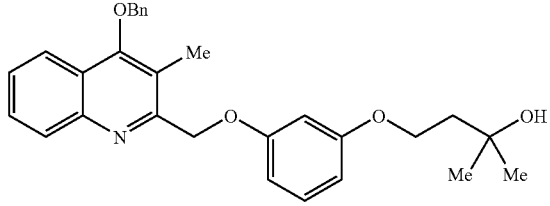 [SMILES: Cc1c(COc2cccc(OCCC(C)(C)O)c2)nc2ccccc2c1OCc1ccccc1] | ESI+: 458 |
| 308 | 16 | 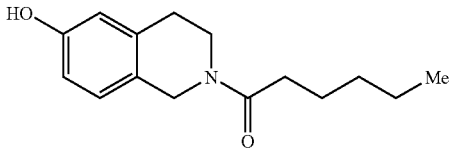 [SMILES: CCCCCC(=O)N1CCc2cc(O)ccc2C1] | EI+: 247 |
| 309 | 21 | 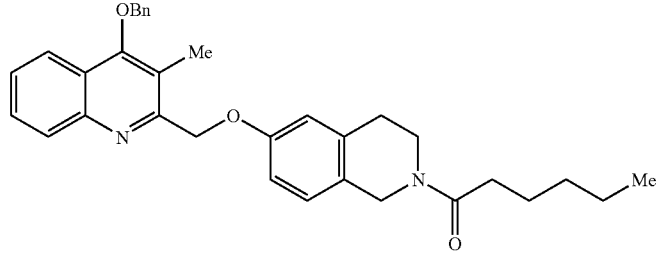 [SMILES: CCCCCC(=O)N1CCc2cc(OCc3nc4ccccc4c(OCc4ccccc4)c3C)ccc2C1] | ESI+: 509 |
| 50 | 50 | 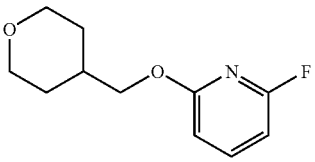 [SMILES: Fc1cccc(OCC2CCOCC2)n1] | EI+: 211 |
| 310 | 26 | 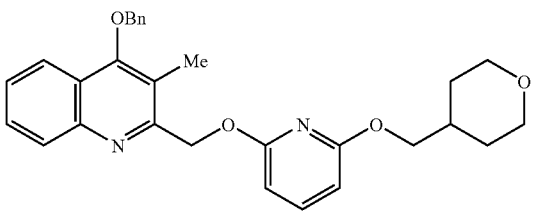 [SMILES: Cc1c(COc2cccc(OCC3CCOCC3)n2)nc2ccccc2c1OCc1ccccc1] | ESI+: 471 |
| 311 | 16 | 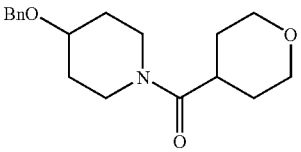 [SMILES: O=C(C1CCOCC1)N1CCC(OCc2ccccc2)CC1] | ESI+: 304 |

TABLE 49

| PEx | PSyn | Str | DATA |
|---|---|---|---|
| 312 | 24 | (structure) | ESI+: 214 |
| 313 | 21 | (structure) | ESI+: 493 |
| 314 | 16 | (structure) | ESI+: 318 |
| 315 | 24 | (structure) | ESI+: 228 |
| 316 | 21 | (structure) | ESI+: 507 |
| 317 | 16 | (structure) | EI+: 213 |

TABLE 50

| PEx | PSyn | Str | DATA |
|---|---|---|---|
| 318 | 21 | (structure) | ESI+: 475 |

TABLE 50-continued

| PEx | PSyn | Str | DATA |
|---|---|---|---|
| 319 | 42 | BnO-C6H4-O-piperidine-N-Boc | FAB+: 384 |
| 320 | 35 | HO-C6H4-O-piperidine-N-Boc | FAB+: 294 |
| 321 | 43 | BnO-C6H4-O-piperidine-NH · HCl | ESI+: 284 |
| 322 | 16 | BnO-C6H4-O-piperidine-N-C(O)Me | EI+: 325 |
| 323 | 35 | HO-C6H4-O-piperidine-N-C(O)Me | EI+: 235 |
| 324 | 21 | 4-OBn-3-Me-quinoline-2-CH2-O-C6H4-O-piperidine-N-C(O)Me | ESI+: 497 |

TABLE 51

| PEx | PSyn | Str | DATA |
|---|---|---|---|
| 325 | 16 | BnO-C6H4-O-piperidine-N-C(O)-tetrahydropyran | ESI+: 396 |
| 326 | 35 | HO-C6H4-O-piperidine-N-C(O)-tetrahydropyran | EI+: 305 |

TABLE 51-continued
| PEx | PSyn | Str | DATA |
|---|---|---|---|
| 327 | 21 | 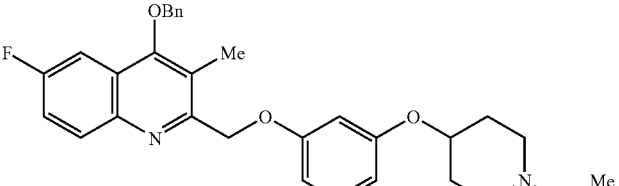 | ESI+: 567 |
| 328 | 16 | | ESI+: 410 |
| 329 | 35 | | EI+: 319 |
| 330 | 21 | | ESI+: 581 |
TABLE 52
| PEx | PSyn | Str | DATA |
|---|---|---|---|
| 331 | 21 | 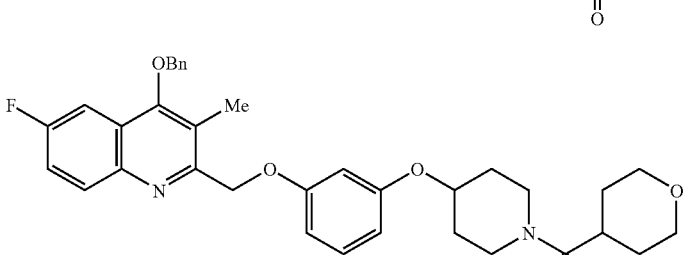 | ESI+: 515 |
| 332 | 21 | | ESI+: 585 |

TABLE 52-continued
| PEx | PSyn | Str | DATA |
|---|---|---|---|
| 333 | 21 | 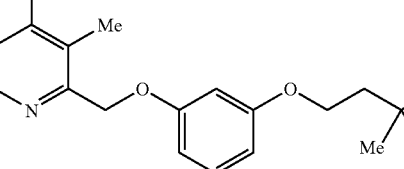 | ESI+: 599 |
| 334 | 21 | | ESI+: 489 |
| 335 | 21 | | NMR1: 2.04(3H, s), 2.44(3H, s), 3.06-3.13(2H, m), 3.13-3.20(2H, m), 3.51-3.60(4H, m), 5.13(2H, s), 5.34(2H, s), 6.5$_2$-$_6$.61(2H, m), 6.66-6.71(1H, m), 7.14(1H, dd, J = 8.4, 8.4 Hz), 7.38-7.47(3H, m), 7.50-7.57(2H, m), 7.61-7.70(2H, m), 8.10(1H, dd, J = 10.0, 5.2 Hz) |
TABLE 53
| PEx | PSyn | Str | DATA |
|---|---|---|---|
| 336 | 21 | 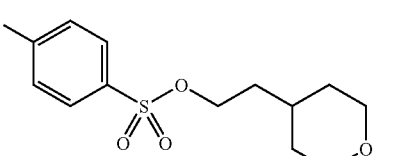 | ESI+: 476 |
| 52 | 52 | 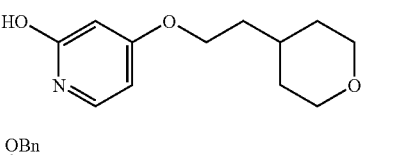 | NMR2: 1.14-1.30(2H, m), 1.43-1.53(2H, m), 1.54-1.71(3H, m), 2.46(3H, s), 3.26-3.37(2H, m), 3.86-3.94(2H, m), 4.08(2H, t, J = 6.3 Hz), 7.35(2H, d, J = 8.2 Hz), 7.80(2H, d, J = 8.2 Hz) |
| 32 | 32 | | ESI+: 224 |
| 337 | 21 | 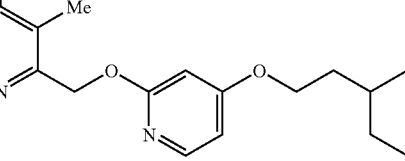 | ESI+: 485 |

TABLE 53-continued

| PEx | PSyn | Str | DATA |
|-----|------|-----|------|
| 338 | 42 | BnO-C6H4-O-CH2-C(O)-Me | EI+: 256 |
| 53 | 53 | BnO-C6H4-O-CH2-C(Me)2-OH | EI+: 272 |

TABLE 54

| PEx | PSyn | Str | DATA |
|-----|------|-----|------|
| 339 | 35 | HO-C6H4-O-CH2-C(Me)2-OH | EI+: 182 |
| 340 | 21 | 4-OBn, 6-F, 3-Me-quinolin-2-yl-CH2-O-C6H4-O-CH2-C(Me)2-OH | ESI+: 462 |
| 341 | 21 | 4-OBn, 6-F, 3-Me-quinolin-2-yl-CH2-O-pyridin-2-yl-O-CH2CH2-(tetrahydropyran-4-yl) | ESI+: 503 |
| 342 | 16 | 6-HO-1,2,3,4-tetrahydroisoquinolin-2-yl-C(O)-CH2-(tetrahydropyran-4-yl) | ESI+: 276 |
| 343 | 21 | 4-OBn, 6-F, 3-Me-quinolin-2-yl-CH2-O-(1,2,3,4-tetrahydroisoquinolin-6-yl-2-C(O)-CH2-tetrahydropyran-4-yl) | ESI+: 555 |

TABLE 54-continued
| PEx | PSyn | Str | DATA |
|---|---|---|---|
| 344 | 51 | 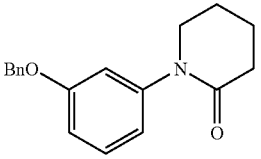 [SMILES: O=C1CCCCN1c1cccc(OCc2ccccc2)c1] | ESI+: 282 |
TABLE 55
| PEx | PSyn | Str | DATA |
|---|---|---|---|
| 345 | 35 | 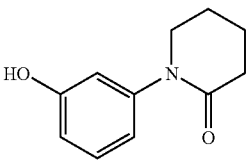 [SMILES: O=C1CCCCN1c1cccc(O)c1] | ESI+: 192 |
| 346 | 21 | 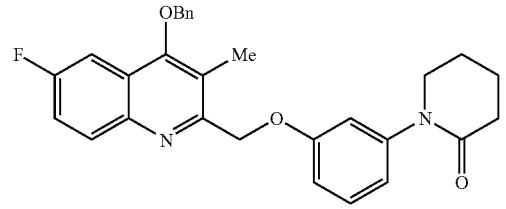 [SMILES: Cc1c(COc2cccc(N3CCCCC3=O)c2)nc2ccc(F)cc2c1OCc1ccccc1] | ESI+: 471 |
| 347 | 32 | 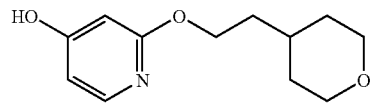 [SMILES: Oc1ccnc(OCCC2CCOCC2)c1] | ESI−: 222 |
| 348 | 21 | 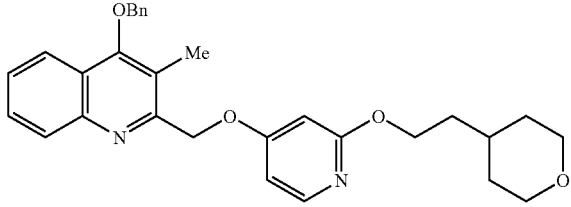 [SMILES: Cc1c(COc2ccnc(OCCC3CCOCC3)c2)nc2ccccc2c1OCc1ccccc1] | ESI+: 485 |
| 349 | 32 | 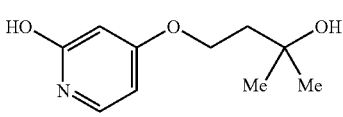 | FAB+: 198 |
| 350 | 21 | 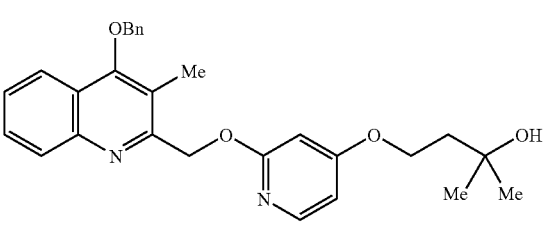 [SMILES: Cc1c(COc2cc(OCCC(C)(C)O)ccn2)nc2ccccc2c1OCc1ccccc1] | ESI+: 459 |
| 351 | 42 | 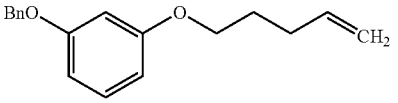 [SMILES: C=CCCCOc1cccc(OCc2ccccc2)c1] | EI+: 268 |

TABLE 56

| PEx | PSyn | Str | DATA |
|---|---|---|---|
| 54 | 54 | | EI+: 284 |
| 352 | 53 | | EI+: 300 |
| 353 | 24 | | EI+: 210 |
| 354 | 21 | | ESI+: 472 |
| 355 | 21 | | ESI+: 490 |
| 356 | 16 | | FAB+: 262 |
| 357 | 21 | | ESI+: 541 |

TABLE 57

| PEx | PSyn | Str | DATA |
|---|---|---|---|
| 358 | 16 | | FAB+: 276 |

TABLE 57-continued
| PEx | PSyn | Str | DATA |
|---|---|---|---|
| 359 | 21 | 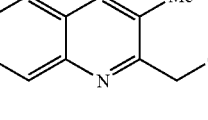 | ESI+: 555 |
| 360 | 16 | 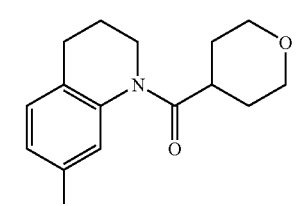 | FAB+: 262 |
| 361 | 21 | 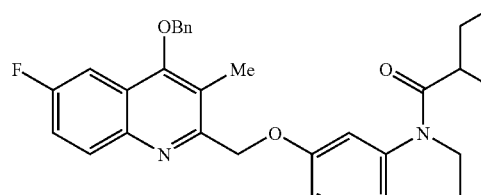 | ESI+: 541 |
| 362 | 16 | 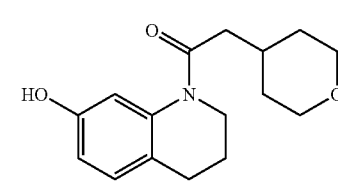 | FAB+: 276 |
| 363 | 21 | 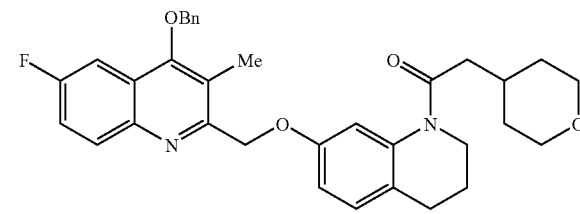 [SMILES: Cc1c(COc2ccc3c(c2)N(C(=O)CC2CCOCC2)CCC3)nc2ccc(F)cc2c1OCc1ccccc1] | ESI+: 555 |
TABLE 58
| PEx | PSyn | Str | DATA |
|---|---|---|---|
| 364 | 16 | 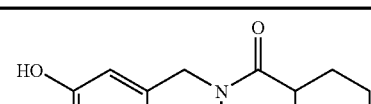 | FAB+: 262 |
| 365 | 21 | 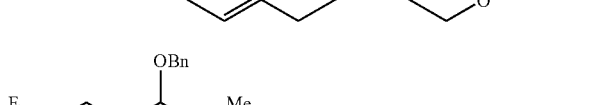 | ESI+: 541 |

TABLE 58-continued

| PEx | PSyn | Str | DATA |
|---|---|---|---|
| 366 | 16 | | EI+: 275 |
| 367 | 21 | | ESI+: 555 |
| 368 | 16 | | FAB+: 262 |
| 369 | 21 | | ESI+: 541 |

TABLE 59

| PEx | PSyn | Str | DATA |
|---|---|---|---|
| 370 | 16 | | ESI+: 276 |
| 371 | 21 | | ESI+: 555 |

TABLE 59-continued

| PEx | PSyn | Str | DATA |
|---|---|---|---|
| 372 | 16 | | FAB+: 262 |
| 373 | 21 | | ESI+: 541 |
| 374 | 52 | | CI+: 301 |
| 375 | 32 | | EI+: 328 |
| 376 | 35 | | EI+: 238 |

TABLE 60

| PEx | PSyn | Str | DATA |
|---|---|---|---|
| 377 | 21 | | ESI+: 500 |
| 378 | 52 | | EI+: 270 |
| 379 | 32 | | EI+: 209 |

TABLE 60-continued
| PEx | PSyn | Str | DATA |
|---|---|---|---|
| 380 | 21 | 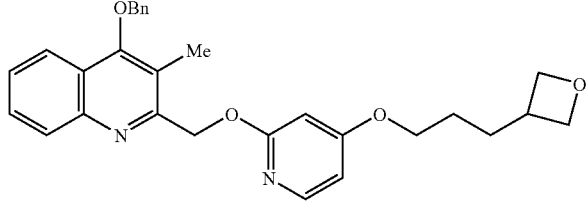 [SMILES: Cc1c(COc2cc(OCCCC3COC3)ccn2)nc2ccccc2c1OCc1ccccc1] | ESI+: 471 |
| 381 | 21 | 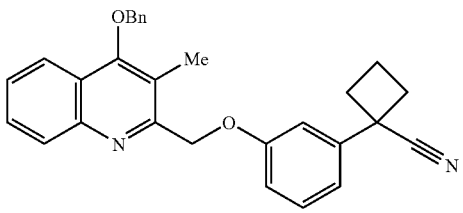 [SMILES: Cc1c(COc2cccc(C3(C#N)CCC3)c2)nc2ccccc2c1OCc1ccccc1] | ESI+: 435 |
| 382 | 32 | 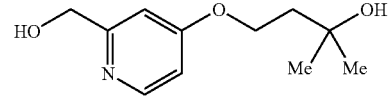 [SMILES: CC(C)(O)CCOc1ccnc(CO)c1] | ESI+: 212 |
TABLE 61
| PEx | PSyn | Str | DATA |
|---|---|---|---|
| 383 | 33 | 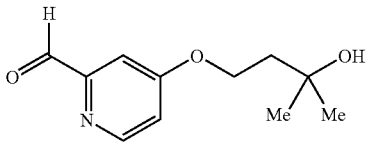 [SMILES: CC(C)(O)CCOc1ccnc(C=O)c1] | NMR2: 1.33(6H, s), 2.04(2H, t, J = 6.1 Hz), 3.91(1H, br s), 4.29(2H, t, J = 6.6 Hz), 7.03(1H, dd, J = 5.6, 2.5 Hz), 7.49(1H, d, J = 2.5 Hz), 8.59(1H, d, J = 5.6 Hz), 10.04(1H, s) |
| 384 | 25 | 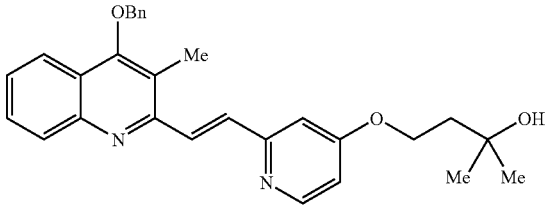 [SMILES: Cc1c(/C=C/c2cc(OCCC(C)(C)O)ccn2)nc2ccccc2c1OCc1ccccc1] | ESI+: 455 |
| 385 | 32 | 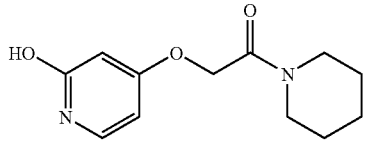 [SMILES: O=C(COc1ccnc(O)c1)N1CCCCC1] | ESI+: 237 |
| 386 | 21 | 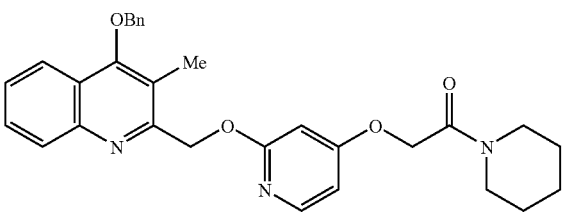 [SMILES: Cc1c(COc2cc(OCC(=O)N3CCCCC3)ccn2)nc2ccccc2c1OCc1ccccc1] | ESI+: 498 |

TABLE 61-continued

| PEx | PSyn | Str | DATA |
|---|---|---|---|
| 387 | 45 | (2-hydroxypyridin-4-yl)-C(O)NH-CH2CH2-(tetrahydropyran-4-yl) | ESI−: 249 |
| 388 | 21 | 4-OBn-3-Me-quinolin-2-yl-CH2-O-(pyridin-2-yl)-4-C(O)NH-CH2CH2-(tetrahydropyran-3-yl) | ESI−: 510 |

TABLE 62

| PEx | PSyn | Str | DATA |
|---|---|---|---|
| 389 | 32 | HO-(pyridin-2-yl)-4-O-CH2CH2CH2-O-Me | ESI+: 184 |
| 390 | 21 | 4-OBn-3-Me-quinolin-2-yl-CH2-O-(pyridin-2-yl)-4-O-CH2CH2CH2-O-Me | ESI+: 445 |
| 391 | 32 | HO-(pyridin-2-yl)-4-O-CH2CH2-(4-OH-tetrahydropyran-4-yl) | ESI+: 240 |
| 392 | 21 | 4-OBn-3-Me-quinolin-2-yl-CH2-O-(pyridin-2-yl)-4-O-CH2CH2-(4-OH-tetrahydropyran-4-yl) | ESI+: 501 |
| 393 | 32 | tBuO-C(O)-N(tetrahydroisoquinoline)-6-O-CH2-(tetrahydropyran-4-yl) | NMR2: 1.36-1.54(2H, m), 1.49(9H, s), 1.70-1.81(2H, m), 2.05(1H, m), 2.79(2H, t, J = 6 Hz), 3.44(2H, ddd, J = 11.7, 11.7, 1.7 Hz), 3.62(2H, br s), 3.78(2H, d, J = 6.5 Hz), 3.96-4.06(2H, m), 4.50(2H, s), 6.66(1H, d, J = 2 Hz), 6.74(1H, dd, J = 8.5, 2 Hz), 7.01(1H, d, J = 8.5 Hz) |

TABLE 62-continued
| PEx | PSyn | Str | DATA |
|---|---|---|---|
| 394 | 43 | 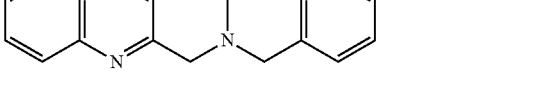 | ESI+: 248 |
TABLE 63
| PEx | PSyn | Str | DATA |
|---|---|---|---|
| 395 | 55 | 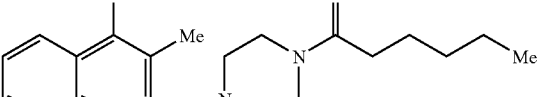 | ESI+: 509 |
| 55 | 55 | 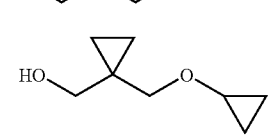 | ESI+: 446 |
| 396 | 26 | 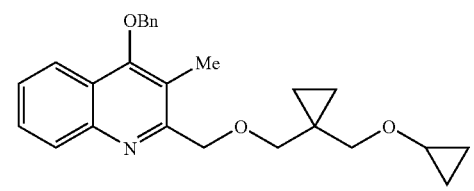 [SMILES: Cc1c(COCC2(COC3CC3)CC2)nc2ccccc2c1OCc1ccccc1] | CI+: 143 |
| 397 | 21 | 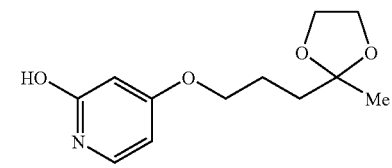 [SMILES: CC1(CCCOc2ccnc(O)c2)OCCO1] | ESI+: 404 |
| 398 | 32 | 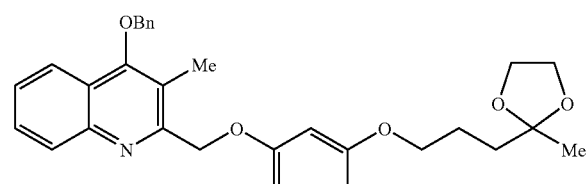 | ESI+: 240 |
| 399 | 21 | 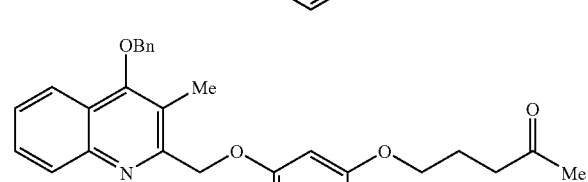 | ESI+: 501 |
| 400 | 49 | | ESI+: 457 |

TABLE 64
| PEx | PSyn | Str | DATA |
|---|---|---|---|
| 401 | 52 | 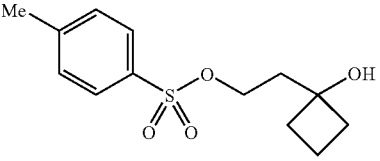 [SMILES: Cc1ccc(S(=O)(=O)OCCC2(O)CCC2)cc1] | CI+: 271 |
| 402 | 32 | 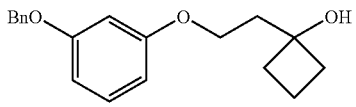 [SMILES: OC1(CCOc2cccc(OCc3ccccc3)c2)CCC1] | EI+: 298 |
| 403 | 35 | 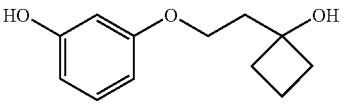 [SMILES: Oc1cccc(OCCC2(O)CCC2)c1] | NMR2: 1.50-1.63(2H, m), 1.73-1.87(1H, m), 2.05-2.19(6H, m), 4.19(2H, t, J = 5.9 Hz), 5.73(1H, s), 6.40(1H, m), 6.48(2H, m), 7.14(1H, m) |
| 404 | 21 | 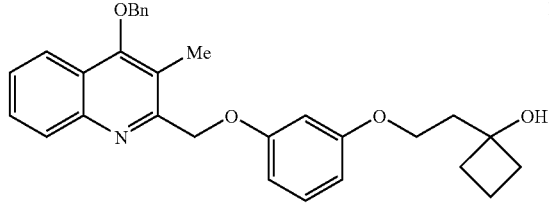 [SMILES: Cc1c(COc2cccc(OCCC3(O)CCC3)c2)nc2ccccc2c1OCc1ccccc1] | ESI+: 470 |
| 405 | 32 | 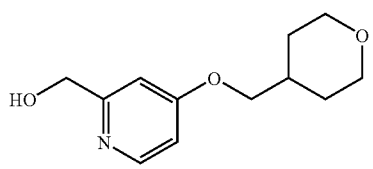 [SMILES: OCc1cc(OCC2CCOCC2)ccn1] | ESI+: 224 |
| 406 | 33 | 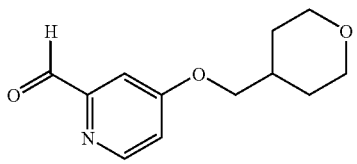 [SMILES: O=Cc1cc(OCC2CCOCC2)ccn1] | NMR2: 1.41-1.54(2H, m), 1.72-1.81(2H, m), 2.05-2.18(1H, m), 3.40-3.51(2H, m), 3.93(2H, d, J = 6.5 Hz), 4.04(2H, dd, J = 11.6, 4.3 Hz), 7.01(1H, dd, J = 5.6, 2.6 Hz), 7.46(1H, d, J = 2.5 Hz), 8.59(1H, d, J = 5.6 Hz), 10.04 (1H, s) |
TABLE 65
| PEx | PSyn | Str | DATA |
|---|---|---|---|
| 407 | 25 | 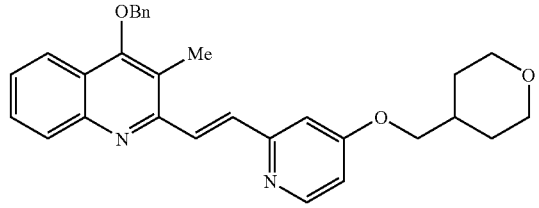 [SMILES: Cc1c(/C=C/c2cc(OCC3CCOCC3)ccn2)nc2ccccc2c1OCc1ccccc1] | ESI+: 467 |
| 56 | 56 | 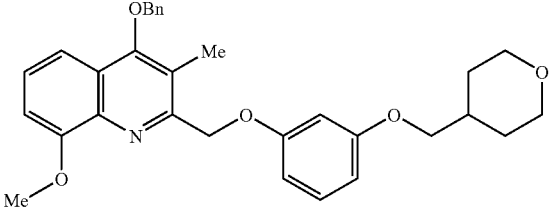 [SMILES: COc1cccc2c(OCc3ccccc3)c(C)c(COc3cccc(OCC4CCOCC4)c3)nc12] | ESI+: 500 |

TABLE 65-continued

| PEx | PSyn | Str | DATA |
|---|---|---|---|
| 408 | 51 | BnO-phenyl-morpholin-3-one | ESI+: 284 |
| 409 | 35 | HO-phenyl-morpholin-3-one | ESI+: 194 |
| 410 | 21 | 4-OBn-3-Me-quinoline-2-CH2-O-phenyl-morpholin-3-one | ESI+: 455 |
| 411 | 32 | HO-pyridine-O-CH2CH2-C(Me)2-OMe | ESI+: 212 |
| 412 | 21 | 4-OBn-3-Me-quinoline-2-CH2-O-pyridine-O-CH2CH2-C(Me)2-OMe | ESI+: 473 |

TABLE 66

| PEx | PSyn | Str | DATA |
|---|---|---|---|
| 413 | 29 | Br-pyridine-O-CH2CH2-tetrahydropyran | ESI+: 286, 288 |
| 414 | 57 | HO-pyridine-O-CH2CH2-tetrahydropyran | ESI+: 224 |
| 415 | 21 | 4-OBn-3-Me-quinoline-2-CH2-O-pyridine-O-CH2CH2-tetrahydropyran | ESI+: 485 |

TABLE 66-continued

| PEx | PSyn | Str | DATA |
|---|---|---|---|
| 416 | 53 | | ESI+: 473 |
| 417 | 32 | | FAB+: 168 |
| 418 | 21 | | ESI+: 429 |
| 419 | 53 | | ESI+: 445 |

TABLE 67

| PEx | PSyn | Str | DATA |
|---|---|---|---|
| 420 | 32 | | ESI+: 196 |
| 421 | 21 | | ESI+: 457 |
| 422 | 21 | | ESI+: 512 |

TABLE 67-continued

| PEx | PSyn | Str | DATA |
|---|---|---|---|
| 423 | 32 | 5-bromo-3-(3-hydroxy-3-methylbutoxy)pyridine | ESI+: 260, 262 |
| 424 | 57 | 3-hydroxy-5-(3-hydroxy-3-methylbutoxy)pyridine | ESI+: 198 |
| 425 | 21 | 4-(benzyloxy)-3-methyl-2-{[(5-(3-hydroxy-3-methylbutoxy)pyridin-3-yl)oxy]methyl}quinoline | ESI+: 459 |
| 426 | 66 | 3-(benzyloxy)phenyl 2-(4-methoxytetrahydro-2H-pyran-4-yl)ethyl ether | EI+: 342 |
| 427 | 35 | 3-hydroxyphenyl 2-(4-methoxytetrahydro-2H-pyran-4-yl)ethyl ether | EI+: 252 |

TABLE 68

| PEx | PSyn | Str | DATA |
|---|---|---|---|
| 428 | 21 | 4-(benzyloxy)-3-methyl-2-({3-[2-(4-methoxytetrahydro-2H-pyran-4-yl)ethoxy]phenoxy}methyl)quinoline | ESI+: 514 |
| 429 | 32 | tert-butyl 4-(3-hydroxy-3-methylbutoxy)piperidine-1-carboxylate | EI+: 287 |
| 430 | 43 | 4-(3-hydroxy-3-methylbutoxy)piperidine HCl | ESI+: 188 |
| 431 | 51 | 1-[3-(benzyloxy)phenyl]-4-(3-hydroxy-3-methylbutoxy)piperidine | EI+: 369 |

TABLE 68-continued
| PEx | PSyn | Str | DATA |
|---|---|---|---|
| 432 | 35 | 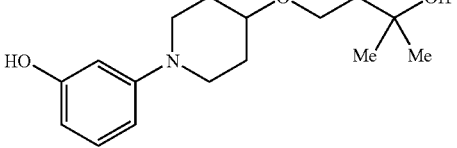 | EI+: 279 |
| 433 | 21 | 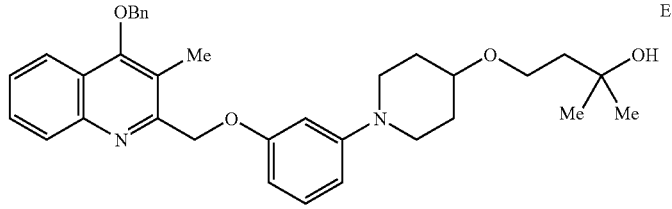 | ESI+: 541 |
| 434 | 52 | 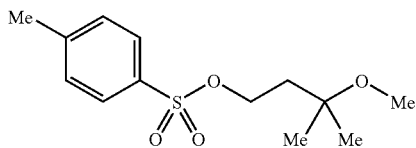 [SMILES: COC(C)(C)CCOS(=O)(=O)c1ccc(C)cc1] | FAB+: 273 |
TABLE 69
| PEx | PSyn | Str | DATA |
|---|---|---|---|
| 435 | 32 | 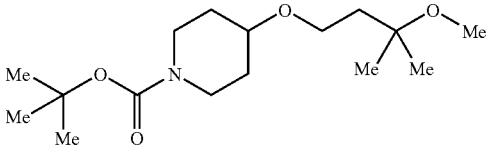 [SMILES: COC(C)(C)CCOC1CCN(C(=O)OC(C)(C)C)CC1] | EI+: 301 |
| 436 | 43 | 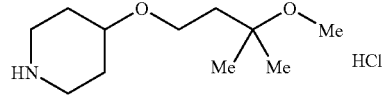 [SMILES: COC(C)(C)CCOC1CCNCC1 ; Cl] | ESI+: 202 |
| 437 | 51 | 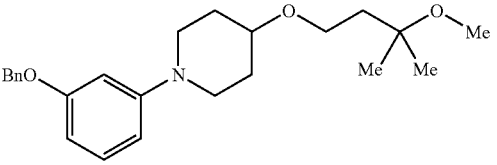 [SMILES: COC(C)(C)CCOC1CCN(c2cccc(OCc3ccccc3)c2)CC1] | EI+: 383 |
| 438 | 35 | 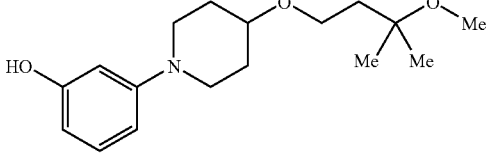 | EI+: 293 |
| 439 | 21 | 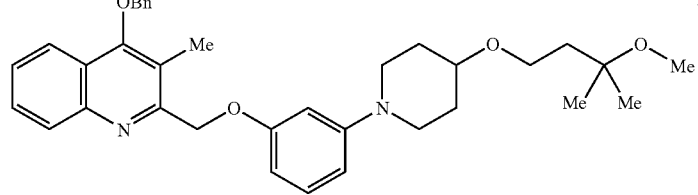 | ESI+: 555 |

TABLE 69-continued
| PEx | PSyn | Str | DATA |
|---|---|---|---|
| 440 | 52 | 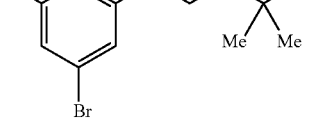 | EI+: 256 |
| 441 | 32 | 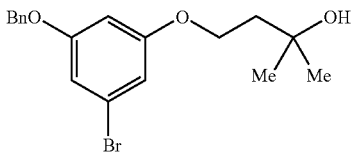 [SMILES: CC(C)(O)CCOc1cc(Br)cc(OCc2ccccc2)c1] | FAB+: 196 |
| 442 | 21 | 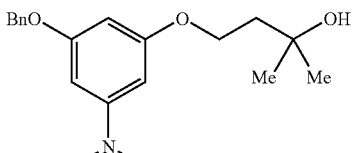 | ESI+: 457 |
TABLE 70
| PEx | PSyn | Str | DATA |
|---|---|---|---|
| 443 | 32 | 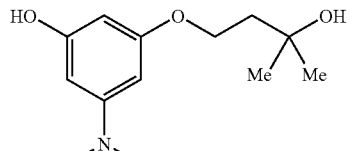 | EI+: 276, 278 |
| 444 | 26 | | NMR2: 1.30(6H, s), 1.97(2H, t, J = 6.3 Hz), 4.12(2H, t, J = 6.3 Hz), 4.70(1H, m), 5.01(2H, s), 6.46(1H, m), 6.69(1H, m), 6.76(1H, m), 7.38(5H, m) |
| 445 | 51 | | EI+: 371 |
| 446 | 35 | | EI+: 281 |

TABLE 70-continued
| PEx | PSyn | Str | DATA |
|---|---|---|---|
| 447 | 21 | 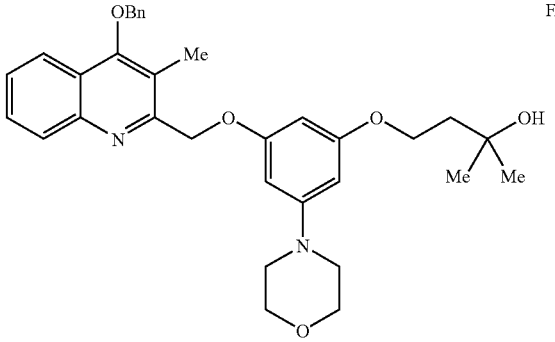 | FAB+: 543 |
TABLE 71
| PEx | PSyn | Str | DATA |
|---|---|---|---|
| 448 | 32 | 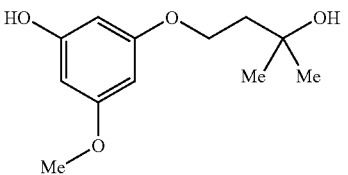 [SMILES: COc1cc(O)cc(OCCC(C)(C)O)c1] | NMR2: 1.32(6H, s), 1.98(2H, t, J = 6.0 Hz), 3.76(3H, s), 4.15(2H, t, J = 6.0 Hz), 5.97-6.02(1H, m), 6.0$_{2-6}$.08(2H, m) |
| 449 | 21 | 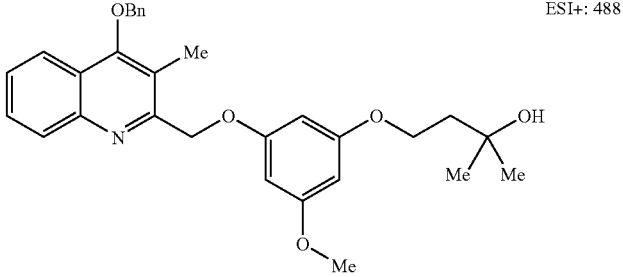 | ESI+: 488 |
| 450 | 51 | 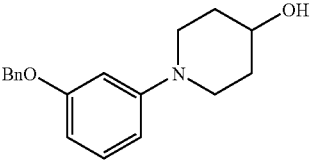 [SMILES: OC1CCN(c2cccc(OCc3ccccc3)c2)CC1] | EI+: 283 |
| 451 | 35 | 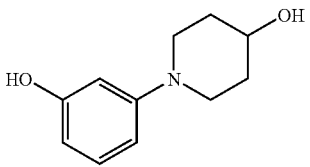 [SMILES: Oc1cccc(N2CCC(O)CC2)c1] | EI+: 193 |
| 452 | 21 | 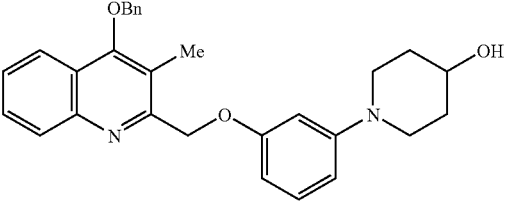 [SMILES: Cc1c(COc2cccc(N3CCC(O)CC3)c2)nc2ccccc2c1OCc1ccccc1] | ESI+: 455 |

TABLE 72

| PEx | PSyn | Str | DATA |
|---|---|---|---|
| 453 | 51 | BnO-phenyl-N(piperidine-4-OH, 4-Me) | NMR2: 1.29(3H, s), 1.56(1H, s), 1.64-1.81(4H, m), 3.14-3.22(2H, m), 3.30-3.37(2H, m), 5.04(2H, s), 6.46(1H, dd, J = 1.6, 7.5 Hz), 6.56-6.60(2H, m), 7.16(1H, t, J = 8.6 Hz), 7.29-7.45(5H, m) |
| 454 | 35 | HO-phenyl-N(piperidine-4-OH, 4-Me) | EI+: 207 |
| 455 | 21 | 4-OBn-3-Me-quinoline-2-CH2-O-phenyl-N(piperidine-4-OH, 4-Me) | FAB+: 469 |
| 456 | 20 | BnO-pyridine-CH=CH-tetrahydropyran (cis) | NMR2: 1.44-1.57(2H, m), 1.66-1.74(2H, m), 3.39-3.54(3H, m), 3.92-4.01(2H, m), 5.12(2H, s), 5.58(1H, dd, J = 11.9, 9.5 Hz), 6.32(1H, d, J = 11.7 Hz), 7.10(1H, d, J = 8.8 Hz), 7.20(1H, dd, J = 8.6, 2.9 Hz), 7.29-7.46(5H, m), 8.37(1H, d, J = 3.2 Hz) ESI+: 296 |

TABLE 73

| PEx | PSyn | Str | DATA |
|---|---|---|---|
| 457 | 20 | BnO-pyridine-CH=CH-tetrahydropyran (trans) | NMR2: 1.46-1.66(2H, m), 1.68-1.77(2H, m), 2.34-2.48(1H, m), 3.42-3.52(2H, m), 3.98-4.05(2H, m), 5.11(2H, s), 6.42(1H, d, J = 16.0 Hz), 6.52(1H, dd, J = 16.0, 6.3 Hz), 7.17-7.50(7H, m), 8.30-8.33(1H, m) ESI+: 296 |
| 458 | 35 | HO-pyridine-CH2CH2-tetrahydropyran | ESI+: 208 |
| 459 | 21 | 4-OBn-3-Me-quinoline-2-CH2-O-pyridine-CH2CH2-tetrahydropyran | ESI+: 469 |

TABLE 73-continued
| PEx | PSyn | Str | DATA |
|---|---|---|---|
| 58 | 58 | 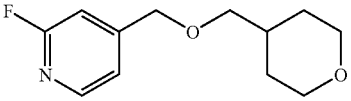 [SMILES: Fc1cc(COCC2CCOCC2)ccn1] | ESI+: 226 |
| 460 | 26 | 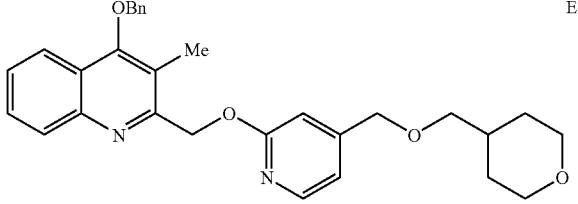 | ESI+: 485 |
TABLE 74
| PEx | PSyn | Str | DATA |
|---|---|---|---|
| 59 | 59 | 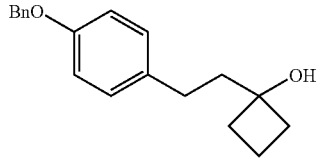 [SMILES: OC1(CCc2ccc(OCc3ccccc3)cc2)CCC1] | NMR2: 1.51-1.65(2H, m), 1.72-1.83(1H, m), 1.87-1.94(2H, m), 1.97-2.16(4H, m), 2.62-2.70(2H, m), 5.05(2H, s), 6.91(2H, d, J = 8.3 Hz), 7.14(2H, d, J = 8.7 Hz), 7.31-7.47(5H, m) |
| 461 | 35 | 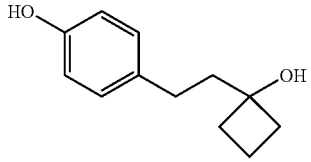 [SMILES: Oc1ccc(CCC2(O)CCC2)cc1] | ESI−: 191 |
| 462 | 21 | 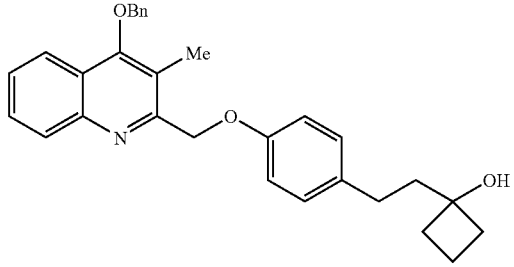 [SMILES: Cc1c(COc2ccc(CCC3(O)CCC3)cc2)nc2ccccc2c1OCc1ccccc1] | ESI+: 454 |
| 463 | 21 | 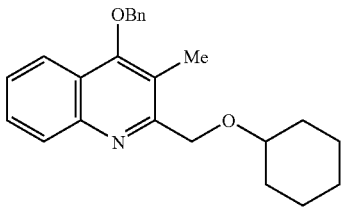 [SMILES: Cc1c(COC2CCCCC2)nc2ccccc2c1OCc1ccccc1] | ESI+: 362 |
| 464 | 21 | 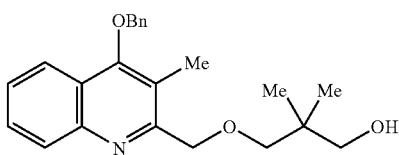 [SMILES: Cc1c(COCC(C)(C)CO)nc2ccccc2c1OCc1ccccc1] | EI+: 365 |

TABLE 74-continued

| PEx | PSyn | Str | DATA |
|---|---|---|---|
| 60 | 60 | (4-OBn, 3-Me quinoline)-2-CH₂-O-CH₂-C(Me)(Me)-CH₂-O-C(=O)-N(morpholine) | ESI+: 479 |

TABLE 75

| PEx | PSyn | Str | DATA |
|---|---|---|---|
| 465 | 21 | (4-OBn, 3-Me quinoline)-2-CH₂-O-CH₂CH₂-C(OH)(cyclohexyl) | ESI+: 406 |
| 466 | 16 | 4-hydroxypiperidine-N-C(=O)-cyclopentyl | NMR2: 1.40-1.57(2H, m), 1.52-1.63(2H, m), 1.69-1.79(2H, m), 1.78-1.86(4H, m), 1.85-199(2H, m), 2.91(1H, q, J = 8.1 Hz), 3.08-3.34(2H, m), 3.74-3.90(1H, m), 3.88-4.01(1H, m), 4.06-4.23(1H, m) |
| 467 | 21 | (4-OBn, 3-Me quinoline)-2-CH₂-O-(piperidin-4-yl)-N-C(=O)-cyclopentyl | ESI+: 459 |
| 468 | 21 | (4-OBn, 3-Me quinoline)-2-CH₂-O-(cyclohexyl)-NH-C(=O)-O-CH₂-Me | ESI+: 449 |
| 469 | 21 | (4-OBn, 3-Me quinoline)-2-CH₂-O-CH₂-(cyclopropyl)-CH₂-OH | FAB+: 364 |

TABLE 76
| PEx | PSyn | Str | DATA |
|---|---|---|---|
| 470 | 60 | 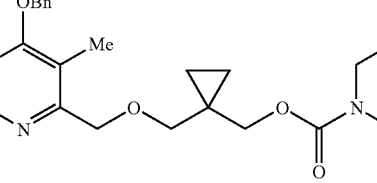 | ESI+: 477 |
| 471 | 20 | 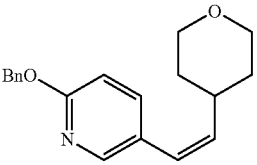 [SMILES: C(=C/C1CCOCC1)/c1ccc(OCc2ccccc2)nc1] | NMR2: 1.46-1.66(4H, m), 2.68-2.81(1H, m), 3.38-3.48(2H, m), 3.92–4.00(2H, m), 5.39(2H, s), 5.52(1H, dd, J = 11.6, 10.0 Hz), 6.27(1H, d, J = 11.6 Hz), 6.80(1H, d, J = 8.6 Hz), 7.28-7.43(3H, m), 7.43-7.50(3H, m), 8.09(1H, d, J = 2.3 Hz) |
| 472 | 20 | | NMR2: 1.53-1.62(2H, m), 1.66-1.74(2H, m), 2.29-2.43(1H, m), 3.42-3.51(2H, m), 3.98-4.04(2H, m), 5.37(2H, s), 6.05(1H, dd, J = 16.0, 6.7 Hz), 6.32(1H, d, J = 16.2 Hz), 6.77(1H, d, J = 8.6 Hz), 7.29-7.42(3H, m), 7.43-7.48(2H, m), 7.66(1H, dd, J = 8.7, 3.0 Hz), 8.08(1H, d, J = 2.5 Hz) |
| 473 | 35 | | ESI+: 208 |
TABLE 77
| PEx | PSyn | Str | DATA |
|---|---|---|---|
| 474 | 21 | 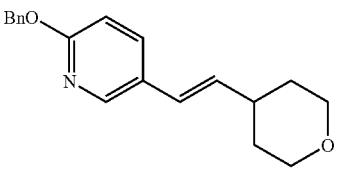 [SMILES: C(=C\C1CCOCC1)/c1ccc(OCc2ccccc2)nc1] | ESI+: 469 |
| 475 | 33 | 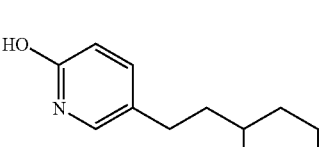 | NMR2: 0.68-0.85(2H, m), 0.89-1.05(2H, m), 1.49-1.72(2H, m), 1.68-1.84(1H, m), 1.88-2.06(2H, m), 2.45-2.63(1H, m), 2.80-3.17(1H, m), 3.07-3.46(1H, m), 3.92–4.50(2H, m), 9.70(1H, s) |

TABLE 77-continued

| PEx | PSyn | Str | DATA |
|-----|------|-----|------|
| 476 | 25 | (4-OBn, 3-Me quinoline)-2-CH=CH-(4-piperidinyl)-N-C(O)-cyclopropyl | ESI+: 427 |
| 477 | 36 | cyclopentyl-C(O)-N(piperazine)N-C(O)-N(imidazole) | NMR2: 1.50-1.66(2H, m), 1.71-1.83(2H, m), 1.77-1.94(4H, m), 2.91(1H, q, J = 8.7 Hz), 3.53-3.71(6H, m), 3.67-3.80(2H, m), 7.14(1H, s), 7.22(1H, s), 7.92(1H, s) |
| 478 | 37 | (4-OBn, 3-Me quinoline)-2-CH2-O-C(O)-N(piperazine)N-C(O)-cyclopentyl | ESI+: 488 |

TABLE 78

| PEx | PSyn | Str | DATA |
|-----|------|-----|------|
| 479 | 36 | (tetrahydropyran-4-yl)-CH2-NH-C(O)-N(imidazole) | NMR2: 1.28-1.41(1H, m), 1.35-1.46(1H, m), 1.59-1.73(2H, m), 1.81-2.02(1H, m), 3.33-3.46(2H, m), 3.34(2H, dd, J = 6.6, 6.6 Hz), 3.93-4.06(2H, m), 6.12–6.25(1H, m), 7.10(1H, s), 7.36(1H, s), 8.16(1H, s) |
| 480 | 22 | (4-OBn, 3-Me quinoline)-2-CH2-O-C(O)-NH-CH2-(tetrahydropyran-4-yl) | ESI+: 421 |
| 481 | 21 | (4-OBn, 3-Me quinoline)-2-CH2-O-(tetrahydropyran-4-yl) | ESI+: 364 |
| 482 | 16 | 6-HO-tetrahydroisoquinoline-2-C(O)-CH2-C(OH)(Me)(Me) | ESI+: 250 |

TABLE 78-continued
| PEx | PSyn | Str | DATA |
|---|---|---|---|
| 483 | 21 | 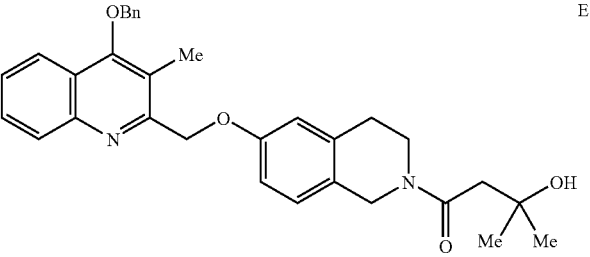 | ESI+: 511 |
TABLE 79
| PEx | PSyn | Str | DATA |
|---|---|---|---|
| 484 | 16 | 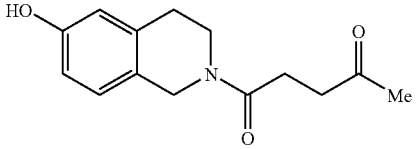 [SMILES: CC(=O)CCC(=O)N1CCc2cc(O)ccc2C1] | ESI+: 248 |
| 485 | 21 | 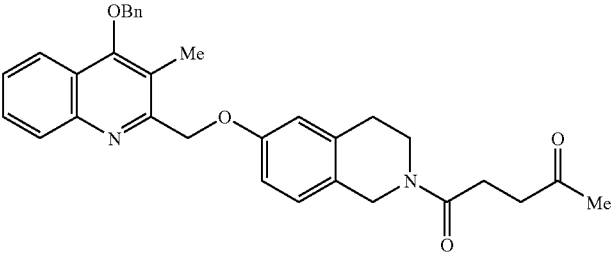 [SMILES: CC(=O)CCC(=O)N1CCc2cc(OCc3nc4ccccc4c(OCc4ccccc4)c3C)ccc2C1] | ESI+: 509 |
| 486 | 53 | 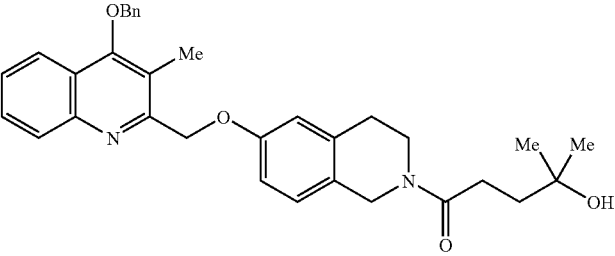 [SMILES: Cc1c(COc2ccc3c(c2)CCN(C(=O)CCC(C)(C)O)C3)nc2ccccc2c1OCc1ccccc1] | ESI+: 525 |
| 487 | 20 | 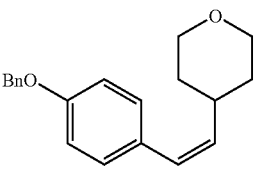 [SMILES: C(=C/C1CCOCC1)/c1ccc(OCc2ccccc2)cc1] | NMR2: 1.47-1.72(4H, m), 2.75-2.88(1H, m), 3.36-3.48(2H, m), 3.9$_{2-4}$.00(2H, m), 5.08(2H, s), 5.40(1H, dd, J = 11.7, 10.3 Hz), 6.32(1H, d, J = 11.7 Hz), 6.95(2H, d, J = 8.9 Hz), 7.18(2H, d, J = 8.9 Hz), 7.28-7.47(5H, m) |
| 488 | 35 | 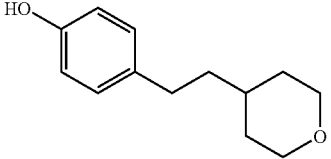 | NMR2: 1.24-1.37(2H, m), 1.44-1.69(5H, m), 2.56(2H, dd, J = 8.0, 7.6 Hz), 3.32-3.40(2H, m), 3.96(2H, dd, J = 11.4, 4.2 Hz), 4.65(1H, s), 6.75(2H, d, J = 8.5 Hz), 7.04(2H, d, J = 8.5 Hz) |

TABLE 80

| PEx | PSyn | Str | DATA |
|---|---|---|---|
| 489 | 21 | (structure) | ESI+: 468 |
| 61 | 61 | (structure) | NMR2: 1.71-1.88(6H, m), 1.88-2.06(4H, m), 2.82-2.89(2H, m), 5.19(2H, s), 7.05(2H, d, J = 8.8 Hz), 7.28(2H, d, J = 8.4 Hz), 7.43-7.61(5H, m) |
| 490 | 35 | (structure) | NMR2: 1.56-1.74(6H, m), 1.74-1.91(4H, m), 2.65-2.74(2H, m), 6.75(2H, d, J = 8.3 Hz), 7.08(2H, d, J = 8.3 Hz) |
| 491 | 21 | (structure) | ESI+: 468 |
| 492 | 52 | (structure) | FAB+: 259 |
| 493 | 26 | (structure) | ESI+: 366 |

TABLE 81
| PEx | PSyn | Str | DATA |
|---|---|---|---|
| 494 | 21 | 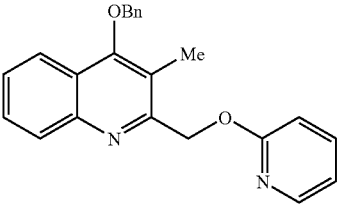 [SMILES: Cc1c(COc2ccccn2)nc2ccccc2c1OCc1ccccc1] | NMR2: 2.46(3H, s), 5.10(2H, s), 5.66(2H, s), 6.86(1H, d, J = 7.6 Hz), 6.88-6.94(1H, m), 7.37-7.47(3H, m), 7.48-7.52(2H, m), 7.51-7.55(1H, m), 7.60(1H, ddd, J = 9.2, 7.2, 2.4 Hz), 7.63-7.70(1H, m), 8.04-8.08(1H, m), 8.08-8.15(1H, m), 8.17-8.22(1H, m) |
| 495 | 26 | 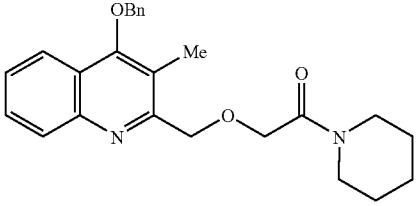 [SMILES: Cc1c(COCC(=O)N2CCCCC2)nc2ccccc2c1OCc1ccccc1] | ESI+: 405 |
| 496 | 25 | 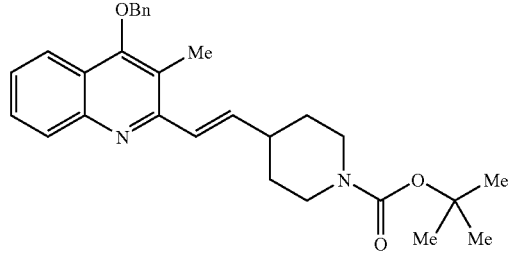 [SMILES: Cc1c(/C=C/C2CCN(C(=O)OC(C)(C)C)CC2)nc2ccccc2c1OCc1ccccc1] | NMR2: 1.42-1.55(11H, m), 1.82-1.91(2H, m), 2.40(3H, s), 2.41-2.49(1H, m), 2.74-2.90(2H, m), 4.06-4.30(2H, m), 5.05(2H, s), 6.81(1H, dd, J = 15.4, 1.2 Hz), 7.04(1H, dd, J = 15.5, 6.8 Hz), 7.37-7.47(4H, m), 7.49-7.53(2H, m), 7.59-7.64(1H, m), 7.97-8.05(2H, m) ESI+: 459 |
TABLE 82
| PEx | PSyn | Str | DATA |
|---|---|---|---|
| 497 | 43 | 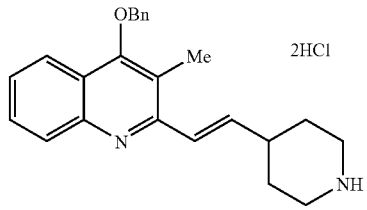 [SMILES: Cc1c(/C=C/C2CCNCC2)nc2ccccc2c1OCc1ccccc1 ; "2HCl"] | NMR1: 1.64-1.82(2H, m), 1.97-2.08(2H, m), 2.44(3H, s), 2.65-2.78(1H, m), 2.90-3.08(2H, m), 3.27-3.36(2H, m), 5.29(2H, s), 6.93(1H, d, J = 15.9 Hz), 7.17(1H, dd, J = 15.5, 5.6 Hz), 7.38-7.50(3H, m), 7.53-7.59(2H, m), 7.66-7.76(1H, m), 7.87-7.97(1H, m), 8.12(1H, d, J = 8.1 Hz), 8.3$_{1-8}$.43(1H, m), 8.6$_{3-8}$.79(1H, m), 8.79-8.94(1H, m) ESI+: 359 |
| 498 | 16 | 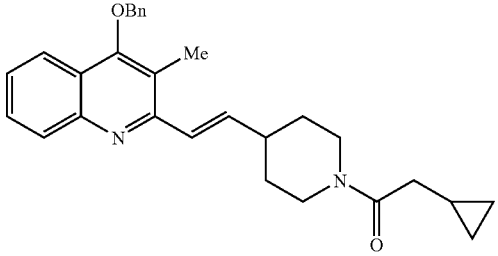 [SMILES: Cc1c(/C=C/C2CCN(C(=O)CC3CC3)CC2)nc2ccccc2c1OCc1ccccc1] | ESI+: 441 |

TABLE 82-continued
| PEx | PSyn | Str | DATA |
|---|---|---|---|
| 499 | 16 | 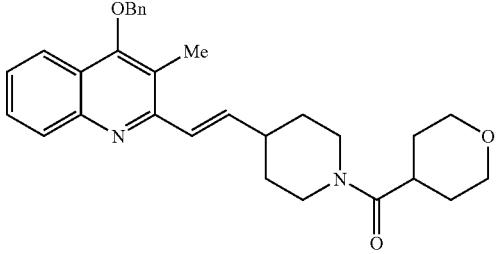 [SMILES: Cc1c(/C=C/C2CCN(C(=O)C3CCOCC3)CC2)nc2ccccc2c1OCc1ccccc1] | ESI+: 471 |
TABLE 83
| PEx | PSyn | Str | DATA |
|---|---|---|---|
| 62 | 62 | 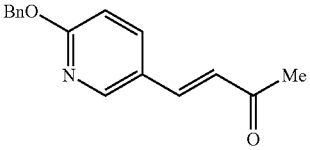 [SMILES: CC(=O)/C=C/c1ccc(OCc2ccccc2)nc1] | NMR2: 2.38(3H, s), 5.42(2H, s), 6.64(1H, d, J = 16.1 Hz), 6.85(1H, d, J = 8.8 Hz), 7.28-7.42(3H, m), 7.43-7.51(3H, m), 7.82(1H, dd, J = 8.6, 2.5 Hz), 8.31(1H, d, J = 2.5 Hz) |
| 500 | 35 | 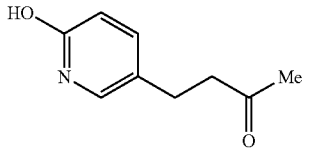 [SMILES: CC(=O)CCc1ccc(O)nc1] | NMR2: 2.14(3H, s), 2.61-2.73(4H, m), 6.54(1H, d, J = 9.4 Hz), 7.17(1H, d, J = 2.4 Hz), 7.35(1H, dd, J = 9.3, 2.4 Hz) ESI+: 166 |
| 501 | 21 | 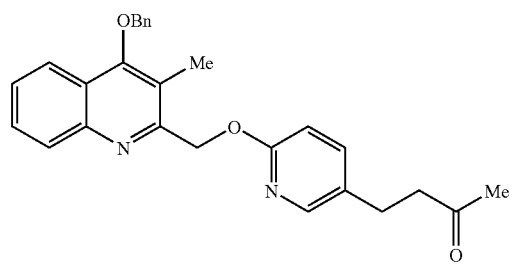 [SMILES: CC(=O)CCc1ccc(OCc2nc3ccccc3c(OCc3ccccc3)c2C)nc1] | ESI+: 427 |
| 502 | 53 | 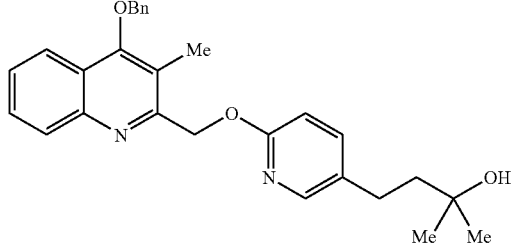 [SMILES: Cc1c(COc2ccc(CCC(C)(C)O)cn2)nc2ccccc2c1OCc1ccccc1] | ESI+: 443 |
| 503 | 16 | 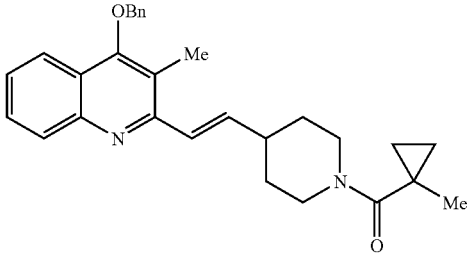 [SMILES: Cc1c(/C=C/C2CCN(C(=O)C3(C)CC3)CC2)nc2ccccc2c1OCc1ccccc1] | ESI+: 441 |

TABLE 84
| PEx | PSyn | Str | DATA |
|---|---|---|---|
| 504 | 16 | 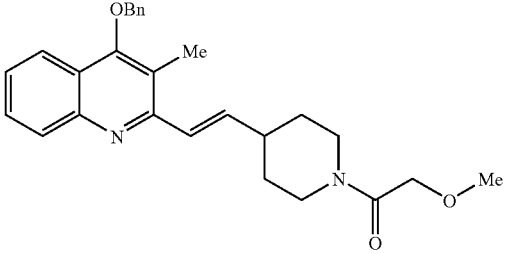 [SMILES: COCC(=O)N1CCC(/C=C/c2nc3ccccc3c(OCc3ccccc3)c2C)CC1] | ESI+: 431 |
| 505 | 21 | 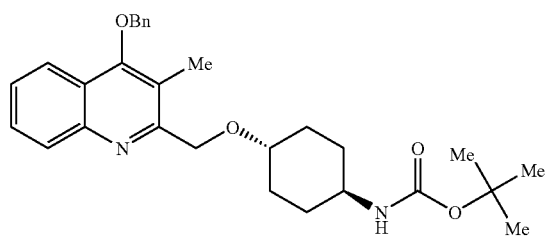 [SMILES: Cc1c(CO[C@H]2CC[C@H](NC(=O)OC(C)(C)C)CC2)nc2ccccc2c1OCc1ccccc1] | ESI+: 477 |
| 506 | 43 | 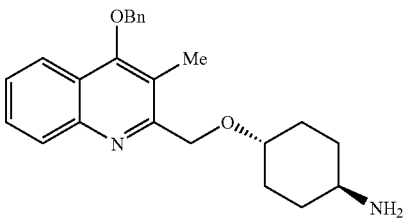 [SMILES: Cc1c(CO[C@H]2CC[C@H](N)CC2)nc2ccccc2c1OCc1ccccc1] | ESI+: 377 |
| 63 | 63 | 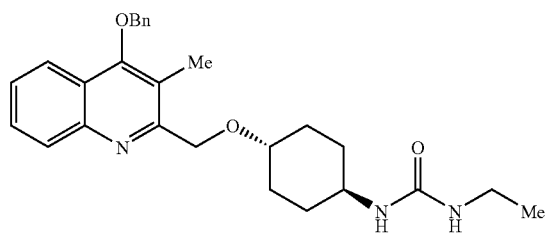 [SMILES: CCNC(=O)N[C@H]1CC[C@H](OCc2nc3ccccc3c(OCc3ccccc3)c2C)CC1] | ESI+: 448 |
| 64 | 64 | 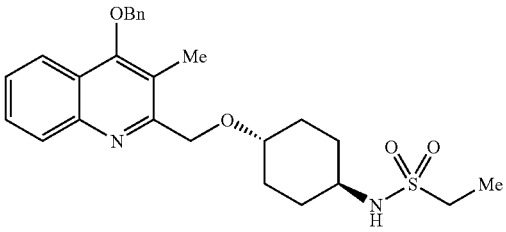 [SMILES: CCS(=O)(=O)N[C@H]1CC[C@H](OCc2nc3ccccc3c(OCc3ccccc3)c2C)CC1] | ESI+: 469 |

TABLE 85

| PEx | PSyn | Str | DATA |
|---|---|---|---|
| 65 | 65 | quinoline-OBn, Me, CH2-O-cyclohexyl-N-(2-oxopyrrolidin-1-yl) | ESI+: 445 |
| 507 | 25 | quinoline-OBn, Me, CH=CH-piperidine-N-C(O)O-CH2-Ph | ESI+: 493 |
| 508 | 16 | quinoline-OBn, Me, CH2-O-cyclohexyl-NH-C(O)-cyclopentyl | ESI+: 473 |
| 509 | 66 | quinoline-OBn, Me, CH2-O-cyclohexyl-N(Me)-C(O)O-Et | ESI+: 463 |
| 510 | 26 | quinoline-OBn, Me, CH2-O-thiadiazole-(4-F-phenyl) | ESI+: 458 |

TABLE 86

| PEx | PSyn | Str | DATA |
|---|---|---|---|
| 511 | 21 | quinoline-OBn, Me, CH2-O-CH2CH2-NH-cyclohexyl | FAB+: 405 |

TABLE 86-continued

| PEx | PSyn | Str | DATA |
|---|---|---|---|
| 512 | 16 | | FAB+: 517 |
| 513 | 25 | | ESI+: 507 |
| 514 | 16 | | ESI+: 457 |
| 515 | 53 | | ESI+: 473 |
| 516 | 26 | | ESI+: 436, 438 |

TABLE 87

| PEx | PSyn | Str | DATA |
|---|---|---|---|
| 67 | 67 | | ESI+: 416 |

TABLE 87-continued

| PEx | PSyn | Str | DATA |
|---|---|---|---|
| 68 | 68 | (4-OBn-3-Me-quinolin-2-yl)methoxy-pyrimidine-5-carboxylic acid | ESI+: 402 |
| 517 | 45 | (4-OBn-3-Me-quinolin-2-yl)methoxy-pyrimidine-5-carboxamide, N-cyclopentyl | ESI+: 469 |
| 518 | 45 | (4-OBn-3-Me-quinolin-2-yl)methoxy-pyrimidine-5-carbonyl-(8-azaspiro[4.5]decane) | ESI+: 523 |
| 519 | 45 | (4-OBn-3-Me-quinolin-2-yl)methoxy-pyrimidine-5-carboxamide, N-cyclopropylmethyl | ESI+: 455 |

TABLE 88

| PEx | PSyn | Str | DATA |
|---|---|---|---|
| 66 | 66 | (4-OBn-3-Me-quinolin-2-yl)methoxy-cyclohexyl-N-Me-cyclopentanecarboxamide | ESI+: 487 |

TABLE 88-continued

| PEx | PSyn | Str | DATA |
|---|---|---|---|
| 520 | 51 | BnO-phenyl-pyrrolidin-2-one | NMR2: 2.10-2.20(2H, m), 2.61(2H, t, J = 8.2 Hz), 3.84(2H, t, J = 7.1 Hz), 5.08(2H, s), 6.75-6.79(1H, m), 7.13-7.17(1H, m), 7.24-7.47(7H, m)<br>ESI+: 268 |
| 521 | 35 | HO-phenyl-pyrrolidin-2-one | ESI+: 178 |
| 522 | 21 | 4-OBn-3-Me-quinoline-2-CH₂O-phenyl-pyrrolidin-2-one | ESI+: 439 |
| 523 | 51 | BnO-phenyl-piperidin-2-one | ESI+: 282 |
| 524 | 35 | HO-phenyl-piperidin-2-one | ESI+: 192 |

TABLE 89

| PEx | PSyn | Str | DATA |
|---|---|---|---|
| 525 | 21 | 4-OBn-3-Me-quinoline-2-CH₂O-phenyl-piperidin-2-one | ESI+: 453 |
| 526 | 51 | BnO-phenyl-azepan-2-one | ESI+: 296 |
| 527 | 35 | HO-phenyl-azepan-2-one | ESI+: 206 |

TABLE 89-continued

| PEx | PSyn | Str | DATA |
|---|---|---|---|
| 528 | 21 | (structure) | ESI+: 467 |
| 529 | 37 | (structure) | ESI+: 393 |
| 530 | 36 | (structure) | NMR2: 1.27(6H, s), 1.64-1.88(2H, m), 1.76-1.87(2H, m), 1.84-2.05(2H, m), 1.87-2.50(2H, m), 3.37-3.57(2H, m), 3.57-3.71(1H, m), 3.68-3.82(3H, m), 7.10(1H, s), 7.19(1H, s), 7.86(1H, s) |

TABLE 90

| PEx | PSyn | Str | DATA |
|---|---|---|---|
| 531 | 37 | (structure) | ESI+: 493 |
| 532 | 36 | (structure) | NMR2: 1.68-1.81(2H, m), 1.81-1.97(2H, m), 3.38(3H, s), 3.40-3.53(2H, m), 3.47-3.58(1H, m), 3.65-3.81(2H, m), 7.10(1H, s), 7.19(1H, s), 7.86(1H, s) |
| 533 | 37 | (structure) | ESI+: 421 |
| 534 | 36 | (structure) | NMR2: 1.19(6H, s), 1.66-1.79(2H, m), 1.80(2H, t, J = 7.2 Hz), 1.83-1.96(2H, m), 3.19(3H, s), 3.47(2H, ddd, J = 13.2, 7.8, 3.9 Hz), 3.56(2H, t, J = 7.2 Hz), 3.57-3.65(1H, m), 3.75(2H, ddd, J = 12.6, 7.8, 3.3 Hz), 7.09(1H, s), 7.19(1H, s), 7.86(1H, s) |

TABLE 90-continued
| PEx | PSyn | Str | DATA |
|---|---|---|---|
| 535 | 37 | 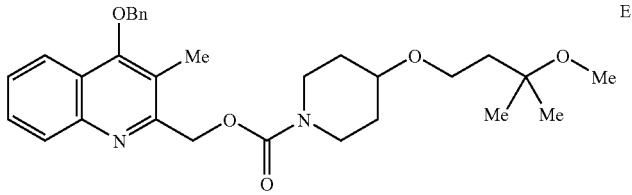 | ESI+: 507 |
TABLE 91
| PEx | PSyn | Str | DATA |
|---|---|---|---|
| 536 | 21 | 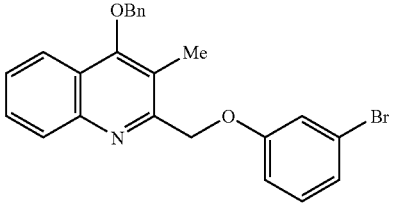 [SMILES: Cc1c(COc2cccc(Br)c2)nc2ccccc2c1OCc1ccccc1] | ESI+: 434, 436 |
| 537 | 51 | 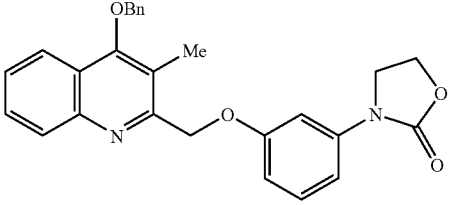 [SMILES: Cc1c(COc2cccc(N3CCOC3=O)c2)nc2ccccc2c1OCc1ccccc1] | ESI+: 441 |
| 538 | 21 | 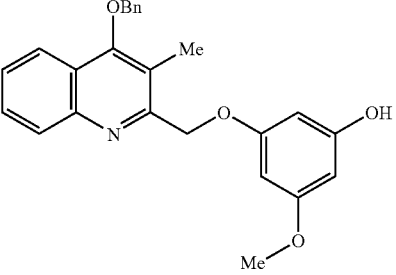 [SMILES: COc1cc(O)cc(OCc2nc3ccccc3c(OCc3ccccc3)c2C)c1] | ESI+: 402 |
| 69 | 69 | 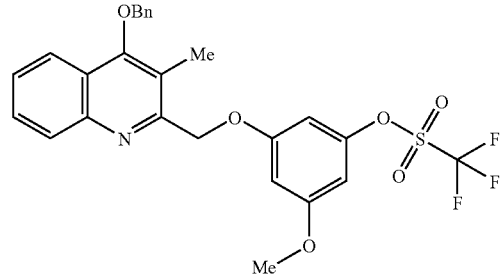 [SMILES: COc1cc(OCc2nc3ccccc3c(OCc3ccccc3)c2C)cc(OS(=O)(=O)C(F)(F)F)c1] | ESI+: 534 |

TABLE 91-continued

| PEx | PSyn | Str | DATA |
|---|---|---|---|
| 539 | 51 | (4-(benzyloxy)-3-methylquinolin-2-yl)methoxy linked to 3-methoxy-5-(3-oxomorpholin-4-yl)phenyl | ESI+: 485 |

TABLE 92

| PEx | PSyn | Str | DATA |
|---|---|---|---|
| 540 | 16 | 4-(benzyloxy)-3-methylquinolin-2-yl-CH2-O-trans-cyclohexyl-NHC(O)CH2-cyclopentyl | ESI+: 487 |
| 541 | 16 | 4-(benzyloxy)-3-methylquinolin-2-yl-CH2-O-trans-cyclohexyl-NHC(O)CH2-cyclopropyl | ESI+: 459 |
| 542 | 16 | 4-(benzyloxy)-3-methylquinolin-2-yl-CH2-O-trans-cyclohexyl-NHC(O)-(1-methylcyclopropyl) | ESI+: 459 |
| 543 | 16 | 4-(benzyloxy)-3-methylquinolin-2-yl-CH2-O-trans-cyclohexyl-NHC(O)CH2-(tetrahydropyran-4-yl) | ESI+: 503 |

TABLE 92-continued
| PEx | PSyn | Str | DATA |
|---|---|---|---|
| 544 | 16 | 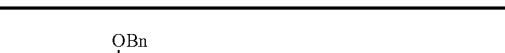 | ESI+: 489 |
TABLE 93
| PEx | PSyn | Str | DATA |
|---|---|---|---|
| 545 | 16 | | ESI+: 477 |
| 546 | 65 | | ESI+: 481 |
| 547 | 21 | | ESI+: 452, 454 |
| 548 | 51 | | ESI+: 473 |
| 549 | 36 | | NMR2: 1.70-1.86(2H, m), 1.91-2.05(2H, m), 2.09(3H, s), 3.52(2H, ddd, J = 12.9, 7.8, 3.9 Hz), 3.80(2H, ddd, J = 12.9, 7.5, 3.9 Hz), 4.99-5.11(1H, m), 7.11(1H, s), 7.17-7.22(1H, m), 7.87(1H, s) |

TABLE 94

| PEx | PSyn | Str | DATA |
|---|---|---|---|
| 550 | 37 | 4-OBn, 3-Me quinoline-2-CH2-O-C(O)-N(piperidine-4-OAc) | ESI+: 449 |
| 551 | 6 | 4-OBn, 3-Me quinoline-2-CH2-O-C(O)-N(piperidine-4-OH) | ESI+: 407 |
| 552 | 21 | 4-OBn, 3-Me quinoline-2-CH2-O-(3-OH-5-Me-phenyl) | ESI+: 386 |
| 553 | 69 | 4-OBn, 3-Me quinoline-2-CH2-O-(3-OTf-5-Me-phenyl) | ESI+: 518 |
| 554 | 51 | 4-OBn, 3-Me quinoline-2-CH2-O-(3-(3-oxomorpholin-4-yl)-5-Me-phenyl) | ESI+: 469 |

TABLE 95

| PEx | PSyn | Str | DATA |
|---|---|---|---|
| 555 | 66 | 4-OBn, 3-Me quinoline-2-CH2-O-C(O)-N(Me)(CH2-tetrahydropyran-4-yl) | ESI+: 435 |

TABLE 95-continued
| PEx | PSyn | Str | DATA |
|---|---|---|---|
| 556 | 25 | 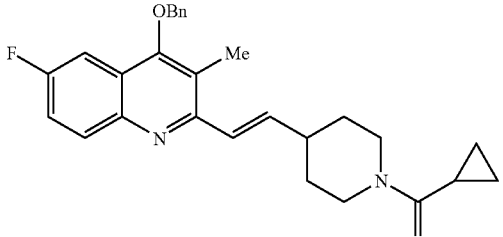 | ESI+: 445 |
| 557 | 64 | 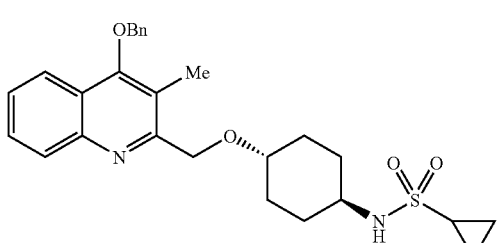 | ESI+: 481 |
| 558 | 51 | 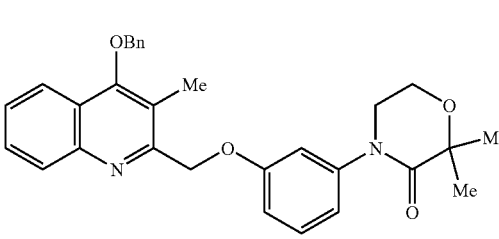 | ESI+: 483 |
| 559 | 51 | 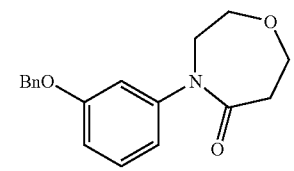 [SMILES: O=C1CCOCCN1c1cccc(OCc2ccccc2)c1] | ESI+: 298 |
| 560 | 35 | 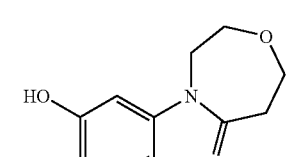 | ESI+: 208 |
TABLE 96
| PEx | PSyn | Str | DATA |
|---|---|---|---|
| 561 | 21 | 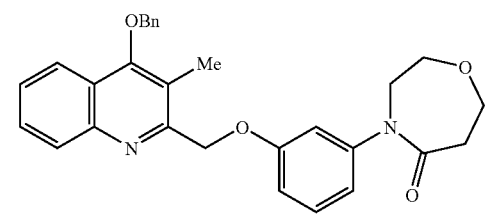 [SMILES: Cc1c(COc2cccc(N3CCOCCC3=O)c2)nc2ccccc2c1OCc1ccccc1] | ESI+: 469 |

TABLE 96-continued

| PEx | PSyn | Str | DATA |
|---|---|---|---|
| 562 | 21 | (structure) | ESI+: 487 |
| 563 | 55 | (structure) | ESI+: 462 |
| 564 | 43 | (structure) 2HCl | ESI+: 362 |
| 565 | 16 | (structure) | ESI+: 446 |

TABLE 97

| Ex | Str |
|---|---|
| 1 | (structure) |
| 24 | (structure) |
| 25 | (structure) |
| 26 | (structure) |
| 27 | (structure) |
| 28 | (structure) |

TABLE 97-continued

| Ex | Str |
|---|---|
| 29 | 3-methyl-2-(4-(4-cyanophenoxy)butyl)quinolin-4(1H)-one |
| 30 | 3-methyl-2-(5-cyclopropoxypentyl)quinolin-4(1H)-one |
| 31 | 3-methyl-2-(2-(3-((tetrahydro-2H-pyran-4-yl)methoxy)phenyl)ethyl)quinolin-4(1H)-one |
| 32 | 3-methyl-2-(4-((6-(trifluoromethyl)pyrimidin-4-yl)oxy)butyl)quinolin-4(1H)-one |
| 2 | 3-methyl-2-((3-((tetrahydro-2H-pyran-4-yl)methoxy)phenoxy)methyl)quinolin-4(1H)-one |
| 33 | 3-methyl-2-(((4-methoxyphenethyl)amino)methyl)quinolin-4(1H)-one · HCl |

TABLE 98

| Ex | Str |
|---|---|
| 34 | 3-methyl-2-((hexylamino)methyl)quinolin-4(1H)-one · HCl |
| 35 | N-((3-methyl-4-oxo-1,4-dihydroquinolin-2-yl)methyl)-N-(4-methoxyphenethyl)acetamide |
| 36 | N-((3-methyl-4-oxo-1,4-dihydroquinolin-2-yl)methyl)-N-hexylacetamide |
| 37 | 3-methyl-2-(((4-phenylbutyl)amino)methyl)quinolin-4(1H)-one · HCl |
| 38 | 3-methyl-2-(((4-(4-methoxyphenyl)butyl)amino)methyl)quinolin-4(1H)-one · HCl |
| 39 | 3-methyl-2-(((3-phenylpropyl)amino)methyl)quinolin-4(1H)-one · HCl |
| 40 | 3-methyl-2-((heptyloxy)methyl)quinolin-4(1H)-one |
| 41 | (3-methyl-4-oxo-1,4-dihydroquinolin-2-yl)methyl pentylcarbamate |
| 42 | 3-methyl-2-((3-(cyclopropylmethoxy)propoxy)methyl)quinolin-4(1H)-one |

TABLE 98-continued

| Ex | Str |
|---|---|
| 43 | 3-methyl-2-((4-(2,3-dihydrobenzo[b][1,4]dioxin-6-yl)butoxy)methyl)quinolin-4(1H)-one |
| 44 | 3-methyl-2-(((4-(pyridin-3-yloxy)butoxy)methyl))quinolin-4(1H)-one |
| 45 | 3-methyl-2-(((4-(propylcarbamoyloxy)butoxy)methyl))quinolin-4(1H)-one |
| 46 | 2-(((4-hydroxybutoxy)methyl))-3-methylquinolin-4(1H)-one |
| 47 | 3-methyl-2-(((4-phenoxybutoxy)methyl))quinolin-4(1H)-one |

TABLE 99

| Ex | Str |
|---|---|
| 48 | 3-methyl-2-(((4-(4,4,4-trifluorobutoxy)butoxy)methyl))quinolin-4(1H)-one |
| 49 | 2-(((4-(4-cyanophenoxy)butoxy)methyl))-3-methylquinolin-4(1H)-one |
| 50 | 2-(((4-(4-(2-methoxyethyl)phenoxy)butoxy)methyl))-3-methylquinolin-4(1H)-one |
| 51 | 2-(((4-(4-fluorophenoxy)butoxy)methyl))-3-methylquinolin-4(1H)-one |
| 52 | 2-(((4-((2,2-dimethyl-2,3-dihydrobenzofuran-7-yl)oxy)butoxy)methyl))-3-methylquinolin-4(1H)-one |

TABLE 99-continued

| Ex | Str |
|---|---|
| 53 | 3-methyl-2-((4-(2-cyclopropylethoxy)butoxy)methyl)quinolin-4(1H)-one |
| 54 | 3-methyl-2-((4-((3-methyloxetan-3-yl)methoxy)butoxy)methyl)quinolin-4(1H)-one |
| 55 | 3-methyl-2-((4-(3-methoxy-3-methylbutoxy)butoxy)methyl)quinolin-4(1H)-one |
| 56 | 3-methyl-2-((4-(3,3,3-trifluoropropoxy)butoxy)methyl)quinolin-4(1H)-one |
| 57 | 2-((4-tert-butoxybutoxy)methyl)-3-methylquinolin-4(1H)-one |
| 58 | tert-butyl 4-(4-((3-methyl-4-oxo-1,4-dihydroquinolin-2-yl)methoxy)butoxy)piperidine-1-carboxylate |
| 59 | 3-methyl-2-((4-(3-morpholinophenoxy)butoxy)methyl)quinolin-4(1H)-one |
| 60 | 2-((4-cyclopropoxybutoxy)methyl)-3-methylquinolin-4(1H)-one |

TABLE 99-continued
| Ex | Str |
|---|---|
| 61 | 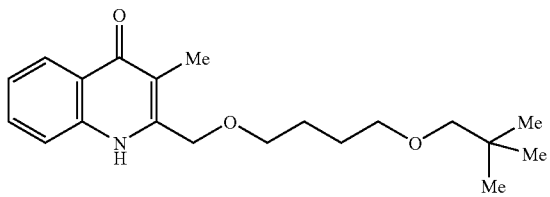 [SMILES: Cc1c(COCCCCOCC(C)(C)C)[nH]c2ccccc2c1=O] |
TABLE 100
| Ex | Str |
|---|---|
| 62 | 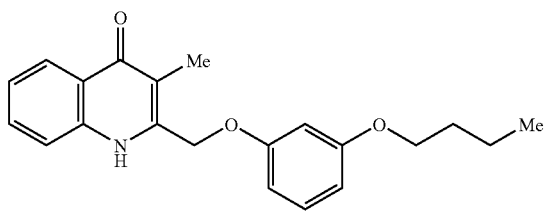 [SMILES: CCCCOc1cccc(OCc2[nH]c3ccccc3c(=O)c2C)c1] |
| 63 | 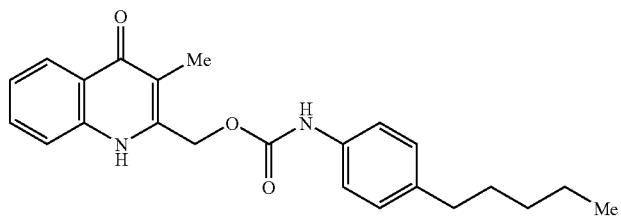 [SMILES: CCCCCc1ccc(NC(=O)OCc2[nH]c3ccccc3c(=O)c2C)cc1] |
| 64 | 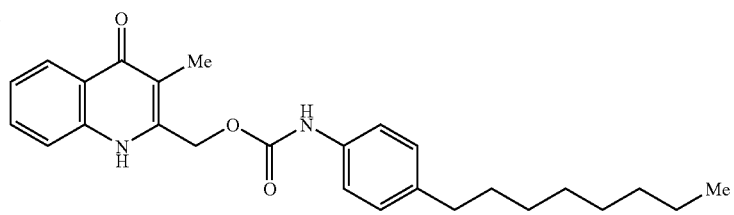 [SMILES: CCCCCCCCc1ccc(NC(=O)OCc2[nH]c3ccccc3c(=O)c2C)cc1] |
| 65 | 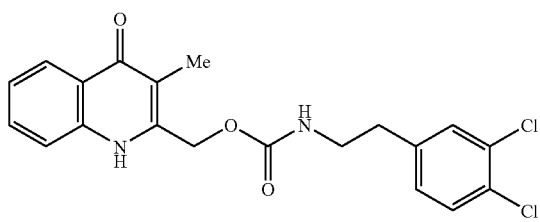 [SMILES: Cc1c(COC(=O)NCCc2ccc(Cl)c(Cl)c2)[nH]c2ccccc2c1=O] |
| 66 | 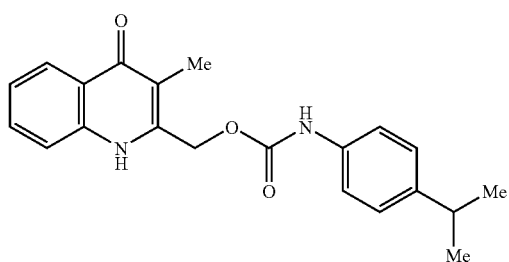 [SMILES: Cc1c(COC(=O)Nc2ccc(C(C)C)cc2)[nH]c2ccccc2c1=O] |

TABLE 100-continued

| Ex | Str |
|---|---|
| 67 | (structure) |
| 68 | (structure) |
| 69 | (structure) |
| 70 | (structure) |
| 71 | (structure) |
| 72 | (structure) |
| 73 | (structure) |

TABLE 100-continued
| Ex | Str |
|---|---|
| 74 | 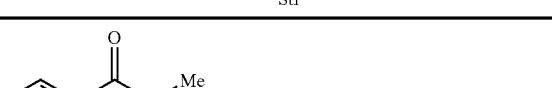 |
TABLE 101
| Ex | Str |
|---|---|
| 75 | |
| 76 | |
| 77 | |
| 78 | |
TABLE 101-continued
| Ex | Str |
|---|---|
| 79 | |
| 80 | |
| 81 | |
| 82 | |
| 83 | |

TABLE 101-continued
| Ex | Str |
|---|---|
| 84 | 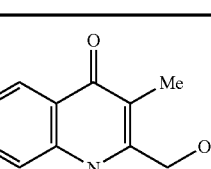 |
| 85 | |
TABLE 102
| Ex | Str |
|---|---|
| 86 | |
| 87 | |
| 88 | |
| 89 | |
| 90 | |
TABLE 102-continued
| Ex | Str |
|---|---|
| 91 | 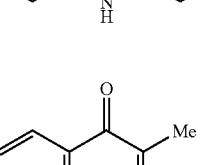 |
| 92 | |
| 93 | |
| 94 | |
| 95 | |
| 96 | |

TABLE 103

| Ex | Str |
|---|---|
| 97 | 6-bromo-3-methyl-2-((3-((tetrahydro-2H-pyran-4-yl)methoxy)phenoxy)methyl)quinolin-4(1H)-one |
| 98 | 2-((3-((1-acetylpiperidin-4-yl)methoxy)phenoxy)methyl)-3-methylquinolin-4(1H)-one |
| 99 | 2-((3-(benzyloxy)phenoxy)methyl)-3-methylquinolin-4(1H)-one |
| 100 | 3,6-dimethyl-2-((3-((tetrahydro-2H-pyran-4-yl)methoxy)phenoxy)methyl)quinolin-4(1H)-one |
| 101 | 6-methoxy-3-methyl-2-((3-((tetrahydro-2H-pyran-4-yl)methoxy)phenoxy)methyl)quinolin-4(1H)-one |
| 102 | 6-chloro-3-methyl-2-((3-((tetrahydro-2H-pyran-4-yl)methoxy)phenoxy)methyl)quinolin-4(1H)-one |
| 103 | 3-methyl-2-((3-((1-(methylsulfonyl)piperidin-4-yl)methoxy)phenoxy)methyl)quinolin-4(1H)-one |

TABLE 103-continued
| Ex | Str |
|---|---|
| 104 | 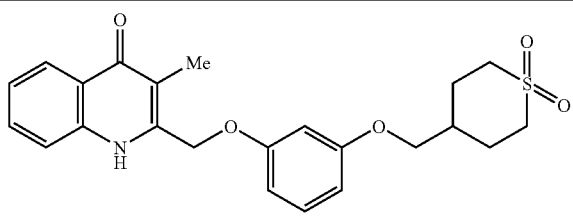 |
| 105 | 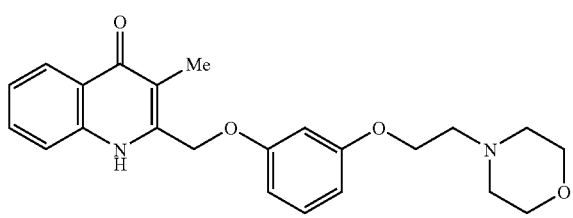 [SMILES: Cc1c(COc2cccc(OCCN3CCOCC3)c2)[nH]c2ccccc2c1=O] |
| 106 | 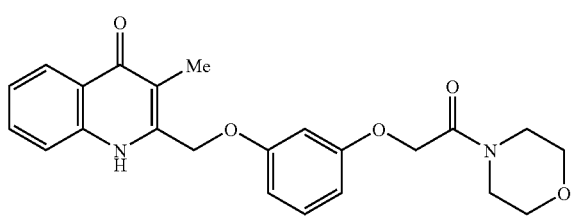 [SMILES: Cc1c(COc2cccc(OCC(=O)N3CCOCC3)c2)[nH]c2ccccc2c1=O] |
| 107 | 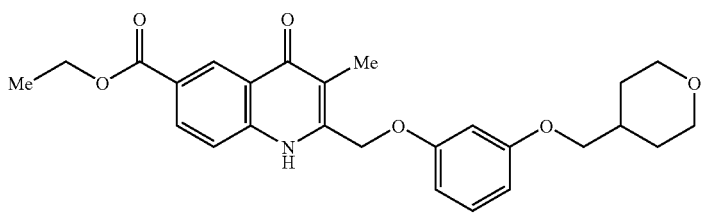 [SMILES: CCOC(=O)c1ccc2[nH]c(COc3cccc(OCC4CCOCC4)c3)c(C)c(=O)c2c1] |
| 108 | 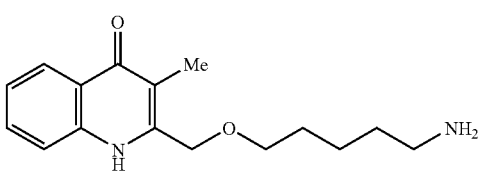 [SMILES: Cc1c(COCCCCCN)[nH]c2ccccc2c1=O] |
| 109 | 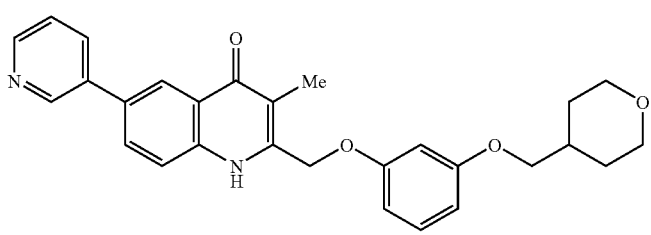 [SMILES: Cc1c(COc2cccc(OCC3CCOCC3)c2)[nH]c2ccc(-c3cccnc3)cc2c1=O] |

TABLE 104
| Ex | Str |
|---|---|
| 110 | 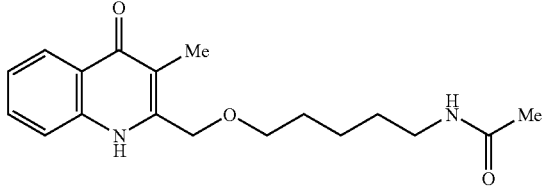 [SMILES: CC(=O)NCCCCCOCc1[nH]c2ccccc2c(=O)c1C] |
| 111 | 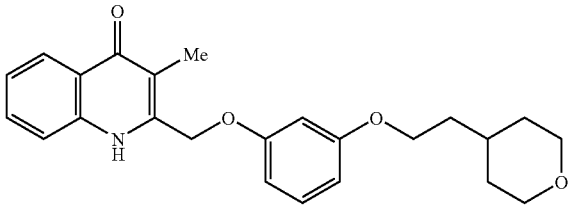 [SMILES: Cc1c(COc2cccc(OCCC3CCOCC3)c2)[nH]c2ccccc2c1=O] |
| 112 | 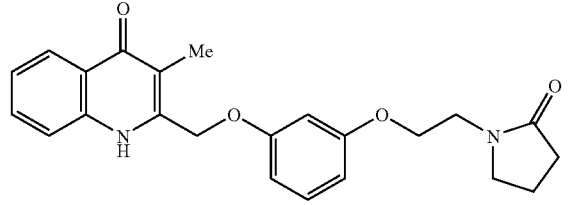 [SMILES: Cc1c(COc2cccc(OCCN3CCCC3=O)c2)[nH]c2ccccc2c1=O] |
| 113 | 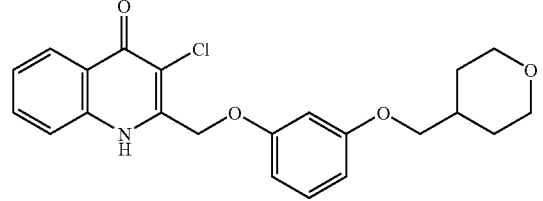 [SMILES: O=c1c(Cl)c(COc2cccc(OCC3CCOCC3)c2)[nH]c2ccccc12] |
| 114 | 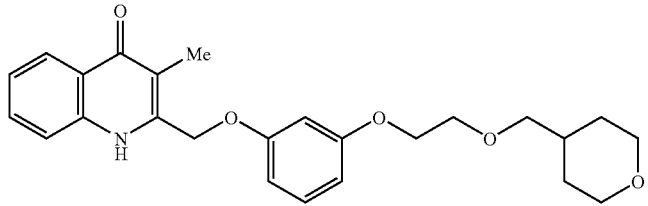 [SMILES: Cc1c(COc2cccc(OCCOCC3CCOCC3)c2)[nH]c2ccccc2c1=O] |
| 115 | 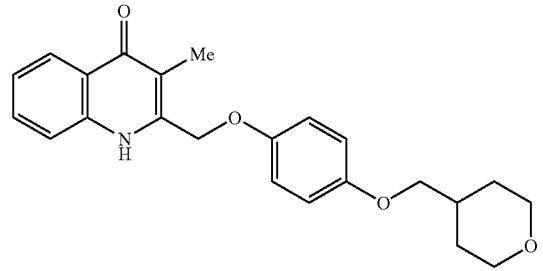 [SMILES: Cc1c(COc2ccc(OCC3CCOCC3)cc2)[nH]c2ccccc2c1=O] |
| 116 | 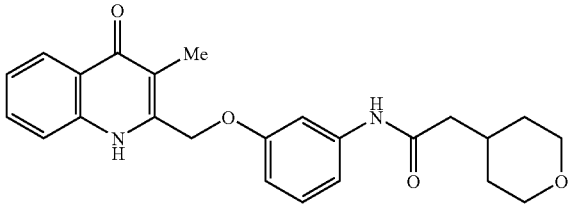 [SMILES: Cc1c(COc2cccc(NC(=O)CC3CCOCC3)c2)[nH]c2ccccc2c1=O] |

TABLE 104-continued

| Ex | Str |
|---|---|
| 117 | (3-methyl-4-oxo-1,4-dihydroquinolin-2-yl)methoxy phenyl acetyl morpholine |
| 118 | 3-isopropyl-2-((3-((tetrahydro-2H-pyran-4-yl)methoxy)phenoxy)methyl)quinolin-4(1H)-one |
| 119 | 3-methyl-2-((3-fluoro-5-((tetrahydro-2H-pyran-4-yl)methoxy)phenoxy)methyl)quinolin-4(1H)-one |
| 120 | 3-methyl-6-(pyrimidin-5-yl)-2-((3-((tetrahydro-2H-pyran-4-yl)methoxy)phenoxy)methyl)quinolin-4(1H)-one |
| 121 | 3-methyl-2-((3-(2-(pyridin-3-yl)ethoxy)phenoxy)methyl)quinolin-4(1H)-one |

TABLE 105

| Ex | Str |
|---|---|
| 122 | 3-methyl-2-((3-(3-(tetrahydro-2H-pyran-4-yl)propoxy)phenoxy)methyl)quinolin-4(1H)-one |

TABLE 105-continued

| Ex | Str |
|---|---|
| 123 | 3-methyl-2-({3-[2-(pyridin-2-yl)ethoxy]phenoxy}methyl)quinolin-4(1H)-one |
| 124 | 6-(2-oxopiperidin-1-yl)-3-methyl-2-({3-[(tetrahydro-2H-pyran-4-yl)methoxy]phenoxy}methyl)quinolin-4(1H)-one |
| 125 | 6-fluoro-3-methyl-2-[(3-{2-[(tetrahydro-2H-pyran-4-yl)methoxy]ethoxy}phenoxy)methyl]quinolin-4(1H)-one |
| 126 | 3-methyl-2-({3-[(4-oxocyclohexyl)methoxy]phenoxy}methyl)quinolin-4(1H)-one |
| 127 | 3-methyl-2-({3-[2-(pyridin-4-yl)ethoxy]phenoxy}methyl)quinolin-4(1H)-one |
| 128 | 6-fluoro-3-methyl-2-{[(1-hexanoylpiperidin-4-yl)oxy]methyl}quinolin-4(1H)-one |
| 129 | 6-fluoro-2-{[(5-cyclopropoxypentyl)oxy]methyl}-3-methylquinolin-4(1H)-one |

TABLE 105-continued

| Ex | Str |
|---|---|
| 130 | |
| 131 | |
| 132 | |
| 133 | |

TABLE 106

| Ex | Str |
|---|---|
| 134 | |
| 135 | |

TABLE 106-continued
| Ex | Str |
|---|---|
| 136 | 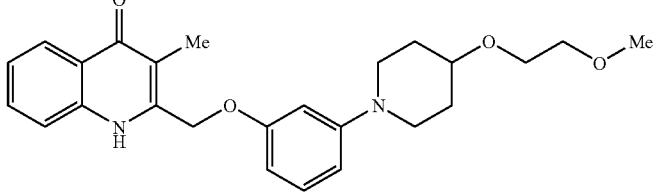 |
| 137 | 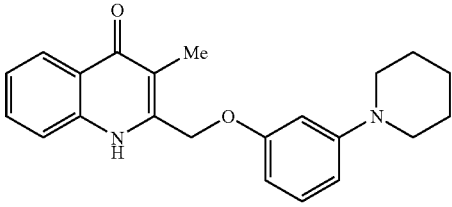 [SMILES: Cc1c(COc2cccc(N3CCCCC3)c2)[nH]c2ccccc2c1=O] |
| 138 | 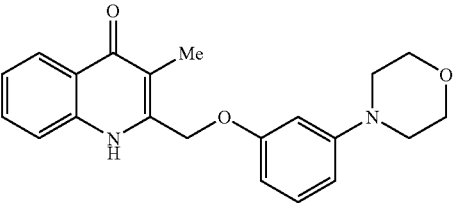 [SMILES: Cc1c(COc2cccc(N3CCOCC3)c2)[nH]c2ccccc2c1=O] |
| 139 | 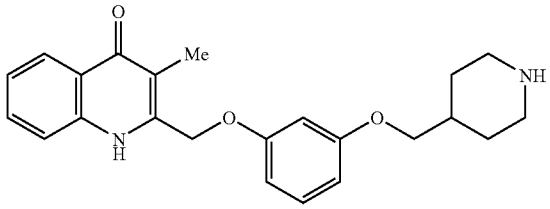 [SMILES: Cc1c(COc2cccc(OCC3CCNCC3)c2)[nH]c2ccccc2c1=O] |
| 140 | 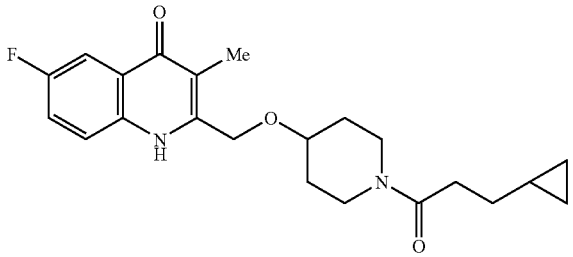 [SMILES: Cc1c(COC2CCN(C(=O)CCC3CC3)CC2)[nH]c2ccc(F)cc2c1=O] |
| 141 | 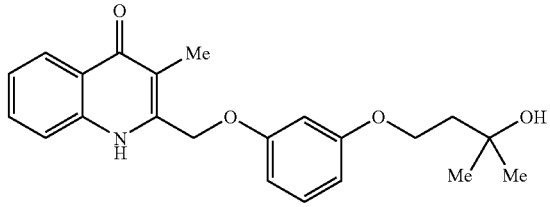 [SMILES: Cc1c(COc2cccc(OCCC(C)(C)O)c2)[nH]c2ccccc2c1=O] |

TABLE 106-continued

| Ex | Str |
|---|---|
| 142 | |
| 143 | |
| 144 | |

TABLE 107

| Ex | Str |
|---|---|
| 145 | |
| 146 | |
| 147 | |

TABLE 107-continued

| Ex | Str |
|---|---|
| 148 | |
| 149 | |
| 150 | |
| 151 | |
| 152 | |
| 153 | |

TABLE 107-continued

| Ex | Str |
|---|---|
| 154 | 6-fluoro-3-methyl-2-[[3-(4-acetylpiperazin-1-yl)phenoxy]methyl]-1H-quinolin-4-one |
| 155 | 6-fluoro-3-methyl-2-[[3-(3-hydroxy-3-methylbutoxy)phenoxy]methyl]-1H-quinolin-4-one |
| 156 | 6-fluoro-3-methyl-2-[[3-(2-hydroxy-2-methylpropoxy)phenoxy]methyl]-1H-quinolin-4-one |
| 157 | 6-fluoro-3-methyl-2-[[4-[2-(tetrahydropyran-4-yl)ethoxy]pyridin-2-yloxy]methyl]-1H-quinolin-4-one |

TABLE 108

| Ex | Str |
|---|---|
| 158 | 6-fluoro-3-methyl-2-[[2-[2-(tetrahydropyran-4-yl)acetyl]-1,2,3,4-tetrahydroisoquinolin-6-yloxy]methyl]-1H-quinolin-4-one |
| 159 | 6-fluoro-3-methyl-2-[[3-(2-oxopiperidin-1-yl)phenoxy]methyl]-1H-quinolin-4-one |

TABLE 108-continued

| Ex | Str |
|---|---|
| 160 | 3-methyl-2-[[2-[2-(tetrahydropyran-4-yl)ethoxy]pyridin-4-yl]oxymethyl]-1H-quinolin-4-one |
| 161 | 2-[[3-(4-hydroxy-4-methylpentoxy)phenoxy]methyl]-3-methyl-1H-quinolin-4-one |
| 162 | 6-fluoro-2-[[3-(4-hydroxy-4-methylpentoxy)phenoxy]methyl]-3-methyl-1H-quinolin-4-one |
| 163 | 6-fluoro-3-methyl-2-[[1-(tetrahydropyran-4-ylcarbonyl)-1,2,3,4-tetrahydroquinolin-5-yl]oxymethyl]-1H-quinolin-4-one |
| 164 | 6-fluoro-3-methyl-2-[[1-[2-(tetrahydropyran-4-yl)acetyl]-1,2,3,4-tetrahydroquinolin-5-yl]oxymethyl]-1H-quinolin-4-one |
| 165 | 6-fluoro-3-methyl-2-[[1-(tetrahydropyran-4-ylcarbonyl)-1,2,3,4-tetrahydroquinolin-7-yl]oxymethyl]-1H-quinolin-4-one |
| 166 | 6-fluoro-3-methyl-2-[[1-[2-(tetrahydropyran-4-yl)acetyl]-1,2,3,4-tetrahydroquinolin-7-yl]oxymethyl]-1H-quinolin-4-one |

TABLE 108-continued

| Ex | Str |
|---|---|
| 167 | |
| 168 | |
| 169 | |
| 170 | |

TABLE 109

| Ex | Str |
|---|---|
| 171 | |
| 172 | |

TABLE 109-continued

| Ex | Str |
|---|---|
| 173 | |
| 174 | |
| 175 | |
| 176 | |
| 177 | |
| 178 | |
| 179 | |

TABLE 109-continued

| Ex | Str |
|---|---|
| 180 | |
| 181 | |
| 182 | |
| 183 | |

TABLE 110

| Ex | Str |
|---|---|
| 184 | |
| 185 | |
| 186 | |

TABLE 110-continued

| Ex | Str |
|---|---|
| 187 | 3-methyl-2-({[2-({2-[(tetrahydro-2H-pyran-4-yl)ethyl]oxy}pyridin-4-yl)oxy]methyl})quinolin-4(1H)-one |
| 188 | 2-({[2-({4-hydroxy-4-methylpentyl}oxy)pyridin-4-yl]oxy}methyl)-3-methylquinolin-4(1H)-one |
| 189 | 2-({[2-({2-hydroxy-2-methylpropyl}oxy)pyridin-4-yl]oxy}methyl)-3-methylquinolin-4(1H)-one |
| 190 | 3-methyl-2-({[2-({(3-methyloxetan-3-yl)methyl}oxy)pyridin-4-yl]oxy}methyl)quinolin-4(1H)-one |
| 191 | ethyl 4-{3-[(3-methyl-4-oxo-1,4-dihydroquinolin-2-yl)methoxy]phenyl}piperazine-1-carboxylate |
| 192 | 2-({[5-({3-hydroxy-3-methylbutyl}oxy)pyridin-3-yl]oxy}methyl)-3-methylquinolin-4(1H)-one |
| 193 | 2-({[3-({2-[(4-methoxytetrahydro-2H-pyran-4-yl)ethyl]oxy}phenyl]oxy}methyl)-3-methylquinolin-4(1H)-one |

TABLE 110-continued

| Ex | Str |
|---|---|
| 194 | |
| 195 | |

TABLE 111

| Ex | Str |
|---|---|
| 196 | |
| 197 | |
| 198 | |
| 199 | |
| 200 | |
| 201 | |
| 202 | |

TABLE 111-continued
| Ex | Str |
|---|---|
| 203 | 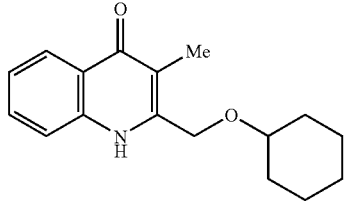 [SMILES: Cc1c(COC2CCCCC2)[nH]c2ccccc2c1=O] |
| 204 | 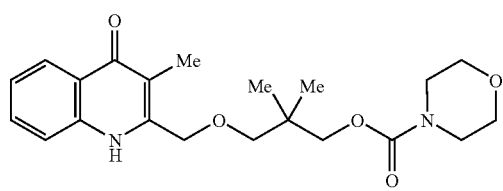 [SMILES: Cc1c(COCC(C)(C)COC(=O)N2CCOCC2)[nH]c2ccccc2c1=O] |
| 205 | 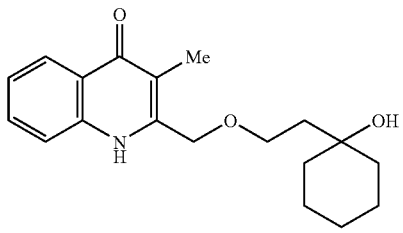 [SMILES: Cc1c(COCCC2(O)CCCCC2)[nH]c2ccccc2c1=O] |
| 206 | 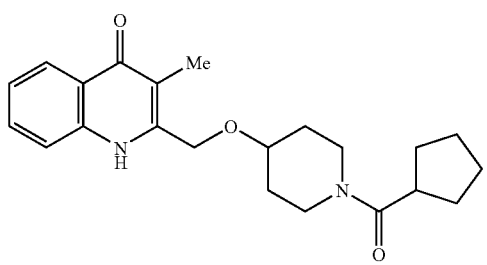 [SMILES: Cc1c(COC2CCN(C(=O)C3CCCC3)CC2)[nH]c2ccccc2c1=O] |
TABLE 112
| Ex | Str |
|---|---|
| 207 | 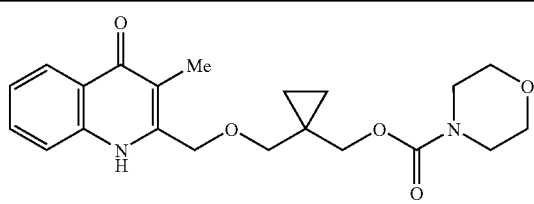 |
| 208 | 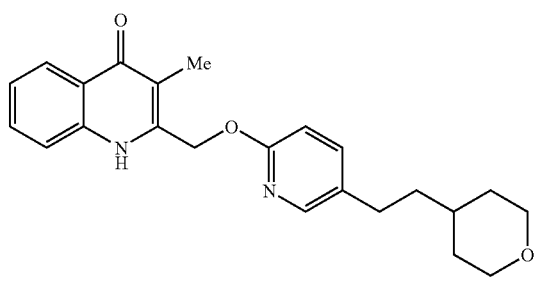 |
| 209 | 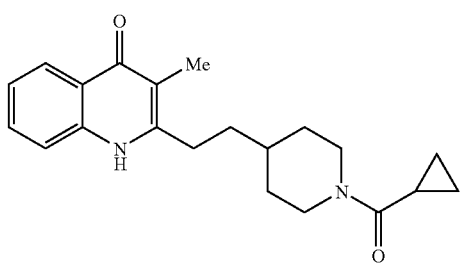 [SMILES: Cc1c(CCC2CCN(C(=O)C3CC3)CC2)[nH]c2ccccc2c1=O] |
| 210 | 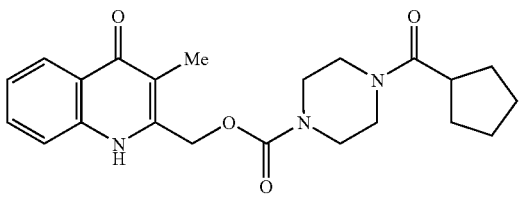 [SMILES: Cc1c(COC(=O)N2CCN(C(=O)C3CCCC3)CC2)[nH]c2ccccc2c1=O] |

TABLE 112-continued

| Ex | Str |
| --- | --- |
| 211 | |
| 212 | |
| 213 | |
| 214 | |
| 215 | |
| 216 | |

TABLE 112-continued

| Ex | Str |
|---|---|
| 217 | 3-methyl-2-((pyridin-2-yloxy)methyl)quinolin-4(1H)-one |
| 218 | 3-methyl-2-((2-oxo-2-(piperidin-1-yl)ethoxy)methyl)quinolin-4(1H)-one |

TABLE 113

| Ex | Str |
|---|---|
| 219 | 2-(2-(1-(2-cyclopropylacetyl)piperidin-4-yl)ethyl)-3-methylquinolin-4(1H)-one HCl |
| 220 | 3-methyl-2-(2-(1-(tetrahydro-2H-pyran-4-carbonyl)piperidin-4-yl)ethyl)quinolin-4(1H)-one HCl |
| 221 | 2-((5-(3-hydroxy-3-methylbutyl)pyridin-2-yloxy)methyl)-3-methylquinolin-4(1H)-one |
| 222 | 3-methyl-2-(2-(1-(1-methylcyclopropanecarbonyl)piperidin-4-yl)ethyl)quinolin-4(1H)-one HCl |

TABLE 113-continued

| Ex | Str |
|---|---|
| 223 | 2-(2-(1-(2-methoxyacetyl)piperidin-4-yl)ethyl)-3-methylquinolin-4(1H)-one HCl |
| 224 | 1-ethyl-3-(trans-4-((3-methyl-4-oxo-1,4-dihydroquinolin-2-yl)methoxy)cyclohexyl)urea |
| 225 | N-(trans-4-((3-methyl-4-oxo-1,4-dihydroquinolin-2-yl)methoxy)cyclohexyl)cyclopentanecarboxamide |
| 226 | ethyl methyl(trans-4-((3-methyl-4-oxo-1,4-dihydroquinolin-2-yl)methoxy)cyclohexyl)carbamate |

TABLE 113-continued

| Ex | Str |
|---|---|
| 227 | (structure) |
| 228 | (structure) |

TABLE 114

| Ex | Str |
|---|---|
| 229 | (structure) |
| 230 | (structure) |
| 231 | (structure) |
| 232 | (structure) |

TABLE 114-continued

| Ex | Str |
|---|---|
| 233 | (structure) |
| 234 | (structure) |
| 235 | (structure) |
| 236 | (structure) |
| 237 | (structure) |
| 238 | (structure) |
| 239 | (structure) |

TABLE 115
| Ex | Str |
|---|---|
| 240 | 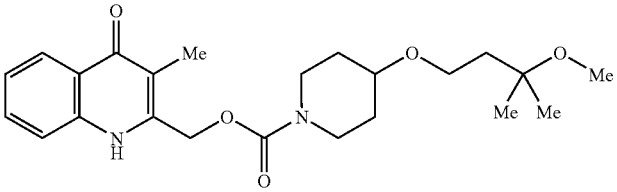 [SMILES: COC(C)(C)CCOC1CCN(C(=O)OCc2[nH]c3ccccc3c(=O)c2C)CC1] |
| 241 | 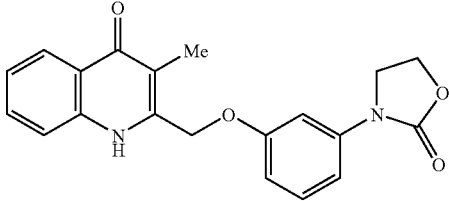 [SMILES: Cc1c(COc2cccc(N3CCOC3=O)c2)[nH]c2ccccc2c1=O] |
| 242 | 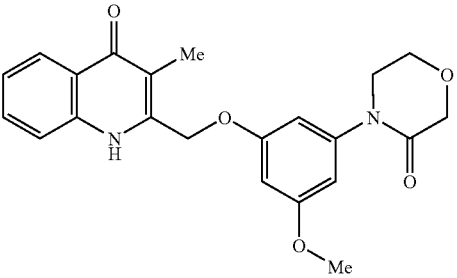 [SMILES: COc1cc(OCc2[nH]c3ccccc3c(=O)c2C)cc(N2CCOCC2=O)c1] |
| 243 | 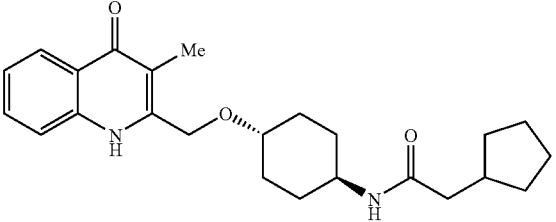 [SMILES: Cc1c(CO[C@H]2CC[C@H](NC(=O)CC3CCCC3)CC2)[nH]c2ccccc2c1=O] |
| 244 | 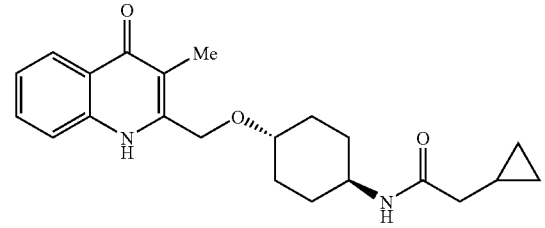 [SMILES: Cc1c(CO[C@H]2CC[C@H](NC(=O)CC3CC3)CC2)[nH]c2ccccc2c1=O] |
| 245 | 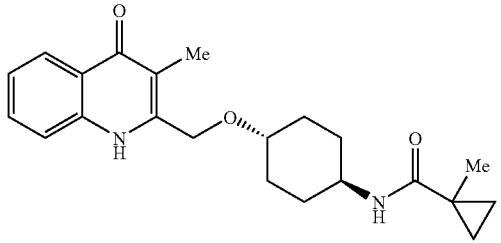 [SMILES: Cc1c(CO[C@H]2CC[C@H](NC(=O)C3(C)CC3)CC2)[nH]c2ccccc2c1=O] |

TABLE 115-continued

| Ex | Str |
|---|---|
| 246 | |
| 247 | |
| 248 | |
| 249 | |
| 250 | |

TABLE 116

| Ex | Str |
|---|---|
| 251 | (structure) |
| 252 | (structure) |
| 253 | (structure) |
| 254 | (structure) |
| 255 | (structure) |
| 256 | (structure) |

TABLE 116-continued

| Ex | Str |
|---|---|
| 257 | (structure) |
| 258 | (structure) |
| 259 | (structure) |
| 3 | (structure) |
| 4 | (structure) |

TABLE 117

| Ex | Str |
|---|---|
| 5 | (structure) |

TABLE 117-continued

| Ex | Str |
|---|---|
| 6 | (3-methyl-4-oxo-1H-quinolin-2-yl)methoxy cyclohexyl ethanesulfonamide |
| 7 | (3-methyl-4-oxo-1H-quinolin-2-yl)methoxy cyclohexyl 2-oxopyrrolidine |
| 8 | (3-methyl-4-oxo-1H-quinolin-2-yl)methoxy pyridinyloxy ethyl tetrahydropyran |
| 9 | (3-methyl-4-oxo-1H-quinolin-2-yl)methoxy phenyl 3-oxomorpholine |
| 10 | (3-methyl-4-oxo-1H-quinolin-2-yl)methoxy phenyl (3-morpholino) propoxy 2-hydroxy-2-methylpropyl |

TABLE 117-continued

| Ex | Str |
|---|---|
| 11 | 2-[2-(piperidin-4-yl)ethyl]-3-methyl-1H-quinolin-4-one |
| 260 | 2-[3-(piperidin-4-yl)propyl]-3-methyl-1H-quinolin-4-one |
| 12 | 2-(heptylsulfanylmethyl)-3-methyl-1H-quinolin-4-one |
| 261 | 2-(heptylsulfinylmethyl)-3-methyl-1H-quinolin-4-one |
| 262 | (3-methyl-4-oxo-1H-quinolin-2-yl)methyl N-(4-phenoxyphenyl)carbamate |

TABLE 118

| Ex | Str |
|---|---|
| 263 | (3-methyl-4-oxo-1H-quinolin-2-yl)methyl N-(4-methylsulfanylphenyl)carbamate |

TABLE 118-continued

| Ex | Str |
|---|---|
| 264 | 3-methyl-2-(((4-(trifluoromethylthio)phenyl)carbamoyloxy)methyl)quinolin-4(1H)-one |
| 265 | 2-(((2,3-dihydrobenzofuran-5-yl)carbamoyloxy)methyl)-3-methylquinolin-4(1H)-one |
| 266 | 3-methyl-2-((3-(((tetrahydro-2H-pyran-4-yl)methylthio)phenoxy)methyl)quinolin-4(1H)-one |
| 267 | 3-cyano-5-((3-methyl-4-oxo-1,4-dihydroquinolin-2-yl)methoxy)phenyl (tetrahydro-2H-pyran-4-yl)methyl ether |
| 268 | 3-methyl-2-(((3-((tetrahydro-2H-pyran-4-yl)methoxy)phenylthio)methyl)quinolin-4(1H)-one |
| 269 | 2-(((3,5-dichloro-6-((tetrahydro-2H-pyran-4-yl)methoxy)pyridin-2-yl)oxy)methyl)-3-methylquinolin-4(1H)-one |

TABLE 118-continued

| Ex | Str |
|---|---|
| 13 | 3-methyl-2-({[(heptanoyl)amino]methyl})quinolin-4(1H)-one |
| 270 | 3-methyl-2-{[3-({1-[(tetrahydro-2H-pyran-4-yl)carbonyl]piperidin-4-yl}methoxy)phenoxy]methyl}quinolin-4(1H)-one |
| 271 | 2-{2-[1-(3-hydroxy-3-methylbutanoyl)piperidin-4-yl]ethyl}-3-methylquinolin-4(1H)-one |
| 272 | 2-{2-[1-(cyclobutylcarbonyl)piperidin-4-yl]ethyl}-3-methylquinolin-4(1H)-one · HCl |

TABLE 119

| Ex | Str |
|---|---|
| 273 | 3-methyl-2-(2-{1-[(tetrahydro-2H-pyran-4-yl)acetyl]piperidin-4-yl}ethyl)quinolin-4(1H)-one · HCl |
| 274 | 2-{3-[1-(cyclopropylcarbonyl)piperidin-4-yl]propyl}-3-methylquinolin-4(1H)-one |

TABLE 119-continued

| Ex | Str |
|---|---|
| 275 | 3-methyl-2-(3-(1-(3-hydroxy-3-methylbutanoyl)piperidin-4-yl)propyl)quinolin-4(1H)-one |
| 14 | pentyl ((3-methyl-4-oxo-1,4-dihydroquinolin-2-yl)methyl)carbamate |
| 276 | ethyl 4-(2-(3-methyl-4-oxo-1,4-dihydroquinolin-2-yl)ethyl)piperidine-1-carboxylate |
| 277 | ethyl 4-(3-(3-methyl-4-oxo-1,4-dihydroquinolin-2-yl)propyl)piperidine-1-carboxylate |
| 15 | 1-((3-methyl-4-oxo-1,4-dihydroquinolin-2-yl)methyl)-3-pentylurea |
| 278 | N-ethyl-4-((3-((3-methyl-4-oxo-1,4-dihydroquinolin-2-yl)methoxy)phenoxy)methyl)piperidine-1-carboxamide |
| 16 | N-((3-methyl-4-oxo-1,4-dihydroquinolin-2-yl)methyl)hexane-1-sulfonamide |

TABLE 119-continued

| Ex | Str |
|---|---|
| 279 | (structure) |
| 17 | (structure) |
| 18 | (structure) |

TABLE 120

| Ex | Str |
|---|---|
| 280 | (structure) |
| 281 | (structure) |
| 282 | (structure) |

TABLE 120-continued
| Ex | Str |
|---|---|
| 283 | 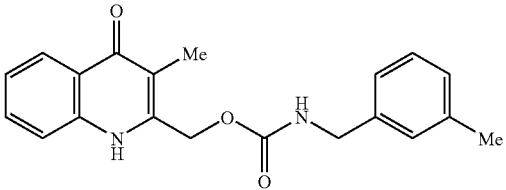 [SMILES: Cc1cccc(CNC(=O)OCc2[nH]c3ccccc3c(=O)c2C)c1] |
| 284 | 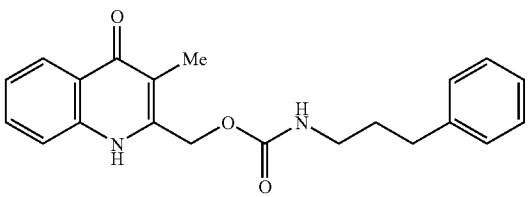 [SMILES: Cc1c(COC(=O)NCCCc2ccccc2)[nH]c2ccccc2c1=O] |
| 285 | 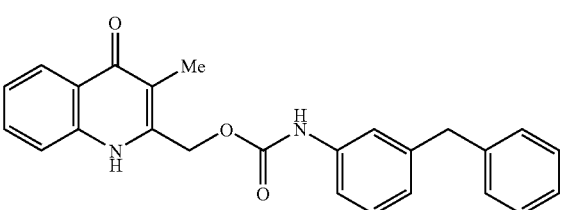 |
| 286 | 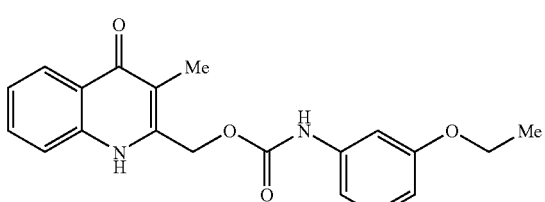 |
| 287 | 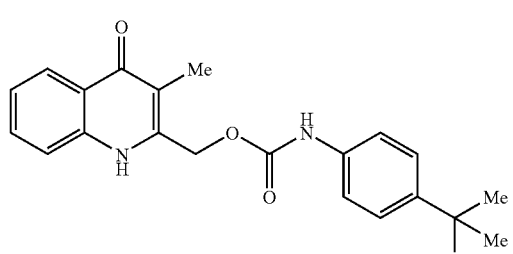 |
| 288 | 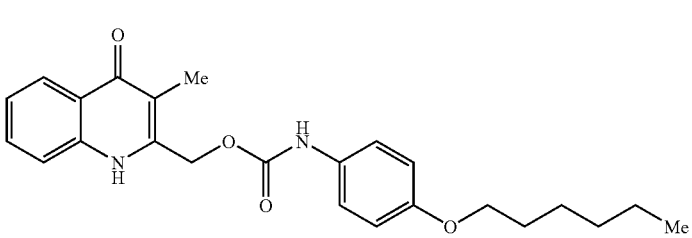 [SMILES: CCCCCCOc1ccc(NC(=O)OCc2[nH]c3ccccc3c(=O)c2C)cc1] |
| 289 | 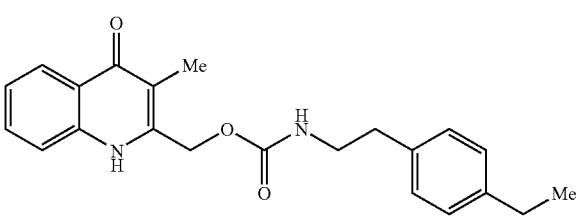 [SMILES: CCc1ccc(CCNC(=O)OCc2[nH]c3ccccc3c(=O)c2C)cc1] |

TABLE 120-continued

| Ex | Str |
|---|---|
| 290 | (3-methyl-4-oxo-1,4-dihydroquinolin-2-yl)methyl (3-phenoxyphenyl)carbamate |
| 291 | (3-methyl-4-oxo-1,4-dihydroquinolin-2-yl)methyl (cyclohexylmethyl)carbamate |

TABLE 121

| Ex | Str |
|---|---|
| 292 | (3-methyl-4-oxo-1,4-dihydroquinolin-2-yl)methyl [4-(trifluoromethoxy)phenyl]carbamate |
| 293 | (3-methyl-4-oxo-1,4-dihydroquinolin-2-yl)methyl [3-(trifluoromethyl)phenyl]carbamate |
| 294 | (3-methyl-4-oxo-1,4-dihydroquinolin-2-yl)methyl [2-(4-methoxyphenyl)ethyl]carbamate |
| 295 | (3-methyl-4-oxo-1,4-dihydroquinolin-2-yl)methyl 2,3-dihydro-1,4-benzodioxin-6-ylcarbamate |
| 19 | 2-{[(heptylsulfonyl)methyl]}-3-methylquinolin-4(1H)-one |

TABLE 121-continued

| Ex | Str |
|---|---|
| 296 | 3-methyl-2-[(3-{[(tetrahydro-2H-pyran-4-yl)methyl]sulfonyl}phenoxy)methyl]quinolin-4(1H)-one |
| 297 | 3-methyl-2-{[(3-{[(tetrahydro-2H-pyran-4-yl)methoxy]phenyl}sulfonyl)methyl]}quinolin-4(1H)-one |
| 20 | 4-[(3-methyl-4-oxo-1,4-dihydroquinolin-2-yl)methoxy]-2-[(tetrahydro-2H-pyran-4-ylmethoxy)]benzoic acid |
| 298 | 3,5-bis[(tetrahydro-2H-pyran-4-ylmethoxy)]-... benzoic acid derivative |

TABLE 121-continued

| Ex | Str |
|---|---|
| 299 | (3-methyl-4-oxo-1H-quinolin-2-yl)methoxy – 3,5-disubstituted phenyl with (tetrahydropyran-4-yl)methoxy and CH₂COOH |

TABLE 122

| Ex | Str |
|---|---|
| 21 | 3-methyl-2-{[4-((tetrahydropyran-4-yl)methoxy)-2-(morpholine-4-carbonyl)phenoxy]methyl}-1H-quinolin-4-one |
| 300 | 3-methyl-2-{[3,5-bis((tetrahydropyran-4-yl)methoxy)phenyl with piperidine-1-carbonyl]methyl}-1H-quinolin-4-one |
| 301 | 3-methyl-2-{[4-((tetrahydropyran-4-yl)methoxy)-2-(piperidine-1-carbonyl)phenoxy]methyl}-1H-quinolin-4-one |
| 22 | 3-methyl-2-{[3,5-bis((tetrahydropyran-4-yl)methoxy)phenyl with 1H-tetrazol-5-yl]methyl}-1H-quinolin-4-one |
| 23 | 6-carboxy-3-methyl-2-{[3-((tetrahydropyran-4-yl)methoxy)phenoxy]methyl}-1H-quinolin-4-one |

TABLE 123

| Ex | Syn | DATA |
|---|---|---|
| 1 | 1 | NMR1: 1.47-1.57(2H, m), 1.64-1.81(4H, m), 2.00(3H, s), 2.71(2H, t, J = 8.0 Hz), 3.95(2H, t, J = 6.4 Hz), 6.89-6.94(2H, m), 7.05-7.12(2H, m), 7.21-7.26(1H, m), 7.48(1H, d, J = 8.1 Hz), 7.54-7.59(1H, m), 8.05(1H, d, J = 7.1 Hz), 11.33(1H, s) FAB+: 340 |
| 24 | 1 | NMR1: 1.54-1.72(4H, m), 1.99(3H, s), 2.70(2H, t, J = 7.3 Hz), 3.23(3H, s), 3.40-3.50(6H, m), 7.21-7.26(1H, m), 7.47-7.51(1H, m), 7.54-7.60(1H, m), 8.0$_{3-8}$.07(1H, m), 11.32(1H, s) FAB+: 290 |
| 25 | 1 | NMR1: 1.24(3H, t, J = 6.8 Hz), 1.45-1.60(2H, m), 1.64-1.76(2H, m), 1.72-1.83(2H, m), 2.00(3H, s), 2.71(2H, dd, J = 8.0, 8.0 Hz), 3.95(2H, q, J = 6.8 Hz), 3.96(2H, dd, J = 6.0, 6.0 Hz), 6.79-6.89(2H, m), 6.89-6.98(2H, m), 7.23(1H, dd, J = 7.2, 7.2 Hz), 7.49(1H, d, J = 8.0 Hz), 7.57(1H, td, J = 7.2, 1.2 Hz), 8.05(1H, d, J = 7.2 Hz), 11.33(1H, s) FAB+: 366 |

TABLE 123-continued

| Ex | Syn | DATA |
|---|---|---|
| 26 | 1 | NMR1: 1.47-1.57(2H, m), 1.65-1.82(4H, m), 2.00(3H, s), 2.71(2H, t, J = 7.6 Hz), 4.03(2H, t, J = 6.4 Hz), 6.95-7.02(1H, m), 7.13-7.29(2H, m), 7.48(1H, d, J = 8.0 Hz), 7.53-7.58(1H, m), 8.05(1H, d, J = 7.1 Hz), 11.33(1H, s)<br>FAB+: 358 |
| 27 | 1 | NMR1: 1.48-1.58(2H, m), 1.62-1.72(2H, m), 1.74-1.83(2H, m), 2.01(3H, s), 2.80(2H, t, J = 7.8 Hz), 4.04(2H, t, J = 6.7 Hz), 6.96-7.02(1H, m), 7.14-7.29(3H, m), 7.46-7.53(1H, m), 7.88(1H, d, J = 7.9 Hz), 11.29(1H, s)<br>FAB+: 376 |

TABLE 124

| Ex | Syn | DATA |
|---|---|---|
| 28 | 1 | NMR1: 1.46-1.58(2H, m), 1.63-1.75(2H, m), 1.72-1.84(2H, m), 2.00(3H, s), 2.71(2H, dd, J = 7.2, 7.2 Hz), 4.03(2H, dd, J = 6.8, 6.8 Hz), 6.94-7.04(1H, m), 7.17(1H, td, J = 10.0, 5.2 Hz), 7.25(1H, ddd, J = 11.6, 8.8, 2.8 Hz), 7.48(1H, td, J = 8.8, 2.8 Hz), 7.57(1H, dd, J = 9.2, 5.2 Hz), 7.68(1H, dd, J = 9.2, 2.8 Hz), 11.50(1H, br s)<br>FAB+: 376<br>mp: 201-203° C. |
| 29 | 1 | NMR1: 1.46-1.57(2H, m), 1.64-1.75(2H, m), 1.75-1.84(2H, m), 2.00(3H, s), 2.66-2.75(2H, m), 4.08(2H, t, J = 6.5 Hz), 7.08(2H, d, J = 8.8 Hz), 7.21-7.26(1H, m), 7.46-7.50(1H, m), 7.54-7.59(1H, m), 7.74(2H, d, J = 8.8 Hz), 8.02-8.07(1H, m), 11.32(1H, s)<br>FAB+: 347 |
| 30 | 1 | NMR1: 0.35-0.44(4H, m), 1.33-1.43(2H, m), 1.49-1.68(4H, m), 1.99(3H, s), 2.64-2.70(2H, m), 3.18-3.24(1H, m), 3.42(2H, t, J = 6.4 Hz), 7.20-7.26(1H, m), 7.47-7.51(1H, m), 7.54-7.59(1H, m), 8.02-8.07(1H, m), 11.32(1H, s)<br>FAB+: 286 |
| 31 | 1 | NMR1: 1.22-1.35(2H, m), 1.60-1.68(2H, m), 1.89-2.02(4H, m), 2.85-3.00(4H, m), 3.27-3.38(2H, m), 3.75(2H, d, J = 6.5 Hz), 3.83-3.90(2H, m), 6.75-6.86(3H, m), 7.16-7.27(2H, m), 7.47-7.52(1H, m), 7.55-7.61(1H, m), 8.03-8.08(1H, m), 11.37(1H, s)<br>FAB+: 378 |
| 32 | 1 | NMR1: 1.46-1.56(2H, m), 1.64-1.76(2H, m), 1.76-1.87(2H, m), 2.00(3H, s), 2.66-2.75(2H, m), 4.45(2H, t, J = 6.5 Hz), 7.20-7.27(1H, m), 7.44-7.51(2H, m), 7.53-7.60(1H, m), 8.02-8.08(1H, m), 8.98(1H, s), 11.32(1H, s)<br>FAB+: 392<br>mp: 173-175° C. |

TABLE 125

| Ex | Syn | DATA |
|---|---|---|
| 2 | 2 | NMR1: 1.25-1.37(2H, m), 1.66(2H, d, J = 12.7 Hz), 1.92-2.03(1H, m), 2.05(3H, s), 3.26-3.36(2H, m), 3.80(2H, d, J = 6.4 Hz), 3.80-3.90(2H, m), 5.16(2H, s), 6.56-6.61(1H, m), 6.66-6.70(2H, m), 7.19-7.32(2H, m), 7.58-7.67(2H, m), 8.09(1H, d, J = 8.0 Hz), 11.59(1H, s)<br>FAB+: 380<br>mp: 200-202° C. |
| 33 | 2 | NMR1: 2.15(3H, s), 2.96-3.03(2H, m), 3.23-3.33(2H, m), 3.73(2H, s), 4.38-4.45(2H, m), 5.60(2H, br s), 6.90(2H, d, J = 8.6 Hz), 7.19(2H, d, J = 8.6 Hz), 7.33-7.38(1H, m), 7.65-7.70(2H, m), 8.14(1H, d, J = 7.9 Hz), 9.73(2H, br s)<br>FAB+: 323 |
| 34 | 2 | NMR1: 0.86(3H, t, J = 6.9 Hz), 1.21-1.37(8H, m), 1.65-1.74(2H, m), 2.13(3H, s), 3.00-3.10(2H, m), 4.35(2H, t, J = 5.9 Hz), 5.87(2H, br s), 7.31-7.37(1H, m), 7.61-7.70(2H, m), 8.12(1H, d, J = 7.7 Hz), 9.50(2H, br s)<br>FAB+: 287 |
| 35 | 2 | NMR1: 1.95(3H, s), 1.96(3H, s), 2.75(2H, t, J = 7.4 Hz), 3.43(2H, t, J = 7.6 Hz), 3.70(3H, s), 4.66(2H, s), 6.83(2H, d, J = 8.6 Hz), 7.08(2H, d, J = 8.6 Hz), 7.28(1H, t, J = 7.9 Hz), 7.57-7.67(2H, m), 8.07(1H, d, J = 7.8 Hz), 11.08(1H, br s)<br>FAB+: 365 |
| 36 | 2 | NMR1: 0.79(3H, t, J = 7.0 Hz), 1.08-1.26(10H, m), 1.92-2.03(3H, m), 2.07-2.14(3H, m), 3.14-3.28(2H, m), 4.60-4.68(2H, m), 7.27(1H, t, J = 6.4 Hz), 7.55-7.80(2H, m), 8.07(1H, d, J = 7.8 Hz) 11.06(1H, br s)<br>FAB+: 329 |
| 37 | 2 | NMR1: 1.60-1.76(4H, m), 2.12(3H, s), 2.61(2H, t, J = 7.1 Hz), 3.03-3.15(2H, m), 4.35(2H, t, J = 5.9 Hz), 5.25(2H, br s), 7.15-7.36(6H, m), 7.62-7.70(2H, m), 8.12(1H, d, J = 7.9 Hz), 9.49(2H, br s)<br>FAB+: 321 |

TABLE 126

| Ex | Syn | DATA |
|---|---|---|
| 38 | 2 | NMR1: 1.56-1.75(4H, m), 2.12(3H, s), 2.54(2H, t, J = 7.2 Hz), 3.03-3.12(2H, m), 3.71(3H, s), 4.35(2H, t, J = 5.7 Hz), 5.46(2H, br s), 6.83(2H, d, J = 8.5 Hz), 7.12(2H, d, J = 8.6 Hz), 7.31-7.37(1H, m), 7.62-7.71(2H, m), 8.12(1H, d, J = 7.9 Hz), 9.48(2H, br s)<br>FAB+: 351 |
| 39 | 2 | NMR1: 2.02(2H, quint, J = 7.7 Hz), 2.12(3H, s), 2.70(2H, t, J = 7.7 Hz), 3.02-3.11(2H, m), 4.37(2H, t, J = 5.7 Hz), 5.50(2H, br s), 7.16-7.37(6H, m), 7.62-7.71(2H, m), 8.12(1H, d, J = 7.8 Hz), 9.61(2H, br s)<br>FAB+: 307 |
| 40 | 2 | NMR1: 0.83(3H, t, J = 6.9 Hz), 1.19-1.35(8H, m), 1.54-1.62(2H, m), 2.00(3H, s), 3.51(2H, t, J = 6.5 Hz), 4.56(2H, s), 7.26(1H, t, J = 7.3 Hz), 7.56-7.61(1H, m), 7.66(1H, d, J = 8.4 Hz), 8.07(1H, d, J = 8.1 Hz), 11.32(1H, s)<br>FAB+: 288 |
| 41 | 2 | NMR1: 0.85(3H, t, J = 7.2 Hz), 1.15-1.30(4H, m), 1.35-1.45(2H, m), 2.02(3H, s), 2.99(2H, q, J = 6.3 Hz), 5.06(2H, s), 7.25-7.36(2H, m), 7.55-7.64(2H, m), 8.07(1H, d, J = 7.8 Hz), 11.57(1H, s)<br>FAB+: 303 |
| 42 | 2 | NMR1: 0.08-0.14(2H, m), 0.38-0.45(2H, m), 0.89-0.99(1H, m), 1.50-1.67(4H, m), 2.00(3H, s), 3.16(2H, d, J = 6.8 Hz), 3.36(2H, t, J = 6.2 Hz), 3.53(2H, t, J = 6.4 Hz), 4.57(2H, s), 7.24-7.30(1H, m), 7.55-7.62(1H, m), 7.67(1H, d, J = 8.3 Hz), 8.07(1H, d, J = 8.1 Hz), 11.32(1H, s)<br>FAB+: 316 |
| 43 | 2 | NMR1: 1.27-1.37(2H, m), 1.46-1.55(2H, m), 1.55-1.64(2H, m), 1.99(3H, s), 2.43(2H, t, J = 7.5 Hz), 3.50(2H, t, J = 6.5 Hz), 4.18(4H, s), 4.55(2H, s), 6.56-6.60(1H, m), 6.6$_2$-$_6$.65(1H, m), 6.68-6.72(1H, m), 7.24-7.30(1H, m), 7.56-7.62(1H, m), 7.64-7.69(1H, m), 8.0$_{5-8}$.10(1H, m), 11.31(1H, s)<br>FAB+: 394<br>mp: 135-137° C. |

TABLE 127

| Ex | Syn | DATA |
|---|---|---|
| 44 | 2 | NMR1: 1.70-1.86(4H, m), 2.01(3H, s), 3.60(2H, t, J = 6 Hz), 4.06(2H, t, J = 6 Hz), 4.59(2H, s), 7.24-7.36(3H, m), 7.56-7.62(1H, m), 7.64-7.69(1H, m), 8.0$_{5-8}$.10(1H, m), 8.12-8.16(1H, m), 8.24-8.28(1H, m), 11.33(1H, s)<br>FAB+: 339 |
| 45 | 2 | NMR1: 0.77-0.87(3H, m), 1.30-1.68(6H, m), 2.00(3H, s), 2.87-2.95(2H, m), 3.50-3.60(2H, m), 3.90-3.97(2H, m), 4.57(2H, s), 7.02-7.10(1H, m), 7.27(1H, t, J = 7.8 Hz), 7.56-7.62(1H, m), 7.66(1H, d, J = 8.2 Hz), 8.07(1H, d, J = 8.2 Hz), 11.31(1H, s)<br>FAB+: 347 |
| 46 | 2 | NMR1: 1.44-1.52(2H, m), 1.58-1.67(2H, m), 2.00(3H, s), 3.40(2H, q, J = 5.2 Hz), 3.53(2H, t, J = 6.5 Hz), 4.40(1H, t, J = 5.0 Hz), 4.56(2H, s), 7.24-7.30(1H, m), 7.56-7.62(1H, m), 7.66(1H, d, J = 8.1 Hz), 8.06-8.10(1H, m), 11.32(1H, s)<br>FAB+: 262 |
| 47 | 2 | NMR1: 1.70-1.83(4H, m), 2.01(3H, s), 3.59(2H, t, J = 6.0 Hz), 3.97(2H, t, J = 6.0 Hz), 4.59(2H, s), 6.86-6.92(3H, m), 7.22-7.30(3H, m), 7.56-7.62(1H, m), 7.66(1H, d, J = 8.2 Hz), 8.06-8.10(1H, m), 11.33(1H, s)<br>FAB+: 338 |
| 48 | 2 | NMR1: 1.50-1.72(6H, m), 2.00(3H, s), 2.18-2.32(2H, m), 3.34-3.40(4H, m), 3.53(2H, t, J = 6.4 Hz), 4.56(2H, s), 7.24-7.29(1H, m), 7.56-7.62(1H, m), 7.66(1H, d, J = 8.2 Hz), 8.0$_{5-8}$.09(1H, m), 11.32(1H, s)<br>FAB+: 372 |
| 49 | 2 | NMR1: 1.70-1.86(4H, m), 2.01(3H, s), 3.59(2H, t, J = 6.0 Hz), 4.08(2H, t, J = 6.4 Hz), 4.59(2H, s), 7.06(2H, d, J = 8.6 Hz), 7.27(1H, t, J = 7.4 Hz), 7.56-7.68(2H, m), 7.72(2H, d, J = 8.6 Hz), 8.08(1H, d, J = 8.4 Hz), 11.34(1H, s)<br>FAB+: 363 |

TABLE 128

| Ex | Syn | DATA |
|---|---|---|
| 50 | 2 | NMR1: 1.70-1.82(4H, m), 2.01(3H, s), 2.70(2H, t, J = 7.0 Hz), 3.22(3H, s), 3.46(2H, t, J = 7.0 Hz), 3.58(2H, t, J = 6.0 Hz), 3.93(2H, t, J = 6.2 Hz), 4.58(2H, s), 6.79(2H, d, J = 8.6 Hz), 7.08(2H, d, J = 8.6 Hz), 7.24-7.30(1H, m), 7.57-7.62(1H, m), 7.66(1H, d, J = 8.2 Hz), 8.06-8.10(1H, m), 11.33(1H, s)<br>FAB+: 396 |
| 51 | 2 | NMR1: 1.66-1.84(4H, m), 2.00(3H, s), 3.58(2H, dd, J = 6.0, 6.0 Hz), 3.94(2H, dd, J = 6.0, 6.0 Hz), 4.59(2H, br s), 6.90(2H, dd, J = 8.8, 4.4 Hz), 7.07(2H, dd, J = 8.8, 8.8 Hz), 7.23-7.31(1H, m), 7.55-7.63(1H, m), 87.67(1H, d, J = 8.0 Hz), 8.0$_{5-8}$.11(1H, m), 11.36(1H, br s)<br>FAB+: 356 |

TABLE 128-continued

| Ex | Syn | DATA |
|---|---|---|
| 52 | 2 | NMR1: 1.38(6H, s), 1.67-1.82(4H, m), 2.01(3H, s), 2.96(2H, s), 3.56(2H, dd, J = 5.2, 5.2 Hz), 3.97(2H, dd, J = 5.2, 5.2 Hz), 4.58(2H, s), 6.67(1H, dd, J = 8.0, 6.4 Hz), 6.71-6.78(2H, m), 7.23-7.31(1H, m), 7.55-7.63(1H, m), 7.67(1H, d, J = 8.0 Hz), 8.08(1H, d, J = 8.0 Hz), 11.33(1H, s)<br>FAB+: 408<br>mp: 139-140° C. |
| 53 | 2 | NMR1: −0.02-0.02(2H, m), 0.32-0.38(2H, m), 0.62-0.72(1H, m), 1.35(2H, q, J = 6.8 Hz), 1.53-1.66(4H, m), 2.00(3H, s), 3.33-3.39(2H, m), 3.53(2H, t, J = 6.4 Hz), 4.56(2H, s), 7.24-7.28(1H, m), 7.56-7.61(1H, m), 7.66(1H, d, J = 8.2 Hz), 8.06-8.09(1H, m), 11.31(1H, s)<br>FAB+: 330<br>mp: 155-157° C. |
| 54 | 2 | NMR1: 1.19(3H, s), 1.54-1.69(4H, m), 2.00(3H, s), 3.38(2H, s), 3.43(2H, t, J = 6.0 Hz), 3.54(2H, t, J = 6.4 Hz), 4.16(2H, d, J = 5.4 Hz), 4.33(2H, d, J = 5.5 Hz), 4.57(2H, s), 7.24-7.29(1H, m), 7.56-7.62(1H, m), 7.66(1H, d, J = 8.2 Hz), 8.06-8.10(1H, m), 11.33(1H, s)<br>FAB+: 346 |

TABLE 129

| Ex | Syn | DATA |
|---|---|---|
| 55 | 2 | NMR1: 1.06(6H, s), 1.50-1.67(6H, m), 2.00(3H, s), 3.04(3H, s), 3.34-3.40(4H, m), 3.53(2H, t, J = 6.4 Hz), 4.56(2H, s), 7.27(1H, t, J = 7.0 Hz), 7.56-7.62(1H, m), 7.66(1H, d, J = 8.2 Hz), 8.08(1H, d, J = 8.2 Hz), 11.32(1H, s)<br>FAB+: 362 |
| 56 | 2 | NMR1: 1.52-1.67(4H, m), 2.00(3H, s), 2.43-2.56(2H, m), 3.40(2H, t, J = 6.0 Hz), 3.50-3.58(4H, m), 4.56(2H, s), 7.24-7.29(1H, m), 7.56-7.62(1H, m), 7.67(1H, d, J = 8.3 Hz), 8.08(1H, d, J = 7.9 Hz), 11.32(1H, s)<br>FAB+: 358 |
| 57 | 2 | NMR1: 1.08(9H, s), 1.44-1.52(2H, m), 1.58-1.66(2H, m), 2.00(3H, s), 3.25-3.31(2H, m), 3.52(2H, t, J = 6.6 Hz), 4.56(2H, s), 7.24-7.29(1H, m), 7.56-7.61(1H, m), 7.67(1H, d, J = 8.2 Hz), 8.07(1H, d, J = 7.2 Hz), 11.32(1H, s)<br>FAB+: 318 |
| 58 | 2 | NMR1: 1.19-1.33(2H, m), 1.38(9H, s), 1.47-1.59(2H, m), 1.58-1.69(2H, m), 1.65-1.79(2H, m), 2.00(3H, s), 2.88-3.08(2H, m), 3.32-3.44(3H, m), 3.47-3.64(4H, m), 4.56(2H, s), 7.22-7.31(1H, m), 7.59(1H, ddd, J = 6.8, 6.8, 1.6 Hz), 7.67(1H, d, J = 8.0 Hz), 8.08(1H, dd, J = 8.0, 1.6 Hz), 11.32(1H, s)<br>ESI+: 445 |
| 59 | 2 | NMR1: 1.68-1.84(4H, m), 2.01(3H, s), 3.06(4H, dd, J = 4.8, 4.8 Hz), 3.59(2H, dd, J = 6.4, 6.4 Hz), 3.70(4H, dd, J = 4.8, 4.8 Hz), 3.94(2H, dd, J = 6.4, 6.4 Hz), 4.59(2H, s), 6.35(1H, dd, J = 9.2, 2.0 Hz), 6.41(1H, dd, J = 2.0, 2.0 Hz), 6.49(1H, dd, J = 9.2, 2.0 Hz), 7.08(1H, dd, J = 8.4, 8.4 Hz), 7.23-7.31(1H, m), 7.55-7.63(1H, m), 7.67(1H, d, J = 8.4 Hz), 8.08(1H, dd, J = 8.4, 1.2 Hz), 11.34(1H, br s)<br>ESI+: 423 |

TABLE 130

| Ex | Syn | DATA |
|---|---|---|
| 60 | 2 | NMR1: 0.34-0.42(4H, m), 1.49-1.65(4H, m), 2.00(3H, s), 3.17-3.22(1H, m), 3.41(2H, t, J = 6 Hz), 3.52(2H, t, J = 6 Hz), 4.56(2H, s), 7.24-7.29(1H, m), 7.56-7.62(1H, m), 7.64-7.69(1H, m), 8.05-8.10(1H, m), 11.31(1H, s)<br>FAB+: 302 |
| 61 | 2 | NMR1: 0.83(9H, s), 1.54-1.67(4H, m), 2.00(3H, s), 2.98(2H, s), 3.33-3.38(2H, m), 3.54(2H, t, J = 6.5 Hz), 4.56(2H, s), 7.26(1H, t, J = 7.2 Hz), 7.56-7.61(1H, m), 7.66(1H, d, J = 8.2 Hz), 8.07(1H, d, J = 7.0 Hz), 11.30(1H, s)<br>FAB+: 332 |
| 62 | 2 | NMR1: 0.92(3H, t, J = 7.5 Hz), 1.37-1.47(2H, m), 1.64-1.72(2H, m), 2.05(3H, s), 3.95(2H, t, J = 6.5 Hz), 5.15(2H, s), 6.55-6.59(1H, m), 6.65-6.69(2H, m), 7.17-7.31(2H, m), 7.58-7.66(2H, m), 8.09(1H, d, J = 7.6 Hz), 11.57(1H, s)<br>FAB+: 338 |
| 63 | 2 | NMR1: 0.85(3H, t, J = 7.2 Hz), 1.18-1.35(4H, m), 1.44-1.61(2H, m), 2.08(3H, s), 2.43-2.56(2H, m), 5.20(2H, s), 7.10(2H, d, J = 8.0 Hz), 7.25-7.32(1H, m), 7.37(2H, d, J = 8.0 Hz), 7.58(1H, d, J = 8.0 Hz), 7.60-7.66(1H, m), 8.09(1H, d, J = 8.0 Hz), 9.75(1H, s), 11.68(1H, s)<br>ESI+: 379<br>mp: 215-216° C. |

TABLE 130-continued

| Ex | Syn | DATA |
|---|---|---|
| 64 | 2 | NMR1: 0.85(3H, t, J = 7.2 Hz), 1.16-1.33(10H, m), 1.45-1.58(2H, m), 2.08(3H, s), 2.44-2.56(2H, m), 5.20(2H, s), 7.09(2H, d, J = 8.0 Hz), 7.24-7.32(1H, m), 7.37(2H, d, J = 8.0 Hz), 7.58(1H, d, J = 8.0 Hz), 7.60-7.67(1H, m), 8.09(1H, d, J = 8.0 Hz), 9.75(1H, s), 11.68(1H, s)<br>ESI+: 421 |
| 65 | 2 | NMR1: 2.01(3H, s), 2.74(2H, dd, J = 6.4, 6.4 Hz), 3.19-3.30(2H, m), 5.05(2H, s), 7.16-7.22(1H, m), 7.28(1H, dd, J = 7.2, 7.2 Hz), 7.38-7.48(1H, m), 7.49(1H, s), 7.50(1H, d, J = 8.4 Hz), 7.56(1H, d, J = 7.2 Hz), 7.58-7.66(1H, m), 8.08(1H, d, J = 8.4 Hz), 11.58(1H, br s)<br>ESI+: 405, 407 |

TABLE 131

| Ex | Syn | DATA |
|---|---|---|
| 66 | 2 | NMR1: 1.16(3H, s), 1.17(3H, s), 2.08(3H, s), 2.82(1H, qq, J = 6.8, 6.8 Hz), 5.20(2H, s), 7.16(2H, d, J = 8.8 Hz), 7.29(1H, dd, J = 7.2, 7.2 Hz), 7.39(2H, d, J = 8.8 Hz), 7.58(1H, d, J = 8.0 Hz), 7.60-7.67(1H, m), 8.09(1H, d, J = 8.0 Hz), 9.75(1H, s), 11.67(1H, s)<br>FAB+: 351<br>mp: 254-256° C. |
| 67 | 2 | NMR1: 1.88-1.97(2H, m), 2.05(3H, m), 2.35-2.46(2H, m), 4.04(2H, t, J = 6.2 Hz), 5.16(2H, s), 6.58-6.62(1H, m), 6.68-6.72(2H, m), 7.21-7.32(2H, m), 7.58-7.67(2H, m), 8.09(1H, d, J = 8.0 Hz), 11.60(1H, s)<br>FAB+: 392 |
| 68 | 2 | NMR1: 0.83(3H, t, J = 7 Hz), 1.43-1.53(2H, m), 2.05(3H, s), 2.75(2H, t, J = 7 Hz), 3.32(2H, t, J = 7 Hz), 3.52(2H, t, J = 7 Hz), 5.15(2H, s), 7.02(2H, d, J = 8 Hz), 7.20(2H, d, J = 8 Hz), 7.26-7.32(1H, m), 7.58-7.68(2H, m), 8.07-8.12(1H, m), 11.59(1H, s)<br>FAB+: 352 |
| 69 | 2 | NMR1: 1.16(6H, s), 1.90(2H, t, J = 7.2 Hz), 2.06(3H, s), 3.10(3H, s), 4.01(2H, t, J = 7.1 Hz), 5.17(2H, s), 6.56-6.60(1H, m), 6.66-6.70(2H, m), 7.19-7.33(2H, m), 7.59-7.67(2H, m), 8.09(1H, d, J = 7.9 Hz), 11.58(1H, s)<br>FAB+: 382 |
| 70 | 2 | NMR1: 1.18(3H, t, J = 7.2 Hz), 2.03(3H, s), 2.41-2.48(4H, m), 3.36-3.45(4H, m), 3.60(2H, s), 4.04(2H, q, J = 7.2 Hz), 7.21-7.29(1H, m), 7.58(1H, ddd, J = 6.8, 6.8, 1.6 Hz), 7.67(1H, d, J = 8.4 Hz), 8.07(1H, dd, J = 8.4, 1.6 Hz), 11.18(1H, s)<br>FAB+: 330 |
| 71 | 2 | NMR1: 1.30(3H, t, J = 7.0 Hz), 1.73-1.85(4H, m), 2.01(3H, s), 2.71-2.80(2H, m), 3.94-4.03(4H, m), 6.43-6.51(3H, m), 7.14(1H, t, J = 8.0 Hz), 7.21-7.26(1H, m), 7.48-7.52(1H, m), 7.55-7.60(1H, m), 8.0$_3$-$_8$.07(1H, m), 11.36(1H, s)<br>FAB+: 352 |

TABLE 132

| Ex | Syn | DATA |
|---|---|---|
| 72 | 2 | NMR1: 0.35-0.43(4H, m), 1.29-1.38(2H, m), 1.43-1.52(2H, m), 1.54-1.63(2H, m), 2.00(3H, s), 3.16-3.22(1H, m), 3.39(2H, t, J = 6.7 Hz), 3.51(2H, t, J = 6.7 Hz), 4.56(2H, s), 7.23-7.30(1H, m), 7.56-7.62(1H, m), 7.64-7.69(1H, m), 8.0$_5$-$_8$.10(1H, m), 11.32(1H, s)<br>FAB+: 316 |
| 73 | 2 | NMR1: 1.36(3H, s), 2.06(3H, s), 4.04(2H, s), 4.30(2H, d, J = 5.7 Hz), 4.48(2H, d, J = 5.7 Hz), 5.17(2H, s), 6.64(1H, dd, J = 2.0, 8.1 Hz), 6.69-6.77(2H, m), 7.22-7.32(2H, m), 7.59-7.67(2H, m), 8.09(1H, d, J = 7.6 Hz), 11.58(1H, s)<br>FAB+: 366 |
| 74 | 2 | NMR1: 0.86(3H, t, J = 7.0 Hz), 1.19-1.34(4H, m), 1.38-1.56(4H, m), 1.81-1.96(2H, m), 2.01(3H, s), 2.29(2H, t, J = 7.0 Hz), 3.00-3.10(1H, m), 3.14-3.24(1H, m), 3.64-3.75(2H, m), 3.86-3.96(1H, m), 4.63(2H, s), 7.24-7.30(1H, m), 7.57-7.62(1H, m), 7.65-7.69(1H, m), 8.0$_5$-$_8$.10(1H, m), 11.27(1H, s)<br>FAB+: 371 |
| 75 | 2 | NMR1: 2.11(3H, s), 5.37(2H, s), 7.25-7.34(2H, m), 7.57-7.68(6H, m), 8.03(1H, d, J = 8.9 Hz), 8.10-8.14(3H, m), 11.68(1H, s)<br>FAB+: 410 |
| 76 | 2 | NMR1: 2.10(3H, s), 5.34(2H, s), 7.07(1H, s), 7.30(1H, t, J = 8.1 Hz), 7.60-7.70(7H, m), 7.84(1H, d, J = 9.1 Hz), 8.10-8.13(3H, m), 11.63(1H, s)<br>FAB+: 410 |
| 77 | 2 | NMR1: 1.27-1.40(2H, m), 1.31(3H, t, J = 7.2 Hz), 1.67(2H, d, J = 12.8 Hz), 1.95-2.05(1H, m), 2.07(3H, s), 3.28-3.36(2H, m), 3.85-3.91(4H, m), 4.31(2H, q, J = 7.0 Hz), 6.99(1H, t, J = 2.4 Hz), 7.11-7.13(1H, m), 7.24-7.32(2H, m), 7.60-7.68(2H, m), 8.09(1H, d, J = 7.8 Hz), 11.56(1H, s)<br>FAB+: 452 |

TABLE 133

| Ex | Syn | DATA |
|---|---|---|
| 78 | 2 | NMR1: 1.28(3H, t, J = 6.8 Hz), 1.34-1.44(2H, m), 1.70(2H, d, J = 12.8 Hz), 1.92-2.05(1H, m), 2.07(3H, s), 3.32(2H, t, J = 11.6 Hz), 3.85-3.92(4H, m), 4.21(2H, q, J = 6.8 Hz), 5.25(2H, s), 6.75(1H, dd, J = 2.4, 8.8 Hz), 6.80(1H, d, J = 2.4 Hz), 7.25-7.36(1H, m), 7.60-7.65(2H, m), 7.72(1H, d, J = 8.0 Hz), 8.10(1H, d, J = 7.6 Hz), 11.58(1H, s)<br>FAB+: 452 |
| 79 | 2 | NMR1: 1.23-1.36(2H, m), 1.64(2H, d, J = 12.9 Hz), 1.90-2.04(1H, m), 2.05(3H, s), 3.25-3.32(2H, m), 3.82-3.92(4H, m), 5.25(2H, s), 7.18(1H, t, J = 8.3 Hz), 7.27-7.31(1H, m), 7.38(1H, t, J = 11.0 Hz), 7.58-7.66(2H, m), 8.09(1H, d, J = 7.9 Hz), 11.69(1H, s)<br>FAB+: 416 |
| 80 | 2 | NMR1: 1.25-1.37(2H, m), 1.66(2H, d, J = 12.7 Hz), 1.90-2.03(1H, m), 2.05(3H, s), 3.27-3.35(4H, m), 3.60(3H, s), 3.81(2H, d, J = 6.5 Hz), 3.87(2H, dd, J = 2.9, 11.4 Hz), 5.14(2H, s), 6.50(1H, s), 6.60(2H, d, J = 1.5 Hz), 7.26-7.31(1H, m), 7.57-7.67(2H, m), 8.04(1H, d, J = 7.6 Hz), 11.61(1H, s)<br>FAB+: 452 |
| 81 | 2 | NMR1: 2.04(3H, s), 2.62(2H, t, J = 8.0 Hz), 2.81(2H, t, J = 8.0 Hz), 3.22-3.41(4H, m), 3.38-3.53(4H, m), 5.16(2H, s), 7.12-7.20(1H, m), 7.19-7.33(5H, m), 7.57(1H, d, J = 8.0 Hz), 7.61(1H, ddd, J = 8.0, 8.0, 1.2 Hz), 8.08(1H, d, J = 8.0 Hz), 11.65(1H, br s)<br>ESI+: 434 |
| 82 | 2 | NMR1: 2.05(3H, s), 3.03(2H, t, J = 6.8 Hz), 4.62(2H, t, J = 6.8 Hz), 5.16(2H, s), 7.05(2H, d, J = 8.5 Hz), 7.26-7.32(3H, m), 7.48(1H, s), 7.59-7.67(2H, m), 8.09(1H, d, J = 8.2 Hz), 8.99(1H, s), 11.59(1H, s)<br>FAB+: 456 |
| 83 | 2 | NMR1: 0.66-0.78(4H, m), 1.88-2.02(1H, m), 2.05(3H, s), 3.33-3.44(2H, m), 3.37-3.58(4H, m), 3.60-3.80(2H, m), 5.17(2H, s), 7.24-7.33(1H, m), 7.58(1H, d, J = 8.0 Hz), 7.62(1H, ddd, J = 8.0, 8.0, 1.6 Hz), 8.08(1H, d, J = 8.0 Hz), 11.62(1H, s)<br>ESI+: 370 |

TABLE 134

| Ex | Syn | DATA |
|---|---|---|
| 84 | 2 | NMR1: 1.04(3H, t, J = 7.3 Hz), 2.06(3H, s), 3.05-3.13(2H, m), 5.11(2H, s), 6.13-6.19(1H, m), 6.63(1H, dd, J = 2.2, 8.2 Hz), 6.90-6.95(1H, m), 7.15(1H, t, J = 8.2 Hz), 7.24-7.31(2H, m), 7.56-7.66(2H, m), 8.07-8.11(1H, m), 8.51(1H, s)<br>FAB+: 352 |
| 85 | 2 | NMR1: 0.82(3H, t, J = 7.3 Hz), 1.20-1.30(2H, m), 1.36-1.44(2H, m), 1.76-1.85(2H, m), 2.00(3H, s), 3.27-3.34(2H, m), 3.42(2H, t, J = 6.2 Hz), 3.57(2H, t, J = 6.4 Hz), 4.57(2H, s), 7.27(1H, t, J = 6.9 Hz), 7.55-7.64(1H, m), 7.67(1H, d, J = 8.2 Hz), 8.08(1H, d, J = 7.2 Hz), 11.34(1H, s)<br>FAB+: 304 |
| 86 | 2 | NMR1: 1.60-1.70(2H, m), 2.00(3H, s), 2.41-2.55(4H, m), 2.87-2.95(2H, m), 3.02-3.09(2H, m), 7.11-7.29(6H, m), 7.48(1H, d, J = 8.2 Hz), 7.52-7.58(1H, m), 7.94-7.99(1H, m), 8.04(1H, d, J = 8.2 Hz), 11.41(1H, s)<br>FAB+: 349<br>mp: 260-264° C. |
| 87 | 2 | NMR1: 1.23-1.37(2H, m), 1.61-1.69(2H, m), 1.90-2.02(1H, m), 2.06(3H, s), 3.26-3.35(2H, m), 3.80(2H, d, J = 6.5 Hz), 3.84-3.90(2H, m), 5.23(2H, s), 6.5$_2$-$_6$.57(1H, m), 6.91(1H, dd, J = 2.9, 7.2 Hz), 7.12-7.18(1H, m), 7.27-7.32(1H, m), 7.58-7.65(2H, m), 8.04(1H, d, J = 7.8 Hz), 11.70(1H, s)<br>FAB+: 398 |
| 88 | 2 | NMR1: 1.25-1.38(2H, m), 1.61-1.70(2H, m), 1.95-2.05(1H, m), 2.05(3H, s), 3.28-3.36(2H, m), 3.82-3.94(4H, m), 5.16(2H, s), 6.6$_2$-$_6$.68(1H, m), 6.92(1H, dd, J = 2.9, 7.3 Hz), 7.13-7.20(1H, m), 7.26-7.32(1H, m), 7.59-7.67(2H, m), 8.09(1H, d, J = 7.9 Hz), 11.57(1H, s)<br>FAB+: 398 |

TABLE 135

| Ex | Syn | DATA |
|---|---|---|
| 89 | 2 | NMR1: 1.21-1.38(2H, m), 1.65(2H, d, J = 12.5 Hz), 1.90-2.00(1H, m), 2.05(3H, s), 2.26(3H, s), 3.25-3.35(2H, m), 3.80(2H, d, J = 6.4 Hz), 3.83-3.92(2H, m), 5.13(2H, s), 6.42(1H, s), 6.49(1H, s), 6.53(1H, s), 7.26-7.33(1H, m), 7.58-7.69(2H, m), 8.10(1H, d, J = 7.9 Hz), 11.57(1H, s)<br>FAB+: 394 |
| 90 | 2 | NMR1: 1.25-1.37(2H, m), 1.60-1.67(2H, m), 1.94-2.04(1H, m), 2.05(3H, s), 3.27-3.36(2H, m), 3.83-3.90(2H, m), 4.11(2H, d, J = 6.6 Hz), 5.23(2H, s), 6.54(1H, d, J = 2.2 Hz), 6.74(1H, dd, J = 2.3, 5.9 Hz), 7.26-7.34(1H, m), 7.61-7.64(2H, m), 8.01(1H, d, J = 5.9 Hz), 8.09(1H, d, J = 8.1 Hz), 11.61(1H, s)<br>FAB+: 381 |

TABLE 135-continued

| Ex | Syn | DATA |
|---|---|---|
| 91 | 2 | NMR1: 1.17-1.30(2H, m), 1.85-1.44(2H, m), 1.92-2.02(1H, m), 2.04(3H, s), 3.16-3.26(2H, m), 3.72(2H, d, J = 7.3 Hz), 3.80-3.86(2H, m), 5.13(2H, s), 6.0$_2$-6.07(2H, m), 7.27-7.32(1H, m), 7.56-7.66(2H, m), 8.09(1H, d, J = 7.8 Hz), 10.62(1H, s)<br>FAB+: 381 |
| 92 | 2 | NMR1: 1.25-1.35(2H, m), 1.62-1.68(2H, m), 1.90-2.04(1H, m), 2.05(3H, s), 3.26-3.37(2H, m), 3.72(3H, s), 3.80(2H, d, J = 6.5 Hz), 3.83-3.90(2H, m), 5.14(2H, s), 6.14-6.17(1H, m), 6.26-6.31(2H, m), 7.26-7.31(1H, m), 7.59-7.67(2H, m), 8.07-8.12(1H, m), 11.61(1H, s)<br>FAB+: 410 |
| 93 | 2 | NMR1: 1.23-1.36(2H, m), 1.60-1.67(2H, m), 1.88-2.00(1H, m), 2.04(3H, s), 3.27-3.30(2H, m), 3.75(2H, d, J = 6.4 Hz), 3.83-3.90(2H, m), 5.09(2H, s), 5.99(1H, t, J = 2.0 Hz), 6.09(1H, t, J = 2.1 Hz), 6.14(1H, t, J = 2.2 Hz), 7.26-7.32(1H, m), 7.59-7.67(2H, m), 8.07-8.12(1H, m), 9.50(1H, s), 11.55(1H, s)<br>FAB+: 396 |

TABLE 136

| Ex | Syn | DATA |
|---|---|---|
| 94 | 2 | NMR1: 1.27-1.39(2H, m), 1.64-1.71(2H, m), 1.95-2.05(1H, m), 2.06(3H, s), 3.27-3.37(2H, m), 3.84-3.91(4H, m), 5.20(2H, s), 6.83-6.86(1H, m), 7.10-7.12(1H, m), 7.20-7.22(1H, m), 7.27-7.32(1H, m), 7.39(1H, s), 7.58-7.67(2H, m), 7.96(1H, s), 8.09(1H, d, J = 7.8 Hz), 11.59(1H, s)<br>FAB+: 423 |
| 95 | 2 | NMR1: 1.26-1.44(2H, m), 1.68(2H, d, J = 12.7 Hz), 1.93-2.05(1H, m), 2.07(3H, s), 2.58(3H, s), 3.28-2.27(2H, m), 3.83-3.97(4H, m), 5.25(2H, s), 6.98(1H, s), 7.14(1H, s), 7.26(1H, s), 7.27-7.34(1H, m), 7.58-7.70(2H, m), 8.10(1H, d, J = 8.0 Hz), 11.60(1H, s)<br>FAB+: 422 |
| 96 | 2 | NMR1: 1.31(2H, dddd, J = 12.8, 12.8, 12.8, 4.4 Hz), 1.57-1.73(2H, m), 1.88-2.04(1H, m), 2.06(3H, s), 3.21-3.43(2H, m), 3.82(2H, d, J = 5.6 Hz), 3.87(2H, dd, J = 11.6, 3.6 Hz), 5.17(2H, s), 6.53-6.63(1H, m), 6.64-6.73(2H, m), 7.22(1H, dd, J = 8.4, 8.4 Hz), 7.54(1H, ddd, J = 8.4, 8.4, 2.8 Hz), 7.68-7.81(1H, m), 7.74(1H, s), 11.73(1H, br s)<br>FAB+: 398 |
| 97 | 2 | NMR1: 1.31(2H, dddd, J = 12.8, 12.8, 12.8, 4.0 Hz), 1.66(2H, d, J = 12.8 Hz), 1.89-2.02(1H, m), 2.06(3H, s), 3.24-3.41(2H, m), 3.82(2H, d, J = 6.0 Hz), 3.83-3.93(2H, m), 5.16(2H, s), 6.55-6.63(1H, m), 6.63-6.73(2H, m), 7.23(1H, dd, J = 8.8, 8.8 Hz), 7.66(1H, d, J = 8.8 Hz), 7.77(1H, dd, J = 8.8, 2.0 Hz), 8.18(1H, d, J = 2.0 Hz), 11.75(1H, s)<br>FAB+: 458, 460 |
| 98 | 2 | NMR1: 1.05-1.13(1H, m), 1.18-1.26(1H, m), 1.76(2H, t, J = 17.5 Hz), 1.96-2.02(1H, m), 1.99(3H, s), 2.05(3H, s), 2.52-2.56(1H, m), 3.02(1H, t, J = 11.7 Hz), 3.82-3.84(3H, m), 4.39(1H, d, J = 13.1 Hz), 5.16(2H, s), 6.59(1H, dd, J = 8.1, 1.8 Hz), 6.67-6.89(2H, m), 7.20-7.24(1H, m), 7.27-7.31(1H, m), 7.60-7.66(2H, m), 8.10(1H, d, J = 7.9 Hz), 11.59(1H, s)<br>ESI+: 421 |

TABLE 137

| Ex | Syn | DATA |
|---|---|---|
| 99 | 2 | NMR1: 2.05(3H, s), 5.10(2H, s), 5.16(2H, s), 6.66-6.72(2H, m), 6.78(1H, t, J = 2.3 Hz), 7.22-7.45(7H, m), 7.60-7.66(2H, m), 8.10(1H, d, J = 7.6 Hz), 11.59(1H, s)<br>ESI+: 372 |
| 100 | 2 | NMR1: 1.25-1.37(2H, m), 1.62-1.70(2H, m), 1.91-2.02(1H, m), 2.04(3H, s), 2.40(3H, s), 3.27-3.36(2H, m), 3.80-3.90(4H, m), 5.14(2H, s), 6.56-6.66(1H, m), 6.65-6.70(2H, m), 7.19-7.25(1H, m), 7.45(1H, dd, J = 2.0, 8.5 Hz), 7.56(1H, d, J = 8.4 Hz), 7.89(1H, s), 11.51(1H, s)<br>FAB+: 394 |
| 101 | 2 | NMR1: 1.25-1.37(2H, m), 1.62-1.70(2H, m), 1.90-2.02(1H, m), 2.06(3H, s), 3.28-3.35(2H, m), 3.80-3.90(7H, m), 5.15(2H, s), 6.56-6.60(1H, m), 6.65-6.70(2H, m), 7.19-7.30(2H, m), 7.49(1H, d, J = 3.0 Hz), 7.62(1H, d, J = 9.0 Hz), 11.58(1H, s)<br>FAB+: 410 |
| 102 | 2 | NMR1: 1.32(2H, dddd, J = 12.0, 12.0, 12.0, 4.0 Hz), 1.60-1.72(2H, m), 1.90-2.04(1H, m), 2.06(3H, s), 3.24-3.39(2H, m), 3.82(2H, d, J = 6.8 Hz), 3.83-3.93(2H, m), 5.17(2H, s), 6.55-6.63(1H, m), 6.63-6.73(2H, m), 7.23(1H, dd, J = 8.4, 8.4 Hz), 7.66(1H, dd, J = 8.4, 2.0 Hz), 7.73(1H, d, J = 8.4 Hz), 8.03(1H, d, J = 2.0 Hz), 11.75(1H, s)<br>ESI+: 414, 416 |

TABLE 137-continued

| Ex | Syn | DATA |
|---|---|---|
| 103 | 2 | NMR1: 1.29-1.37(2H, m), 1.85-1.87(3H, m), 2.06(3H, s), 2.71(2H, t, J = 11.2 Hz), 2.85(3H, s), 3.59(2H, d, J = 11.7 Hz), 3.86(2H, d, J = 5.9 Hz), 5.17(2H, s), 6.59(1H, d, J = 7.2 Hz), 6.68-6.70(2H, m), 7.20-7.30(2H, m), 7.59-7.67(2H, m), 8.10(1H, d, J = 8.1 Hz), 11.69(1H, s)<br>ESI+: 457 |
| 104 | 2 | NMR1: 1.71-1.80(2H, m), 2.05(3H, s), 2.02-2.14(3H, m), 3.05-3.08(2H, m), 3.15-3.18(2H, m), 3.88(2H, d, J = 6.1 Hz), 5.16(2H, s), 6.59-6.61(1H, m), 6.69-6.70(2H, m), 7.21-7.31(2H, m), 7.60-7.66(2H, m), 8.10(1H, d, J = 7.8 Hz), 11.59(1H, s)<br>ESI+: 428 |

TABLE 138

| Ex | Syn | DATA |
|---|---|---|
| 105 | 2 | NMR1: 2.06(3H, s), 2.46(4H, br s), 2.68(2H, br s), 3.57(4H, br s), 4.08(2H, t, J = 5.4 Hz), 5.17(2H, s), 6.58-6.61(1H, m), 6.68-6.70(2H, m), 7.22(1H, t, J = 8.2 Hz), 7.27-7.31(1H, m), 7.60-7.67(2H, m), 8.10(1H, d, J = 7.9 Hz), 11.62(1H, s)<br>FAB+: 395 |
| 106 | 2 | NMR1: 2.06(3H, s), 3.45(4H, br s), 3.56(4H, br s), 4.82(2H, s), 5.15(2H, s), 6.59(1H, dd, J = 2.2, 8.2 Hz), 6.68-6.72(2H, m), 7.23(1H, t, J = 8.2 Hz), 7.27-7.31(1H, m), 7.60-7.65(2H, m), 8.10(1H, d, J = 7.8 Hz), 11.64(1H, s)<br>ESI+: 409 |
| 107 | 2 | NMR1: 1.36(3H, t, J = 6.8 Hz), 1.62-1.71(2H, m), 1.89-2.04(1H, m), 2.07(3H, s), 3.27-3.36(4H, m), 3.82(2H, d, J = 6.8 Hz), 3.84-3.91(2H, m), 4.35(2H, q, J = 6.8 Hz), 5.18(2H, s), 5.56-6.63(1H, m), 6.65-6.70(1H, m), 6.69(1H, d, J = 2.0 Hz), 7.23(1H, dd, J = 8.4, 8.4 Hz), 7.75(1H, d, J = 8.4 Hz), 8.13(1H, dd, J = 8.8, 2.0 Hz), 8.72(1H, d, J = 2.0 Hz), 11.88(1H, br s)<br>ESI+: 452 |
| 108 | 2 | NMR1: 1.27-1.38(4H, m), 1.53-1.62(2H, m), 2.00(3H, s), 3.36(2H, s), 3.51(2H, t, J = 6.7 Hz), 4.56(2H, s), 7.24-7.29(1H, m), 7.56-7.61(1H, m), 7.67(1H, d, J = 8.0 Hz), 8.07(1H, dd, J = 1.2, 8.2 Hz)<br>FAB+: 275 |
| 109 | 2 | NMR1: 1.32(2H, dddd, J = 12.4, 12.4, 12.4, 4.0 Hz), 1.61-1.73(2H, m), 1.90-2.04(1H, m), 2.09(3H, s), 3.25-3.41(2H, m), 3.83(2H, d, J = 6.4 Hz), 3.83-3.94(2H, m), 5.20(2H, s), 6.56-6.63(1H, m), 6.66-6.75(2H, m), 7.23(1H, dd, J = 8.4, 8.4 Hz), 7.52(1H, dd, J = 8.4, 5.2 Hz), 7.80(1H, d, J = 8.4 Hz), 8.03(1H, dd, J = 8.4, 2.0 Hz), 8.1$_{1-8}$.18(1H, m), 8.38(1H, d, J = 2.0 Hz), 8.59(1H, d, J = 4.0 Hz), 8.95(1H, br s), 11.72(1H, s)<br>ESI+: 457 |

TABLE 139

| Ex | Syn | DATA |
|---|---|---|
| 110 | 2 | NMR1: 1.25-1.44(4H, m), 1.54-1.63(2H, m), 1.77(3H, s), 2.00(3H, s), 3.00(2H, q, J = 6.0 Hz), 3.51(2H, t, J = 6.5 Hz), 4.56(2H, s), 7.27(1H, t, J = 7.8 Hz), 7.59(1H, t, J = 7.0 Hz), 7.67(1H, d, J = 8.3 Hz), 7.75-7.80(1H, s), 8.08(1H, d, J = 8.0 Hz), 11.32(1H, s)<br>FAB+: 317 |
| 111 | 2 | NMR1: 1.16-1.26(2H, m), 1.58-1.68(5H, m), 2.05(3H, s), 3.25-3.30(2H, m), 3.82(2H, dd, J = 3.1, 11.2 Hz), 4.00(2H, t, J = 6.2 Hz), 5.16(2H, s), 6.57-6.59(1H, m), 6.67-6.68(2H, m), 7.22(1H, t, J = 8.5 Hz), 7.27-7.31(1H, m), 7.60-7.66(2H, m), 8.09(1H, d, J = 7.9 Hz), 11.59(1H, s)<br>ESI+: 394 |
| 112 | 2 | NMR1: 1.86-1.94(2H, m), 2.06(3H, s), 2.21(2H, t, J = 8.1 Hz), 3.43(2H, t, J = 7.0 Hz), 3.53(2H, t, J = 5.5 Hz), 4.07(2H, t, J = 5.5 Hz), 5.17(2H, s), 6.58-6.61(1H, m), 6.69-6.71(2H, m), 7.21-7.25(1H, m), 7.27-7.31(1H, m), 7.60-7.66(2H, m), 8.10(1H, d, J = 7.6 Hz), 11.61(1H, s)<br>ESI+: 393 |
| 113 | 2 | NMR1: 1.31(2H, dddd, J = 12.0, 12.0, 12.0, 4.0 Hz), 1.60-1.72(2H, m), 1.90-2.06(1H, m), 3.23-3.40(2H, m), 3.83(2H, d, J = 6.4 Hz), 3.83-3.92(2H, m), 5.31(2H, s), 6.56-6.64(1H, m), 6.64-6.74(2H, m), 7.23(1H, dd, J = 8.4, 8.4 Hz), 7.41(1H, dd, J = 7.6, 7.6 Hz), 7.67-7.76(1H, m), 7.79(1H, d, J = 8.4 Hz), 8.15(1H, d, J = 8.4 Hz), 12.22(1H, s)<br>FAB+: 400, 402 |
| 114 | 2 | NMR1: 1.11-1.25(2H, m), 1.55(2H, d, J = 12.9 Hz), 1.72-1.85(1H, m), 2.06(3H, s), 3.20-3.33(4H, m), 3.66-3.72(1H, m), 3.77-3.86(2H, m), 4.04-4.12(2H, m), 5.16(2H, s), 6.59(1H, d, J = 9.2 Hz), 6.65-6.74(2H, m), 7.23(1H, t, J = 8.7 Hz), 7.26-7.32(1H, m), 7.58-7.69(2H, m), 8.09(1H, d, J = 7.8 Hz), 11.61(1H, s)<br>ESI+: 424 |

TABLE 140

| Ex | Syn | DATA |
|---|---|---|
| 115 | 2 | NMR1: 1.26-1.35(2H, m), 1.64-1.67(2H, m), 1.93-1.97(1H, m), 2.04(3H, s), 3.30-3.34(2H, m), 3.77(2H, d, J = 6.4 Hz), 3.85-3.87(2H, m), 5.11(2H, s), 6.90(2H, d, J = 9.0 Hz), 7.03(2H, d, J = 9.2 Hz), 7.26-7.30(1H, m), 7.58-7.67(2H, m), 8.09(1H, d, J = 7.8 Hz), 11.56(1H, s)<br>ESI+: 380 |
| 116 | 2 | NMR1: 1.19-1.29(2H, m), 1.56-1.60(2H, m), 2.00-2.03(1H, m), 2.06(3H, s), 2.24(2H, d, J = 7.1 Hz), 3.27-3.32(2H, m), 3.82(2H, dd, J = 2.6, 11.3 Hz), 5.15(2H, s), 6.79(1H, dd, J = 2.0, 8.1 Hz), 7.16(1H, d, J = 8.1 Hz), 7.22-7.31(2H, m), 7.50(1H, br s), 7.59-7.67(2H, m), 8.10(1H, d, J = 8.1 Hz), 9.95(1H, s), 11.62(1H, s)<br>ESI+: 407 |
| 117 | 2 | NMR1: 2.05(3H, s), 3.43-3.46(6H, m), 3.50-3.53(2H, m), 3.71(2H, s), 5.16(2H, s), 6.88(1H, d, J = 7.7 Hz), 6.98-6.99(2H, m), 7.26-7.31(2H, m), 7.59-7.67(2H, m), 8.10(1H, d, J = 8.1 Hz), 11.61(1H, s)<br>ESI+: 393 |
| 118 | 2 | NMR1: 1.25-1.38(8H, m), 1.62-1.70(2H, m), 1.91-2.03(1H, m), 3.05-3.13(1H, m), 3.27-3.36(2H, m), 3.78-3.90(4H, m), 5.13(2H, s), 6.56-6.60(1H, m), 6.65-6.69(2H, m), 7.19-7.29(2H, m), 7.56-7.64(2H, m), 8.07(1H, d, J = 8.4 Hz), 11.51(1H, s)<br>FAB+: 408 |
| 119 | 2 | NMR1: 1.24-1.37(2H, m), 1.65(2H, d, J = 11.0 Hz), 1.90-2.10(4H, m), 3.26-3.39(2H, m), 3.77-3.93(4H, m), 5.13-5.22(2H, m), 6.48(1H, d, J = 10.9 Hz), 6.55(1H, s), 6.60(1H, d, J = 10.8 Hz), 7.27-7.33(1H, m), 7.59-7.69(2H, m), 8.10(1H, d, J = 8.0 Hz), 11.60(1H, br s)<br>ESI+: 398 |
| 120 | 2 | NMR1: 1.32(2H, dddd, J = 12.0, 12.0, 12.0, 4.4 Hz), 1.61-1.72(2H, m), 1.91-2.05(1H, m), 2.09(3H, s), 3.26-3.37(2H, m), 3.83(2H, d, J = 6.4 Hz), 3.83-3.92(2H, m), 5.20(2H, s), 6.56-6.63(1H, m), 6.66-6.75(2H, m), 7.23(1H, dd, J = 8.4, 8.4 Hz), 7.82(1H, d, J = 8.4 Hz), 8.08(1H, dd, J = 8.4, 2.4 Hz), 8.44(1H, d, J = 2.4 Hz), 9.20(3H, s), 11.74(1H, s)<br>ESI+: 458 |

TABLE 141

| Ex | Syn | DATA |
|---|---|---|
| 121 | 2 | NMR1: 2.05(3H, s), 3.05(2H, t, J = 6.6 Hz), 4.21(2H, t, J = 6.6 Hz), 5.15(2H, s), 6.58-6.60(1H, m), 6.68-6.70(2H, m), 7.22(1H, t, J = 8.4 Hz), 7.27-7.35(2H, m), 7.60-7.65(2H, m), 7.75(1H, d, J = 7.8 Hz), 8.10(1H, d, J = 7.7 Hz), 8.43-8.45(1H, m), 8.54(1H, d, J = 1.8 Hz), 11.58(1H, s)<br>ESI+: 387 |
| 122 | 2 | NMR1: 1.08-1.21(2H, m), 1.29-1.38(2H, m), 1.41-1.53(1H, m), 1.57(2H, d, J = 13.1 Hz), 1.66-1.77(2H, m), 2.05(3H, s), 3.26(2H, t, J = 11.5 Hz), 3.83(2H, dd, J = 11.2, 3.6 Hz), 3.94(2H, dd, J = 6.5, 6.4 Hz), 5.16(2H, s), 6.58(1H, d, J = 9.2 Hz), 6.34-6.71(2H, m), 7.21(1H, dd, J = 8.6, 8.5 Hz), 7.29(1H, ddd, J = 8.1, 7.9, 1.4 Hz), 7.57-7.69(2H, m), 8.10(1H, d, J = 7.9 Hz), 11.58(1H, s)<br>ESI+: 408 |
| 123 | 2 | NMR1: 2.05(3H, s), 3.18(2H, t, J = 6.6 Hz), 4.36(2H, t, J = 6.6 Hz), 5.15(2H, s), 6.58-6.60(1H, m), 6.67-6.69(2H, m), 7.20-7.31(3H, m), 7.36(1H, d, J = 7.8 Hz), 7.59-7.66(2H, m), 7.72(1H, dt, J = 1.9, 7.6 Hz), 8.09-8.11(1H, m), 8.50-8.52(1H, m), 11.58(1H, s)<br>ESI+: 387 |
| 124 | 2 | NMR1: 1.31(2H, dddd, J = 11.6, 11.6, 11.6, 4.0 Hz), 1.60-1.71(2H, m), 1.81-1.95(4H, m), 1.93-2.04(1H, m), 2.05(3H, s), 2.41(2H, d, J = 5.6, 5.6 Hz), 3.25-3.38(1H, m), 3.65(2H, dd, J = 5.6, 5.6 Hz), 3.82(2H, d, J = 6.4 Hz), 3.83-3.92(2H, m), 5.17(2H, s), 6.55-6.63(1H, m), 6.64-6.73(2H, m), 7.22(1H, dd, J = 8.4, 8.4 Hz), 7.54(1H, dd, J = 8.4, 2.4 Hz), 7.64(1H, d, J = 8.4 Hz), 7.91(1H, d, J = 2.4 Hz), 8.31(1H, s), 11.63(1H, s)<br>ESI+: 477 |
| 125 | 2 | NMR1: 1.18(2H, dddd, J = 12.8, 12.8, 12.8, 4.0 Hz), 1.50-1.61(2H, m), 1.71-1.84(1H, m), 2.06(3H, s), 3.20-3.28(2H, m), 3.30(2H, d, J = 6.4 Hz), 3.64-3.73(2H, m), 3.77-3.87(2H, m), 4.04-4.13(2H, m), 5.17(2H, s), 6.56-6.64(1H, m), 6.65-6.73(2H, m), 7.23(1H, dd, J = 8.8, 8.8 Hz), 7.54(1H, ddd, J = 8.8, 8.8, 2.4 Hz), 7.74(1H, ddd, J = 8.8, 8.8, 3.2 Hz), 7.74(1H, d, J = 3.6 Hz), 11.76(1H, br s)<br>ESI+: 442 |

TABLE 142

| Ex | Syn | DATA |
|---|---|---|
| 126 | 2 | NMR1: 1.44-1.54(2H, m), 2.06(3H, s), 2.06-2.10(2H, m), 2.22-2.26(3H, m), 2.38-2.46(2H, m), 3.90(2H, d, J = 6.4 Hz), 5.17(2H, s), 6.59-6.62(1H, m), 6.68-6.71(2H, m), 7.21-7.31(2H, m), 7.60-7.66(2H, m), 8.10(1H, d, J = 7.9 Hz), 11.60(1H, s)<br>ESI+: 392 |

TABLE 142-continued

| Ex | Syn | DATA |
| --- | --- | --- |
| 127 | 2 | NMR1: 2.05(3H, s), 3.06(2H, t, J = 6.5 Hz), 4.24(2H, t, J = 6.5 Hz), 5.15(2H, s), 6.58-6.61(1H, m), 6.68-6.70(2H, m), 7.20-7.24(1H, m), 7.27-7.31(1H, m), 7.34(2H, d, J = 5.7 Hz), 7.60-7.65(2H, m), 8.10(1H, d, J = 7.9 Hz), 8.49(2H, d, J = 4.6 Hz), 11.58(1H, s)<br>ESI+: 387 |
| 128 | 2 | NMR1: 0.88(3H, t, J = 7.6 Hz), 1.18-1.34(4H, m), 1.36-1.58(4H, m), 1.80-1.90(1H, m), 1.89-1.98(1H, m), 2.01(3H, s), 2.29(2H, dd, J = 8.0, 8.0 Hz), 2.98-3.10(1H, m), 3.13-3.25(1H, m), 3.61-3.77(2H, m), 3.85-3.99(1H, m), 4.64(2H, s), 7.53(1H, ddd, J = 8.8, 8.8, 3.2 Hz), 7.71(1H, dd, J = 8.8, 3.2 Hz), 7.78(1H, dd, J = 8.8, 5.3 Hz), 11.40(1H, s)<br>ESI+: 389 |
| 129 | 2 | NMR1: 0.29-0.45(4H, m), 1.26-1.39(2H, m), 1.41-1.53(2H, m), 1.52-1.66(2H, m), 2.00(2H, s), 3.15-3.24(2H, m), 3.39(2H, t), 3.52(2H, t), 4.57(2H, s), 7.52(1H, ddd), 7.71(1H, dd), 7.78(1H, s), 11.47(1H, s)<br>ESI+: 334 |
| 130 | 2 | NMR1: 1.22-1.36(2H, m), 1.59-1.68(2H, m), 1.93-2.05(1H, m), 2.06(3H, s), 3.27-3.36(2H, m), 3.82-3.93(4H, m), 5.38(2H, s), 6.49(1H, d, J = 2.0 Hz), 6.67(1H, dd, J = 2.0, 5.9 Hz), 7.24-7.32(1H, m), 7.58-7.65(2H, m), 8.01(1H, d, J = 5.9 Hz), 8.09(1H, d, J = 8.0 Hz), 11.60(1H, s)<br>ESI+: 381 |
| 131 | 2 | NMR1: 2.06(3H, s), 2.44-2.47(4H, m), 2.67(2H, t, J = 5.8 Hz), 3.57-3.58(4H, m), 4.07(2H, t, J = 5.7 Hz), 5.17(2H, s), 6.58-6.61(1H, m), 6.67-6.70(2H, m), 7.22(1H, t, J = 8.2 Hz), 7.53(1H, dt, J = 3.2, 8.4 Hz), 7.71-7.77(2H, m), 11.8(1H, br s)<br>ESI+: 413 |

TABLE 143

| Ex | Syn | DATA |
| --- | --- | --- |
| 132 | 2 | NMR1: 1.30-1.35(2H, m), 1.65-1.68(2H, m), 2.00-2.03(1H, m), 2.07(3H, s), 3.29-3.35(2H, m), 3.85-3.89(2H, m), 3.92(2H, d, J = 6.5 Hz), 5.27(2H, s), 7.19-7.21(1H, m), 7.56(1H, dt, J = 2.9, 9.2 Hz), 7.71-7.76(2H, m), 7.99(1H, d, J = 2.4 Hz), 8.07(1H, d, J = 2.3 Hz), 11.8(1H, s)<br>ESI+: 399 |
| 133 | 2 | NMR1: 1.59(4H, t, J = 5.4 Hz), 1.66(2H, t, J = 6.9 Hz), 1.87(2H, sept., J = 7.7 Hz), 2.06(3H, s), 3.16-3.23(4H, m), 3.72(2H, t, J = 6.7 Hz), 5.14(2H, s), 6.48(1H, dd, J = 2.0, 7.9 Hz), 6.56-6.62(1H, m), 7.13(1H, t, J = 8.2 Hz), 7.26-7.31(1H, m), 7.59-7.67(2H, m), 8.09(1H, d, J = 7.5 Hz), 11.6(1H, br s)<br>ESI+: 405 |
| 134 | 2 | NMR1: 0.85(3H, t, J = 7.2 Hz), 1.13-1.33(4H, m), 1.38-1.52(2H, m), 2.00(3H, s), 2.03(2H, t, J = 7.6 Hz), 3.77(1H, dd, J = 10.0, 3.6 Hz), 3.96-4.10(1H, m), 4.04(1H, d, J = 10.0 Hz), 4.32(1H, dd, J = 10.0, 7.2 Hz), 4.40-4.52(1H, m), 4.59(2H, s), 7.54(1H, ddd, J = 8.8, 8.8, 3.2 Hz), 7.71(1H, dd, J = 8.8, 3.2 Hz), 7.77(1H, dd, J = 8.8, 4.4 Hz), 11.49(1H, s)<br>ESI+: 361 |
| 135 | 2 | NMR1: 1.27-1.38(2H, m), 1.65-1.68(2H, m), 1.97-2.03(1H, m), 2.07(3H, s), 3.29-3.35(2H, m), 3.87(2H, dd, J = 2.9, 11.2 Hz), 3.92(2H, d, J = 6.4 Hz), 5.26(2H, s), 7.20(1H, t, J = 2.3 Hz), 7.27-7.32(1H, m), 7.60-7.66(2H, m), 7.98(1H, d, J = 2.3 Hz), 8.07(1H, d, J = 2.3 Hz), 8.09(1H, d, J = 8.1 Hz), 11.6(1H, s)<br>ESI+: 381 |
| 136 | 2 | NMR1: 1.44-1.51(2H, m), 1.87(2H, m), 2.06(3H, s), 2.84-2.89(2H, m), 3.25(3H, s), 3.42-3.56(7H, m), 5.14(2H, s), 6.49(1H, dd, J = 2.0, 8.1 Hz), 6.57-6.59(1H, m), 6.63(1H, m), 7.12(1H, t, J = 8.2 Hz), 7.26-7.30(1H, m), 7.59-7.67(2H, m), 8.09(1H, d, J = 7.7 Hz), 11.6(1H, s)<br>ESI+: 423 |

TABLE 144

| Ex | Syn | DATA |
| --- | --- | --- |
| 137 | 2 | NMR1: 1.52-1.59(6H, m), 2.06(3H, s), 3.11-3.15(4H, m), 5.14(2H, s), 6.48(1H, dd, J = 2.1, 8.1 Hz), 6.56(1H, d, J = 8.2 Hz), 6.60-6.61(1H, m), 7.13(1H, t, J = 8.2 Hz), 7.29(1H, t, J = 7.2 Hz), 7.59-7.67(2H, m), 8.09(1H, d, J = 8.1 Hz), 11.6(1H, s)<br>ESI+: 349 |
| 138 | 2 | NMR1: 2.06(3H, s), 3.09-3.12(4H, m), 3.71-3.74(4H, m), 5.15(2H, s), 6.54-6.61(2H, m), 6.63-6.65(1H, m), 7.17(1H, t, J = 8.2 Hz), 7.27-7.31(1H, m), 7.59-7.66(2H, m), 8.09(1H, d, J = 7.8 Hz), 11.6(1H, s)<br>ESI+: 351 |
| 139 | 2 | NMR1: 1.06-1.19(2H, m), 1.62-1.70(2H, m), 1.72-1.84(1H, m), 2.05(3H, s), 2.40-2.50(2H, m), 2.90-2.97(2H, m), 3.77(2H, d, J = 6.4 Hz), 5.16(2H, s), 6.55-6.59(1H, m), 6.65-6.69(2H, m), 7.18-7.32(2H, m), 7.59-7.67(2H, m), 8.09(1H, d, J = 7.8 Hz), 11.50(1H, s)<br>FAB+: 379 |

TABLE 144-continued

| Ex | Syn | DATA |
|---|---|---|
| 140 | 2 | NMR1: 0.00-0.09(2H, m), 0.29-0.45(2H, m), 0.63-0.78(1H, m), 1.31-1.43(2H, m), 1.38-1.49(1H, m), 1.47-1.62(1H, m), 1.80-2.00(2H, m), 2.01(3H, s), 2.38(2H, dd, J = 8.0, 8.0 Hz), 2.98-3.12(1H, m), 3.14-3.29(1H, m), 3.63-3.79(2H, m), 3.86-4.00(1H, m), 4.64(2H, s), 7.53(1H, ddd, J = 8.8, 8.8, 3.2 Hz), 7.71(1H, dd, J = 8.8, 3.2 Hz), 7.78(1H, dd, J = 8.8, 4.4 Hz), 11.40(1H, s)<br>ESI+: 387 |
| 141 | 2 | NMR1: 1.15(6H, s), 1.82(2H, t, J = 7.0 Hz), 2.05(3H, s), 4.07(2H, t, J = 7.0 Hz), 4.36(1H, s), 5.16(2H, s), 6.58(1H, dd, J = 1.8, 8.1 Hz), 6.66-6.68(2H, m), 7.22(1H, t, J = 8.7 Hz), 7.28(1H, m), 7.59-7.66(2H, m), 8.09(1H, d, J = 7.8 Hz), 11.6(1H, s)<br>ESI+: 368 |

TABLE 145

| Ex | Syn | DATA |
|---|---|---|
| 142 | 2 | NMR1: 0.82-0.88(3H, m), 1.27(4H, m), 2.05(3H, s), 2.36(2H, t, J = 7.6 Hz), 2.74(1H, t, J = 5.8 Hz), 2.84(1H, t, J = 5.7 Hz), 3.35(2H, s), 3.64(2H, t, J = 5.8 Hz), 4.55(2H, d, J = 18.2 Hz), 5.15(2H, s), 6.94(2H, s), 7.13-7.16(1H, m), 7.28(1H, t, J = 6.8 Hz), 7.59-7.67(2H, m), 8.10(1H, d, J = 7.7 Hz), 11.6(1H, s)<br>ESI+: 419 |
| 143 | 2 | NMR1: 1.14-1.27(2H, m), 1.50-1.58(2H, m), 1.82-1.93(1H, m), 2.07(3H, s), 3.17-3.25(2H, m), 3.78-3.84(2H, m), 4.01(2H, d, J = 6.6 Hz), 5.39(2H, s), 6.40(1H, d, J = 7.8 Hz), 6.51(1H, d, J = 7.8 Hz), 7.25-7.29(1H, m), 7.57-7.68(3H, m), 7.08(1H, d, J = 7.6 Hz), 11.53(1H, s)<br>FAB+: 381<br>mp: 221-223° C. |
| 144 | 2 | NMR1: 1.35-1.66(6H, m), 1.82-1.99(2H, m), 2.01(3H, s), 2.80-2.95(1H, m), 2.98-3.14(1H, m), 3.18-3.34(1H, m), 3.39(2H, dd, J = 12.0, 2.2 Hz), 3.67-3.75(1H, m), 3.75-3.88(3H, m), 3.87-4.01(1H, m), 4.64(2H, s), 7.52(1H, ddd, J = 8.8, 8.8, 2.8 Hz), 7.71(1H, dd, J = 10.0, 2.8 Hz), 7.79(1H, dd, J = 8.8, 4.8 Hz), 11.44(1H, br s)<br>ESI+: 403 |
| 145 | 2 | NMR1: 1.19(2H, ddd, J = 24.0, 12.0, 4.4 Hz), 1.37-1.55(2H, m), 1.51-1.62(2H, m), 1.80-1.98(3H, m), 2.01(3H, s), 2.25(2H, d, J = 7.2 Hz), 3.00-3.11(1H, m), 3.15-3.25(1H, m), 3.22-3.31(3H, m), 3.64-3.75(1H, m), 3.75-3.84(2H, m), 3.88-3.99(1H, m), 4.64(2H, s), 7.53(1H, ddd, J = 8.8, 8.8, 3.2 Hz), 7.71(1H, dd, J = 8.8, 2.8 Hz), 7.78(1H, dd, J = 8.8, 4.4 Hz), 11.39(1H, s)<br>ESI+: 417 |
| 146 | 2 | NMR1: 0.85(3H, t, J = 7.1 Hz), 0.97-1.10(2H, m), 1.21-1.28(4H, m), 1.44-1.50(2H, m), 1.71(2H, t, J = 15.2 Hz), 1.87(1H, m), 2.01(3H, s), 2.25(2H, t, J = 7.7 Hz), 2.50(1H, m), 2.95(1H, t, J = 11.3 Hz), 3.36(2H, m), 3.83(1H, d, J = 13.4 Hz), 4.37(1H, d, J = 13.0 Hz), 4.56(2H, s), 7.25-7.29(1H, m), 7.57-7.67(2H, m), 8.07-8.09(1H, m), 11.4(1H, s)<br>ESI+: 385 |

TABLE 146

| Ex | Syn | DATA |
|---|---|---|
| 147 | 2 | NMR1: 1.45-1.60(2H, m), 1.84-1.97(2H, m), 2.01(3H, s), 2.06(3H, s), 3.19-3.35(2H, m), 3.63(1H, m), 3.82(1H, m), 4.60(1H, m), 5.16(2H, s), 6.64(1H, dd, J = 1.8, 8.1 Hz), 6.69(1H, dd, J = 2.0, 8.2 Hz), 6.72(1H, t, J = 2.3 Hz), 7.23(1H, t, J = 8.2 Hz), 7.28(1H, ddd, J = 1.9, 6.2, 8.0 Hz), 7.59-7.65(2H, m), 8.08-8.10(1H, m), 11.6(1H, s)<br>ESI+: 407 |
| 148 | 2 | NMR1: 1.49-1.63(6H, m), 1.96(2H, m), 2.05(3H, s), 2.91(1H, m), 3.21-3.41(4H, m), 3.82-3.85(4H, m), 4.61(1H, m), 5.16(2H, s), 6.65(1H, dd, J = 1.8, 8.0 Hz), 6.67(1H, dd, J = 2.1, 8.0 Hz), 6.72(1H, t, J = 2.3 Hz), 7.23(1H, t, J = 8.1 Hz), 7.28(1H, ddd, J = 2.0, 6.0, 8.2 Hz), 7.61-7.63(2H, m), 8.09(1H, d, J = 7.9 Hz), 11.6(1H, s)<br>ESI+: 477 |
| 149 | 2 | NMR1: 1.19(2H, dq, J = 4.3, 12.7 Hz), 1.40-1.59(4H, m), 1.91(3H, m), 2.05(3H, s), 2.26(2H, d, J = 6.3 Hz), 3.20-3.40(4H, m), 3.60-3.82(4H, m), 4.60(1H, m), 5.16(2H, s), 6.63(1H, dd, J = 1.7, 8.1 Hz), 6.69(1H, dd, J = 2.0, 8.0 Hz), 6.72(1H, t, J = 2.1 Hz), 7.23(1H, t, J = 8.2 Hz), 7.29(1H, ddd, J = 1.9, 5.9, 8.0 Hz), 7.59-7.65(2H, m), 8.09(1H, d, J = 7.8 Hz), 11.6(1H, s)<br>ESI+: 491 |
| 150 | 2 | NMR1: 1.47(1H, m), 1.59(1H, m), 1.84-1.93(2H, m), 2.01(3H, s), 2.05(3H, s), 3.17-3.22(1H, m), 3.28-3.35(1H, m), 3.64(1H, m), 3.82(1H, m), 4.60(1H, m), 5.17(2H, s), 6.64(1H, dd, J = 1.9, 8.2 Hz), 6.69(1H, dd, J = 2.1, 8.0 Hz), 6.73(1H, t, J = 2.3 Hz), 7.23(1H, t, J = 8.2 Hz), 7.55(1H, dt, J = 3.0, 8.7 Hz), 7.71-7.76(2H, m), 11.7(1H, s)<br>ESI+: 425 |

TABLE 146-continued

| Ex | Syn | DATA |
|---|---|---|
| 151 | 2 | NMR1: 1.49-1.64(6H, m), 1.89(2H, m), 2.06(3H, s), 2.89(1H, m), 3.34-3.41(4H, m), 3.75-3.89(4H, m), 4.62(1H, m), 5.17(2H, s), 6.63-6.72(3H, m), 7.24(1H, t, J = 8.2 Hz), 7.55(1H, dt, J = 3.0, 8.5 Hz), 7.71-7.76(2H, m), 11.7(1H, s)<br>ESI+: 495 |

TABLE 147

| Ex | Syn | DATA |
|---|---|---|
| 152 | 2 | NMR1: 1.19(2H, dq, J = 4.4, 12.0 Hz), 1.45-1.59(4H, m), 1.88-1.98(3H, m), 2.06(3H, s), 2.26(2H, d, J = 6.5 Hz), 3.18-3.36(4H, m), 3.69-3.89(4H, m), 4.61(1H, m), 5.17(2H, s), 6.63-6.72(3H, m), 7.23(1H, t, J = 8.2 Hz), 7.54(1H, dt, J = 3.0, 8.6 Hz), 7.71-7.76(2H, m), 11.7(1H, s)<br>ESI+: 509 |
| 153 | 2 | NMR1: 1.31(2H, dddd, J = 12.4, 12.4, 12.4, 4.4 Hz), 1.58-1.71(2H, m), 1.92-2.06(1H, m), 2.06(3H, s), 3.23-3.42(1H, m), 3.86(2H, dd, J = 11.6, 3.6 Hz), 3.91(2H, d, J = 6.8 Hz), 5.39(2H, s), 6.49(1H, d, J = 2.0 Hz), 6.67(2H, dd, J = 5.6, 2.0 Hz), 7.54(1H, ddd, J = 8.4, 8.4, 8.4 Hz), 7.67-7.77(1H, m), 7.72(1H, d, J = 8.4 Hz), 8.01(1H, d, J = 6.4 Hz), 11.75(1H, s)<br>ESI+: 399 |
| 154 | 2 | NMR1: 2.04(3H, s), 2.06(3H, s), 3.05-3.14(2H, m), 3.14-3.22(2H, m), 3.51-3.63(4H, m), 5.17(2H, s), 6.57(1H, dd, J = 8.4, 2.0 Hz), 6.62(1H, dd, J = 8.4, 2.0 Hz), 6.64-6.69(1H, m), 7.18(1H, dd, J = 8.4, 8.4 Hz), 7.54(1H, ddd, J = 8.4, 8.4, 2.8 Hz), 7.73(1H, dd, J = 8.8, 2.8 Hz), 7.76(1H, dd, J = 8.8, 4.8 Hz), 11.76(1H, br s)<br>ESI+: 410 |
| 155 | 2 | NMR1: 1.16(6H, s), 1.82(2H, t, J = 7.2 Hz), 2.06(3H, s), 4.07(2H, t, J = 6.8 Hz), 4.37(1H, s), 5.18(2H, s), 6.58(1H, dd, J = 1.2, 8.0 Hz), 6.67(2H, m), 7.20-7.24(1H, m), 7.52-7.57(1H, m), 7.71-7.77(2H, m), 11.7(1H, s)<br>ESI+: 386 |
| 156 | 2 | NMR1: 1;19(6H, s), 2.06(3H, s), 3.70(2H, s), 4.61(1H, s), 5.18(2H, s), 6.59(1H, m), 6.69(2H, m), 7.22(1H, t, J = 8.3 Hz), 7.52-7.57(1H, m), 7.71-7.77(2H, m), 11.7(1H, s)<br>ESI+: 372 |

TABLE 148

| Ex | Syn | DATA |
|---|---|---|
| 157 | 2 | NMR1: 1.12-1.31(2H, m), 1.60(2H, d, J = 12.4 Hz), 1.61-1.76(3H, m), 2.06(3H, s), 3.27(2H, ddd, J = 12.0, 12.0, 2.0 Hz), 3.82(2H, dd, J = 11.2, 3.2 Hz), 4.09(2H, dd, J = 6.0, 6.0 Hz), 5.39(2H, s), 6.49(1H, d, J = 2.0 Hz), 6.66(1H, dd, J = 6.0, 2.0 Hz), 7.54(1H, ddd, J = 8.4, 8.4, 3.2 Hz), 7.67-7.75(1H, m), 7.72(1H, d, J = 8.4 Hz), 8.00(1H, d, J = 5.6 Hz), 11.76(1H, s)<br>ESI+: 413 |
| 158 | 2 | NMR1: 1.16-1.25(2H, m), 1.57(2H, d, J = 12.8 Hz), 1.95(1H, m), 2.05(3H, s), 2.33(2H, d, J = 6.8 Hz), 2.75(1H, t, J = 5.9 Hz), 2.84(1H, t, J = 5.8 Hz), 3.23-3.28(2H, m), 3.65(2H, m), 3.80(2H, m), 4.54(1H, s), 4.60(1H, s), 5.16(2H, s), 6.94(2H, m), 7.15(1H, m), 7.51-7.57(1H, m), 7.71-7.78(2H, m), 11.7(1H, s)<br>ESI+: 465 |
| 159 | 2 | NMR1: 1.78-1.93(4H, m), 2.06(3H, s), 2.34-2.43(2H, m), 3.55-3.64(2H, m), 5.18(2H, s), 6.88-6.95(1H, m), 7.00(1H, dd, J = 8.4, 2.4 Hz), 7.04-7.09(1H, m), 7.34(1H, dd, J = 8.4, 8.4 Hz), 7.55(1H, ddd, J = 8.4, 8.4, 2.8 Hz), 7.68-7.79(1H, m), 7.71-7.76(1H, m), 11.76(1H, br s)<br>ESI+: 381 |
| 160 | 2 | NMR2: 1.30-1.42(2H, m), 1.58-1.81(5H, m), 2.16(3H, s), 3.34-3.44(2H, m), 3.92-4.00(2H, m), 4.34(2H, t, J = 6.2 Hz), 5.17(2H, s), 6.30(1H, d, J = 2.2 Hz), 6.61(1H, dd, J = 5.8, 2.2 Hz), 7.31-7.40(2H, m), 7.59(1H, ddd, J = 7, 7, 1 Hz), 8.04(1H, d, J = 5.8 Hz), 8.39(1H, d, J = 8 Hz), 8.92(1H, s)<br>ESI+: 395 |
| 161 | 2 | NMR1: 1.10(6H, s), 1.43-1.51(2H, m), 1.69-1.80(2H, m), 2.06(3H, s), 3.95(2H, t, J = 6.4 Hz), 4.17(1H, s), 5.16(2H, s), 6.57(1H, d, J = 8.1 Hz), 6.64-6.69(2H, m), 7.22(1H, dd, J = 8.1, 8.1 Hz), 7.26-7.32(1H, m), 7.58-7.68(2H, m), 8.09(1H, d, J = 8.2 Hz), 11.59(1H, s)<br>ESI+: 382 |

TABLE 149

| Ex | Syn | DATA |
|---|---|---|
| 162 | 2 | NMR1: 1.10(6H, s), 1.43-1.51(2H, m), 1.69-1.80(2H, m), 2.06(3H, s), 3.95(2H, t, J = 6.3 Hz), 4.17(1H, s), 5.17(2H, s), 6.58(1H, d, J = 8.4 Hz), 6.65-6.70(2H, m), 7.22(1H, dd, J = 9.1, 8.4 Hz), 7.51-7.59(1H, m), 7.70-7.79(2H, m), 11.74(1H, s)<br>ESI+: 400 |
| 163 | 2 | NMR1: 1.52-1.54(2H, m), 1.63(2H, dq, J = 4.3, 13.3 Hz), 1.79-1.85(2H, m), 2.97(3H, s), 2.66(2H, t, J = 6.9 Hz), 3.06-3.14(1H, m), 3.21-3.26(2H, m), 3.66(2H, t, J = 5.9 Hz), 3.81-3.84(2H, m), 5.19(2H, s), 6.97(1H, d, J = 8.2 Hz), 7.00-7.09(1H, m), 7.20(1H, t, J = 8.2 Hz), 7.54(1H, dt, J = 2.9, 8.4 Hz), 7.68-7.75(2H, m), 11.8(1H, s)<br>ESI+: 451 |
| 164 | 2 | NMR1: 1.03-1.17(2H, m), 1.54(2H, d, J = 12.6 Hz), 1.78-1.85(2H, m), 1.95-2.01(1H, m), 2.07(3H, s), 2.43(2H, d, J = 6.8 Hz), 2.65(2H, t, J = 7.0 Hz), 3.23-3.32(2H, m), 3.64-3.67(2H, m), 3.75-3.80(2H, m), 5.19(2H, s), 6.96(1H, d, J = 8.3 Hz), 7.08(1H, br s), 7.18(1H, t, J = 8.1 Hz), 7.55(1H, dt, J = 2.6, 8.4 Hz), 7.69-7.75(2H, m), 11.8(1H, s)<br>ESI+: 465 |
| 165 | 2 | NMR1: 1.50-1.54(2H, m), 1.57-1.68(2H, dq, J = 4.2, 13.4 Hz), 1.81-1.89(2H, m), 2.05(3H, s), 2.64(2H, t, J = 6.6 Hz), 3.05-3.12(1H, m), 3.13-3.24(2H, m), 3.68(2H, t, J = 6.3 Hz), 3.78-3.81(2H, m), 5.17(2H, s), 6.90(1H, dd, J = 2.4, 8.3 Hz), 7.15(1H, d, J = 8.5 Hz), 7.17(1H, br s), 7.51-7.56(1H, m), 7.70-7.78(2H, m), 11.8(1H, s)<br>ESI+: 451 |
| 166 | 2 | NMR1: 0.94-1.12(2H, m), 1.48(2H, d, J = 12.2 Hz), 1.83(2H, sept, J = 6.4 Hz), 1.87-1.99(1H, m), 2.05(3H, s), 2.37(2H, d, J = 6.8 Hz), 2.62(2H, t, J = 6.6 Hz), 3.22(2H, t, J = 10.9 Hz), 3.65(2H, t, J = 6.4 Hz), 3.71-3.75(2H, m), 5.18(2H, s), 6.87(1H, dd, J = 2.4, 8.3 Hz), 7.13(1H, d, J = 8.5 Hz), 7.19(1H, br s), 7.53(1H, dt, J = 3.2, 8.6 Hz), 7.70-7.76(2H, m), 11.7(1H, s)<br>ESI+: 465 |

TABLE 150

| Ex | Syn | DATA |
|---|---|---|
| 167 | 2 | NMR1: 1.53-1.64(4H, m), 2.05(3H, s), 2.67-2.71(1H, m), 2.78-2.81(1H, m), 2.93-2.99(1H, m), 3.37-3.43(2H, m), 3.64-3.67(1H, m), 3.72-3.75(1H, m), 3.84-3.87(2H, m), 4.59(1H, s), 4.72(1H, s), 5.16(2H, s), 6.9$_{1-6}$.99(2H, m), 7.13(1H, d, J = 8.4 Hz), 7.54(1H, dt, J = 2.8, 8.6 Hz), 7.72(1H, dd, J = 2.8, 9.5 Hz), 7.75(1H, dd, J = 4.6, 9.1 Hz), 11.7(1H, s)<br>ESI+: 451 |
| 168 | 2 | NMR1: 1.14-1.26(2H, m), 1.58(2H, d, J = 12.8 Hz), 1.87-2.01(1H, m), 2.04(3H, s), 2.33(2H, d, J = 6.8 Hz), 2.67-2.70(1H, m), 2.76-2.80(1H, m), 3.23-3.30(2H, m), 3.65-3.68(2H, m), 3.76-3.83(2H, m), 4.60(1H, s), 4.65(1H, s), 5.16(2H, s), 6.9$_{1-6}$.99(2H, m), 7.13(1H, d, J = 8.4 Hz), 7.52-7.57(1H, m), 7.71-7.77(2H, m), 11.7(1H, s)<br>ESI+: 465<br>mp: 179-182° C. |
| 169 | 2 | NMR1: 1.51-1.60(4H, m), 2.07(3H, s), 2.74-2.84(2H, m), 2.89-3.01(1H, m), 3.19-3.26(2H, m), 3.37-3.43(2H, m), 3.65-3.85(4H, m), 4.53(1H, s), 4.64(1H, s), 6.83-6.85(1H, m), 6.97-7.07(1H, m), 7.17-7.25(1H, m), 7.52-7.60(1H, m), 7.69-7.75(2H, m), 11.8(1H, s)<br>ESI+: 451 |
| 170 | 2 | NMR1: 1.12-1.24(2H, m), 1.51-1.58(2H, m), 1.84-1.98(1H, m), 2.06(3H, s), 2.32(2H, t, J = 6.5 Hz), 2.73-2.82(2H, m), 3.18-3.31(2H, m), 3.64-3.67(2H, m), 3.73-3.80(2H, m), 4.53-4.58(2H, m), 5.19(2H, s), 6.8$_{2-6}$.85(1H, m), 6.97-7.05(1H, m), 7.17-7.24(1H, m), 7.52-7.58(1H, m), 7.67-7.75(2H, m), 11.8(1H, s)<br>ESI+: 465 |
| 171 | 2 | NMR1: 1.51-1.63(4H, m), 2.05(3H, s), 2.74-2.85(2H, m), 2.91-3.01(1H, m), 3.40(2H, t, J = 11.0 Hz), 3.61-3.68(1H, m), 3.71-3.75(1H, m), 3.83-3.86(2H, m), 4.54(1H, s), 4.67(1H, s), 5.16(2H, s), 6.94-6.96(2H, m), 7.14-7.19(1H, m), 7.54(1H, dt, J = 3.0, 8.4 Hz), 7.72(1H, dd, J = 3.0, 9.6 Hz), 7.75(1H, dd, J = 4.6, 9.2 Hz), 11.7(1H,<br>FAB+: 451 |

TABLE 151

| Ex | Syn | DATA |
|---|---|---|
| 172 | 2 | NMR1: 1.43-1.47(2H, m), 1.54-1.62(2H, m), 1.85(2H, t, J = 7.0 Hz), 2.06(3H, s), 3.56(2H, dt, J = 4.0, 10.8 Hz), 3.63(2H, dt, J = 2.4, 10.6 Hz), 4.11(2H, t, J = 7.0 Hz), 4.43(1H, s), 5.16(2H, s), 6.56-6.59(1H, m), 6.66-.669(2H, m), 7.22(1H, t, J = 8.4 Hz), 7.27-7.31(1H, m), 7.59-7.67(2H, m), 8.07-8.10(1H, m), 11.6(1H, s)<br>ESI+: 410 |

TABLE 151-continued

| Ex | Syn | DATA |
|---|---|---|
| 173 | 2 | NMR1: 1.30-1.41(1H, m), 1.44-1.64(2H, m), 1.77-1.86(1H, m), 1.95-2.05(1H, m), 2.06(3H, s), 3.21-3.40(2H, m), 3.70-3.87(2H, m), 3.93(2H, J = 6.7 Hz), 5.38(2H, s), 6.49(1H, d, J = 2.1 Hz), 6.67(1H, dd, J = 6.0, 2.3 Hz), 7.25-7.31(1H, m), 7.60-7.63(2H, m), 8.01(1H, d, J = 5.9 Hz), 8.08(1H, d, J = 7.9 Hz), 11.60(1H, s)<br>ESI+: 381 |
| 174 | 2 | NMR1: 1.95-2.04(1H, m), 2.07(3H, s), 2.23-2.33(1H, m), 2.58-2.77(4H, m), 5.23(2H, s), 7.08-7.13(2H, m), 7.19(1H, t, J = 2.1 Hz), 7.27-7.31(1H, m), 7.42(1H, t, J = 8.0 Hz), 7.59-7.67(2H, m), 8.10(1H, d, J = 7.9 Hz), 11.61(1H, s)<br>ESI+: 345 |
| 175 | 2 | NMR1: 1.14(6H, s), 1.81(2H, t, J = 7.2 Hz), 1.96(3H, s), 2.96-3.12(4H, m), 4.12(2H, t, J = 7.2 Hz), 4.41(1H, s), 6.82(1H, dd, J = 5.6, 2.4 Hz), 6.85(1H, d, J = 2.3 Hz), 7.21-7.27(1H, m), 7.51(1H, d, J = 7.8 Hz), 7.55-7.60(1H, m), 8.05(1H, d, J = 8.2 Hz), 8.32(1H, d, J = 5.8 Hz), 11.47(1H, s)<br>ESI+: 367 |
| 176 | 2 | NMR1: 1.36-1.47(2H, m), 1.46-1.55(2H, m), 1.52-1.64(2H, m), 2.06(3H, s), 3.29-3.38(2H, m), 3.35-3.45(2H, m), 4.92(2H, s), 5.37(2H, s), 6.45(1H, d, J = 2.4 Hz), 6.66(1H, dd, J = 6.0, 2.4 Hz), 7.22-7.33(1H, m), 7.61(2H, d, J = 4.0 Hz), 8.01(1H, d, J = 5.6 Hz), 8.09(1H, d, J = 8.4 Hz), 11.64(1H, s)<br>ESI+: 408 |

TABLE 152

| Ex | Syn | DATA |
|---|---|---|
| 177 | 2 | NMR1: 1.07-1.21(2H, m), 1.38-1.47(2H, m), 1.45-1.57(1H, m), 1.53-1.64(2H, m), 1.93(3H, s), 3.18-3.26(2H, m), 3.25-3.31(2H, m), 3.75-3.87(2H, m), 5.19(2H, s), 6.56(1H, dd, J = 6.8, 2.0 Hz), 6.85(1H, d, J = 2.0 Hz), 7.29(1H, ddd, J = 8.4, 6.8, 1.6 Hz), 7.55-7.60(1H, m), 7.59-7.65(1H, m), 7.73(1H, d, J = 7.6 Hz), 8.08(1H, d, J = 8.4 Hz), 8.61(1H, dd, J = 5.6, 5.6 Hz), 11.53(1H, s)<br>ESI+: 422 |
| 178 | 2 | NMR1: 1.94(2H, q, J = 6.8 Hz), 2.06(3H, s), 3.24(3H, s), 3.44(2H, t, J = 6.8 Hz), 4.09(2H, t, J = 6.8 Hz), 5.38(2H, s), 6.48(1H, d, J = 2.4 Hz), 6.67(1H, dd, J = 6.0, 2.4 Hz), 7.28(1H, ddd, J = 8.0, 6.0, 2.4 Hz), 7.58-7.65(2H, m), 8.01(1H, d, J = 6.0 Hz), 8.07-8.12(1H, m), 11.60(1H, br s)<br>ESI+: 355 |
| 179 | 2 | NMR1: 1.44(2H, d, J = 12.7 Hz), 1.53-1.61(2H, m), 1.86(2H, t, J = 7.0 Hz), 2.06(3H, s), 3.54-3.64(4H, m), 4.20(2H, t, J = 7.1 Hz), 4.47(1H, s), 5.38(2H, s), 6.49(1H, d, J = 2.1 Hz), 6.65(1H, dd, J = 2.2, 5.9 Hz), 7.26-7.30(1H, m), 7.60-7.62(2H, m), 8.00(1H, d, J = 5.8 Hz), 8.08(1H, d, J = 7.8 Hz), 11.6(1H, s)<br>ESI+: 411<br>mp: 189-190° C. |
| 180 | 2 | NMR2: 1.40-1.52(2H, m), 1.73-1.81(2H, m), 2.07(1H, m), 2.13(3H, s), 2.90(2H, t, J = 6 Hz), 2.99(2H, t, J = 6 Hz), 3.45(2H, ddd, J = 11.7, 11.7, 2 Hz), 3.76(2H, s), 3.80(2H, d, J = 6 Hz), 3.81(2H, s), 3.99-4.07(2H, m), 6.72(1H, d, J = 2.2 Hz), 6.75(1H, dd, J = 8, 2.2 Hz), 6.96(1H, d, J = 8 Hz), 7.23-7.33(2H, m), 7.53(1H, ddd, J = 7, 7, 1.5 Hz), 8.39(1H, dd, J = 7, 1.5 Hz), 9.61(1H, s)<br>ESI+: 419 |

TABLE 153

| Ex | Syn | DATA |
|---|---|---|
| 181 | 2 | NMR1: 0.86(3H, t, J = 6.8 Hz), 1.20-1.32(4H, m), 1.44-1.52(2H, m), 2.03(3H, s), 2.25-2.31(2H, m), 2.40-2.48(4H, m), 3.45-3.51(4H, m), 3.60(2H, s), 7.23-7.28(1H, m), 7.56-7.61(1H, m), 7.65-7.70(1H, m), 8.0$_{5-8}$.08(1H, m), 11.21(1H, s)<br>ESI+: 356<br>mp: 171-173° C. |
| 182 | 2 | NMR1: 0.33-0.40(4H, m), 0.43-0.46(4H, m), 2.01(3H, s), 3.19-3.25(1H, m), 3.35(2H, s), 3.38(2H, s), 4.57(2H, s), 7.24-7.29(1H, m), 7.57-7.66(2H, m), 8.06-8.09(1H, m), 11.35(1H, s)<br>ESI+: 314<br>mp: 125-127° C. |
| 183 | 2 | NMR1: 1.45-1.52(1H, m), 1.56-1.64(1H, m), 1.95-2.04(6H, m), 2.05(3H, s), 3.43(1H, br s), 4.06(2H, t, J = 7.2 Hz), 5.17(2H, s), 5.57(1H, dd, J = 2.0, 7.6 Hz), 6.66-6.68(2H, m), 7.19-7.24(1H, m), 7.27-7.31(2H, m), 7.59-7.67(2H, m), 8.08-8.10(1H, m), 11.6(1H, s)<br>ESI+: 380 |
| 184 | 2 | NMR1: 1.21-1.36(2H, m), 1.57-1.67(2H, m), 1.89-2.05(4H, m), 2.96-3.14(4H, m), 3.26-3.35(2H, m), 3.81-3.90(4H, m), 6.79-6.88(2H, m), 7.20-7.28(1H, m), 7.50(1H, d, J = 8.0 Hz), 7.54-7.61(1H, m), 8.05(1H, d, J = 8.4 Hz), 8.33(1H, d, J = 5.5 Hz), 11.47(1H, s)<br>ESI+: 379<br>mp: 212-215° C. |

TABLE 153-continued

| Ex | Syn | DATA |
|---|---|---|
| 185 | 2 | NMR1: 1.25-1.37(2H, m), 1.62-1.72(2H, m), 1.98(1H, m), 2.04(3H, s), 3.27-3.37(2H, m), 3.82(2H, d, J = 6 Hz), 3.83-3.90(2H, m), 4.00(3H, s), 5.26(2H, s), 6.57(1H, dd, J = 8.2 Hz), 6.6$_{2-6}$.68(2H, m), 7.18-7.27(3H, m), 7.66(1H, m), 10.91(1H, s)<br>ESI+: 410 |

TABLE 154

| Ex | Syn | DATA |
|---|---|---|
| 186 | 2 | NMR1: 1.15(6H, s), 1.91(2H, t, J = 7.6 Hz), 2.06(3H, s), 3.10(3H, s), 4.10(2H, t, J = 7.6 Hz), 5.38(2H, s), 6.50(1H, d, J = 2.0 Hz), 6.57(1H, dd, J = 6.0, 2.0 Hz), 7.28(1H, ddd, J = 8.0, 6.0, 2.0 Hz), 7.57-7.66(2H, m), 8.01(1H, d, J = 6.0 Hz), 8.06-8.12(1H, m), 11.59(1H, s)<br>ESI+: 383 |
| 187 | 2 | NMR1: 1.13-1.30(2H, m), 1.55-1.77(5H, m), 2.06(3H, s), 3.28(2H, ddd, J = 11.9, 11.8, 2.0 Hz), 3.83(2H, dd, J = 11.3, 4.0 Hz), 4.10(2H, t, J = 6.5 Hz), 5.26(2H, s), 7.20(1H, dd, J = 2.4, 2.4 Hz), 7.27-7.34(1H, m), 7.59-7.66(2H, m), 7.98(1H, d, J = 2.3 Hz), 8.06(1H, d, J = 2.4 Hz), 8.10(1H, d, J = 8.3 Hz), 11.63(1H, s)<br>ESI+: 395 |
| 188 | 2 | NMR1: 1.09(6H, s), 1.42-1.48(2H, m), 1.70-1.79(2H, m), 2.06(3H, s), 4.0$_{1-4}$.06(2H, m), 4.20(1H, s), 5.38(2H, s), 6.47(1H, d, J = 2.0 Hz), 6.65(1H, dd, J = 2.4, 6.0 Hz), 7.25-7.30(1H, m), 7.58-7.64(2H, m), 8.00(1H, d, J = 6.0 Hz), 8.08(1H, d, J = 8.0 Hz), 11.62(1H, s)<br>ESI+: 383 |
| 189 | 2 | NMR1: 1.18(6H, s), 2.06(3H, s), 3.79(2H, s), 4.69(1H, s), 5.38(2H, s), 6.48(1H, d, J = 2.0 Hz), 6.68(1H, dd, J = 2.0, 6.0 Hz), 7.26-7.31(1H, m), 7.58-7.66(2H, m), 8.01(1H, d, J = 6.0 Hz), 8.08(1H, d, J = 8.4 Hz), 11.61(1H, s)<br>ESI+: 355 |
| 190 | 2 | NMR1: 1.35(3H, s), 2.06(3H, s), 4.14(2H, s), 4.30(2H, d, J = 6.0 Hz), 4.46(2H, d, J = 6.0 Hz), 5.39(2H, s), 6.55(1H, d, J = 2.4 Hz), 6.72(1H, dd, J = 6.0, 2.4 Hz), 7.28(1H, ddd, J = 8.4, 5.2, 3.2 Hz), 7.57-7.66(2H, m), 8.03(1H, d, J = 6.0 Hz), 8.06-8.12(1H, m), 11.61(1H, s)<br>ESI+: 367 |

TABLE 155

| Ex | Syn | DATA |
|---|---|---|
| 191 | 2 | NMR1: 1.20(3H, t, J = 7.2 Hz), 2.06(3H, s), 3.09-3.17(4H, m), 3.44-3.53(4H, m), 4.06(2H, q, J = 7.2 Hz), 5.15(2H, s), 6.57(1H, dd, J = 8.0, 2.4 Hz), 6.61(1H, dd, J = 8.0, 2.4 Hz), 6.66(1H, dd, J = 2.4, 2.4 Hz), 7.17(1H, dd, J = 8.0, 8.0 Hz), 7.29(1H, ddd, J = 8.0, 6.4, 1.6 Hz), 7.63(1H, dddd, J = 8.0, 8.0, 8.0, 1.6 Hz), 7.60-7.68(1H, m), 8.09(1H, d, J = 8.0, 1.2 Hz), 11.59(1H, s)<br>ESI+: 422<br>mp: >234° C.(dec.) |
| 192 | 2 | NMR1: 1.16(6H, s), 1.85(2H, t, J = 7.1 Hz), 2.07(3H, s), 4.16(2H, t, J = 7.2 Hz), 4.42(1H, s), 5.27(2H, s), 7.20(1H, dd, J = 2.4, 2.3 Hz), 7.26-7.34(1H, m), 7.59-7.67(2H, m), 7.97(1H, d, J = 2.3 Hz), 8.06(1H, d, J = 2.4 Hz), 8.10(1H, d, J = 8.0 Hz), 11.63(1H, br s)<br>ESI+: 369 |
| 193 | 2 | NMR1: 1.52-1.59(2H, m), 1.66-1.70(2H, m), 1.94(2H, t, J = 7.0 Hz), 2.06(3H, s), 3.11(3H, s), 3.49-3.59(4H, m), 4.00(2H, t, J = 7.0 Hz), 5.17(2H, s), 6.55-6.60(1H, m), 6.66-6.69(2H, m), 7.20-7.25(1H, m), 7.27-7.31(1H, m), 7.59-7.66(2H, m), 8.07-8.10(1H, m), 11.6(1H, s)<br>FAB+: 424 |
| 194 | 2 | NMR1: 1.10(6H, s), 1.44-1.52(2H, m), 1.62(2H, t, J = 7.2 Hz), 1.84-1.92(2H, m), 2.03(3H, s), 2.85-2.92(2H, m), 3.40-3.44(1H, m), 3.47-3.52(2H, m), 3.53(2H, t, J = 7.1 Hz), 4.12(1H, s), 5.14(2H, s), 6.48(1H, dd, J = 2.1, 8.0 Hz), 6.58(1H, dd, J = 2.0, 8.2 Hz), 6.6$_{1-6}$.63(1H, m), 7.13(1H, t, J = 8.2 Hz), 7.26-7.31(1H, m), 7.59-7.66(2H, m), 8.07-8.10(1H, m), 11.6(1H, s)<br>FAB+: 451<br>mp: 160-163° C. |

TABLE 156

| Ex | Syn | DATA |
| --- | --- | --- |
| 195 | 2 | NMR1: 1.10(6H, s), 1.41-1.54(2H, m), 1.68(2H, t, J = 7.2 Hz), 1.83-1.92(2H, m), 2.05(3H, s), 2.86-2.92(2H, m), 3.07(3H, s), 3.42-3.45(1H, m), 3.45-3.51(2H, m), 3.47(2H, t, J = 7.3 Hz), 5.14(2H, s), 6.48(1H, dd, J = 2.0, 8.0 Hz), 6.57-6.60(1H, m), 6.6$_{1-6}$.63(1H, m), 7.13(1H, t, J = 8.0 Hz), 7.26-7.31(1H, m), 7.59-7.66(2H, m), 8.08-8.09(1H, m), 11.6(1H, s)<br>FAB+: 465 |
| 196 | 2 | NMR1: 2.01-2.02(5H, m), 3.05-3.14(1H, m), 4.02(2H, t, J = 6.4 Hz), 4.33(2H, t, J = 6.0 Hz), 4.6$_{2-4}$.67(2H, m), 5.37(2H, s), 6.46(1H, d, J = 2.2 Hz), 6.6$_{1-6}$.65(1H, dd, J = 2.3, 5.9 Hz), 7.25-7.31(1H, m), 7.60-7.63(2H, m), 8.00(1H, d, J = 5.9 Hz), 8.08(1H, d, J = 8.0 Hz), 11.60(1H, s)<br>ESI+: 367 |
| 197 | 2 | NMR1: 1.15(6H, s), 1.81(2H, t, J = 7.3 Hz), 2.05(3H, s), 3.72(3H, s), 4.04(2H, t, J = 7.2 Hz), 4.36(1H, s), 5.14(2H, s), 6.15(1H, dd, J = 2.1, 2.1 Hz), 6.25-6.30(2H, m), 7.26-7.32(1H, m), 7.58-7.67(2H, m), 8.10(1H, d, J = 8.1 Hz), 11.58(1H, s)<br>ESI+: 398 |
| 198 | 2 | NMR1: 1.37-1.48(2H, m), 1.73-1.82(2H, m), 2.05(3H, s), 2.79-2.87(2H, m), 3.48-3.56(2H, m), 3.56-3.65(1H, m), 4.66(1H, d, J = 4.0 Hz), 5.14(2H, s), 6.47(1H, dd, J = 2.2, 8.1 Hz), 6.57(1H, dd, J = 2.1, 8.2 Hz), 6.60-6.63(1H, m), 7.12(1H, t, J = 8.2 Hz), 7.25-7.30(1H, m), 7.58-7.67(2H, m), 8.09(1H, dd, J = 1.2, 8.2 Hz), 11.60(1H, s)<br>ESI+: 365 |
| 199 | 2 | NMR1: 1.13(3H, s), 1.49-1.55(4H, m), 2.06(3H, s), 3.08-3.16(2H, m), 3.26-3.32(2H, m), 4.27(1H, s), 5.14(2H, s), 6.46(1H, d, J = 2.1, 8.0 Hz), 6.55-6.59(1H, m), 6.59-6.62(1H, m), 7.11(1H, t, J = 8.2 Hz), 7.26-7.30(1H, m), 7.58-7.67(2H, m), 8.09(1H, dd, J = 1.2, 8.2 Hz), 11.57(1H, s)<br>ESI+: 379 |

TABLE 157

| Ex | Syn | DATA |
| --- | --- | --- |
| 200 | 2 | NMR1: 1.09-1.22(2H, m), 1.36-1.51(1H, m), 1.52-1.64(4H, m), 2.06(3H, s), 2.65-2.74(2H, m), 3.18-3.27(2H, m), 3.82(2H, dd, J = 11.0, 3.9 Hz), 5.24(2H, s), 7.24(1H, d, J = 8.5 Hz), 7.27-7.32(1H, m), 7.46(1H, dd, J = 8.5, 2.9 Hz), 7.59-7.66(2H, m), 8.09(1H, d, J = 8.2 Hz), 8.34(1H, d, J = 2.9 Hz), 11.59(1H, br s)<br>ESI+: 379 |
| 201 | 2 | NMR1: 1.16-1.28(2H, m), 1.55-1.62(2H, m), 1.79-1.90(1H, m), 2.06(3H, s), 3.25-3.38(4H, m), 3.80-3.86(2H, m), 4.50(2H, s), 5.41(2H, s), 6.89(1H, s), 6.98(1H, d, J = 5.6 Hz), 7.25-7.31(1H, m), 7.58-7.65(2H, m), 8.08(1H, d, J = 8.0 Hz), 8.16(1H, d, J = 4.8 Hz), 11.61(1H, s)<br>FAB+: 395 |
| 202 | 2 | NMR1: 1.38-1.53(1H, m), 1.56-1.67(1H, m), 1.67-1.76(2H, m), 1.90-1.98(4H, m), 2.05(3H, s), 2.50-2.60(2H, m), 4.90(1H, s), 5.15(2H, s), 7.01(2H, d, J = 8.6 Hz), 7.17(2H, d, J = 6.6 Hz), 7.26-7.31(1H, m), 7.59-7.68(2H, m), 8.09(1H, dd, J = 8.0, 1.0 Hz), 11.60(1H, br s)<br>FAB+: 364 |
| 203 | 2 | NMR1: 1.17-1.37(5H, m), 1.46-1.51(1H, m), 1.66-1.75(2H, m), 1.90-1.98(2H, m), 2.00(3H, s), 33.6-3.48(1H, m), 4.58(2H, s), 7.24-7.28(1H, m), 7.55-7.64(1H, m), 7.66-7.68(1H, m), 8.0$_{5-8}$.09(1H, m), 11.3(1H, s)<br>FAB+: 272 |
| 204 | 2 | NMR1: 0.89(6H, s), 2.01(3H, s), 3.19-3.50(10H, m), 3.84(2H, s), 4.57(2H, s), 7.23-7.31(1H, m), 7.58-7.60(2H, m), 8.06-8.08(1H, m), 11.3(1H, s)<br>FAB+: 389<br>mp: 155-157° C. |
| 205 | 2 | NMR1: 1.13-1.26(1H, m), 1.26-1.50(7H, m), 1.50-1.63(2H, m), 1.72(2H, t, J = 7.0 Hz), 1.98(3H, s), 3.67(2H, t, J = 7.1 Hz), 4.20(1H, s), 4.57(2H, s), 7.23-7.30(1H, m), 7.56-7.63(1H, m), 7.68(1H, d, J = 8.2 Hz), 8.08(1H, dd, J = 8.0, 1.3 Hz), 11.34(1H, s)<br>FAB+: 316<br>mp: 125-127° C. |

TABLE 158

| Ex | Syn | DATA |
| --- | --- | --- |
| 206 | 2 | NMR1: 1.37-1.69(8H, m), 1.67-1.80(2H, m), 1.81-1.97(2H, m), 2.01(3H, s), 2.98(1H, q, J = 7.2 Hz), 3.02-3.12(1H, m), 3.18-3.28(1H, m), 3.64-3.74(1H, m), 3.74-3.84(1H, m), 3.87-3.97(1H, m), 4.63(2H, s), 7.27(1H, ddd, J = 8.0, 6.8, 1.2 Hz), 7.60(1H, ddd, J = 8.0, 6.8, 1.2 Hz), 7.68(1H, d, J = 8.0 Hz), 8.08(1H, dd, J = 8.0, 1.2 Hz), 11.25(1H, s)<br>FAB+: 369 |

TABLE 158-continued

| Ex | Syn | DATA |
|---|---|---|
| 207 | 2 | NMR1: 0.52-0.56(4H, m), 2.00(3H, s), 3.19(4H, br s), 3.40(4H, br s), 3.40(2H, s), 3.98(2H, s), 4.59(2H, s), 7.27(1H, t, J = 8.0 Hz), 7.57-7.65(2H, m), 8.07(1H, d, J = 8.0 Hz), 11.3(1H, s)<br>FAB+: 387 |
| 208 | 2 | NMR1: 1.08-1.23(2H, m), 1.37-1.53(3H, m), 1.56-1.65(2H, m), 2.06(3H, s), 2.52-2.59(2H, m), 3.19-3.28(2H, m), 3.82(2H, dd, J = 10.4, 3.3 Hz), 5.37(2H, s), 6.90(1H, d, J = 8.2 Hz), 7.24-7.31(1H, m), 7.56-7.66(3H, m), 8.04(1H, d, J = 2.3 Hz), 8.09(1H, d, J = 8.1 Hz), 11.60(1H, br s)<br>ESI+: 379 |
| 209 | 2 | NMR1: 0.58-0.78(4H, m), 0.94-1.23(2H, m), 1.49-1.61(2H, m), 1.54-1.67(1H, m), 1.68-1.90(2H, m), 1.92-2.04(1H, m), 2.00(3H, s), 2.50-2.63(1H, m), 2.63-2.77(2H, m), 2.98-3.15(1H, m), 4.18-4.45(2H, m), 7.24(1H, ddd, J = 8.0, 6.4, 1.2 Hz), 7.50(1H, d, J = 8.0 Hz), 7.57(1H, ddd, J = 8.0, 6.4, 1.2 Hz), 8.05(1H, dd, J = 8.0, 1.2 Hz), 11.36(1H, s)<br>ESI+: 339<br>mp: 222-224° C. |
| 210 | 2 | NMR1: 1.42-1.56(2H, m), 1.54-1.69(4H, m), 1.68-1.81(2H, m), 2.04(3H, s), 2.96(1H, q, J = 8.0 Hz), 3.31-3.46(4H, m), 3.41-3.57(4H, m), 5.17(2H, s), 7.28(1H, ddd, J = 8.0, 6.8, 1.2 Hz), 7.57(1H, d, J = 8.0 Hz), 7.62(1H, ddd, J = 8.0, 6.8, 1.2 Hz), 8.08(1H, dd, J = 8.0, 1.2 Hz), 11.61(1H, br s)<br>ESI+: 398 |

TABLE 159

| Ex | Syn | DATA |
|---|---|---|
| 211 | 2 | NMR1: 1.02-1.21(2H, m), 1.44-1.58(2H, m), 1.56-1.71(1H, m), 2.03(3H, s), 2.91(2H, dd, J = 6.0, 6.0 Hz), 3.17-3.28(2H, m), 3.76-3.88(2H, m), 5.07(2H, s), 7.28(1H, ddd, J = 8.0, 6.8, 1.2 Hz), 7.36-7.43(1H, m), 7.56(1H, d, J = 8.0 Hz), 7.61(1H, ddd, J = 8.0, 6.8, 1.2 Hz), 8.08(1H, dd, J = 8.0, 1.2 Hz), 11.56(1H, br s)<br>ESI+: 331 |
| 212 | 2 | NMR1: 1.47-1.57(2H, m), 1.91-1.95(2H, m), 2.01(3H, s), 3.32-3.38(2H, m), 3.62-3.70(1H, m), 3.81-3.86(2H, m), 4.62(2H, s), 7.26(1H, t, J = 7.0 Hz), 7.57-7.61(1H, m), 7.67(1H, d, J = 8.3 Hz), 8.07(1H, d, J = 8.2 Hz), 11.2(1H, s)<br>ESI+: 274<br>mp: 194-196° C. |
| 213 | 2 | NMR1: 1.17(6H, d, J = 8.1 Hz), 2.04(3H, s), 2.50-2.54(2H, m), 1.76-2.85(2H, m), 3.65-3.73(2H, m), 4.56(1H, s), 4.64(1H, s), 4.84(1H, d, J = 8.5 Hz), 5.15(2H, s), 6.93-6.96(2H, m), 7.13-7.17(1H, m), 7.27-7.31(1H, m), 7.58-7.66(2H, m), 8.09(1H, d, J = 7.8 Hz), 11.5(1H, s)<br>ESI+: 421<br>mp: 135-138° C. |
| 214 | 2 | NMR1: 1.09(6H, s), 1.56-1.64(2H, m), 2.05(3H, s), 2.39-2.44(2H, m), 2.71-2.78(1H, m), 2.82-2.90(1H, m), 3.63-3.68(2H, m), 4.00-4.06(1H, m), 4.53(1H, s), 4.60(1H, s), 5.16(2H, s), 6.94(2H, br s), 7.14-7.18(1H, m), 7.26-7.30(1H, m), 7.59-7.66(2H, m), 8.09(1H, d, J = 7.9 Hz), 11.5(1H, s)<br>ESI+: 435 |
| 215 | 2 | NMR1: 1.09-1.22(2H, m), 1.37-1.52(3H, m), 1.55-1.64(2H, m), 2.05(3H, s), 2.51-2.58(2H, m), 3.18-3.28(2H, m), 3.82(2H, dd, J = 11.0, 3.7 Hz), 5.14(2H, s), 7.01(2H, d, J = 8.6 Hz), 7.16(2H, d, J = 8.6 Hz), 7.25-7.31(1H, m), 7.57-7.67(2H, m), 8.09(1H, d, J = 8.0 Hz), 11.55(1H, br s)<br>ESI+: 378 |

TABLE 160

| Ex | Syn | DATA |
|---|---|---|
| 216 | 2 | NMR1: 1.12(6H, s), 1.74(2H, t, J = 6.8 Hz), 1.99(3H, s), 3.66(2H, t, J = 6.8 Hz), 4.38(1H, br s), 4.57(2H, s), 7.27(1H, dd, J = 7.2, 7.2 Hz), 7.55-7.63(1H, m), 7.67(1H, d, J = 8.4 Hz), 8.08(1H, d, J = 8.4 Hz), 11.31(1H, br s)<br>ESI+: 276 |
| 217 | 2 | NMR1: 2.07(3H, s), 5.41(2H, s), 6.97(1H, d, J = 8.0 Hz), 7.06(1H, dd, J = 7.2, 5.2 Hz), 7.24-7.31(1H, m), 7.57-7.65(2H, m), 7.74-7.81(1H, m), 8.09(1H, d, J = 8.0 Hz), 8.20-8.25(1H, m), 11.59(1H, br s)<br>ESI+: 267 |
| 218 | 2 | NMR1: 1.40-1.53(4H, m), 1.52-1.63(2H, m), 1.98(3H, s), 3.24-3.36(2H, m), 3.40-3.50(2H, m), 4.39(2H, s), 4.71(2H, s), 7.27(1H, ddd, J = 8.4, 6.8, 1.6 Hz), 7.60(1H, ddd, J = 8.4, 6.8, 1.6 Hz), 7.62-7.66(1H, m), 8.08(1H, dd, J = 8.4, 1.6 Hz), 11.70(1H, br s)<br>ESI+: 315 |

TABLE 160-continued

| Ex | Syn | DATA |
|---|---|---|
| 219 | 2 | NMR1: 0.08-0.14(2H, m), 0.40-0.48(2H, m), 0.83-1.22(3H, m), 1.51-1.66(3H, m), 1.72-1.84(2H, m), 2.09(3H, s), 2.24(2H, d, J = 6.7 Hz), 2.47-2.59(1H, m), 2.77-2.86(2H, m), 2.93-3.04(1H, m), 3.84(1H, d, J = 13.5 Hz), 4.40(1H, d, J = 12.7 Hz), 7.34-7.42(1H, m), 7.63-7.72(2H, m), 8.17(1H, d, J = 8.1 Hz), 12.36(1H, br s)<br>ESI+: 353 |
| 220 | 2 | NMR1: 0.93-1.16(2H, m), 1.45-1.67(7H, m), 1.73-1.87(2H, m), 2.10(3H, s), 2.47-2.58(1H, m), 2.77-2.92(3H, m), 2.95-3.07(1H, m), 3.33-3.43(2H, m), 3.80-3.87(2H, m), 3.99(1H, d, J = 13.2 Hz), 4.40(1H, d, J = 11.6 Hz), 7.34-7.41(1H, m), 7.63-7.72(2H, m), 8.17(1H, d, J = 8.1 Hz), 12.36(1H, br s)<br>ESI+: 383 |
| 221 | 2 | NMR1: 1.13(6H, s), 1.56-1.64(2H, m), 2.06(3H, s), 2.54-2.62(2H, m), 4.25(1H, s), 5.37(2H, s), 6.89(1H, d, J = 8.6 Hz), 7.25-7.31(1H, m), 7.57-7.65(3H, m), 8.03(1H, d, J = 2.2 Hz), 8.09(1H, d, J = 7.8 Hz), 11.59(1H, br s)<br>ESI+: 353 |

TABLE 161

| Ex | Syn | DATA |
|---|---|---|
| 222 | 2 | NMR1: 0.49-0.56(2H, m), 0.73-0.80(2H, m), 1.01-1.19(2H, m), 1.22(3H, s), 1.53-1.68(3H, m), 1.75-1.85(2H, m), 2.12(3H, s), 2.69-2.90(4H, m), 4.2$_{1-4}$.32(2H, m), 7.36-7.45(1H, m), 7.67-7.74(2H, m), 8.19(1H, d, J = 8.2 Hz), 12.55(1H, br s)<br>ESI+: 353 |
| 223 | 2 | NMR1: 0.97-1.23(2H, m), 1.52-1.68(3H, m), 1.74-1.83(2H, m), 3.13(3H, s), 2.57(1H, t, J = 13.1 Hz), 2.81-2.91(2H, m), 2.96(1H, t, J = 12.3 Hz), 3.28(3H, s), 3.7-3.83(1H, m), 4.03(1H, d, J = 14.0 Hz), 4.10(1H, d, J = 13.7 Hz), 4.34(1H, d, J = 13.0 Hz), 7.40-7.48(1H, m), 7.69-7.79(2H, m), 8.22(1H, d, J = 8.2 Hz), 12.8(1H, br s)<br>ESI+: 343 |
| 224 | 2 | NMR1: 0.96(3H, t, J = 7.2 Hz), 1.10-1.21(2H, m), 1.26-1.40(2H, m), 1.84(2H, d, J = 10.8 Hz), 2.03(2H, d, J = 10.5 Hz), 2.09(3H, s), 2.98(2H, q, J = 7.1 Hz), 3.30-3.38(1H, m), 3.38-3.48(1H, m), 4.70(2H, s), 7.41(1H, t, J = 7.4 Hz), 7.71(1H, t, J = 7.3 Hz), 7.87(1H, d, J = 8.1 Hz), 8.20(1H, d, J = 8.1 Hz), 12.2(1H, s)<br>ESI+: 358<br>mp: >270° C.(dec.) |
| 225 | 2 | NMR1 + TFA: 1.20-1.30(2H, m), 1.39-1.50(4H, m), 1.56-1.63(4H, m), 1.69-1.74(2H, m), 1.83-1.87(2H, m), 2.11-2.13(2H, m), 2.32(3H, s), 2.50-2.53(1H, m), 3.52-3.58(2H, m), 4.95(2H, s), 7.62(1H, d, J = 7.5 Hz), 7.74(1H, t, J = 7.6 Hz), 7.96(1H, t, J = 7.2 Hz), 8.26(1H, d, J = 8.6 Hz), 8.45(1H, d, J = 8.2 Hz)<br>ESI+: 383 |
| 226 | 2 | NMR1: 1.17(3H, t, J = 7.0 Hz), 1.28-1.41(2H, m), 1.47-1.64(4H, m), 2.00(3H, s), 2.13(2H, d, J = 12.0 Hz), 2.68(3H, s), 3.33-3.42(1H, m), 3.82(1H, br s), 4.01(2H, q, J = 7.0 Hz), 4.60(2H, s), 7.24-7.28(1H, m), 7.56-7.62(1H, m), 7.68(1H, d, J = 8.3 Hz), 8.0$_{5-8}$.08(1H, m), 11.2(1H, s)<br>ESI+: 373 |

TABLE 162

| Ex | Syn | DATA |
|---|---|---|
| 227 | 2 | NMR1: 2.03(3H, s), 5.21(2H, s), 7.27-7.39(3H, m), 7.63(2H, d, J = 3.2 Hz), 7.69-7.74(2H, m), 8.08(1H, d, J = 8.4 Hz), 11.74(1H, s)<br>ESI+: 368 |
| 228 | 2 | NMR1: 1.10-1.72(14H, m), 2.00(3H, d, J = 10.7 Hz), 2.75-2.90(1H, m), 3.14(1H, t, J = 2.8 Hz), 3.35-3.85(8H, m), 4.61(2H, d, J = 6.8 Hz), 7.27(1H, t, J = 7.5 Hz), 7.57-7.71(2H, m), 8.08(1H, d, J = 8.1 Hz)<br>ESI+: 427 |
| 229 | 2 | NMR1: 0.91-1.27(9H, m), 1.47-1.65(5H, m), 1.69-1.87(2H, m), 1.99(3H, s), 2.25-2.38(2H, m), 2.64-2.75(2H, m), 2.92-3.09(1H, m), 3.80-3.95(1H, m), 4.21(1H, s), 4.3$_{2-4}$.47(1H, m), 7.23(1H, dd, J = 7.4, 7.2 Hz), 7.48(1H, d, J = 8.2 Hz), 7.56(1H, dd, J = 7.5, 7.2 Hz), 8.05(1H, d, J = 7.9 Hz), 11.29(1H, s)<br>ESI+: 385 |
| 230 | 2 | NMR1: 1.53(4H, br s), 1.69(2H, br s), 1.89(2H, br s), 2.10(3H, s), 4.16-4.27(1H, m), 5.52(2H, s), 7.24-7.32(1H, m), 7.60-7.62(2H, m), 8.08(1H, d, J = 8.0 Hz), 8.43(1H, d, J = 7.0 Hz), 9.02(2H, s), 11.7(1H, s)<br>ESI+: 379<br>mp: >231° C.(dec.) |
| 231 | 2 | NMR1: 1.44(8H, br s), 1.59(4H, br s), 2.10(3H, s), 3.36(2H, br s), 3.59(2H, br s), 5.51(2H, s), 7.25-7.31(1H, m), 7.61-7.62(2H, m), 8.09(1H, d, J = 8.1 Hz), 8.74(2H, s), 11.7(1H, s)<br>ESI+: 433 |

TABLE 162-continued

| Ex | Syn | DATA |
| --- | --- | --- |
| 232 | 2 | NMR1: 0.23(2H, d, J = 4.6 Hz), 0.45(2H, d, J = 8.0 Hz), 0.97-1.09(1H, m), 2.10(3H, s), 3.15(2H, t, J = 6.2 Hz), 5.53(2H, s), 7.24-7.33(1H, m), 7.61-7.62(2H, m), 8.09(1H, d, J = 8.1 Hz), 8.69-8.78(1H, m), 9.05(2H, s), 11.7(1H, s)<br>ESI+: 365<br>mp: >265° C.(dec.) |

TABLE 163

| Ex | Syn | DATA |
| --- | --- | --- |
| 233 | 2 | NMR1: 1.33-1.75(10H, m), 1.93-2.00(2H, m), 2.00(3H, s), 2.01(3H, s), 2.11-2.14(2H, m), 2.89-3.00(2H, m), 3.34-3.41(1H, m), 3.72-3.81(1H, m), 4.23-4.29(1H, m), 4.60(2H, s), 7.26(1H, t, J = 7.6 Hz), 7.59(1H, t, J = 7.4 Hz), 7.67(1H, t, J = 7.2 Hz), 8.07(1H, d, J = 7.8 Hz), 11.2(1H, s)<br>ESI+: 397 |
| 234 | 2 | NMR1: 2.00-2.11(5H, m), 2.45-2.54(2H, m), 3.82(2H, t, J = 7.1 Hz), 5.18(2H, s), 6.89(1H, dd, J = 7.9, 2.2 Hz), 7.22-7.36(3H, m), 7.50(1H, dd, J = 2.2, 2.1 Hz), 7.57-7.68(2H, m), 8.09(1H, d, J = 8.1 Hz), 11.58(1H, br s)<br>ESI+: 349 |
| 235 | 2 | NMR1: 1.77-1.92(4H, m), 2.06(3H, s), 2.36-2.42(2H, m), 3.56-3.62(2H, m), 5.16(2H, s), 6.92(1H, d, J = 7.8 Hz), 6.99(1H, dd, J = 8.3, 2.6 Hz), 7.06(1H, dd, J = 2.3, 2.1 Hz), 7.26-7.36(2H, m), 7.58-7.67(2H, m), 8.10(1H, d, J = 8.1 Hz), 11.58(1H, br s)<br>ESI+: 363 |
| 236 | 2 | NMR1: 1.65-1.77(6H, m), 2.06(3H, s), 2.56-2.62(2H, m), 3.67-3.73(2H, m), 5.17(2H, s), 6.85(1H, d, J = 7.7 Hz), 6.95-7.01(2H, m), 7.24-7.37(2H, m), 7.57-7.68(2H, m), 8.09(1H, d, J = 8.2 Hz), 11.57(1H, s)<br>ESI+: 377 |
| 237 | 2 | NMR1: 2.04(3H, s), 3.33-3.44(4H, m), 3.51-3.61(4H, m), 5.16(2H, s), 7.28(1H, ddd, J = 8.0, 6.8, 1.6 Hz), 7.57(1H, d, J = 8.0 Hz), 7.62(1H, ddd, J = 8.0, 6.8, 1.6 Hz), 8.08(1H, d, J = 8.0 Hz), 11.57(1H, br s)<br>ESI+: 303 |
| 238 | 2 | NMR1: 1.08(6H, s), 1.29-1.43(2H, m), 1.60(2H, t, J = 6.8 Hz), 1.73-1.84(2H, m), 2.03(3H, s), 3.08-3.21(2H, m), 3.40-3.48(1H, m), 3.50(2H, t, J = 6.8 Hz), 3.61-3.71(2H, m), 4.14(1H, s), 5.12(2H, s), 7.28(1H, ddd, J = 8.0, 7.2, 1.6 Hz), 7.57(1H, d, J = 8.0 Hz), 7.61(1H, ddd, J = 8.0, 7.2, 1.6 Hz), 8.0$_{5-8}$.11(1H, m), 11.56(1H, br s)<br>ESI+: 403 |

TABLE 164

| Ex | Syn | DATA |
| --- | --- | --- |
| 239 | 2 | NMR1: 1.30-1.42(2H, m), 1.74-1.85(2H, m), 2.03(3H, s), 3.07-3.20(2H, m), 3.24(3H, s), 3.28-3.42(1H, m), 3.60-3.72(2H, m), 5.12(2H, s), 7.28(1H, ddd, J = 8.0, 6.8, 1.6 Hz), 7.57(1H, d, J = 8.0 Hz), 7.61(1H, ddd, J = 8.0, 6.8, 1.6 Hz), 8.0$_{5-8}$.10(1H, m), 11.60(1H, br s)<br>ESI+: 331 |
| 240 | 2 | NMR1: 1.09(6H, s), 1.30-1.42(2H, m), 1.67(2H, t, J = 7.6 Hz), 1.73-1.84(2H, m), 2.03(3H, s), 3.06(3H, s), 3.08-3.21(2H, m), 3.25-3.37(1H, m), 3.45(2H, t, J = 7.6 Hz), 3.60-3.72(2H, m), 5.12(2H, s), 7.28(1H, ddd, J = 8.0, 6.4, 1.2 Hz), 7.57(1H, d, J = 8.0 Hz), 7.61(1H, ddd, J = 8.0, 6.4, 1.2 Hz), 8.08(1H, d, J = 8.0 Hz), 11.56(1H, s)<br>ESI+: 417 |
| 241 | 2 | NMR1: 2.07(3H, s), 4.0$_{2-4}$.09(2H, m), 4.40-4.47(2H, m), 5.19(2H, s), 6.90(1H, dd, J = 8.3, 2.2 Hz), 7.18(1H, dd, J = 8.3, 1.7 Hz), 7.26-7.32(1H, m), 7.32-7.40(2H, m), 7.58-7.67(2H, m), 8.09(1H, d, J = 8.0 Hz), 11.59(1H, s)<br>ESI+: 351 |
| 242 | 2 | NMR1: 2.06(3H, s), 3.69-3.75(2H, m), 3.76(3H, s), 3.93-3.99(2H, m), 4.19(2H, s), 5.16(2H, s), 6.6$_{1-6}$.67(2H, m), 6.78(1H, dd, J = 2.0, 2.0 Hz), 7.25-7.33(1H, m), 7.58-7.68(2H, m), 8.10(1H, d, J = 7.9 Hz), 11.61(1H, br s)<br>ESI+: 395 |
| 243 | 2 | NMR1: 1.05-1.14(2H, m), 1.14-1.24(2H, m), 1.30-1.39(2H, m), 1.42-1.49(2H, m), 1.49-1.59(2H, m), 1.62-1.69(2H, m), 1.77-1.82(2H, m), 1.99(3H, s), 2.02-2.13(5H, m), 3.37-3.42(1H, m), 3.49-3.56(1H, m), 4.59(2H, s), 7.26(1H, t, J = 8.0 Hz), 7.57-7.61(2H, m), 7.68(1H, d, J = 8.3 Hz), 8.07(1H, d, J = 8.0 Hz), 11.2(1H, s)<br>ESI+: 397 |

TABLE 165

| Ex | Syn | DATA |
|---|---|---|
| 244 | 2 | NMR1: 0.07-0.11(2H, m), 0.37-0.43(2H, m), 0.89-0.96(1H, m), 1.15-1.24(2H, m), 1.30-1.39(2H, m), 1.79-1.82(1H, m), 1.93(2H, d, J = 7.0 Hz), 2.00(3H, s), 2.04-2.07(2H, m), 3.37-3.43(1H, m), 3.49-3.56(1H, m), 4.59(2H, s), 7.26(1H, t, J = 7.9 Hz), 7.52(1H, d, J = 7.7 Hz), 7.56-7.61(1H, m), 7.68(1H, d, J = 8.3 Hz), 8.07(1H, d, J = 8.1 Hz), 11.2(1H, s)<br>ESI+: 369 |
| 245 | 2 | NMR1: 0.44-0.47(2H, m), 0.89-0.92(2H, m), 1.22(3H, s), 1.29-1.35(4H, m), 1.69-1.80(2H, m), 2.00(3H, s), 2.02-2.12(2H, m), 3.32-3.42(1H, m), 3.51-3.63(1H, m), 4.60(2H, s), 7.07(1H, d, J = 7.9 Hz), 7.24-7.29(1H, m), 7.56-7.61(1H, m), 7.68(1H, d, J = 8.3 Hz), 8.07(1H, d, J = 8.1 Hz), 11.2(1H, s)<br>ESI+: 369 |
| 246 | 2 | NMR1: 1.10-1.24(4H, m), 1.29-1.38(2H, m), 1.48-1.51(2H, m), 1.78-1.81(2H, m), 1.81-1.90(1H, m), 1.96(2H, d, J = 7.1 Hz), 2.00(3H, s), 2.03-2.06(2H, m), 3.20-3.29(2H, m), 3.37-3.43(1H, m), 3.48-3.58(1H, m), 3.77-3.81(2H, m), 4.59(2H, s), 7.26(1H, t, J = 7.1 Hz), 7.56-7.61(1H, m), 7.64-7.69(2H, m), 8.07(1H, d, J = 8.2 Hz), 11.2(1H, s)<br>ESI+: 413 |
| 247 | 2 | NMR1: 1.15-1.24(2H, m), 1.30-1.39(2H, m), 1.54-1.58(4H, m), 1.77-1.80(2H, m), 2.04(3H, s), 2.98-2.32(3H, m), 3.23-3.34(4H, m), 3.82-3.85(2H, m), 4.65(2H, s), 7.33(1H, t, J = 7.4 Hz), 7.58-7.66(2H, m), 7.77(1H, d, J = 8.3 Hz), 8.13(1H, d, J = 7.9 Hz), 11.7(1H, s)<br>ESI+: 399 |
| 248 | 2 | NMR1: 1.12(6H, s), 1.12-1.25(2H, m), 1.31-1.40(2H, m), 1.80-1.83(2H, m), 2.00(3H, s), 2.04-2.06(2H, m), 2.16(2H, s), 3.38-3.44(1H, m), 3.55-3.58(1H, m), 4.59(2H, s), 4.81(1H, s), 7.26(1H, t, J = 7.8 Hz), 7.56-7.61(1H, m), 7.67-7.73(2H, m), 8.06-8.08(1H, m), 11.2(1H, s)<br>ESI+: 387 |

TABLE 166

| Ex | Syn | DATA |
|---|---|---|
| 249 | 2 | NMR1: 1.33-1.42(2H, m), 1.49-1.58(2H, m), 1.80-1.83(2H, m), 2.00(3H, s), 2.09-2.12(2H, m), 2.16-2.22(2H, m), 3.14(2H, t, J = 7.7 Hz), 3.19(2H, t, J = 6.7 Hz), 3.23-3.25(1H, m), 3.30-3.40(1H, m), 4.60(2H, s), 7.27(1H, t, J = 7.3 Hz), 7.59(1H, t, J = 7.4 Hz), 7.67(1H, d, J = 8.3 Hz), 8.07(1H, d, J = 8.0 Hz), 11.2(1H, s)<br>ESI+: 391 |
| 250 | 2 | NMR1: 2.06(3H, s), 3.74(2H, dd, J = 5.6, 4.0 Hz), 3.97(2H, dd, J = 5.6, 4.0 Hz), 4.21(2H, s), 5.19(2H, s), 7.01-7.07(2H, m), 7.21(1H, dd, J = 2.0, 2.0 Hz), 7.38(1H, dd, J = 8.0, 8.0 Hz), 7.55(1H, ddd, J = 8.0, 8.0, 2.8 Hz), 7.73(1H, dd, J = 9.6, 2.8 Hz), 7.75(1H, dd, J = 9.6, 4.8 Hz), 11.76(1H, br s)<br>FAB+: 383 |
| 251 | 2 | NMR1: 1.20-1.36(2H, m), 1.62-1.77(2H, m), 2.03(3H, s), 2.97-3.17(2H, m), 3.58-3.68(1H, m), 3.67-3.78(2H, m), 4.71(1H, d, J = 4.0 Hz), 5.12(2H, s), 7.28(1H, ddd, J = 8.0, 6.8, 1.2 Hz), 7.57(1H, d, J = 8.0 Hz), 7.61(1H, d, J = 8.0, 8.0, 1.2 Hz), 8.08(1H, d, J = 8.0 Hz), 11.57(1H, s)<br>ESI+: 317 |
| 252 | 2 | NMR1: 2.06(3H, s), 2.31(3H, s), 3.68-3.74(2H, m), 3.93-3.99(2H, m), 4.19(2H, s), 5.15(2H, s), 6.85-6.90(2H, m), 6.97-7.02(1H, m), 7.25-7.32(1H, m), 7.58-7.67(2H, m), 8.10(1H, d, J = 7.8 Hz), 11.57(1H, br s)<br>ESI+: 379 |
| 253 | 2 | NMR1: 1.52(2H, m), 1.72-1.92(1H, m), 2.04(3H, s), 2.81-2.93(3H, m), 3.13(2H, d, J = 6.8 Hz), 3.15-3.26(2H, m), 3.69-3.87(2H, m), 5.12(2H, s), 7.28(1H, ddd, J = 8.0, 7.2, 1.6 Hz), 7.56(1H, d, J = 8.0 Hz), 7.61(1H, ddd, J = 8.0, 8.0, 1.6 Hz), 8.08(1H, d, J = 8.0 Hz), 11.55(1H, s)<br>ESI+: 345 |
| 254 | 2 | NMR1: 0.63-0.75(4H, m), 0.96-1.27(2H, m), 1.52-2.05(6H, m), 2.00(3H, s), 2.49-2.75(3H, m), 3.01-3.14(1H, m), 4.18-4.43(2H, m), 7.45-7.52(1H, m), 7.55-7.60(1H, m), 7.65-7.71(1H, m), 11.47(1H, s)<br>ESI+: 357 |

TABLE 167

| Ex | Syn | DATA |
|---|---|---|
| 255 | 2 | NMR1: 0.90-0.92(4H, m), 1.28-1.38(4H, m), 1.92-1.95(2H, m), 2.00(3H, s), 2.03-2.06(2H, m), 2.50-2.53(1H, m), 3.15-3.16(1H, m), 3.34-3.42(1H, m), 4.58(2H, s), 6.99(1H, d, J = 7.7 Hz), 7.26(1H, t, J = 7.5 Hz), 7.59(1H, t, J = 8.0 Hz), 7.67(1H, d, J = 8.3 Hz), 8.07(1H, d, J = 8.0 Hz), 11.2(1H, s)<br>ESI+: 391 |

TABLE 167-continued

| Ex | Syn | DATA |
|---|---|---|
| 256 | 2 | NMR1: 1.42(6H, s), 2.06(3H, s), 3.70-3.74(2H, m), 3.93-3.98(2H, m), 5.18(2H, s), 7.00(1H, dd, J = 7.8, 1.7 Hz), 7.03(1H, dd, J = 8.2, 2.5 Hz), 7.15(1H, dd, J = 2.3, 2.2 Hz), 7.27-7.32(1H, m), 7.37(1H, dd, J = 8.1, 8.1 Hz), 7.59-7.67(2H, m), 8.10(1H, d, J = 8.3 Hz), 11.62(1H, br s)<br>ESI+: 393 |
| 257 | 2 | NMR1: 2.06(3H, s), 2.78-2.85(2H, m), 3.75-3.89(6H, m), 5.17(2H, s), 6.87(1H, d, J = 8.4 Hz), 6.97-7.03(2H, m), 7.26-7.38(2H, m), 7.59-7.68(2H, m), 8.10(1H, d, J = 7.6 Hz), 11.65(1H, br s)<br>ESI+: 379 |
| 258 | 2 | NMR1: 2.06(3H, s), 2.78-2.84(2H, m), 3.76-3.87(6H, m), 5.18(2H, s), 6.85-6.90(1H, m), 6.98-7.03(2H, m), 7.31-7.37(1H, m), 7.55(1H, ddd, J = 8.8, 8.6, 3.0 Hz), 7.70-7.78(2H, m), 11.78(1H, br s)<br>ESI+: 397 |
| 259 | 2 | NMR1: 0.83-0.88(6H, m), 1.90-2.00(1H, m), 1.93(3H, s), 2.16-2.21(2H, m), 3.15-3.41(2H, m), 3.63-3.71(2H, m), 4.09-4.21(2H, m), 4.68(2H, s), 7.24-7.29(1H, m), 7.57-7.61(2H, m), 8.06(1H, d, J = 8.0 Hz), 11.27(1H, s)<br>ESI+: 356 |
| 3 | 3 | NMR1: 1.36-1.61(6H, m), 1.67-1.75(4H, m), 2.05(3H, s), 2.58-2.66(2H, m), 4.07(1H, s), 5.14(2H, s), 7.00(2H, d, J = 8.6 Hz), 7.15(2H, d, J = 8.6 Hz), 7.26-7.31(1H, m), 7.58-7.68(2H, m), 8.09(1H, dd, J = 7.8, 1.6 Hz), 11.54(1H, br s)<br>ESI+: 378<br>mp: 200-202° C. |

TABLE 168

| Ex | Syn | DATA |
|---|---|---|
| 4 | 4 | NMR1: 1.15(6H, s), 1.83(2H, t, J = 7.1 Hz), 2.06(3H, s), 4.15(2H, t, J = 7.1 Hz), 4.40(1H, s), 5.38(2H, s), 6.49(1H, d, J = 2.1 Hz), 6.65(1H, dd, J = 2.1, 5.8 Hz), 7.26-7.31(1H, m), 7.58-7.65(2H, m), 8.00(1H, d, J = 5.8 Hz), 8.09(1H, d, J = 7.9 Hz), 11.6(1H, s)<br>ESI+: 369<br>mp: 127-130° C. |
| 5 | 5 | NMR1: 1.14(3H, t, J = 7.1 Hz), 1.16-1.24(2H, m), 1.25-1.37(2H, m), 1.79-1.84(2H, m), 1.99(3H, s), 2.01-2.06(2H, m), 3.25-3.29(2H, m), 3.95(2H, q, J = 7.1 Hz), 4.59(2H, s), 7.00(1H, d, J = 7.7 Hz), 7.27(1H, m), 7.57-7.61(1H, m), 7.67(1H, d, J = 8.2 Hz), 8.07(1H, dd, J = 1.4, 8.2 Hz), 11.2(1H, s)<br>ESI+: 359<br>mp: 268-271° C. |
| 6 | 6 | NMR1: 1.18(3H, t, J = 7.3 Hz), 1.23-1.39(4H, m), 1.85-1.90(2H, m), 1.99(3H, s), 2.02-2.06(2H, m), 2.98(2H, q, J = 7.3 Hz), 3.04-3.13(1H, m), 3.34-3.40(1H, m), 4.58(2H, s), 7.01(1H, d, J = 7.7 Hz), 7.24-7.28(1H, m), 7.57-7.61(1H, m), 7.67(1H, d, J = 8.2 Hz), 8.06-8.08(1H, m), 11.2(1H, s)<br>ESI+: 379<br>mp: 245-247° C. |
| 7 | 7 | NMR1: 1.12-1.63(6H, m), 1.76-1.95(2H, m), 2.00(3H, s), 2.11-2.14(2H, m), 2.18(2H, t, J = 8.2 Hz), 3.26(2H, t, J = 7.1 Hz), 3.35-3.43(1H, m), 3.69-3.77(1H, m), 4.61(2H, s), 7.25-7.28(1H, m), 7.57-7.61(1H, m), 7.68(1H, d, J = 8.3 Hz), 8.06-8.08(1H, m), 11.2(1H, s)<br>ESI+: 355<br>mp: 216-217° C. |

TABLE 169

| Ex | Syn | DATA |
|---|---|---|
| 8 | 8 | NMR2: 1.31-1.43(2H, m), 1.58-1.69(2H, m), 1.72-1.84(3H, m), 2.25(3H, s), 3.40(2H, ddd, J = 12, 12, 2 Hz), 3.94-4.01(2H, m), 4.06(2H, t, J = 6 Hz), 5.50(2H, s), 6.35(1H, d, J = 2 Hz), 6.59(1H, dd, J = 6, 2 Hz), 7.24-7.32(2H, m), 7.55(1H, m), 8.03(1H, d, J = 6 Hz), 8.38(1H, d, J = 7.5 Hz), 9.89(1H, br s)<br>ESI+: 395<br>mp: 137-138° C. |
| 9 | 9 | NMR1: 0.06(3H, s), 3.72-3.76(2H, m), 3.95-4.00(2H, m), 4.21(2H, s), 5.18(2H, s), 7.02-7.07(2H, m), 7.21(1H, dd, J = 2.0, 2.0 Hz), 7.27-7.32(1H, m), 7.38(1H, dd, J = 8.2, 8.0 Hz), 7.59-7.67(2H, m), 8.10(1H, d, J = 8.0 Hz), 11.62(1H, br s)<br>ESI+: 365<br>mp: 221-223° C. |
| 10 | 10 | NMR1: 1.15(6H, s), 1.80(2H, t, J = 7.2 Hz), 2.05(3H, s), 3.07-3.10(4H, m), 3.69-3.72(4H, m), 4.03(2H, t, J = 7.2 Hz), 4.35(1H, s), 5.12(2H, s), 6.12(1H, t, J = 2.0 Hz), 6.17(1H, t, J = 1.9 Hz), 6.24(1H, t, J = 2.0 Hz), 7.26-7.31(1H, m), 7.59-7.66(2H, m), 8.06-8.10(1H, m), 11.6(1H, s)<br>FAB+: 453<br>mp: 189-190° C. |

TABLE 169-continued

| Ex | Syn | DATA |
|---|---|---|
| 11 | 11 | NMR1: 1.00-1.13(2H, m), 1.32-1.45(1H, m), 1.45-1.57(2H, m), 1.62-1.72(2H, m), 1.98(3H, s), 2.44(2H, t, J = 12.1 Hz), 2.63-2.71(2H, m), 2.88-2.97(2H, m), 7.23(1H, dd, J = 7.5, 7.2 Hz), 7.49(1H, d, J = 8.1 Hz), 7.54-7.59(1H, m), 8.04(1H, d, J = 8.2 Hz), 11.32(1H, br s)<br>FAB+: 271 |
| 260 | 11 | NMR1: 0.88-1.03(2H, m), 1.21-1.39(3H, m), 1.52-1.70(4H, m), 1.99(3H, s), 2.34-2.45(2H, m), 2.61-2.71(2H, m), 2.83-2.92(2H, m), 7.23(1H, ddd, J = 7.6, 7.6, 0.9 Hz), 7.49(1H, d, J = 8.1 Hz), 7.56(1H, ddd, J = 7.6, 7.6, 1.2 Hz), 8.04(1H, d, J = 8.3 Hz), 11.28(1H, br s)<br>FAB+: 285 |

TABLE 170

| Ex | Syn | DATA |
|---|---|---|
| 12 | 12 | NMR1: 0.82(3H, t, J = 7.0 Hz), 1.13-1.32(8H, m), 1.46-1.55(2H, m), 2.04(3H, s), 2.57(2H, t, J = 7.4 Hz), 3.81(2H, s), 7.23-7.28(1H, m), 7.52(1H, d, J = 7.9 Hz), 7.53-7.62(1H, m), 7.85(1H, dd, J = 1.4, 8.1 Hz), 11.49(1H, s)<br>FAB+: 304 |
| 261 | 12 | NMR1: 0.86(3H, t, J = 7.0 Hz), 1.20-1.46(8H, m), 1.65-1.75(2H, m), 2.03(3H, s), 2.80-2.98(2H, m), 4.12(1H, d, J = 13.2 Hz), 4.27(1H, d, J = 13.2 Hz), 7.28(1H, t, J = 7.0 Hz), 7.51(1H, d, J = 8.1 Hz), 7.58-7.63(1H, m), 8.06-8.09(1H, m), 11.58(1H, s)<br>FAB+: 320 |
| 262 | 12 | NMR1: 2.09(3H, s), 5.22(2H, s), 6.95(2H, d, J = 7.6 Hz), 7.00(2H, d, J = 7.6 Hz), 7.09(1H, dd, J = 7.6, 7.6 Hz), 7.26-7.32(1H, m), 7.36(2H, dd, J = 7.6, 7.6 Hz), 7.45-7.56(2H, m), 7.59(1H, d, J = 7.6 Hz), 7.60-7.68(1H, m), 8.10(1H, d, J = 8.8 Hz), 9.90(1H, s), 11.70(1H, s)<br>FAB+: 401 |
| 263 | 12 | NMR1: 2.08(3H, s), 3.43(3H, s), 5.21(2H, s), 7.23(2H, d, J = 8.4 Hz), 7.26-7.34(1H, m), 7.45(1H, d, J = 8.4 Hz), 7.58(2H, d, J = 8.4 Hz), 7.60-7.66(1H, m), 8.09(1H, d, J = 8.4 Hz), 9.87(1H, s), 11.68(1H, s)<br>ESI+: 355 |
| 264 | 12 | NMR1: 2.08(3H, s), 5.25(2H, s), 7.29(1H, dd, J = 7.2, 7.2 Hz), 7.58(2H, d, J = 8.0 Hz), 7.60-7.69(2H, m), 7.65(2H, s), 8.10(1H, d, J = 8.0 Hz), 10.27(1H, s), 11.69(1H, s)<br>FAB+: 409 |
| 265 | 12 | NMR1: 2.07(3H, s), 3.14(2H, qq, J = 8.4, 8.4 Hz), 4.48(2H, t, J = 8.4 Hz), 5.17(2H, s), 6.67(1H, d, J = 8.4 Hz), 7.08-7.19(1H, m), 7.24-7.32(1H, m), 7.35(1H, br s), 7.58(1H, d, J = 8.4 Hz), 7.59-7.67(1H, m), 8.0$_5$-8.12(1H, m), 9.60(1H, s), 11.66(1H, s)<br>ESI+: 351 |

TABLE 171

| Ex | Syn | DATA |
|---|---|---|
| 266 | 12 | NMR1: 1.15-1.29(2H, m), 1.63-1.71(3H, m), 2.08(3H, s), 2.91(2H, d, J = 6.4 Hz), 3.15-3.23(2H, m), 3.29-3.32(2H, m), 3.78-3.84(2H, m), 5.20(2H, s), 6.90-6.98(2H, m), 7.03-7.05(1H, m), 7.25-7.32(2H, m), 7.59-7.66(2H, m), 8.09(1H, d, J = 7.6 Hz), 11.57(1H, s)<br>FAB+: 396 |
| 267 | 12 | NMR1: 1.24-1.39(2H, m), 1.66(2H, d, J = 11.0 Hz), 1.93-2.04(1H, m), 2.06(3H, s), 3.27-3.38(2H, m), 3.83-3.95(4H, m), 5.24(2H, s), 7.03-7.06(1H, m), 7.11(1H, s), 7.24(1H, s), 7.27-7.33(1H, m), 7.60-7.68(2H, m), 8.10(1H, d, J = 8.0 Hz), 11.58(1H, s)<br>ESI+: 405 |
| 268 | 12 | NMR1: 1.20-1.32(2H, m), 1.58-1.65(2H, m), 1.90-1.95(4H, m), 3.26-3.36(2H, m), 3.72(2H, d, J = 6.4 Hz), 3.83-3.89(2H, m), 4.26(2H, s), 6.83(1H, dd, J = 2.2, 8.2 Hz), 6.90-6.92(1H, m), 6.98(1H, d, J = 7.9 Hz), 7.20-7.28(2H, m), 7.48(1H, d, J = 8.2 Hz), 7.56-7.62(1H, m), 8.05(1H, d, J = 7.2 Hz), 11.53(1H, s)<br>FAB+: 396 |
| 269 | 12 | NMR1: 1.16-1.29(2H, m), 1.47-1.55(2H, m), 1.81-1.92(1H, m), 2.06(3H, s), 3.16-3.24(2H, m), 3.77-3.84(2H, m), 4.10(2H, d, J = 6.6 Hz), 5.48(2H, s), 7.26-7.32(1H, s), 7.56-7.65(2H, m), 8.08(1H, d, J = 7.6 Hz), 8.13(1H, s), 11.62(1H, s)<br>FAB+: 449 |
| 13 | 13 | NMR1: 0.83(3H, t, J = 6.9 Hz), 1.19-1.28(6H, m), 1.45-1.55(2H, m), 1.98(3H, s), 2.14(2H, t, J = 7.5 Hz), 4.32(2H, d, J = 5.2 Hz), 7.24-7.29(1H, m), 7.55-7.61(2H, m), 8.07(1H, d, J = 8.4 Hz), 8.2$_5$-8.30(1H, m), 11.57(1H, s)<br>FAB+: 301 |

TABLE 172

| Ex | Syn | DATA |
|---|---|---|
| 270 | 13 | NMR1: 0.97-1.31(2H, m), 1.43-1.68(4H, m), 1.68-1.88(2H, m), 1.88-2.04(1H, m), 2.05(3H, s), 2.41-2.63(1H, m), 2.80-2.94(1H, m), 2.95-3.11(1H, m), 3.25-3.47(2H, m), 3.84(4H, d, J = 5.6 Hz), 4.00(1H, d, J = 12.4 Hz), 4.42(1H, d, J = 12.4 Hz), 5.16(2H, s), 6.53-6.62(1H, m), 6.63-6.74(2H, m), 7.22(1H, dd, J = 8.8, 8.8 Hz), 7.25-7.35(1H, m), 7.57-7.69(2H, m), 8.09(1H, d, J = 8.0 Hz), 11.58(1H, s)<br>ESI+: 491 |
| 271 | 13 | NMR1: 0.95-1.21(8H, m), 1.50-1.66(3H, m), 1.73-1.81(2H, m), 1.99(3H, s), 2.44(2H, s), 2.50-2.59(1H, m), 2.65-2.74(2H, m), 2.99(1H, t, J = 12.4 Hz), 3.99(1H, d, J = 13.5 Hz), 4.45(1H, d, J = 12.4 Hz), 4.92(1H, s), 7.23(1H, dd, J = 7.6, 7.5 Hz), 7.49(1H, d, J = 8.2 Hz), 7.34-7.60(1H, m), 8.05(1H, d, J = 7.9 Hz), 11.32(1H, s)<br>ESI+: 371<br>mp: 203-205° C. |
| 272 | 13 | NMR1: 0.94-1.12(2H, m), 1.51-1.66(3H, m), 1.66-1.81(3H, m), 1.81-1.96(1H, m), 2.00-2.22(7H, m), 2.46-2.60(1H, m), 2.80-2.97(3H, m), 3.26-3.38(1H, m), 3.69(1H, d, J = 13.5 Hz), 4.36(1H, d, J = 13.5 Hz), 7.39-7.47(1H, m), 7.69-7.78(2H, m), 8.21(1H, d, J = 8.5 Hz), 12.77(1H, br s)<br>ESI+: 353 |
| 273 | 13 | NMR1: 1.68(5H, m), 1.72-1.84(2H, m), 1.84-1.96(1H, m), 2.14(3H, s), 2.24(2H, d, J = 6.9 Hz), 2.47-2.58(1H, m), 2.82-2.92(2H, m), 2.99(1H, t, J = 12.4 Hz), 3.23-3.33(2H, m), 3.77-3.84(3H, m), 4.41(1H, d, J = 12.9 Hz), 7.42-7.47(1H, m), 7.70-7.80(2H, m), 8.23(1H, d, J = 8.1 Hz), 12.90(1H, br s)<br>ESI+: 397 |

TABLE 173

| Ex | Syn | DATA |
|---|---|---|
| 274 | 13 | NMR1: 0.61-0.74(4H, m), 0.79-1.19(2H, m), 1.27-1.40(2H, m), 1.45-1.60(1H, m), 1.60-1.80(4H, m), 1.88-1.97(1H, m), 1.99(3H, s), 2.62-2.73(2H, m), 2.94-3.10(1H, m), 3.26-3.34(1H, m), 4.1$_{2-4}$.42(2H, m), 7.23(1H, dd, J = 7.5, 7.5 Hz), 7.49(1H, d, J = 8.0 Hz), 7.56(1H, dd, J = 7.5, 7.5 Hz), 8.05(1H, d, J = 8.0 Hz), 11.29(1H, br s)<br>ESI+: 353 |
| 275 | 13 | NMR1: 0.82-1.10(2H, m), 1.15(6H, s), 1.26-1.38(2H, m), 1.45-1.59(1H, m), 1.59-1.75(4H, m), 1.99(3H, s), 2.42(2H, s), 2.62-2.72(2H, m), 2.89-3.00(1H, m), 3.95(1H, d, J = 13.2 Hz), 4.42(1H, d, J = 12.8 Hz), 4.90(1H, s), 7.23(1H, dd, J = 7.5, 7.5 Hz), 7.49(1H, d, J = 8.2 Hz), 7.56(1H, dd, J = 7.7, 7.4 Hz), 8.05(1H, d, J = 8.1 Hz), 11.32(1H, s)<br>ESI+: 385 |
| 14 | 14 | NMR1: 0.60-0.90(3H, m), 1.00-1.35(4H, m), 1.50-1.60(2H, m), 1.99(3H, s), 3.98(2H, t, J = 6.5 Hz), 4.27(2H, t, J = 5.4 Hz), 7.23-7.28(1H, m), 7.55-7.65(3H, m), 8.06(1H, d, J = 7.6 Hz), 11.25(1H, s)<br>FAB+: 303 |
| 276 | 14 | NMR1: 0.99-1.14(2H, m), 1.17(3H, t, J = 7.0 Hz), 1.45-1.60(3H, m), 1.69-1.80(2H, m), 1.99(3H, s), 2.63-2.88(4H, m), 3.9$_{1-4}$.07(4H, m), 7.23(1H, dd, J = 7.6, 7.4 Hz), 7.48(1H, d, J = 8.2 Hz), 7.54-7.59(1H, m), 8.04(1H, d, J = 8.1 Hz), 11.31(1H, br s)<br>ESI+: 343<br>mp: 211-213° C. |
| 277 | 14 | NMR1: 0.89-1.04(2H, m), 1.16(3H, t, J = 7.0 Hz), 1.26-1.37(2H, m), 1.37-1.52(1H, m), 1.58-1.71(4H, m), 1.99(3H, s), 2.61-2.80(4H, m), 3.90-4.05(4H, m), 7.24(1H, dd, J = 7.7, 7.5 Hz), 7.49(1H, d, J = 8.4 Hz), 7.57(1H, dd, J = 7.7, 7.5 Hz), 8.05(1H, d, J = 7.9 Hz), 11.32(1H, br s)<br>ESI+: 357 |

TABLE 174

| Ex | Syn | DATA |
|---|---|---|
| 15 | 15 | NMR1: 0.85(3H, t, J = 7.2 Hz), 1.18-1.42(6H, m), 2.01(3H, s), 3.00(2H, q, J = 6.0 Hz), 4.28(2H, d, J = 5.7 Hz), 6.06(1H, t, J = 5.8 Hz), 6.28-6.35(1H, m), 7.22-7.28(1H, m), 7.55-7.61(2H, m), 8.06(1H, d, J = 8.0 Hz), 11.28(1H, s)<br>FAB+: 302 |
| 278 | 15 | NMR1: 1.00(3H, t, J = 7.6 Hz), 1.05-1.21(2H, m), 1.70(2H, d, J = 13.2 Hz), 1.81-1.95(1H, m), 2.06(3H, s), 2.64(2H, dd, J = 11.6, 11.6 Hz), 3.03(2H, qd, J = 7.6, 7.6 Hz), 3.82(2H, d, J = 6.8 Hz), 3.90-4.03(2H, m), 5.16(2H, s), 6.40(1H, dd, J = 5.6, 5.6 Hz), 6.58(1H, d, J = 8.0 Hz), 6.6$_{2-6}$.73(2H, m), 7.22(1H, dd, J = 8.0, 8.0 Hz), 7.25-7.34(1H, m), 7.63(1H, dd, J = 8.0, 8.0 Hz), 7.64(1H, s), 8.10(1H, d, J = 8.0 Hz), 11.58(1H, s)<br>ESI+: 450 |

TABLE 174-continued

| Ex | Syn | DATA |
|---|---|---|
| 16 | 16 | NMR1: 0.81(3H, t, J = 7.1 Hz), 1.10-1.32(6H, m), 1.56-1.66(2H, m), 2.04(3H, s), 3.00-3.06(2H, m), 4.24(2H, s), 7.25-7.30(1H, m), 7.56-7.65(3H, m), 8.07(1H, d, J = 7.9 Hz), 11.34(1H, s)<br>FAB+: 337 |
| 279 | 16 | NMR1: 1.12-1.28(5H, m), 1.39-1.53(1H, m), 1.53-1.64(2H, m), 1.78-1.88(2H, m), 1.99(3H, s), 2.64-2.74(2H, m), 2.74-2.84(2H, m), 3.02(2H, q, J = 7.4 Hz), 3.56-3.65(2H, m), 7.23(1H, dd, J = 7.6, 7.3 Hz), 7.49(1H, d, J = 8.3 Hz), 7.54-7.60(1H, m), 8.05(1H, d, J = 8.3 Hz), 11.32(1H, br s)<br>ESI+: 363<br>mp: 225-228° C. |
| 17 | 17 | NMR1: 1.60-1.75(4H, m), 1.99(3H, s), 2.70(2H, t, J = 7.8 Hz), 3.47(2H, t, J = 5.8 Hz), 4.45(2H, s), 7.21-7.36(6H, m), 7.48(1H, d, J = 8.0 Hz), 7.54-7.60(1H, m), 8.06(1H, dd, J = 1.3, 8.1 Hz) 11.33(1H, s)<br>FAB+: 322 |
| 18 | 18 | NMR1: 1.94-2.03(2H, m), 2.08(3H, s), 2.75-2.84(4H, m), 5.19(2H, s), 7.09-7.14(1H, m), 7.18-7.24(1H, m), 7.26-7.32(1H, m), 7.36(1H, s), 7.55-7.66(2H, m), 8.06-8.12(1H, m), 9.71(1H, s), 11.67(1H, s)<br>FAB+: 349 |

TABLE 175

| Ex | Syn | DATA |
|---|---|---|
| 280 | 18 | NMR1: 2.09(3H, s), 5.25(2H, s), 7.27-7.32(1H, m), 7.55-7.72(6H, m), 8.09(1H, d, J = 8.0 Hz), 10.31(1H, s), 11.69(1H, s)<br>FAB+: 377<br>mp: 254-257° C. |
| 281 | 18 | NMR1: 0.92(3H, t, J = 7.3 Hz), 1.36-1.47(2H, m), 1.64-1.71(2H, m), 2.07(3H, s), 3.90(2H, t, J = 6.4 Hz), 5.18(2H, s), 6.84-6.86(2H, m), 7.26-7.40(3H, m), 7.56-7.65(2H, m), 8.08(1H, d, J = 7.5 Hz), 9.65(1H, s), 11.66(1H, s)<br>FAB+: 381 |
| 282 | 18 | NMR1: 2.09(3H, s), 5.24(2H, s), 7.26-7.32(1H, m), 7.35(1H, d, J = 7.7 Hz), 7.47(1H, t, J = 8.2 Hz), 7.56-7.68(3H, m), 7.94(1H, s), 8.09(1H, d, J = 7.3 Hz), 10.20(1H, s), 11.68(1H, s)<br>FAB+: 409 |
| 283 | 18 | NMR1: 2.04(3H, s), 2.27(3H, s), 4.18(2H, d, J = 6.2 Hz), 5.10(2H, s), 7.02-7.08(3H, m), 7.19(1H, t, J = 7.2 Hz), 7.25-7.31(1H, m), 7.54-7.64(2H, m), 7.89(1H, t, J = 6.0 Hz), 8.07(1H, d, J = 8.0 Hz), 11.59(1H, s)<br>FAB+: 337<br>mp: 240-243° C. |
| 284 | 18 | NMR1: 1.64-1.75(2H, m), 2.03(3H, s), 2.54-2.60(2H, m), 2.96-3.06(2H, m), 5.07(2H, s), 7.10-7.21(3H, m), 7.23-7.31(3H, m), 7.40-7.45(1H, m), 7.55-7.64(2H, m), 8.07(1H, d, J = 7.7 Hz), 11.59(1H, s)<br>FAB+: 351 |
| 285 | 18 | NMR1: 2.07(3H, s), 3.89(2H, s), 5.19(2H, s), 6.88(1H, d, J = 7.6 Hz), 7.15-7.40(9H, m), 7.55-7.65(2H, m), 8.09(1H, dd, J = 1.2, 8.1 Hz), 9.80(1H, s), 11.65(1H, s)<br>FAB+: 399 |
| 286 | 18 | NMR1: 1.30(3H, t, J = 7.0 Hz), 2.08(3H, s), 3.96(2H, q, J = 7.0 Hz), 5.20(2H, s), 6.55-6.60(1H, m), 6.99-7.06(1H, m), 7.10-7.20(2H, m), 7.26-7.32(1H, m), 7.55-7.66(2H, m), 8.06-8.12(1H, m), 9.83(1H, s), 11.67(1H, s)<br>FAB+: 353 |

TABLE 176

| Ex | Syn | DATA |
|---|---|---|
| 287 | 18 | NMR1: 1.25(9H, s), 2.08(3H, s), 5.20(2H, s), 7.26-7.33(3H, m), 7.34-7.42(2H, m), 7.56-7.66(2H, m), 8.07-8.12(1H, m), 9.76(1H, s), 11.69(1H, s)<br>FAB+: 365 |
| 288 | 18 | NMR1: 0.84-0.90(3H, m), 1.23-1.44(6H, m), 1.63-1.71(2H, m), 2.07(3H, s), 3.87-3.92(2H, m), 5.18(2H, s), 6.83-6.88(2H, m), 7.26-7.40(3H, m), 7.56-7.66(2H, m), 8.07-8.11(1H, m), 8.65(1H, s), 11.66(1H, s)<br>FAB+: 409 |
| 289 | 18 | NMR1: 1.14(3H, t, J = 7.5 Hz), 2.02(3H, s), 2.51-2.57(2H, m), 2.65-2.72(2H, m), 3.17-3.25(2H, m), 5.06(2H, s), 7.09(4H, s), 7.25-7.31(1H, m), 7.40-7.46(1H, m), 7.54-7.65(2H, m), 8.05-8.11(1H, m), 11.58(1H, s)<br>FAB+: 365 |
| 290 | 18 | NMR1: 2.06(3H, s), 5.19(2H, s), 6.63-6.68(1H, m), 6.99-7.04(2H, m), 7.12-7.18(1H, m), 7.19-7.32(4H, m), 7.36-7.43(2H, m), 7.54-7.65(2H, m), 8.06-8.11(1H, m), 9.99(1H, s), 11.68(1H, s)<br>FAB+: 401<br>mp: 194-197° C. |

TABLE 176-continued

| Ex | Syn | DATA |
| --- | --- | --- |
| 291 | 18 | NMR1: 0.76-0.92(2H, m), 1.05-1.24(3H, m), 1.30-1.42(1H, m), 1.55-1.70(5H, m), 2.03(3H, s), 2.85(2H, t, J = 6.3 Hz), 5.05(2H, s), 7.24-7.30(1H, m), 7.34(1H, t, J = 5.8 Hz), 7.54-7.64(2H, m), 8.07(1H, d, J = 7.1 Hz), 11.56(1H, s)<br>FAB+: 329 |
| 292 | 18 | NMR1: 2.08(3H, s), 5.23(2H, s), 7.26-7.35(3H, m), 7.55-7.66(4H, m), 8.07-8.12(1H, m), 10.09(1H, s), 11.69(1H, s)<br>FAB+: 393 |
| 293 | 18 | NMR1: 2.09(3H, s), 5.25(2H, s), 7.26-7.32(1H, m), 7.34-7.40(1H, m), 7.51-7.74(4H, m), 7.93(1H, s), 8.07-8.12(1H, m), 10.26(1H, s), 11.70(1H, s)<br>FAB+: 377 |

TABLE 177

| Ex | Syn | DATA |
| --- | --- | --- |
| 294 | 18 | NMR1: 2.02(3H, s), 2.66(2H, t, J = 7.1 Hz), 3.19(2H, q, J = 6.6 Hz), 3.70(3H, s), 5.06(2H, s), 6.82(2H, d, J = 8.4 Hz), 7.10(2H, d, J = 8.4 Hz), 7.28(1H, t, J = 6.7 Hz), 7.41(1H, t, J = 5.6 Hz), 7.55-7.64(2H, m), 8.08(1H, d, J = 7.8 Hz), 11.58(1H, s)<br>FAB+: 367 |
| 295 | 18 | NMR1: 2.07(3H, s), 4.16-4.24(4H, m), 5.18(2H, s), 6.76(1H, d, J = 8.7 Hz), 6.86-6.92(1H, m), 7.06(1H, s), 7.29(1H, t, J = 7.7 Hz), 7.56-7.65(2H, m), 8.09(1H, d, J = 8.0 Hz), 9.66(1H, s), 11.67(1H, s)<br>FAB+: 367 |
| 19 | 19 | NMR1: 0.86(3H, t, J = 7.1 Hz), 1.19-1.45(8H, m), 1.68-1.78(2H, m), 2.08(3H, s), 3.23-3.29(2H, m), 4.63(2H, s), 7.26-7.32(1H, m), 7.54(1H, d, J = 8.1 Hz), 7.60-7.66(1H, m), 8.06-8.10(1H, m), 11.59(1H, s)<br>FAB+: 336<br>mp: >310° C.(dec.) |
| 296 | 19 | NMR1: 1.23-1.35(2H, m), 1.59-1.66(2H, m), 1.93-2.05(1H, m), 2.08(3H, s), 3.18-3.26(2H, m), 3.30-3.33(2H, m), 3.71-3.77(2H, m), 5.32(2H, s), 7.27-7.32(1H, m), 7.46-7.51(1H, m), 7.54-7.58(1H, m), 7.60-7.67(4H, m), 8.10(1H, d, J = 7.8 Hz), 11.60(1H, s)<br>FAB+: 428 |
| 297 | 19 | NMR1: 1.20-1.33(2H, m), 1.57-1.67(5H, m), 1.88-2.00(1H, m), 3.27-3.37(2H, m), 3.77(2H, d, J = 6.4 Hz), 3.83-3.90(2H, m), 4.80(2H, s), 7.22-7.40(4H, m), 7.46-7.57(2H, m), 7.60-7.65(1H, m), 8.05(1H, d, J = 6.9 Hz), 11.51(1H, s)<br>FAB+: 428 |
| 20 | 20 | NMR1: 1.30-1.41(2H, m), 1.69(2H, d, J = 11.1 Hz), 1.95-2.05(1H, m), 2.07(3H, s), 3.27-3.33(2H, m), 3.83-3.92(4H, m), 5.25(2H, s), 6.7$_{2-6}$.80(2H, m), 7.27-7.32(1H, m), 7.60-7.65(2H, m), 7.72(1H, d, J = 8.7 Hz), 8.10(1H, d, J = 8.1 Hz), 11.63(1H, s), 12.21(1H, s)<br>FAB+: 424 |

TABLE 178

| Ex | Syn | DATA |
| --- | --- | --- |
| 298 | 20 | NMR1: 1.27-1.39(2H, m), 1.67(2H, d, J = 15.2 Hz), 1.90-2.03(1H, m), 2.07(3H, s), 3.22-3.38(2H, m), 3.86-3.91(4H, m), 5.24(2H, s), 6.93-6.95(1H, m), 7.10-7.12(1H, m), 7.24-7.32(2H, m), 7.59-7.68(2H, m), 8.09(1H, d, J = 7.6 Hz), 11.56(1H, s), 13.01(1H, br s)<br>FAB+: 424 |
| 299 | 20 | NMR1: 1.24-1.36(2H, m), 1.62-1.69(2H, m), 1.90-2.00(1H, m), 2.05(3H, s), 3.20-3.40(4H, m), 3.79-3.90(4H, m), 5.14(2H, s), 6.50(1H, s), 6.57-6.62(2H, m), 7.26-7.32(1H, m), 7.59-7.67(2H, m), 8.09(1H, d, J = 7.8 Hz), 11.59(1H, s)<br>FAB+: 438 |
| 21 | 21 | NMR1: 1.22-1.38(2H, m), 1.56-1.69(2H, m), 1.90-2.03(1H, m), 2.07(3H, s), 3.13(2H, s), 3.26-3.72(8H, m), 3.80-3.95(4H, m), 5.21(2H, s), 6.73-6.77(1H, m), 6.78-6.82(1H, m), 7.16(1H, d, J = 8.2 Hz), 7.27-7.33(1H, m), 7.59-7.67(2H, m), 8.10(1H, d, J = 8.2 Hz), 11.63(1H, s)<br>ESI+: 493 |
| 300 | 21 | NMR1: 1.25-1.45(4H, m), 1.45-1.70(6H, m), 1.92-2.03(1H, m), 2.05(3H, s), 3.16-3.23(2H, m), 3.28-3.34(2H, m), 3.50-3.60(2H, m), 3.83-3.90(4H, m), 5.20(2H, s), 6.53(1H, s), 6.65(1H, s), 6.74(1H, t, J = 2.2 Hz), 7.26-7.32(1H, m), 7.60-7.66(2H, m), 8.09(1H, d, J = 7.8 Hz), 11.56(1H, s)<br>FAB+: 491 |
| 301 | 21 | NMR1: 1.25-1.65(10H, m), 1.88-2.00(1H, m), 2.07(3H, s), 3.07-3.12(2H, m), 3.25-3.35(2H, m), 3.40-3.70(2H, m), 3.86-3.90(4H, m), 5.20(2H, s), 6.72(1H, dd, J = 2.3, 8.3 Hz), 6.78(1H, d, J = 2.1 Hz), 7.11(1H, d, J = 8.2 Hz), 7.25-7.33(1H, m), 7.62-7.65(2H, m), 8.10(1H, d, J = 7.9 Hz), 11.61(1H, s)<br>FAB+: 491 |

TABLE 179

| Ex | Syn | DATA |
|---|---|---|
| 22 | 22 | NMR1: 1.27-1.43(2H, m), 1.70(2H, d, J = 11.1 Hz), 1.95-2.07(1H, m), 2.09(3H, s), 3.27-3.45(2H, m), 3.84-3.93(4H, m), 5.22(2H, s), 6.59(1H, t, J = 2.4 Hz), 7.22(1H, s), 7.26-7.32(1H, m), 7.35(1H, s), 7.59-7.65(1H, m), 7.69(1H, d, J = 8.1 Hz), 8.10(1H, d, J = 8.1 Hz), 11.63(1H, s)<br>ESI+: 448 |
| 23 | 23 | NMR1: 1.31(2H, dddd, J = 12.4, 12.4, 12.4, 4.4 Hz), 1.60-1.72(2H, m), 1.90-2.03(1H, m), 2.07(3H, s), 3.26-3.34(2H, m), 3.83(2H, d, J = 6.4 Hz), 3.83-3.92(2H, m), 5.17(2H, s), 6.56-6.63(1H, m), 6.65-6.73(2H, m), 7.23(1H, dd, J = 8.4, 8.4 Hz), 7.72(1H, d, J = 8.4 Hz), 8.11(1H, dd, J = 8.4, 1.6 Hz), 8.71(1H, d, J = 1.6 Hz), 11.83(1H, s), 12.98(1H, br s)<br>FAB+: 424 |

TABLE 180

| No | Str |
|---|---|
| 1 | ![structure] |
| 2 | ![structure] |
| 3 | ![structure] |
| 4 | ![structure] |
| 5 | ![structure] |
| 6 | ![structure] |
| 7 | ![structure] |
| 8 | ![structure] |
| 9 | ![structure] |
| 10 | ![structure] |

TABLE 180-continued

| No | Str |
|---|---|
| 11 | 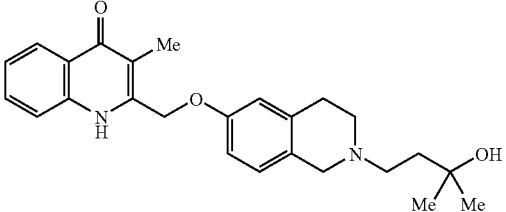 [SMILES: Cc1c(COc2ccc3c(c2)CCN(CCC(C)(C)O)C3)[nH]c2ccccc2c1=O] |

INDUSTRIAL APPLICABILITY

Since the compound which is an active ingredient of the medicament of the present invention has an NAD(P)H oxidase inhibitory action and a superior reactive oxygen species production inhibitory action based thereon, the pharmaceutical composition according to the present invention can be used as an agent for treating and/or preventing diseases associated with NAD(P)H oxidase.

The invention claimed is:

1. A compound of the formula (I) or a salt thereof:

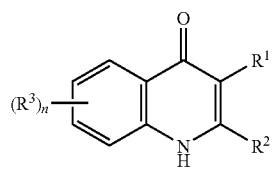

(I)

wherein:
$R^1$: lower alkyl or halogen;
$R^2$: —X—Y—$R^{20}$, —X-a heterocyclic group which may be substituted, or

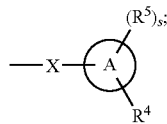

Ring A: aryl;
$R^3$: lower alkyl, halogen, halogeno-lower alkyl, aryl which may be substituted, a heterocyclic group which may be substituted, —$CO_2R^0$, —$OR^0$, or —O-halogeno-lower alkyl, wherein $R^3$s can be the same or different from one another, when n is 2 or 3;
X: $C_{1-10}$ alkylene which may be substituted;
Y: *—C(O)N($R^7$)—, —O—, *—OC(O)—, *—OC(O)N($R^7$)—, —S—, —S(O)—, —S(O)$_2$—, —N($R^8$)—, *—N($R^7$)C(O)—, *—N($R^7$)C(O)O—, —N($R^7$)C(O)N($R^7$)—, or *—N($R^7$)S(O)$_2$—; wherein
* in Y means a binding point to X;
$R^7$: the same or different, and $R^0$, cycloalkyl, or lower alkylene-cycloalkyl;
$R^8$: the same or different, and $R^7$ or —C(O)$R^7$;
$R^0$: the same or different, and H or lower alkyl;
n: 0, 1, 2, or 3;
s: 0, 1, 2, or 3;

$R^{20}$: $C_{1-10}$ alkyl, halogeno-lower alkyl, cycloalkyl which may be substituted, aryl which may be substituted, a heterocyclic group which may be substituted, lower alkylene-cycloalkyl which may be substituted, lower alkylene-aryl which may be substituted, lower alkylene-a heterocyclic group which may be substituted, lower)alkylene-N($R^0$)$_2$, —W—$R^0$, —W—halogeno-lower alkyl, —W-cycloalkyl which may be substituted, —W-aryl which may be substituted, —W-a heterocyclic group which may be substituted, —W-lower alkylene-cycloalkyl which may be substituted, —W-lower alkylene-aryl which may be substituted, or —W-lower alkylene-a heterocyclic group which may be substituted;
W: *-lower alkylene-C(O)N($R^7$)—, *-lower alkylene-C(O)—, *-lower alkylene-O—, *-lower alkylene-OC(O)—, *-lower alkylene-OC(O)N($R^7$)—, *-lower alkylene-O-lower alkylene-O—, *-lower alkylene-S—, *-lower alkylene-S(O)—, *-lower alkylene-S(O)$_2$—, *-lower alkylene-N($R^8$)-, *-lower alkylene-N($R^7$)C(O)—, *-lower alkylene-N($R^7$)C(O)O—, *-lower alkylene-N($R^7$)C(O)N($R^7$)—, or *-lower alkylene-N($R^7$)S(O)$_2$—; wherein
* in W means a binding point to Y;
$R^4$: cycloalkyl which may be substituted, aryl which may be substituted, a heterocyclic group which may be substituted, lower alkylene-cycloalkyl which may be substituted, lower alkylene-aryl which may be substituted, lower alkylene-a heterocyclic group which may be substituted, lower alkylene-O$R^0$, —O-lower alkylene-O$R^0$, -J-cycloalkyl which may be substituted, -J-aryl which may be substituted, -J-a heterocyclic group which may be substituted, -J-lower alkylene-cycloalkyl which may be substituted, -J-lower alkylene-aryl which may be substituted, or -J-lower alkylene-a heterocyclic group which may be substituted;
$R^5$: $C_{1-10}$ alkyl, halogen, halogeno-lower alkyl, cycloalkyl which may be substituted, aryl which may be substituted, a heterocyclic group which may be substituted, —$CO_2R^0$, —CN, oxo, lower alkylene-cycloalkyl which may be substituted, lower alkylene-aryl which may be substituted, lower alkylene-a heterocyclic group which may be substituted, lower alkylene-$CO_2R^0$, -J-$R^0$, -J-halogeno-lower alkyl, -J-cycloalkyl which may be substituted, -J-aryl which may be substituted, -J-a heterocyclic group which may be substituted, -J-lower alkylene-cycloalkyl which may be substituted, -J-lower alkylene-aryl which may be substituted, or -J-lower alkylene-a heterocyclic group which may be substituted, wherein $R^5$s can be the same or different from one another, when s is 2 or 3; and
J: the same or different, and *—C(O)N($R^7$)—, —C(O)—, —O—, —S—, —S(O)—, —S(O)$_2$—, —N($R^8$)—, *—N($R^7$)C(O)—, *—N($R^7$)C(O)O—, —N($R^7$)C(O)N($R^7$)—, *-lower alkylene-C(O)N($R^7$)—, *-lower alkylene-C(O)—, *-lower alkylene-O—, *-lower alkylene-S—, *-lower alkylene-S(O)—, *-lower alkylene-S(O)$_2$—, *-lower alkylene-N($R^8$)—, *-lower alkylene-N($R^7$)C(O)—, *-lower alkylene-N($R^7$)C(O)O—, *-lower alkylene-N($R^7$)C(O)N($R^7$)—, *—O-lower alkylene-C(O)—, —O-lower alkylene-O—, or *—O-lower alkylene-N($R^8$)—; wherein
* in J means a binding point to ring A;
provided that the following compounds are excluded:
3-methyl-2-(5-phenoxypentyl)quinolin-4(1H)-one,
3-ethyl-2-(5-phenoxypentyl)quinolin-4(1H)-one,
3-methyl-2-[2-(4-phenoxypheny)ethyl]quinolin-4(1H)-one, 3-chloro-2-(piperidin-1-ylmethyl)quinolin-4(1H)-one, and 5-({4-[(3,4-dihydro-3-methyl-4-oxoquinolin-2-yl) methoxy]phenyl}methyl)thiazolidine-2,4-dione.

2. The compound or a salt thereof according to claim 1, wherein $R^1$: lower alkyl or halogen;

$R^2$: -lower alkylene-(a heterocyclic group which may be substituted with group(s) selected from Group $G^1$), or -lower alkylene-O—$R^{20}$;

$R^3$: halogen;

n: 0 or 1;

$R^{20}$:: cycloalkyl which may be substituted with at least one group selected from Group $G^1$, aryl which may be substituted with at least one group selected from Group $G^1$, or a heterocyclic group which may be substituted with at least one group selected from Group $G^1$; wherein Group $G^1$: $C_{1-10}$ alkyl, halogen, halogeno-lower alkyl, cycloalkyl which may be substituted, aryl which may be substituted, a heterocyclic group which may be substituted, —$CO_2R^0$, —CN, oxo, lower alkylene-cycloalkyl which may be substituted, lower alkylene-aryl which may be substituted, lower alkylene-a heterocyclic group which may be substituted, lower alkylene-$CO_2R^0$, -$J^1$-$R^0$, -$J^1$-halogeno-lower alkyl, -$J^1$-cycloalkyl which may be substituted, -$J^1$-aryl which may be substituted, -$J^1$-a heterocyclic group which may be substituted, -$J^1$-lower alkylene-cycloalkyl which may be substituted, -$J^1$-lower alkylene-aryl which may be substituted, and -$J^1$-lower alkylene-a heterocyclic group which may be substituted; and $J^1$: —C(O)N($R^7$)—*, —C(O)—, —C(O)-lower alkylene-O—*, —O—, —S—, —S(O)—, —S(O)$_2$—, —N($R^8$)—, —N($R^7$)C(O)—*, —N($R^7$)C(O)O—*, —N($R^7$)C(O)N($R^7$)—, —N($R^7$)S(O)$_2$—*, —N($R^7$)C(O)-lower alkylene-O—*, -lower)alkylene-C(O)N($R^0$)—*, -lower alkylene-C(O)—*, -lower alkylene-O—*, -lower alkylene-OC(O)—*, -lower alkylene-S—*, -lower alkylene-S(O)—*, -lower alkylene-S(O)$_2$—*, -lower alkylene-N($R^8$)—*, -lower alkylene-N($R^7$)C(O)—*, —O-lower alkylene-C(O)—*, —O-lower alkylene-O—, or —O-lower alkylene-N($R^8$)—*; wherein

* in $J^1$ means a binding point to a remnant of the group in Group $G^1$.

3. The compound or a salt thereof according to claim 2, wherein $R^1$: lower alkyl;

$R^2$: -lower alkylene-(piperidyl which may be substituted with at least one group selected from Group $G^1$), or -lower alkylene-O—$R^{20}$; and $R^{20}$: a cyclohexyl which may be substituted with at least one group selected from Group $G^1$, phenyl which may be substituted with at least one group selected from Group $G^1$, pyridyl which may be substituted with at least one group selected from Group $G^1$, tetrahydroquinolinyl which may be substituted with at least one group selected from Group $G^1$, or tetrahydroisoquinolinyl which may be substituted with at least one group selected from Group $G^1$.

4. The compound or a salt thereof according to claim 3, wherein $R^2$ is -lower alkylene-O-(phenyl which may be substituted with at least one group selected from Group $G^1$), or -lower alkylene-O-(pyridyl which may be substituted with at least one group selected from Group $G^1$).

5. The compound or a salt thereof according to claim 4, wherein $R^2$ is -lower alkylene-O-(phenyl which may be substituted with at least one group selected from Group $G^1$).

6. The compound or a salt thereof according to claim 5, wherein $R^2$ is

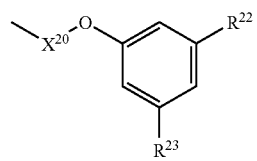

wherein:

$X^{20}$: lower alkylene;

$R^{22}$: a group selected from Group $G^1$; and $R^{23}$: H, lower alkyl, halogen, halogeno-lower alkyl, —$OR^0$, —$CO_2R^0$, —C(O)$R^0$, or —CN.

7. The compound or a salt thereof according to claim 6, wherein $R^{23}$ is H, lower alkyl, halogen, halogeno-lower alkyl, or —$OR^0$.

8. The compound or a salt thereof according to claim 7, wherein $R^{22}$ is lower alkyl, halogen, halogeno-lower alkyl, lower alkylene-a saturated heterocyclic group, lower alkylene-$OR^0$, —$OR^0$, —O-lower alkylene-$OR^0$, —O-halogeno-lower alkyl, cycloalkyl which may be substituted with —O-lower alkylene-oxo, or —O-lower alkylene-a saturated heterocyclic group; provided that the saturated heterocyclic group may be substituted with lower alkyl, —$OR^0$, —C(O)-lower alkyl, or —S(O)$_2$-lower alkyl.

9. The compound or a salt thereof according to claim 8, wherein $R^{22}$ is lower alkylene-a saturated heterocyclic group, lower alkylene-$OR^0$, —O-lower alkylene-$OR^0$, or —O-lower alkylene-a saturated heterocyclic group; provided that the saturated heterocyclic group is selected from oxetanyl, tetrahydrofuranyl, and tetrahydropyranyl, each of which may be substituted with lower alkyl or —$OR^0$.

10. The compound or a salt thereof according to claim 7, wherein $R^{22}$ is

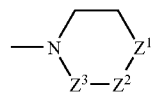

wherein:

$Z^1$: —C($R^0$)$_2$— or —O—;

$Z^2$: a bond,)—C($R^0$)$_2$—, or) —C($R^0$)$_2$C($R^0$)$_2$—; and $Z^3$:))—C($R^0$)$_2$C($R^0$)$_2$—or —C(O)—.

11. The compound or a salt thereof according to claim 5, wherein $R^2$ is

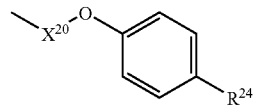

wherein:

$X^{20}$: lower alkylene; and $R^{24}$: a group selected from Group $G^1$.

12. The compound or a salt thereof according to claim 11, wherein $R^{24}$ is lower alkyl, halogen, halogeno-lower alkyl, cyclohexyl which may be substituted with —$OR^0$, lower alkylene-a saturated heterocyclic group, lower alkylene-OR⁰, —OR⁰, —O-lower alkylene-OR⁰, —O-halogeno-lower alkyl, or —O-lower alkylene-a saturated heterocyclic group; provided that the saturated heterocyclic group may be substituted with a lower alkyl, —OR⁰, —C(O)-lower alkyl, or —S(O)₂-lower alkyl.

13. The compound or a salt thereof according to claim 12, wherein $R^{24}$ is lower alkylene-a saturated heterocyclic group, or —O-lower alkylene-a saturated heterocyclic group; provided that the saturated heterocyclic group is selected from oxetanyl, tetrahydrofuranyl, and tetrahydropyranyl, each of which may be substituted with a lower alkyl or —OR⁰.

14. The compound or a salt thereof according to claim 4, wherein $R^2$ is -lower alkylene-O-(pyridyl which may be substituted with at least one group selected from Group $G^1$).

15. The compound or a salt thereof according to claim 14, wherein $R^2$ is

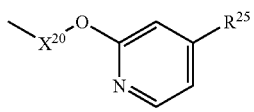

wherein:
$X^{20}$: lower alkylene; and
$R^{25}$: a group selected from Group $G^1$.

16. The compound or a salt thereof according to claim 15, wherein $R^{25}$ is lower alkyl, halogen, halogeno-lower alkyl, lower alkylene-a saturated heterocyclic group, lower alkylene-OR⁰, —OR⁰, —O-lower alkylene-OR⁰, —O-halogeno-lower alkyl, or —O-lower alkylene-a saturated heterocyclic group; provided that the saturated heterocyclic group may be substituted with lower alkyl or —OR⁰.

17. The compound or a salt thereof according to claim 16, wherein $R^{25}$ is lower alkylene-a saturated heterocyclic group, lower alkylene-OR⁰, —O-lower alkylene-OR⁰, or —O-lower alkylene-a saturated heterocyclic group; provided that the saturated heterocyclic group is selected from oxetanyl, tetrahydrofuranyl, and tetrahydropyranyl, each of which may be substituted with lower alkyl or —OR⁰.

18. The compound or a salt thereof according to claim 1, which is selected from the following group:
3-methyl-2-{[3-(tetrahydro-2H-pyran-4-ylmethoxy)phenoxy]methyl}quinolin-4(1H)-one;
N-{trans-4-[(3-methyl-4-oxo-1,4-dihydroquinolin-2-yl)methoxy]cyclohexyl}ethanesulfonamide;
3-methyl-2-[({4-[2-(tetrahydro-2H-pyran-4-yl)ethoxy]pyridin-2-yl}oxy)methyl]quinolin-4(1H)-one;
3-methyl-2-{[3-(3-oxomorpholin-4-yl)phenoxy]methyl}quinolin-4(1H)-one;
4-{4-[(3-methyl-4-oxo-1,4-dihydroquinolin-2-yl)methoxy]butoxy}benzonitrile;
2-({4-[4-(2-methoxyethyl)phenoxy]butoxy}methyl)-3-methylquinolin-4(1H)-one;
2-({3-[(1-acetylpiperidin-4-yl)methoxy]phenoxy}methyl)-3-methylquinolin-4(1H)-one;
3-methyl-2-{[3-(2-pyridin-4-ylethoxy)phenoxy]methyl}quinolin-4(1H)-one;
2-{[3-(3-hydroxy-3-methylbutoxy)phenoxy]methyl}-3-methylquinolin-4(1H)-one;
6-fluoro-3-methyl-2-({[4-(tetrahydro-2H-pyran-4-ylmethoxy)pyridin-2-yl]oxy}methyl)quinolin-4(1H)-one;
2-({[4-(3-hydroxy-3-methylbutoxy)pyridin-2-yl]oxy}methyl)-3-methylquinolin-4(1H)-one;
6-fluoro-3-methyl-2-({[1-(tetrahydro-2H-pyran-4-ylacetyl)-1,2,3,4-tetrahydroquinolin-7-yl]oxy}methyl)quinolin-4(1H)-one;
3-methyl-2-{[6-(tetrahydro-2H-pyran-4-ylmethoxy)-3,4-dihydroisoquinolin-2(1H)-yl]methyl}quinolin-4(1H)-one;
2-({[4-(3-methoxy-3-methylbutoxy)pyridin-2-yl]oxy}methyl)-3-methylquinolin-4(1H)-one;
2-[({4-[(4-hydroxy-4-methylpentyl)oxy]pyridin-2-yl}oxy)methyl]-3-methylquinolin-4(1H)-one;
2-{[3-(4-hydroxypiperidin-1-yl)phenoxy]methyl}-3-methylquinolin-4(1H)-one;
2-{[3-(4-hydroxy-4-methylpiperidin-1-yl)phenoxy]methyl}-3-methylquinolin-4(1H)-one;
N-cyclohexyl-N-{2-[(3-methyl-4-oxo-1,4-dihydroquinolin-2-yl)methoxy]ethyl}tetrahydro-2H-pyrane-4-carboxamide;
ethyl 4-[2-(3-methyl-4-oxo-1,4-dihydroquinolin-2-yl)ethyl]piperidine-1-carboxylate;
2-{2-[1-(ethylsulfonyl)piperidin-4-yl]ethyl}-3-methylquinolin-4(1H)-one; and
(3-methyl-4-oxo-1,4-dihydroquinolin-2-yl)methyl (3-phenylpropyl)carbamate.

19. A pharmaceutical composition comprising the compound or a salt thereof according to claim 1 and a pharmaceutically acceptable excipient.

20. A compound of the formula 2-({[4-(3-hydroxy-3-methylbutoxy)pyridin-2-yl]oxy}methyl)-3-methylquinolin-4(1H)-one or a salt thereof.

21. A method for treating a disease associated with NAD(P)H oxidase, comprising administering to a patient in need thereof an effective amount of a compound or a salt thereof according to claim 20, wherein the disease is selected from the group consisting of diabetes types 1 and 2, impaired glucose tolerance, hyperlipidemia, fatty liver and diabetic complications.

* * * * *